(12) United States Patent
Parham et al.

(10) Patent No.: US 11,208,401 B2
(45) Date of Patent: Dec. 28, 2021

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt Am Main (DE); Anja Jatsch, Frankfurt Am Main (DE); Thomas Eberle, Landau (DE); Tobias Grossmann, Darmstadt (DE); Jonas Valentin Kroeber, Frankfurt Am Main (DE); Lars Dobelmann-Mara, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 172 days.

(21) Appl. No.: 15/580,309

(22) PCT Filed: May 19, 2016

(86) PCT No.: PCT/EP2016/000834
§ 371 (c)(1),
(2) Date: Dec. 7, 2017

(87) PCT Pub. No.: WO2016/198144
PCT Pub. Date: Dec. 15, 2016

(65) Prior Publication Data
US 2018/0162843 A1 Jun. 14, 2018

(30) Foreign Application Priority Data

Jun. 10, 2015 (EP) .................................... 15001718

(51) Int. Cl.
C07D 405/14 (2006.01)
C07D 409/14 (2006.01)
C07D 403/10 (2006.01)
C09K 11/06 (2006.01)
H01L 51/00 (2006.01)
C07D 403/14 (2006.01)
C07D 407/14 (2006.01)

(52) U.S. Cl.
CPC ......... C07D 405/14 (2013.01); C07D 403/10 (2013.01); C07D 403/14 (2013.01); C07D 407/14 (2013.01); C07D 409/14 (2013.01); C09K 11/06 (2013.01); H01L 51/0072 (2013.01); H01L 51/0073 (2013.01); H01L 51/0074 (2013.01); C09K 2211/1029 (2013.01); C09K 2211/1044 (2013.01); C09K 2211/1059 (2013.01); C09K 2211/1088 (2013.01); C09K 2211/1092 (2013.01)

(58) Field of Classification Search
None
See application file for complete search history.

(56) References Cited

U.S. PATENT DOCUMENTS

| 2016/0233436 A1* | 8/2016 | Zeng | H01L 51/0072 |
| 2016/0248023 A1* | 8/2016 | Parham | H01L 51/0072 |

FOREIGN PATENT DOCUMENTS

| JP | 2013131518 A | | 7/2013 |
| KR | 20120033017 A | | 4/2012 |
| KR | 10-2015-0012835 | * | 2/2015 |
| KR | 20150012835 A | | 2/2015 |
| WO | WO-2012036482 A1 | | 3/2012 |
| WO | WO-2012067425 A1 | | 5/2012 |
| WO | WO-2013/154325 A1 | * | 10/2013 |
| WO | WO-2013187689 A1 | | 12/2013 |
| WO | WO-2015/051869 A1 | * | 4/2015 |

OTHER PUBLICATIONS

Machine English translation of Hwang et al. (KR 10-2012-0033017). Aug. 6, 2019.*
Machine English translation of Ji et al. (KR 10-2015-0012835). Apr. 30, 2020.*
International Search Report for PCT/EP2016/000834 dated Aug. 16, 2016.
Written Opinion of the International Searching Authority for PCT/EP2016/000834 dated Aug. 16, 2016.

* cited by examiner

Primary Examiner — Jay Yang
(74) Attorney, Agent, or Firm — Faegre Drinker Biddle & Reath LLP

(57) ABSTRACT

The present invention relates to compounds which are suitable for use in electronic devices, and to electronic devices, in particular organic electroluminescent devices, comprising these compounds. The compounds have a dibenzofuran, dibenzothiophene or a fluorene group substituted in the 1-position, either directly or through a linking group, to a carbon atom of a heteroaromatic group with one or two nitrogen atoms in a bicyclic 6/6 core, or to a carbon or nitrogen atom of a heteroaromatic group with two nitrogen atoms in a bicyclic 5/6 core and is further substituted with a group selected from dibenzofuran, dibenzothiophene, fluorene or carbazole.

26 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2016/000834, filed May 19, 2016, which claims benefit of European Application No. 15001718.4, filed Jun. 10, 2015, both of which are incorporated herein by reference in their entirety.

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence. For quantum-mechanical reasons, an up to four-fold increase in the energy and power efficiency is possible using organometallic compounds as phosphorescence emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties.

There are many materials that can be employed as matrix materials for phosphorescent emitters in organic electroluminescent devices. Further improvements are desirable here, in particular with respect to the efficiency, the lifetime and the thermal stability of the materials. The object of the present invention is the provision of compounds which are suitable for use in an OLED, in particular as matrix material for phosphorescent emitters, but also as electron-transport materials although other uses such as hole-transport and/or electron-blocking materials are also possible. A further object of the present invention is to provide further organic semiconductors for organic electroluminescent devices so as to provide the person skilled in the art with a greater possible choice of materials for the production of OLEDs.

It is known that compounds with aromatic heterocyclic groups such as carbazoles, dibenzofurans, dibenzothiophenes, fluorenes, quinazolines, quinoxalines and benzimidazoles are useful in OLEDs, generally as hosts for light emitting materials or for their charge-carrying properties. Compounds with combinations of at least three of these classes are known.

WO 2012/134124, WO 2012/169821, WO 2013/187689, WO 2012/121561, WO 2012/050371, WO 2012/036482, WO 2012/141499, KR 201310263, KR 2012132815, KR 2012116272, KR 2012109744, KR 2012038060, KR 2013102673 and KR 20120033017 describe OLEDs with quinazolone groups substituted with (among others) dibenzofuran, dibenzothiophene or fluorene groups as well as carbazoyl groups.

US 2014/0114069 discloses OLEDs with quinazoline substituted (either directly or through a link) through the nitrogen of a carbazole group which may be further substituted with dibenzofuran, dibenzothiophene or fluorene groups.

US 2013/0306959 discloses OLED with compounds of the formula A-B-(Cz)$_n$ where A, B and C are all aromatic heterocyclic groups, where A and B can include (among many others) quinazolines, quinoxalines, benzimidazoles, dibenzofurans and dibenzothiophenes and Cz can also include carbazoles as well.

CN 103467447 discloses OLEDs with quinazoline compounds substituted with carbazole groups and can be further substituted with (among others) dibenzofuran, dibenzothiophene and fluorene groups.

WO 2013/154325 and WO 2014/104585 disclose OLEDs with bis-carbazolyl groups that may be substituted with (among others) quinazolines, dibenzofurans, dibenzothiophenes and fluorenes.

WO 2014/088290 discloses OLEDs with carbazole groups that have an annulated benzene ring which can be substituted with quinazolines, quinoxalines, dibenzofurans, dibenzothiophenes and fluorenes.

KR 2014013351, US 2014/0027744 and US 2012/0133274 describe OLEDs with compounds that may contain combinations of 2-(N-phenylbenzimidazole), N-phenylcarbazole, dibenzofuran and dibenzothiophene groups.

JP 2012-222268 discloses OLEDs with compounds with combinations of carbazole, dibenzofuran, dibenzothiophene and N-benzimidazole groups.

WO 2013/022145 discloses OLEDs with compounds with N-phenylbenzimidazole and carbazole groups which may be substituted with (among other) dibenzofuran and dibenzothiophene groups.

WO 2010/044607 discloses OLEDs with compounds with N-phenylbenzimidazole and carbazole groups which may be substituted with (among other) dibenzofuran, dibenzothiophene and fluorene groups.

JP 2012-049518 discloses OLEDs with substituted dibenzofuran, dibenzothiophene and N-phenylcarbazole groups.

KR 2012104067 discloses dibenzothiophene derivatives substituted in the 1-position with quinoline and N-(1-phenylbenzimidazole) groups. The benzimidazole may be connected either directly through the nitrogen or through an aryl linking group to the nitrogen.

WO 2011/106344 discloses dibenzofuran, dibenzothiophene or fluorene compounds substituted in the 1- or 4-positions with a N-(1-phenylbenzimidazole) as ligands for phosphorescent metal complexes.

Begoin et al., Helv. Chem. Acta., 96, 853 (2013) discloses 1-(N-(1-phenylbenzimidazole)) substituted dibenzofurans and dibenzothiophenes.

Additional general disclosures for compounds with a combination of three different kinds of aromatic heterocyclic groups can be found in WO 2012/033108; JP 20141883315; US 2011/0147792; KR 2014122680; KR 2014127073; US 2014/0284584; WO 2012/033108; US 2014/001460; KR 2014080002 and U.S. Pat. No. 8,685,543.

U.S. Pat. No. 7,651,790 discloses OLEDs with a compound of A-C-B where A is a hole-transporting group (including, among others, carbazoles), B is an electron-transporting group (including triazines, fluorenes and spiro-fluorenes among others) and C is a bond or a linking group.

Lee et al., Chem. Europ. J., 19, 1194 (2013) compares the effects on OLED performance of attaching a N-phenylcarbazole group (through the phenyl group) in the 2, 3 or 4 positions of a dibenzofuran.

Surprisingly, it has been found that certain compounds described in greater detail below achieve this object, are highly suitable for use in OLEDs and result in improvements in the organic electroluminescent device. The improvements here relate, in particular, to the lifetime of the device, although other characteristics can also be improved. The present invention therefore relates to these compounds and to electronic devices, in particular organic electroluminescent devices, which comprise compounds of this type.

The present invention relates to a compound according to Formula (1) or (2):

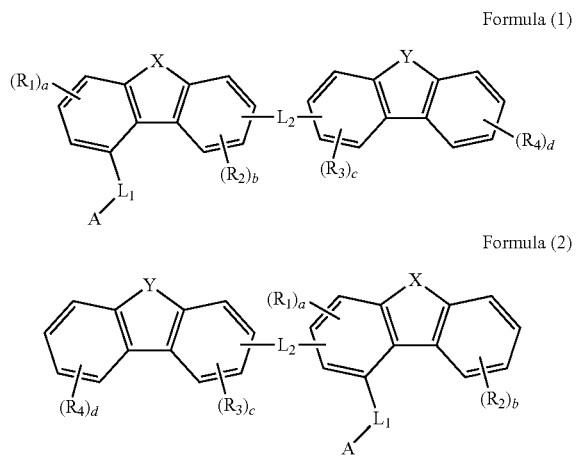

Formula (1)

Formula (2)

where:

X is an oxygen, sulfur or $CZ_1Z_2$;

Y is an oxygen, sulfur, $CZ_1Z_2$ or $NAr_1$;

$Z_1$ and $Z_2$ are on each occurrence, identically or differently, H, D, F, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R_5$, where one or more, preferably non-adjacent $CH_2$ groups may be replaced by $(R_5)C=C(R_5)$, $C\equiv C$, $Si(R_5)_2$, $Ge(R_5)_2$, $Sn(R_5)_2$, $C=O$, $C=S$, $C=Se$, $C=N(R_5)$, $P(=O)(R_5)$, SO, SO2, $N(R_5)_2$, O, S or $CON(R_5)_2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R_5$, or an aryloxy or heteroaryloxy group having 5 to 60 aromatic ring atoms, which may be substituted by one or more radicals $R_5$, where $Z_1$ and $Z_2$ may be connected together to form a spiro ring system;

$R_1$, $R_2$, $R_3$ and $R_4$ is on each occurrence, identically or differently, selected from the group consisting of H, D, F, Cl, Br, I, CN, $Si(R_5)_3$, a straight-chain alkyl, alkoxy or thioalkyl group having 1 to 40 C atoms or a branched or cyclic alkyl, alkoxy or thioalkyl with 3-40 C atoms which may be substituted by one or more radicals $R_5$, wherein each one or more non-adjacent $CH_2$ groups by may be replaced $Si(R_5)_2$, $C=NR_5$, $P(=O)(R_5)$, SO, $SO_2$, $NR_5$, O, S or $CONR_5$ and where one or more H atoms may be replaced by D, F, Cl, Br or I, an aromatic or heteroaromatic ring system having 6 to 40 carbon atoms which may be substituted by one or more radicals $R_5$, an aryloxy group having 5 to 60 aromatic ring atoms which may be substituted by one or more radicals $R_5$, or an aralkyl group having 5 to 60 aromatic ring atoms, which may be substituted by one or more radicals $R_5$, where two or more adjacent substituents $R_1$, $R_2$, $R_3$ and $R_4$ can form a mono- or poly-cyclic, aliphatic, aromatic or heteroaromatic ring system with one another and which may be substituted with one or more radicals $R_5$; where $R_5$ is selected from the group consisting of H, D, F, an aliphatic hydrocarbon radical having 1 to 20 carbon atoms or an aromatic or heteroaromatic ring system having 5 to 30 C atoms; $R_6$ is the same as $R_1$ but excluding H or D;

$Ar_1$ and $Ar_2$ are on each occurrence, identically or differently, an aromatic or heteroaromatic ring system having 5 to 30 aromatic ring atoms, which may be substituted by one or more radicals $R_5$ and where optionally two or more adjacent substituents $R_5$ can form a mono- or polycyclic-aliphatic, aromatic or heteroaromatic ring system with one another;

a, b, c are on each occurrence, identically or differently, are 0, 1, 2 or 3 where a is not 3 in Formula (2) and d is independently 0, 1, 2, 3 or 4;

$L_1$ and $L_2$ are on each occurrence, identically or differently, a direct bond or an aromatic or heteroaromatic ring system having 5-30 aromatic ring atoms, which may be substituted by one or more non-aromatic radicals $R_5$;

A is a heterocyclic group according to Formula $A_1$:

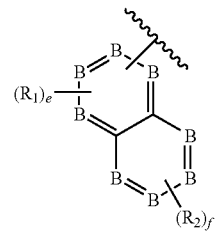

$A_1$ where only one or two of B are nitrogen atoms and the others are carbon atoms, $R_1$ and $R_2$ are as previously defined, e is 0, 1, 2 or 3, f is 0, 1, 2, 3 or 4, and wherein $A_1$ is connected to the remainder of the compound through a carbon atom; or A is a heterocyclic group selected from the group of Formula $A_2$ or $A_3$:

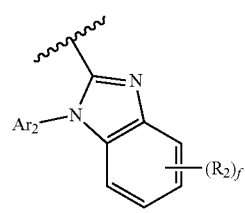

$A_2$

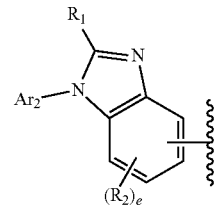

$A_3$ where $Ar_2$, $R_1$, $R_2$, e and f are as previously defined; or A is a heterocyclic group according to $A_4$:

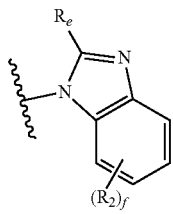

where $Ar_2$, $R_2$, $R_6$, e and f are as previously defined.

In the sense of this invention, the following numbering system for the central nucleus to which A is attached (X=O, S or $CZ_1Z_2$) will be used:

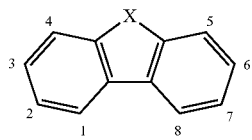

For convenience, the same numbering system will also be used for a carbazole substituent ($X=NAr_1$).

The compounds of Formulae (1) or (2) can be generally described as having a central nucleus that is a dibenzofuran (X=O), a dibenzothiophene (X=S) or a fluorene ($X=CZ_1Z_2$). The 1-position of the compound of Formulae (1) and (2) is connected (either directly or through a linking group $L_1$) to a carbon atom of a heteroaromatic group with one or two nitrogen atoms in a bicyclic 6/6 core. Alternatively, the 1-position is connected (either directly or through a linking group $L_1$) to a carbon or nitrogen atom of a heteroaromatic group with two nitrogen atoms in a bicyclic 5/6 core, which is a benzimidazole. In either of these alternatives, the compounds of Formulae (1) and (2) also have at least one substituent selected from a dibenzofuran (Y=O), dibenzothiophene (Y=S), fluorene ($Y=CZ_1Z_2$) or carbazole ($Y=NAr_1$) attached via any of its 1- to 8-positions to any of the 2- to 8-positions of the central nucleus.

In the sense of the invention, the terms "dibenzofuran, dibenzothiophene, fluorene (including spirofluorene), or carbazole" include not only the parent heterocycle but also include any analogues that have annulated monocyclic- or polycyclic-, aliphatic, aromatic or heteroaromatic rings. An annulated ring is one that has two adjacent ring atoms in common with another ring.

An aryl group in the context of this invention contains from 6 to 24 carbon atoms; a heteroaryl group within the meaning of this invention containing from 2 to 24 carbon atoms and at least one heteroatom, with the proviso that the sum of carbon atoms and hetero atoms is at least 5. The heteroatoms are preferably selected from N, O and S. Among an aryl or heteroaryl group is either a simple aromatic ring, for example benzene, or a simple heteroaromatic ring, for example pyridine, pyrimidine, thiophene, etc., or a fused aryl or heteroaryl, such as naphthalene, anthracene, phenanthrene, quinoline, isoquinoline, etc.

An aromatic ring system in the sense of this invention contains from 6 to 40 carbon atoms in the ring system. A heteroaromatic ring system in the sense of this invention contains 1 to 40 carbon atoms and at least one heteroatom in the ring system, with the proviso that the sum of carbon atoms and hetero atoms is at least 5 results. The heteroatoms are preferably selected from N, O and S. An aromatic or heteroaromatic ring system in the context of this invention is to be understood as a system that does not necessarily contain only aryl or heteroaryl groups, but in which a plurality of aryl or heteroaryl groups are connected by a non-aromatic moiety, such as, for example, a C, N or O atom or a carbonyl group. For example, systems such as 9,9'-spirobifluorene, 9,9-diarylfluorene, triarylamine, stilbene, etc., are aromatic ring systems for the purposes of this invention. Also included are systems in which two or more aryl groups are connected, for example, by a linear or cyclic alkyl group or by a silyl group. Furthermore, to systems in which two or more aryl or heteroaryl groups are directly bonded to each other, such, for example, biphenyl, terphenyl or quaterphenyl be understood also as an aromatic or heteroaromatic ring system.

For the purposes of this invention, a cyclic alkyl, alkoxy or thioalkoxy means a monocyclic, bicyclic or a polycyclic group.

In the present invention, a C1 to C40 alkyl group, in which individual H atoms or $CH_2$ groups may be substituted by the above-mentioned groups, include methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neo-pentyl, cyclopentyl, n hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo [2,2,2] octyl, 2-bicyclo [2.2.2] octyl, 2-(2,6-dimethyl) octyl, 3-(3,7-dimethyl) octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl) cyclohex-1-yl, 1-(n-butyl)cyclohex-1-yl, 1-(N-hexyl)-cyclohex-1-yl, 1-(n-octyl)-cyclohex-1-yl and 1-(n-decyl)cyclohex-1-yl. Examples of an alkenyl group include ethenyl, propenyl, butenyl, pentenyl, cyclopentenyl, hexenyl, cyclohexenyl, heptenyl, cycloheptenyl, octenyl, cyclooctenyl or cyclooctadienyl. Examples of an alkynyl group include, for example, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms which may be substituted with residues above yet and which can be linked via any position on the aromatic or heteroaromatic compounds, for example, groups are understood to be derived from benzene, naphthalene, anthracene, benzanthracene, phenanthrene, benzophenanthrene, pyrene, chrysene, perylene, fluoranthene, benzfluoranthen, naphthacene, pentacene, benzopyrene, biphenyl, biphenyl, terphenyl, fluorene, spirobifluorene, dihydrophenanthrene, dihydropyrene, tetrahydropyrene, cis- or trans-indenofluorene, cis- or trans-Monobenzoindenofluoren, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, chinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazin, pyrimidine, benzpyrimidine, quinoxaline, 1,5-diaza-anthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In the above, $R_1$ to $R_4$ refers to a first substituent and $R_5$ is a secondary substituent on $R_1$-$R_4$ or in the case of structure $A_4$, a first substituent. Any of $R_1$-$R_4$ and $R_5$ can be chosen independently from the groups as described. Adjacent radicals or adjacent substituents in the sense of the present application are taken to mean substituents which are bonded to C atoms which are in turn bonded directly to one another or substituents which are bonded to the same C atom.

In compounds which are processed by vacuum evaporation, the alkyl groups preferably have not more than five C atoms, particularly preferably not more than 4 C atoms, very particularly preferably not more than 1 C atom. For compounds which are processed from solution, suitable compounds are also those which are substituted by alkyl groups, in particular branched alkyl groups, having up to 10 C atoms or which are substituted by oligoarylene groups, for example ortho-, meta-, para- or branched terphenyl or quaterphenyl groups.

If the compounds of the formula (1) or (2) or the preferred embodiments are used as matrix material for a phosphorescent emitter or in a layer which is directly adjacent to a phosphorescent layer, it is furthermore preferred for $R_1$-$R_6$, $Z_1$, $Z_2$, $Ar_1$ and $Ar_2$ of the compound to contain no condensed aryl or heteroaryl groups in which more than two six-membered rings are condensed directly onto one another. It is generally advantageous for the triplet energy of the compound used as a matrix material or in an adjacent layer to be the same or greater than the phosphorescent material in the emitting layer.

The compounds according to the invention described above, in particular compounds which are substituted by reactive leaving groups, such as bromine, iodine, chlorine, boronic acid or boronic acid ester, or by reactive, polymerisable groups, such as olefins, styrenes, acrylates or oxetanes, can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the compounds according to the invention indicated above, where one or more bonds from the compound according to the invention to the polymer, oligomer or dendrimer are present at one or more positions instead of substituents. Depending on the linking of the compound according to the invention, this forms a side chain of the oligomer or polymer or is linked in the main chain or forms the core of a dendrimer. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formula (1) or the preferred embodiments indicated above are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example hole-transport units, in particular those based on triarylamines, and/or electron-transport units. In addition, the polymers may contain triplet emitters, either copolymerised or mixed in as a blend. In particular, the combination of the oligomers, polymers or dendrimers according to the invention with triplet emitters leads to particularly good results.

X and Y may be the same or different in any combination. In particular, all of the following combinations (shown for Formula (1), but it should be understood that the same combinations apply to Formula (2) as well) are possible:

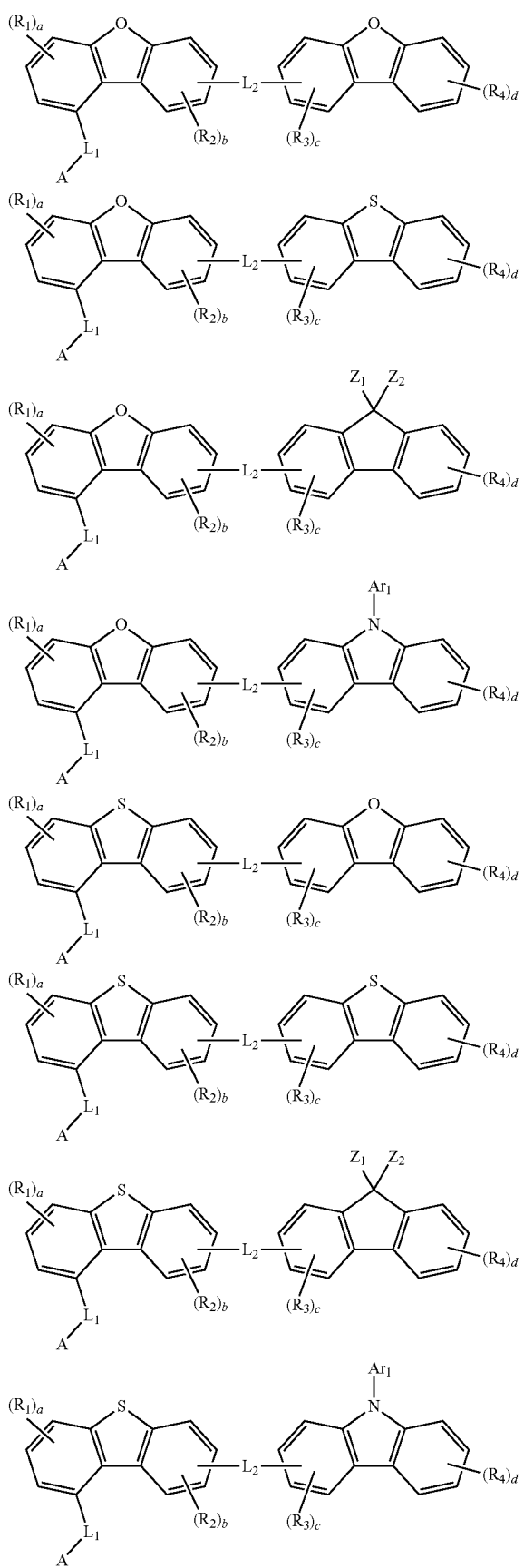
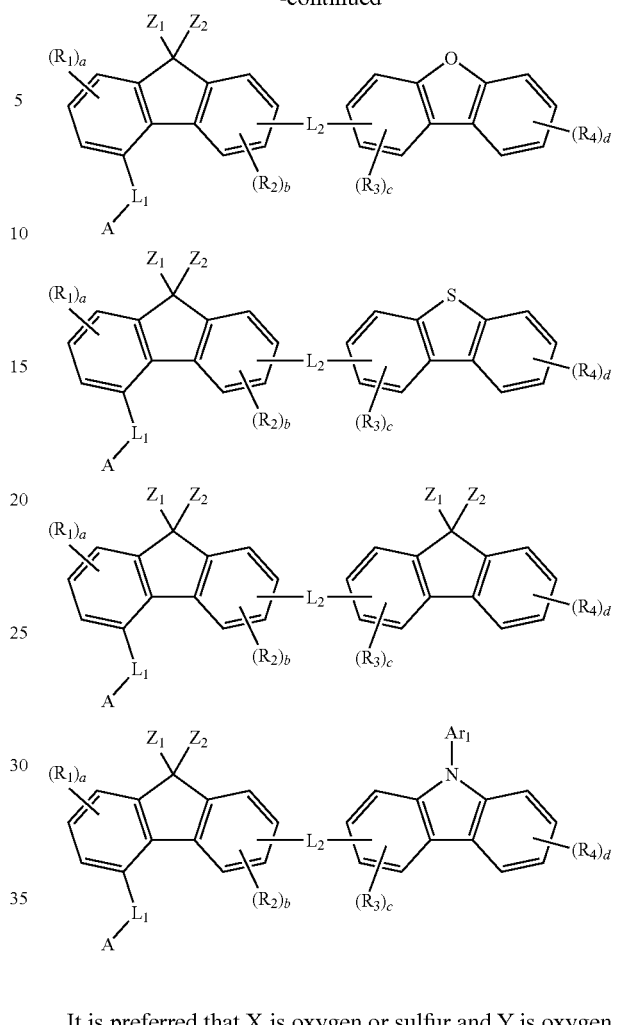
It is preferred that X is oxygen or sulfur and Y is oxygen, sulfur, $CZ_1Z_2$ or $NAr_1$ in both Formulae (1) and (2). It is also preferred that Y is $NAr_1$ and X is oxygen, sulfur or $CZ_1Z_2$ in both Formulae (1) and (2). It is most preferred that X is oxygen and Y is $NAr_1$ as shown in Formulae (3) and (4):
(3)
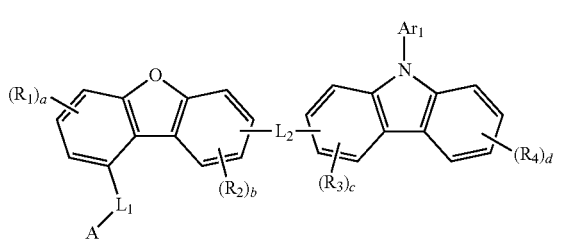
(4)
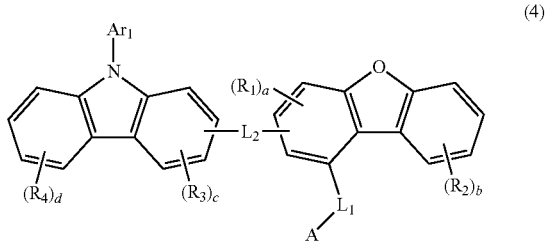

In any of Formulae (1)-(4), it is preferred that c is 0, d is 0, 1 or 2 and when d is 2, the two $R_4$ groups are adjacent and form a monocyclic- or polycyclic, aromatic or heteroaromatic annulated ring system.

Whenever X or Y (or both) is $CZ_1Z_2$ (a fluorene derivative), it is preferred that $Z_1$ and $Z_2$ are on each occurrence, identically or differently, an alkyl group of 1-10 carbon atoms or an aryl group of between 6-30 carbon atoms. For both alkyl and aryl groups, the two Z groups may be attached together to form a spiro ring system. Examples of suitable alkyl groups for $Z_1$ and $Z_2$ are methyl, ethyl, hexyl and decyl. Of these, methyl groups are highly preferred. Examples of aryl groups are phenyl and naphthyl. The aryl groups may be further substituted with additional alkyl, aryl or heteroatoms. Of these, substituted or unsubstituted phenyl groups such as p-methylphenyl are preferred. Particularly preferred are 9,9'-diphenyl groups. It is preferred for both X and Y that $Z_1$ and $Z_2$ are identical, although X and Y may individually have the same or different identical Z groups.

Two identical or different $Z_1$ and $Z_2$ groups may also be connected together to form a 9,9'-spiro ring system. For example, two alkyl Z groups can be connected to form spiro compounds such as 9,9'-cyclopentyl or 9,9'-cyclohexyl:

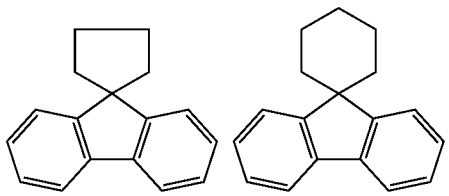

Alternatively, two aryl Z groups may be connected to form spiro compounds such as a 9,9'-spirobifluorene:

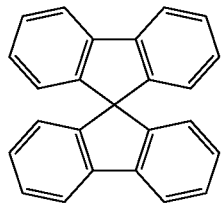 [SMILES: c1ccc2c(c1)-c1ccccc1C21c2ccccc2-c2ccccc21]

which may be further substituted. Particularly preferred are unsubstituted 9,9'-spirobifluorenes. Also contemplated are unsymmetrical spiro compounds where $Z_1$ is an alkyl and $Z_2$ is an aryl such as:

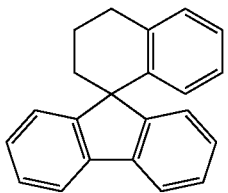 [SMILES: c1ccc2c(c1)CCCC21c2ccccc2-c2ccccc21]

Further contemplated are spirofluorene derivatives where the spiro group is further elaborated with additional substituents or forms heterocyclic spiro groups. Some examples of this type of heterocyclic spirofluorene derivative are:

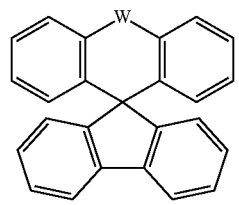

where W is oxygen, sulfur, N-Aryl, $SO_2$ or C=O.

The group containing Y is connected through any of the 1- to 8-positions to the central nucleus (which contains X and the $-L_1$-A group) and not through the 9-position. It is understood that when Y is $NAr_1$, the carbazole group is not connected to the central nucleus through the $Ar_1$ group or the nitrogen of the carbazole group either. It is preferred for Formulae (1) and (2) that the 7-position of the group containing X is connected (either directly or through $L_2$) to the 2-position of the group containing Y.

$L_2$ is a linking group that connects the group containing X to the group containing Y. It may be a direct bond so that a carbon atom of the group containing X (in any of the 2- to 8-positions) is connected via a single bond to a carbon atom in the group containing Y (in any of the 1- to 8-positions). If $L_2$ is not a direct bond, then it is an aromatic or heteroaromatic ring system having 5-30 aromatic ring atoms, which may be substituted by one or more non-aromatic radicals $R_5$. For example, $L_2$ can be a meta- or para-phenylene group, a polycyclic aromatic group such as naphthyl or a fluorene, or a polycyclic heteroaromatic group such as dibenzofuran or dibenzothiophene, any of which can be further substituted. If $L_2$ is an aromatic or heteroaromatic ring system, then $L_2$ is connected to both the group containing X and the group containing Y by single bonds. Thus, it is understood that the group containing X and the group containing Y are not annulated to each other. It is preferred that $L_2$ is a direct bond as shown in Formulae (5) and (6):

(5)

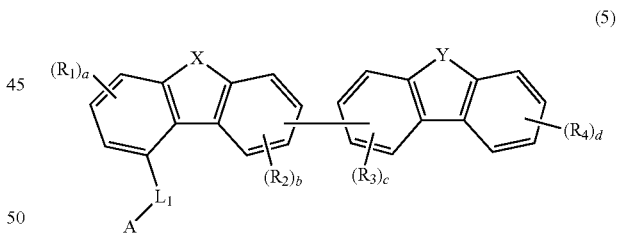

(6)

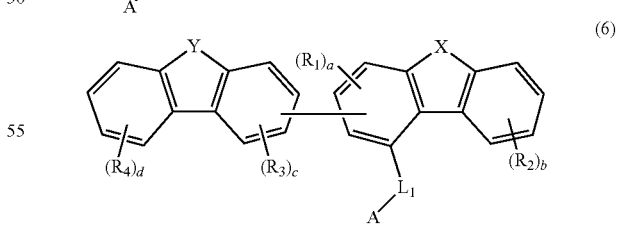

The group containing X may be substituted with $R_1$ and $R_2$ substituents. The group containing Y may be substituted with $R_3$ and $R_4$ substituents. If there are any two adjacent $R_1$-$R_4$ groups, they may be combined to form an annulated monocyclic or polycyclic aromatic or heteroaromatic ring. For example, any two adjacent $R_3$ or $R_4$ groups may be represented by the following annulated groups:

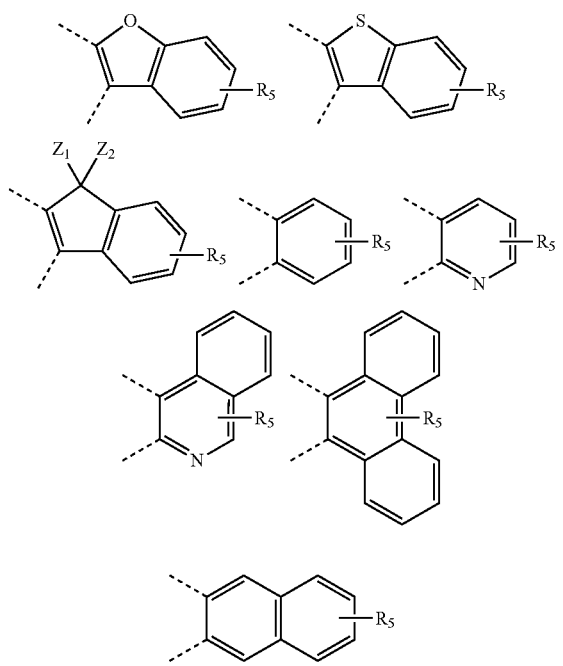

The group -L₁-A is located in the 1-position of the group containing X and L₁ is selected independently of L₂. It may be a direct bond so that a carbon atom in the 1-position of the group containing X is connected to A by a single bond. Alternatively, if L₁ is not a direct bond, then it is an aromatic or heteroaromatic ring system having 5-30 aromatic ring atoms, which may be substituted by one or more non-aromatic radicals R₅. For example, L₁ can be a meta- or para-phenylene group, a polycyclic aromatic group such as naphthyl or a fluorene, or a polycyclic heteroaromatic group such as dibenzofuran or dibenzothiophene, any of which can be further substituted. If L₁ is an aromatic or heteroaromatic ring system, then L₁ is connected to both the group containing X and A by single bonds. It is preferred that L₁ is a single bond as in Formulae (7) and (8):

(7)
(8)

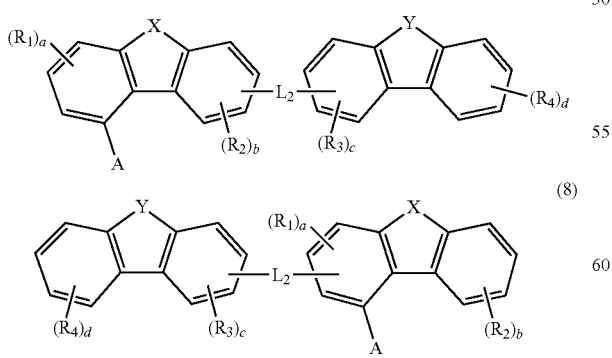

One option for A is a heterocyclic group according to Formula A₁:

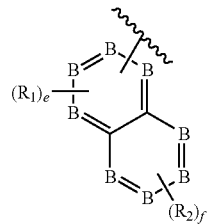

where only one or two of B are nitrogen atoms and the others are carbon atoms. If there is no substituent on the carbon atom, an H atom is bound to the corresponding carbon atom. The site where A₁ is connected to L₁ or the group containing X is where B is a carbon atom and not a nitrogen. A preferred version of A₁ is according to formula W:

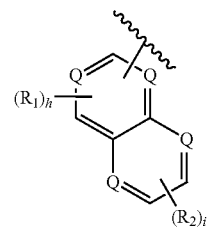

where at least one but at most only two Q are nitrogen and the others are carbon and h and i are independently 0, 1 or 2. This embodiment corresponds to formulae (9) and (10):

(9)
(10)

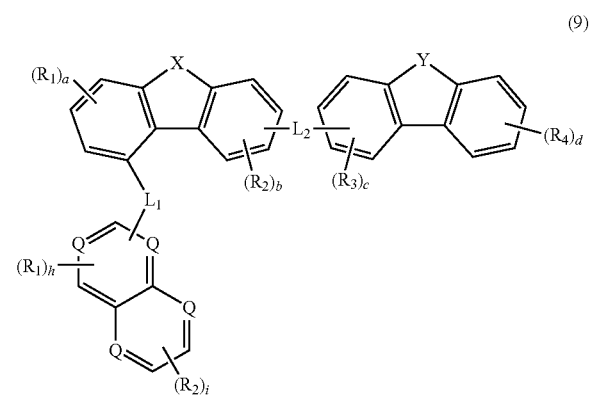

where at most only two Q are nitrogen and the others are carbon and h and i are independently 0, 1 or 2.

In one embodiment of Formulae (9) and (10) where only one Q is nitrogen, then W is a quinoline derivative according to formula A₁-a:

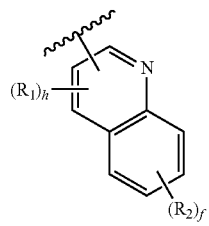

A₁-a

In this embodiment, one preferred structure for the quinoline derivative is:

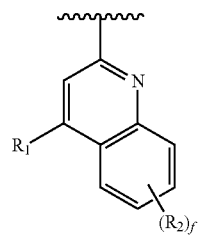

and a specific example of a suitable structure for a quinoline derivative of this embodiment is:

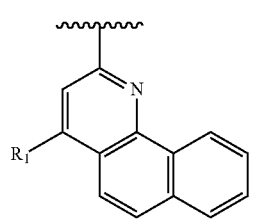

In this embodiment of Formulae (9) and (10) with A₁-a, the most preferred structure is where f is 0.

In another embodiment of Formulae (9) and (10) where one Q is nitrogen, then W is an isoquinoline derivative according to formula A₁-b:

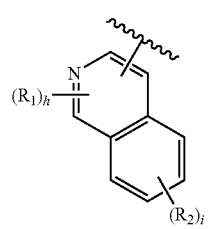

A₁-b

In this embodiment, two preferred structures for the isoquinoline derivative are:

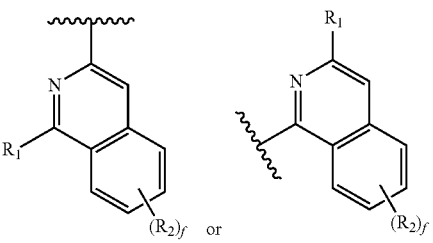

and the most preferred structures for Formulae (9) and (10) with A₁-b are where f is 0.

In Formulas (9) and (10) when two Q are nitrogen, then W can be a quinazoline derivative according to A₁-c:

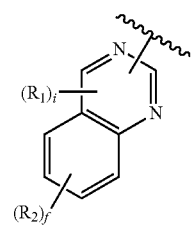

A₁-c where i is 0 or 1. In this embodiment, three preferred structures for A₁-c are:

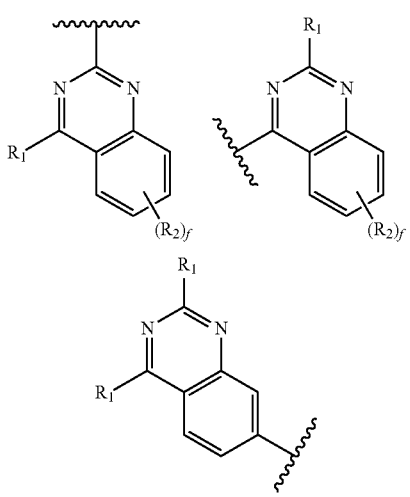

and some specific examples of preferred structures include:

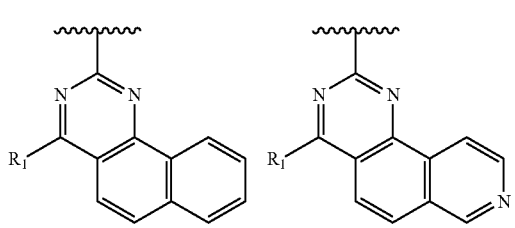

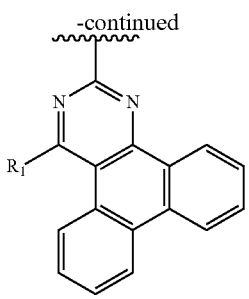

In this embodiment of Formulae (9) and (10) with $A_1$-c, it is most preferred that f is 0.

In another embodiment when two Q of W are nitrogen, then W can be a naphthyridine derivative according to $A_1$-d:

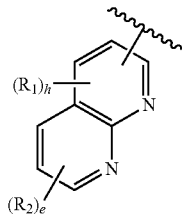

$A_1$-d

In this embodiment, a preferred structure for $A_1$-d is:

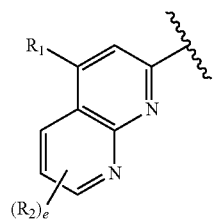

and the most preferred for Formulae (9) and (10) with $A_1$-d are where e is 0.

In yet another embodiment when two Q of W are nitrogen, then W can be a pyrido[3,2-b]-pyridine derivative according to $A_1$-e:

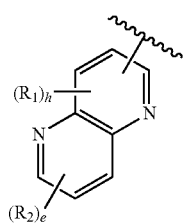

$A_1$-e and where preferred structures are:

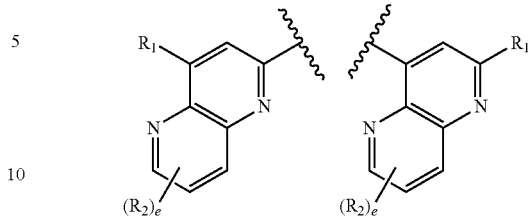

and the most preferred for Formulae (9) and (10) with A1-e are where e is 0.

In $A_1$-a, $A_1$-b, $A_1$-c, $A_1$-d or $A_1$-e, it is understood any two adjacent $R_1$ or $R_2$ groups may be combined to form an annulated monocyclic or polycyclic aromatic or heteroaromatic ring. In the sense of the invention, it is understood that a derivative encompasses such annulated groups.

Of these embodiments, the preferred are according to Formulae (11)-(12) with $A_1$-a, Formulae (13)-(14) with $A_1$-c, Formulae (15)-(16) with $A_1$-d and Formulae (17)-(18) with $A_1$-e:

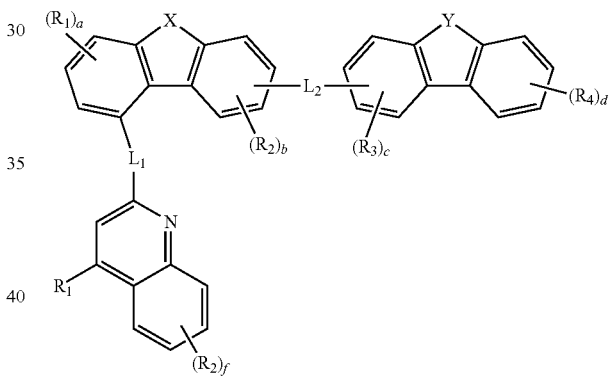

(11)

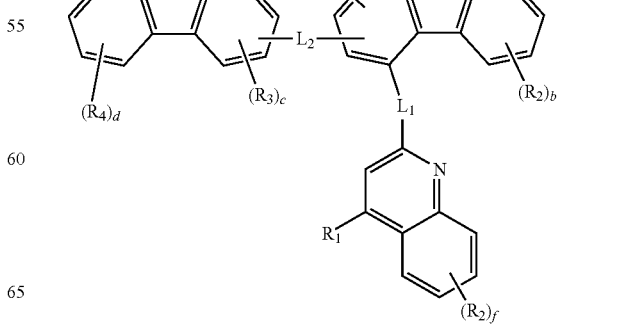

(12)

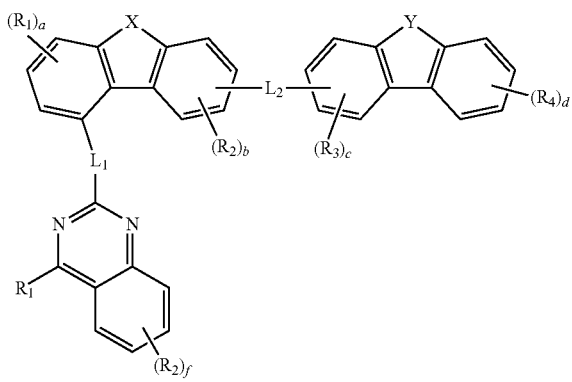

(13)

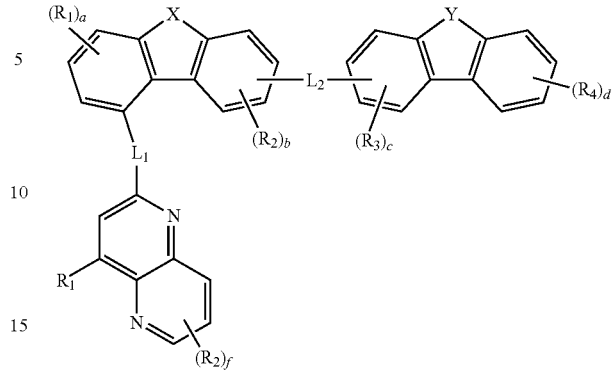

(17)

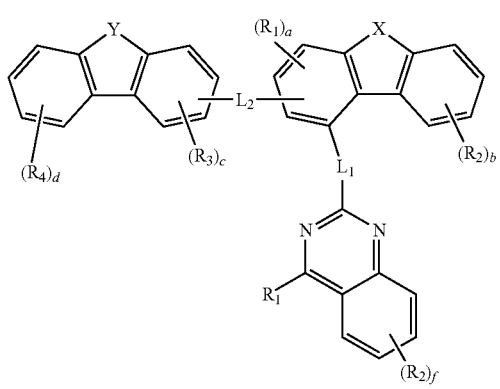

(14)

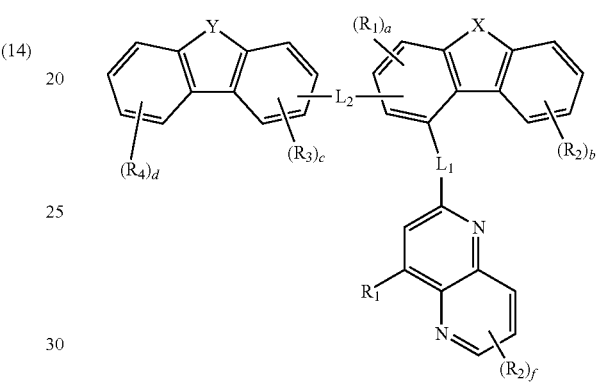

(18)

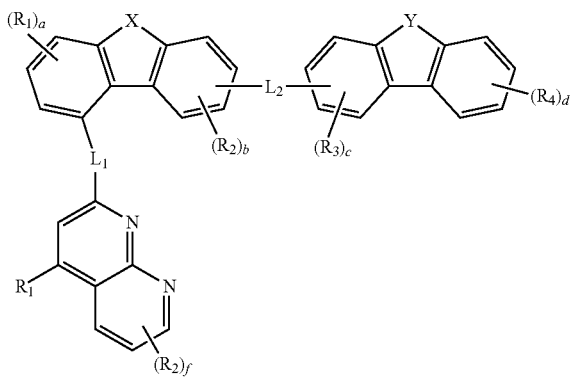

(15)

In Formulae (11)-(18), it is preferred that f is 0.

In some embodiments, A can be a benzimidazole derivative as illustrated in $A_2$, $A_3$ and $A_4$. The benzimidazole derivative can be attached to the 1-position of the group containing X (either directly or via $L_1$) by a carbon atom as in $A_2$ or $A_3$, or through the 1-nitrogen as in $A_4$.

One preferred embodiment is according to $A_2$ as shown in Formulae (19) and (20)

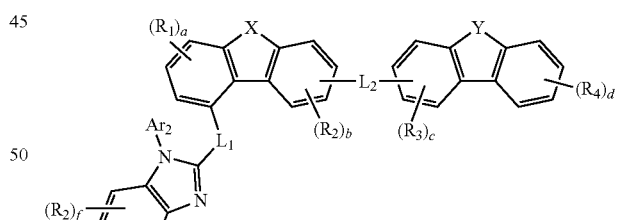

(19)

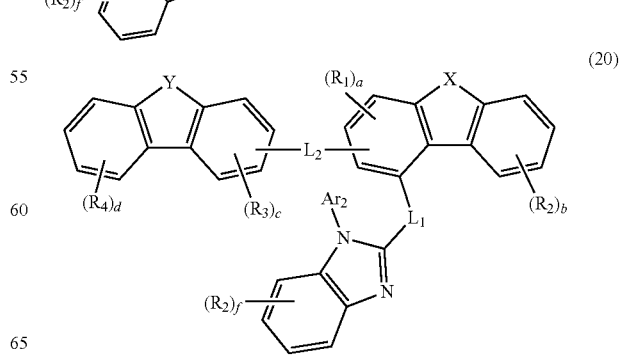

(20)

(16)

For Formula (19) and (20), it is preferred that f is 0. In another embodiment related to (19) and (20), it is preferred that Ar$_2$ is phenyl. In yet another embodiment related to (19) and (20), it is preferred that L$_1$ is a direct bond or a phenyl group.

Another preferred embodiment is according to A$_4$ as shown in Formulae (21) and (22):

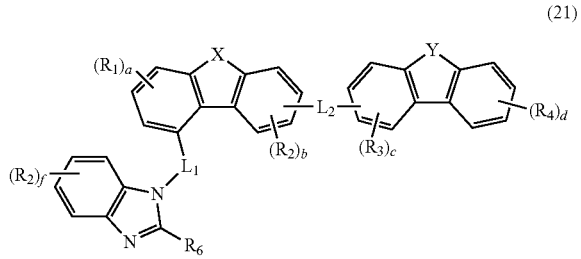
(21)

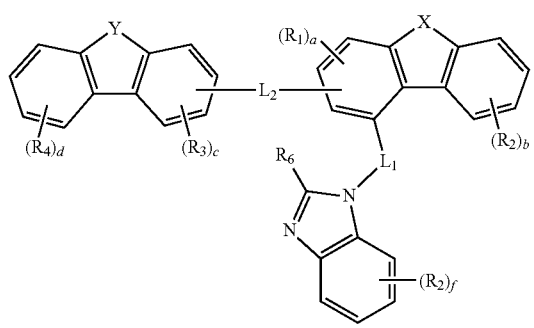
(22)

For Formula (21) and (22), it is preferred that f is 0. In another embodiment related to (21) and (22), it is preferred that R$_1$ is phenyl. In yet another embodiment related to (21) and (22), it is preferred that L$_1$ is a direct bond or a phenyl group. It is preferred in another embodiment of (21) and (22) that R$_6$ is an alkyl group of 1 to 12 C atoms or an aromatic or heteroaromatic ring system having 5 to 30 aromatic ring atoms, and most preferably, phenyl.

Other preferred embodiments are where the A group is attached to a different ring of the group containing X than the group containing Y as in Formulae (1), (3), (5), (7), (9), (11), (13), (15), (17), (19) or (21). In any of these embodiments, it is preferred that a and b are both 0, and more preferred that a, b and c are all 0. It is most preferred that a, b and c is 0, d is 0 or 2 and when d is 2, the two R$_4$ groups are adjacent and form a monocyclic- or polycyclic-aromatic or heteroaromatic annulated ring system The preferred embodiments mentioned above can be combined with one another in any combination as desired. In a particularly preferred embodiment of the invention, multiple preferences mentioned above can occur simultaneously. For example, the following formulae include some preferred combinations of features.

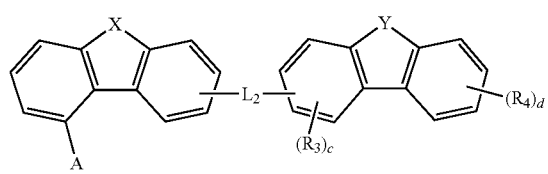
(22)

In one embodiment according to Formula (22), it is most preferred that X is oxygen and Y is NAr$_1$. In another embodiment according to Formula (22), it is most preferred that L$_2$ is a direct bond. In yet another embodiment according to Formula (22), it is most preferred that c is 0, d is 0 or 2 and when d is 2, the two R$_4$ groups are adjacent and form a monocyclic- or polycyclic-aromatic or heteroaromatic annulated ring system. In yet another embodiment according to Formula (22), it is most preferred that A is a quinazoline group according to A$_1$-b.

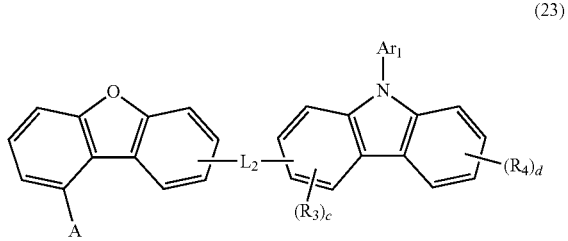
(23)

In one embodiment according to Formula (23), it is preferred that c is 0. In another embodiment according to Formula (23), it is preferred that L$_2$ is a direct bond. In yet another embodiment according to Formula (23), it is most preferred that c is 0, d is 0 or 2 and when d is 2, the two R$_4$ groups are adjacent and form a monocyclic- or polycyclic-aromatic or heteroaromatic annulated ring system. In yet another embodiment according to Formula (23), it is preferred that A is a quinazoline group, and more preferably, A is a quinoline derivative according to A$_1$-a, and even more preferably where h and f are 0. In yet another embodiment according to Formula (23), it is preferred that A is a quinazoline group according to A$_1$-b, and more preferably where i and f are 0.

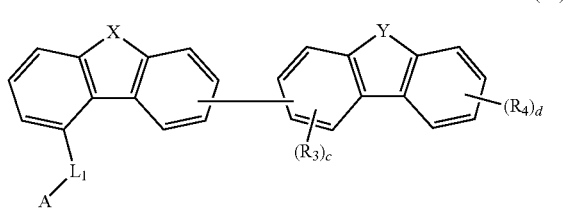
(24)

In one embodiment according to Formula (24), it is preferred that X is oxygen and Y is NAr$_1$. In yet another embodiment according to Formula (23), L$_1$ is a meta- or para-phenyl group. In yet another embodiment according to Formula (23), it is most preferred that c is 0, d is 0 or 2 and when d is 2, the two R$_4$ groups are adjacent and form a monocyclic- or polycyclic, aromatic or heteroaromatic annulated ring system. In yet another embodiment according to Formula (24), it is most preferred that A is a quinazoline group according to A$_1$-b where f is 0 or a benzimidazole according to A$_4$ where L$_1$ is a direct bond or a meta- or para-phenyl group and f is 0. For Formula (24), if A is according to A$_4$, it is most preferred that L$_1$ is a meta- or para-phenyl group and Ar$_1$ is a phenyl group.

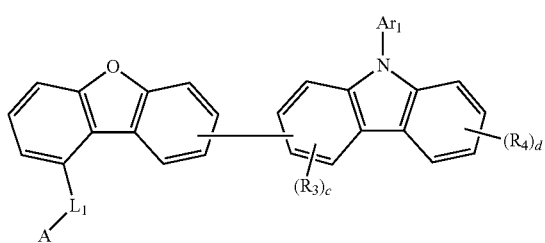

(25)

In one embodiment according to Formula (25), it is preferred that A is according to $A_2$, $A_3$ or $A_4$, and more preferred where e and f are 0. In yet another embodiment according to Formula (25), $L_1$ is a meta- or para-phenyl group. In yet another embodiment according to Formula (25), it is most preferred that c is 0, d is 0 or 2 and when d is 2, the two $R_4$ groups are adjacent and form a monocyclic- or polycyclic-aromatic or heteroaromatic annulated ring system. In yet another embodiment according to Formula (25), it is most preferred that A is a benzimidazole according to $A_4$ where $L_1$ is a direct bond or a meta- or para-phenyl group and f is 0. For Formula (25), if A is according to $A_4$, it is most preferred that $L_1$ is a meta- or para-phenyl group and $Ar_2$ is a phenyl group.

Examples of compounds in accordance with the embodiments indicated above are the compounds shown in the following table.

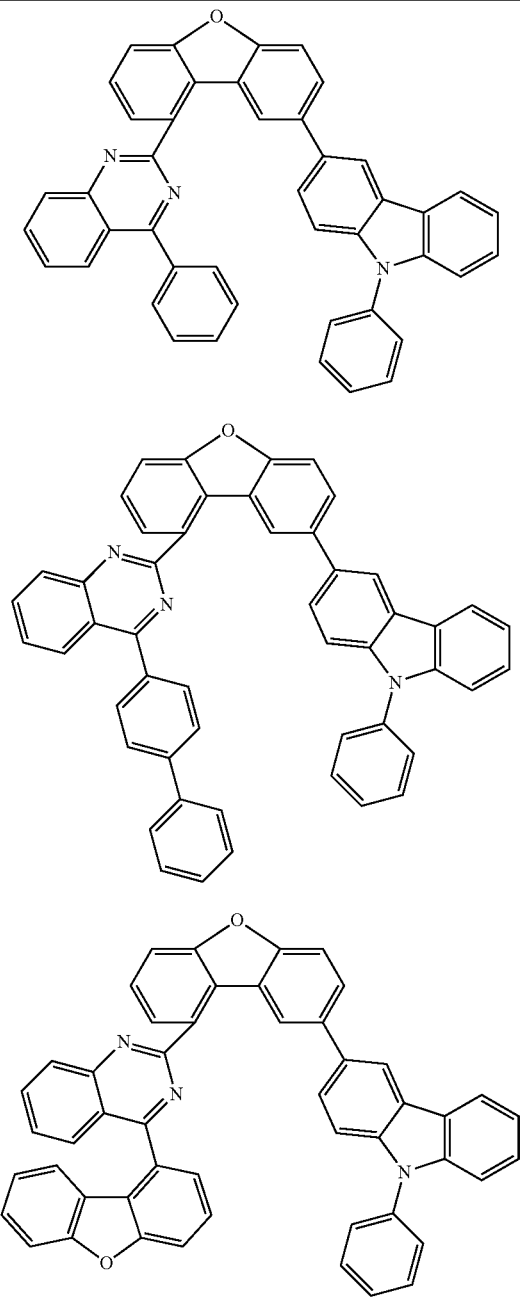

-continued
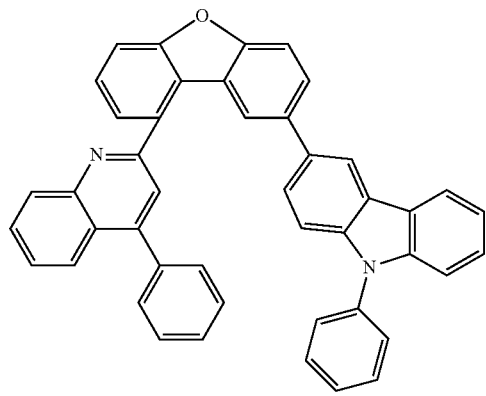 [SMILES: c1ccc(-c2cc(-c3cccc4oc5ccc(-c6ccc7c(c6)c6ccccc6n7-c6ccccc6)cc5c34)nc3ccccc23)cc1]
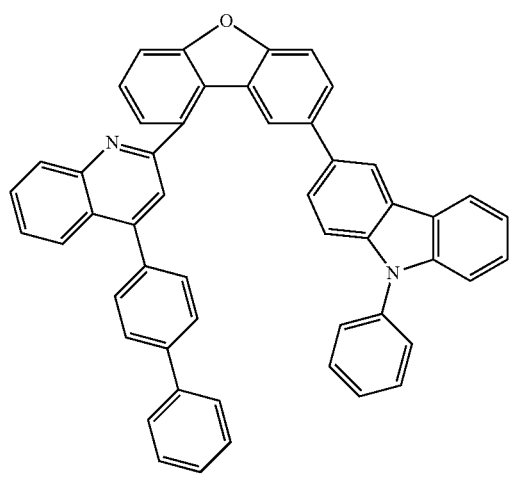 [SMILES: c1ccc(-c2ccc(-c3cc(-c4cccc5oc6ccc(-c7ccc8c(c7)c7ccccc7n8-c7ccccc7)cc6c45)nc4ccccc34)cc2)cc1]
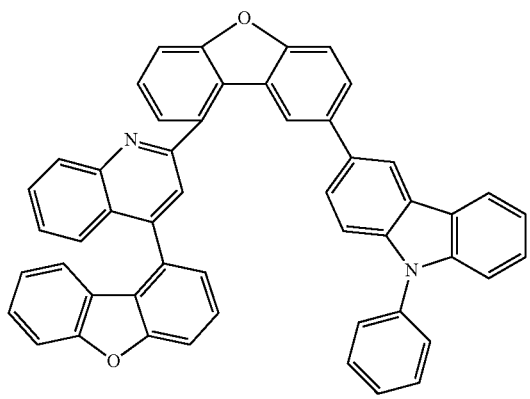
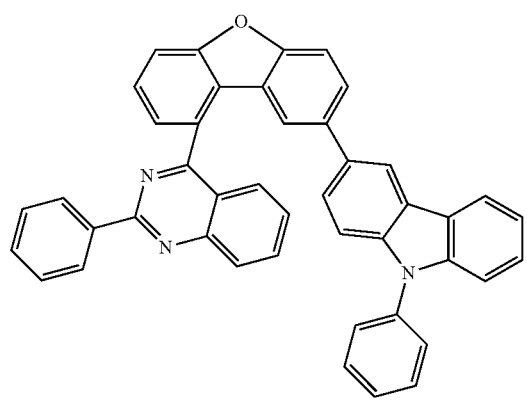 [SMILES: c1ccc(-c2nc(-c3cccc4oc5ccc(-c6ccc7c(c6)c6ccccc6n7-c6ccccc6)cc5c34)c3ccccc3n2)cc1]

-continued
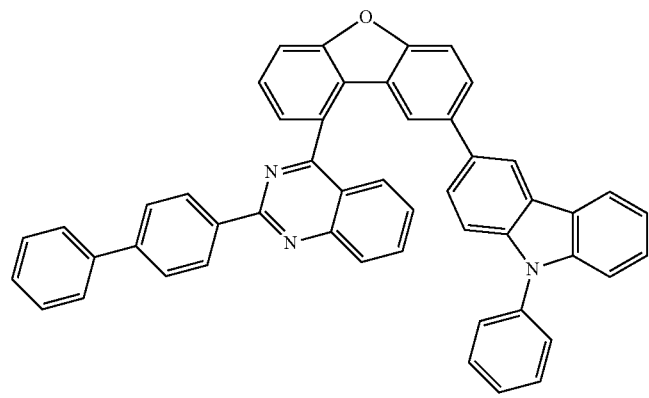 [SMILES: c1ccc(-c2ccc(-c3nc(-c4cccc5oc6ccc(-c7ccc8c(c7)c7ccccc7n8-c7ccccc7)cc6c45)c4ccccc4n3)cc2)cc1]
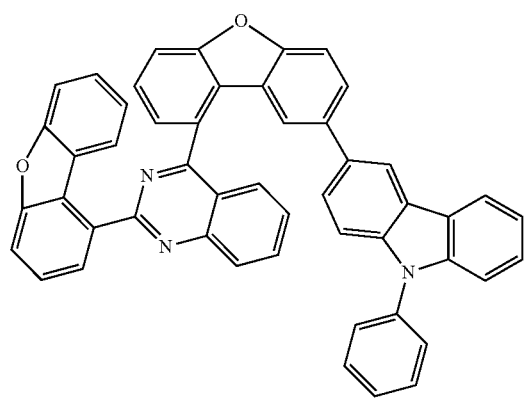 [SMILES: c1ccc(-n2c3ccccc3c3cc(-c4ccc5oc6cccc(-c7nc(-c8cccc9oc%10ccccc%10c89)nc8ccccc78)c6c5c4)ccc32)cc1]
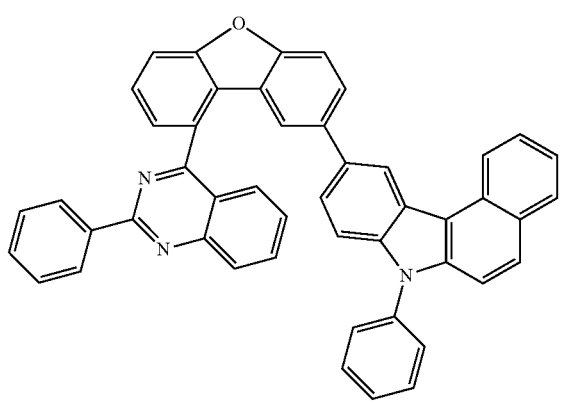 [SMILES: c1ccc(-c2nc(-c3cccc4oc5ccc(-c6ccc7c(c6)c6c8ccccc8ccc6n7-c6ccccc6)cc5c34)c3ccccc3n2)cc1]
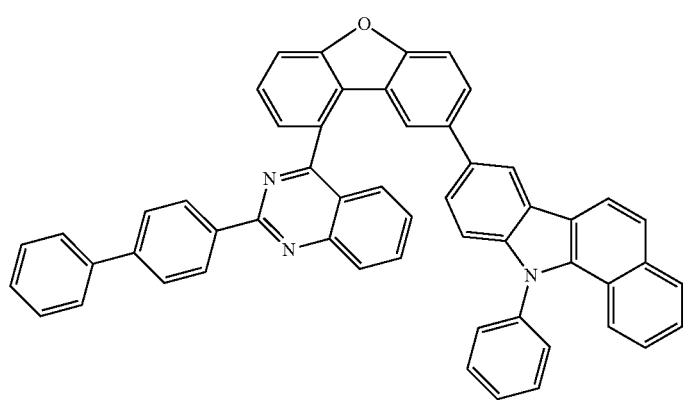 [SMILES: c1ccc(-c2ccc(-c3nc(-c4cccc5oc6ccc(-c7ccc8c(c7)c7ccc9ccccc9c7n8-c7ccccc7)cc6c45)c4ccccc4n3)cc2)cc1]

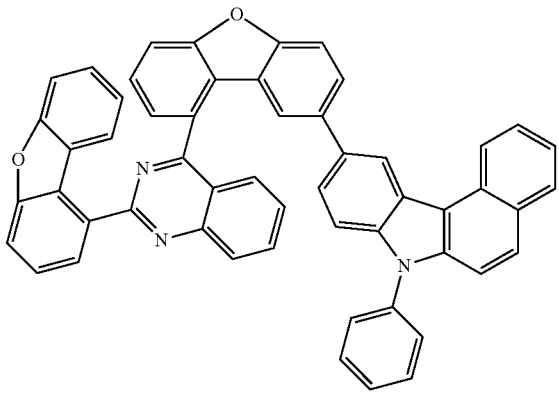 [SMILES: c1ccc(-n2c3ccc(-c4ccc5oc6cccc(-c7nc(-c8cccc9oc%10ccccc%10c89)nc8ccccc78)c6c5c4)cc3c3c4ccccc4ccc32)cc1]

-continued
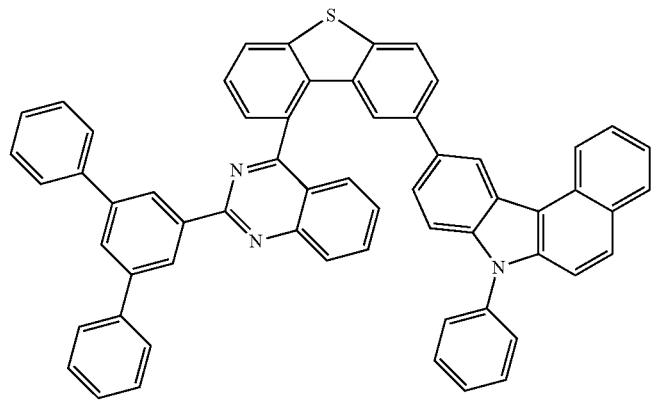 [SMILES: c1ccc(-c2cc(-c3ccccc3)cc(-c3nc(-c4cccc5sc6ccc(-c7ccc8c(c7)c7c9ccccc9ccc7n8-c7ccccc7)cc6c45)c4ccccc4n3)c2)cc1]
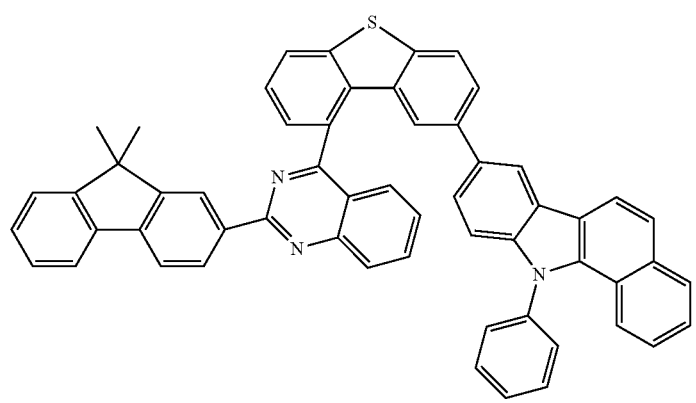 [SMILES: CC1(C)c2ccccc2-c2ccc(-c3nc(-c4cccc5sc6ccc(-c7ccc8c(c7)c7ccc9ccccc9c7n8-c7ccccc7)cc6c45)c4ccccc4n3)cc21]
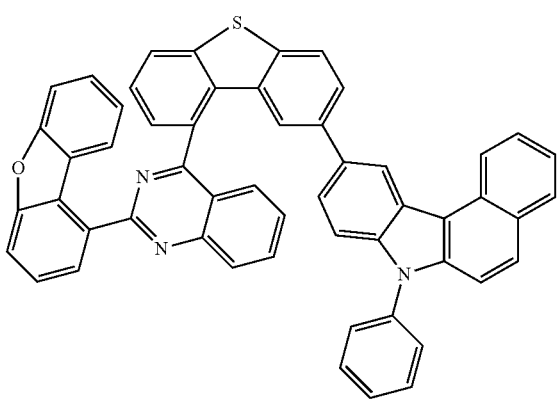
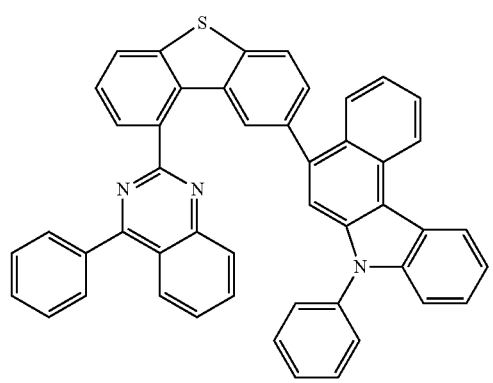 [SMILES: c1ccc(-c2nc(-c3cccc4sc5ccc(-c6cc7c(c8ccccc68)c6ccccc6n7-c6ccccc6)cc5c34)nc3ccccc23)cc1]

-continued
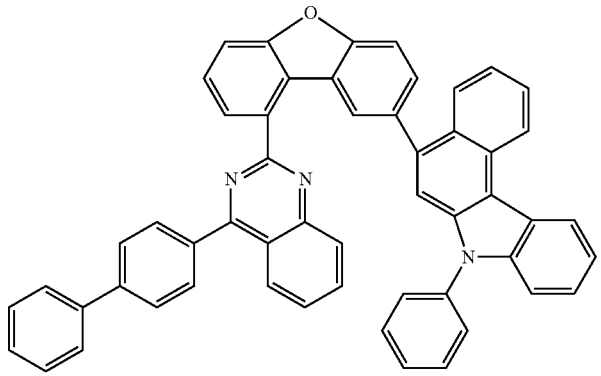 [SMILES: c1ccc(-c2ccc(-c3nc(-c4cccc5oc6ccc(-c7cc8c(c9ccccc79)c7ccccc7n8-c7ccccc7)cc6c45)nc4ccccc34)cc2)cc1]
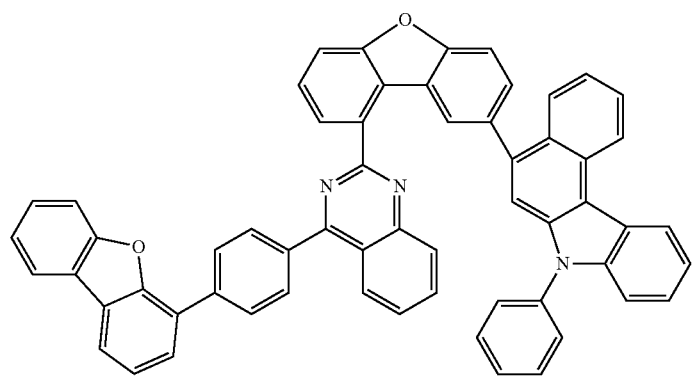 [SMILES: c1ccc(-n2c3ccccc3c3c4ccccc4c(-c4ccc5oc6cccc(-c7nc(-c8ccc(-c9cccc%10c9oc9ccccc9%10)cc8)c8ccccc8n7)c6c5c4)cc32)cc1]
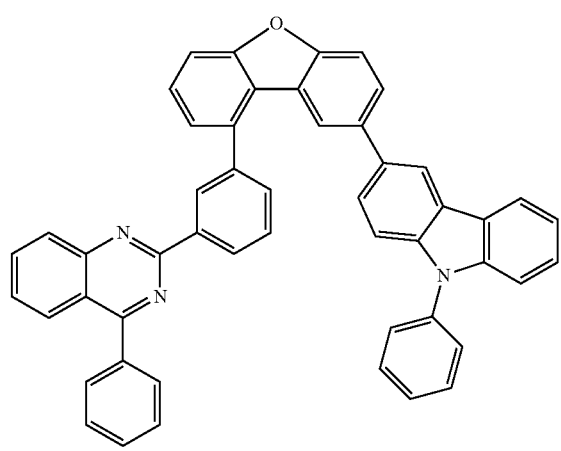 [SMILES: c1ccc(-c2nc(-c3cccc(-c4cccc5oc6ccc(-c7ccc8c(c7)c7ccccc7n8-c7ccccc7)cc6c45)c3)nc3ccccc23)cc1]

-continued
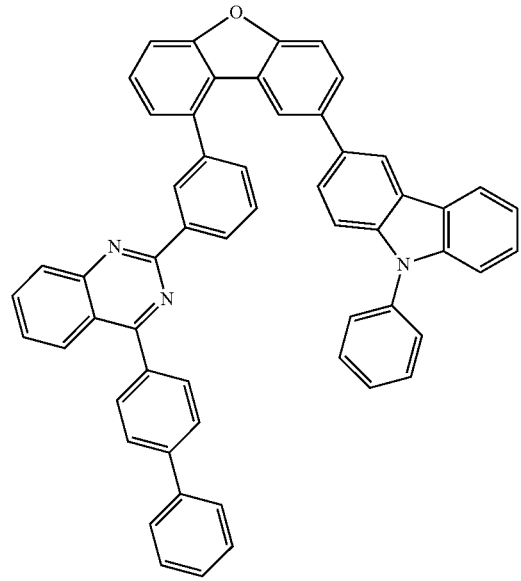 [SMILES: c1ccc(-c2ccc(-c3nc(-c4cccc(-c5cccc6oc7ccc(-c8ccc9c(c8)c8ccccc8n9-c8ccccc8)cc7c56)c4)nc4ccccc34)cc2)cc1]
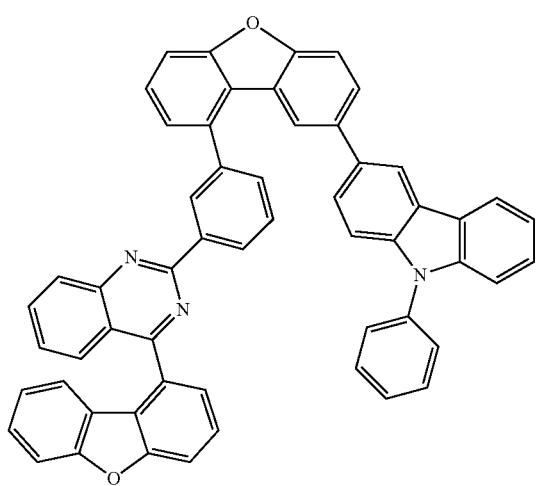 [SMILES: c1ccc(-n2c3ccccc3c3cc(-c4ccc5oc6cccc(-c7cccc(-c8nc(-c9cccc%10oc%11ccccc%11c9%10)c9ccccc9n8)c7)c6c5c4)ccc32)cc1]
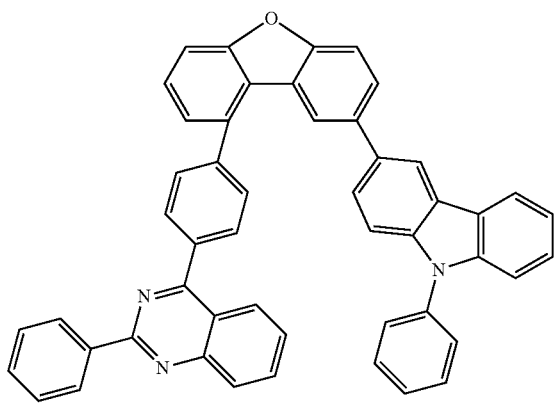 [SMILES: c1ccc(-c2nc(-c3ccc(-c4cccc5oc6ccc(-c7ccc8c(c7)c7ccccc7n8-c7ccccc7)cc6c45)cc3)c3ccccc3n2)cc1]

-continued
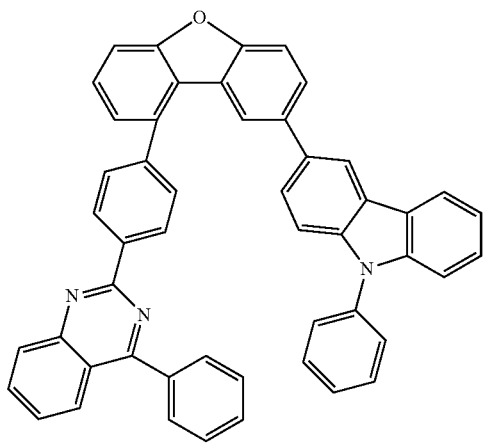 [SMILES: c1ccc(-c2nc(-c3ccc(-c4cccc5oc6ccc(-c7ccc8c(c7)c7ccccc7n8-c7ccccc7)cc6c45)cc3)nc3ccccc23)cc1]
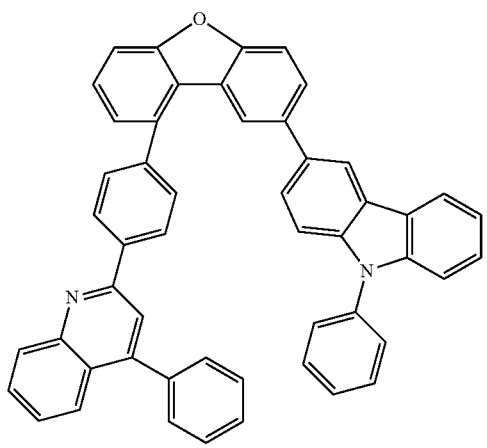 [SMILES: c1ccc(-c2cc(-c3ccc(-c4cccc5oc6ccc(-c7ccc8c(c7)c7ccccc7n8-c7ccccc7)cc6c45)cc3)nc3ccccc23)cc1]
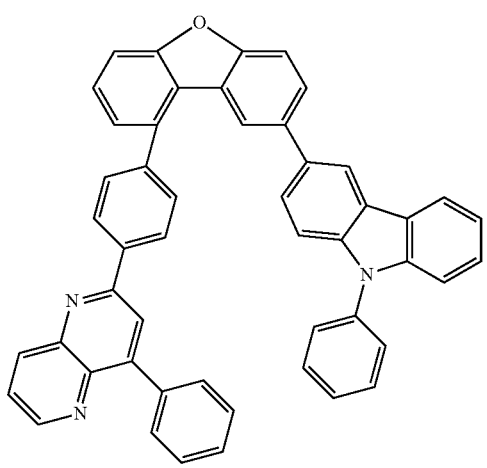 [SMILES: c1ccc(-c2cc(-c3ccc(-c4cccc5oc6ccc(-c7ccc8c(c7)c7ccccc7n8-c7ccccc7)cc6c45)cc3)nc3cccnc23)cc1]

-continued
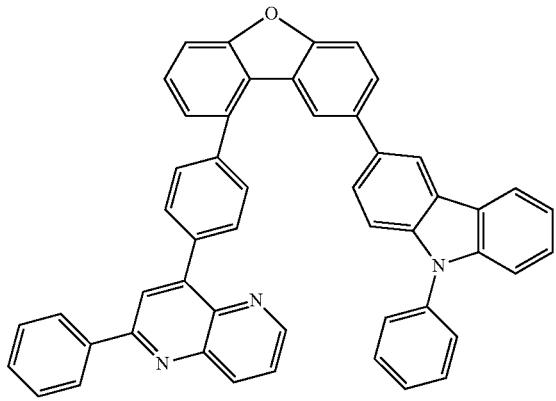 [SMILES: c1ccc(-c2cc(-c3ccc(-c4cccc5oc6ccc(-c7ccc8c(c7)c7ccccc7n8-c7ccccc7)cc6c45)cc3)c3ncccc3n2)cc1]
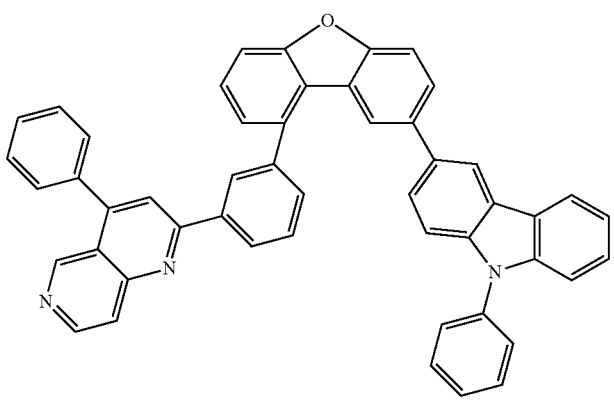 [SMILES: c1ccc(-c2cc(-c3cccc(-c4cccc5oc6ccc(-c7ccc8c(c7)c7ccccc7n8-c7ccccc7)cc6c45)c3)nc3ccncc23)cc1]
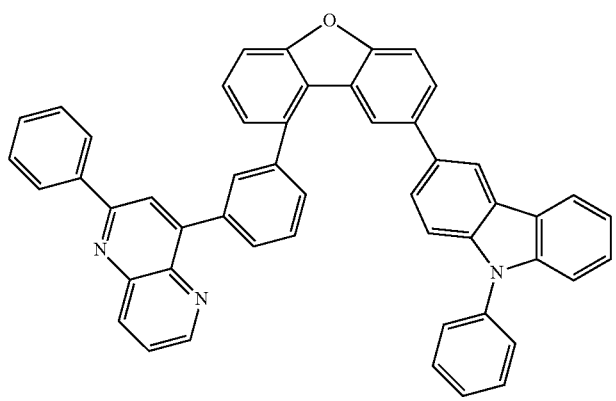 [SMILES: c1ccc(-c2cc(-c3cccc(-c4cccc5oc6ccc(-c7ccc8c(c7)c7ccccc7n8-c7ccccc7)cc6c45)c3)c3ncccc3n2)cc1]
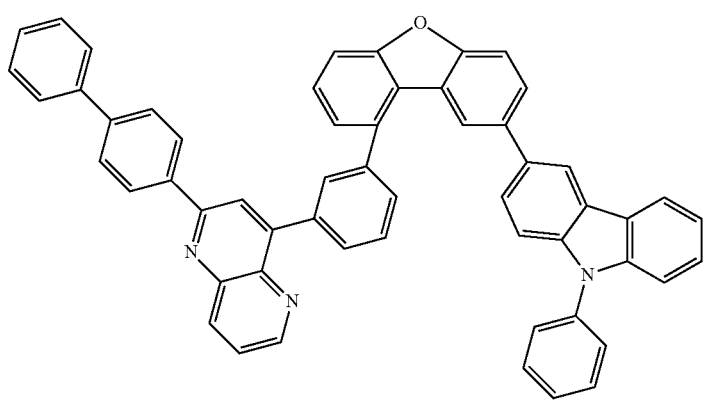 [SMILES: c1ccc(-c2ccc(-c3cc(-c4cccc(-c5cccc6oc7ccc(-c8ccc9c(c8)c8ccccc8n9-c8ccccc8)cc7c56)c4)c4ncccc4n3)cc2)cc1]

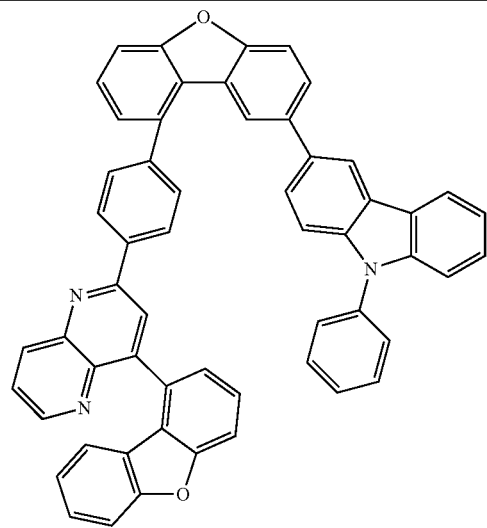
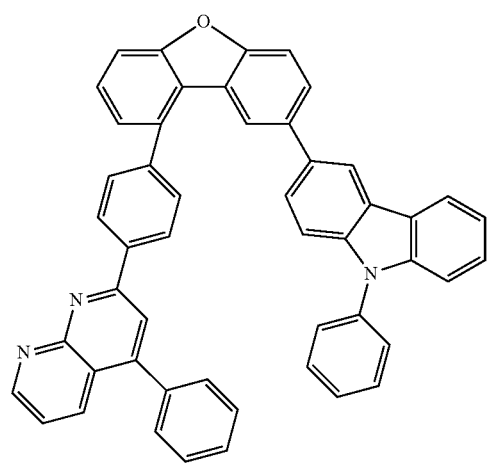 [SMILES: c1ccc(-c2cc(-c3ccc(-c4cccc5oc6ccc(-c7ccc8c(c7)c7ccccc7n8-c7ccccc7)cc6c45)cc3)nc3ncccc23)cc1]
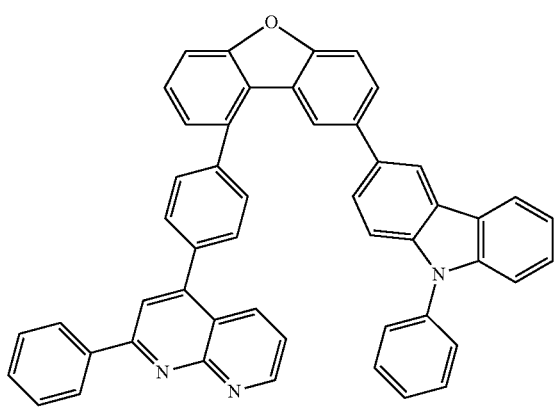

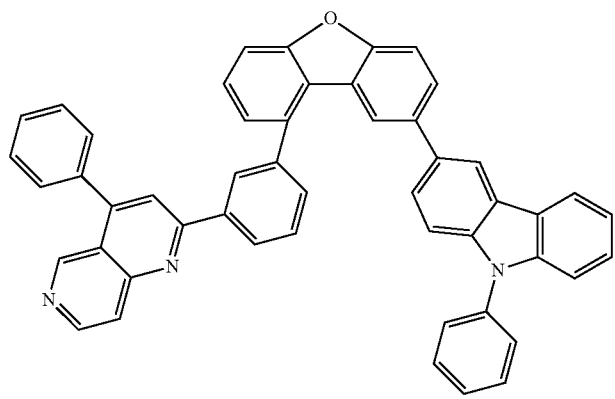 [SMILES: c1ccc(-c2cc(-c3cccc(-c4cccc5oc6ccc(-c7ccc8c(c7)c7ccccc7n8-c7ccccc7)cc6c45)c3)nc3ccncc23)cc1]
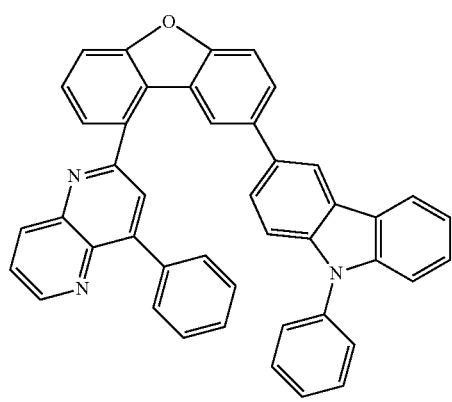 [SMILES: c1ccc(-c2cc(-c3cccc4oc5ccc(-c6ccc7c(c6)c6ccccc6n7-c6ccccc6)cc5c34)nc3cccnc23)cc1]
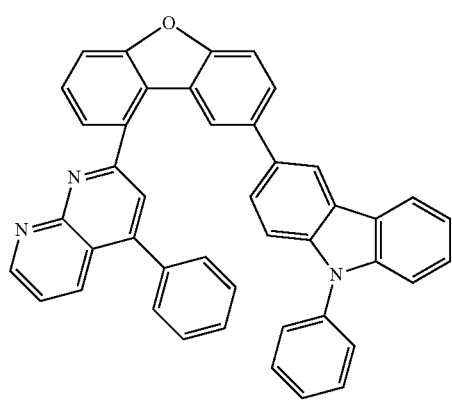
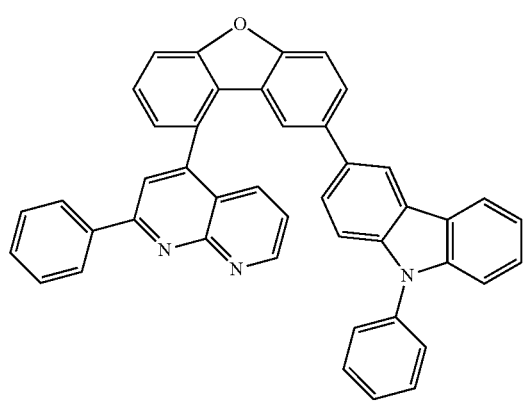 [SMILES: c1ccc(-c2cc(-c3cccc4oc5ccc(-c6ccc7c(c6)c6ccccc6n7-c6ccccc6)cc5c34)c3cccnc3n2)cc1]

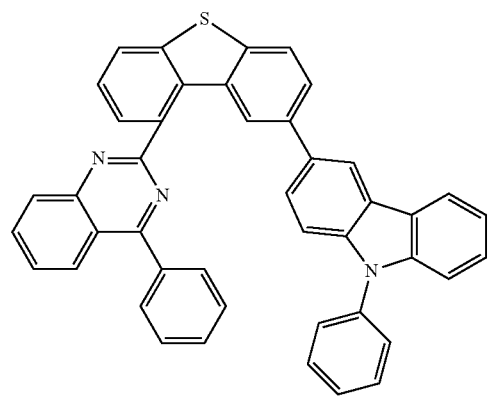
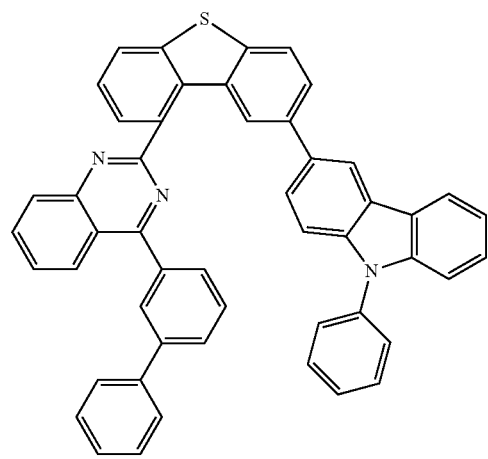 [SMILES: c1ccc(-c2cccc(-c3nc(-c4cccc5sc6ccc(-c7ccc8c(c7)c7ccccc7n8-c7ccccc7)cc6c45)nc4ccccc34)c2)cc1]
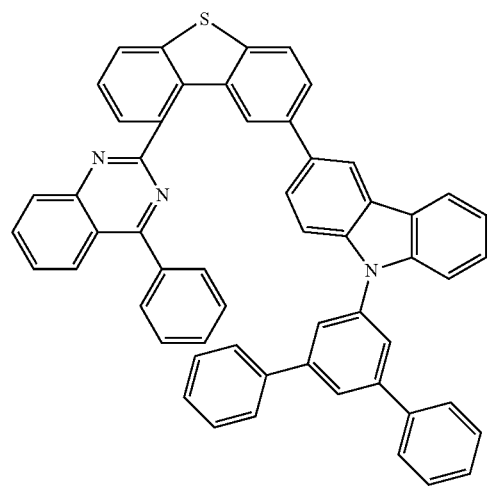

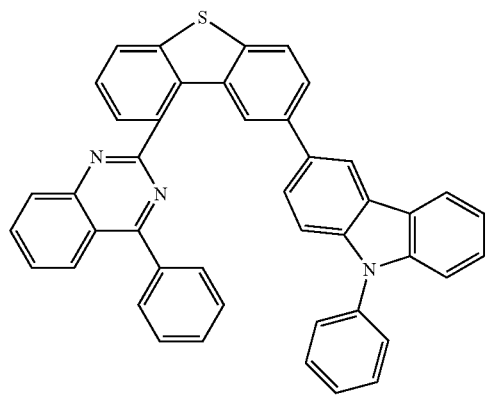 [SMILES: c1ccc(-c2nc(-c3cccc4sc5ccc(-c6ccc7c(c6)c6ccccc6n7-c6ccccc6)cc5c34)nc3ccccc23)cc1]
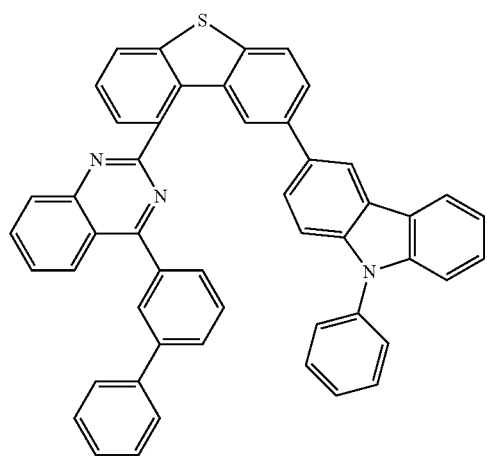 [SMILES: c1ccc(-c2cccc(-c3nc(-c4cccc5sc6ccc(-c7ccc8c(c7)c7ccccc7n8-c7ccccc7)cc6c45)nc4ccccc34)c2)cc1]
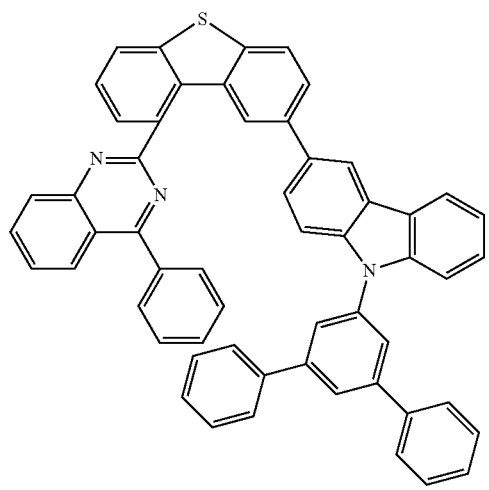

-continued
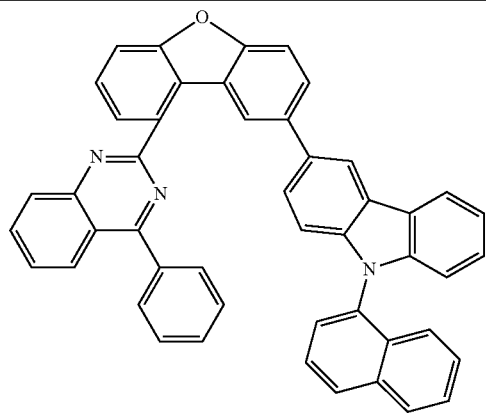
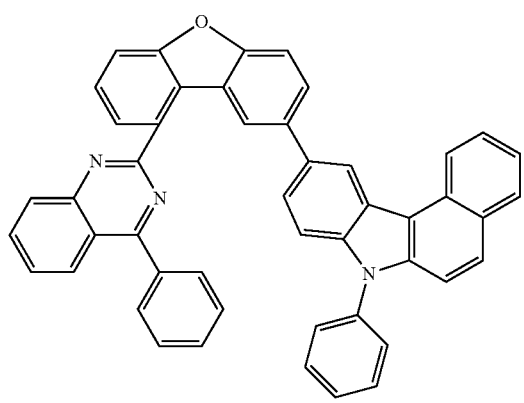 [SMILES: c1ccc(-c2nc(-c3cccc4oc5ccc(-c6ccc7c(c6)c6c8ccccc8ccc6n7-c6ccccc6)cc5c34)nc3ccccc23)cc1]
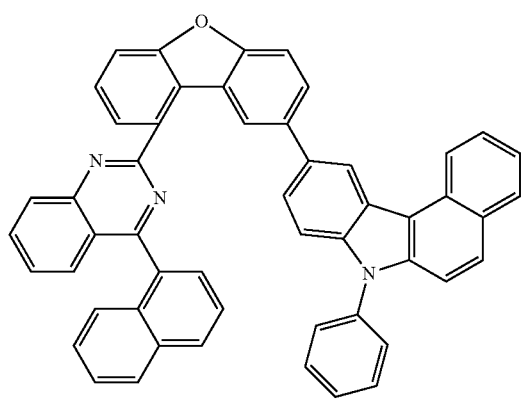 [SMILES: c1ccc(-n2c3ccc(-c4ccc5oc6cccc(-c7nc(-c8cccc9ccccc89)c8ccccc8n7)c6c5c4)cc3c3c4ccccc4ccc32)cc1]
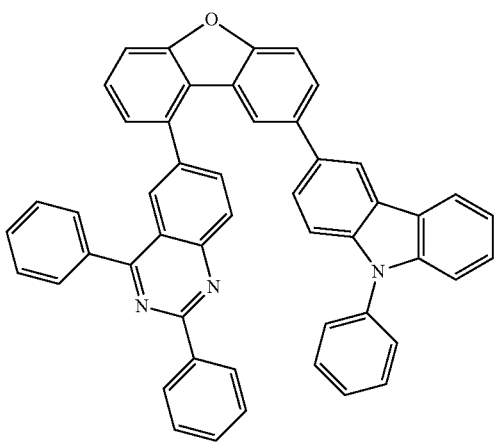 [SMILES: c1ccc(-c2nc(-c3ccccc3)c3cc(-c4cccc5oc6ccc(-c7ccc8c(c7)c7ccccc7n8-c7ccccc7)cc6c45)ccc3n2)cc1]

-continued
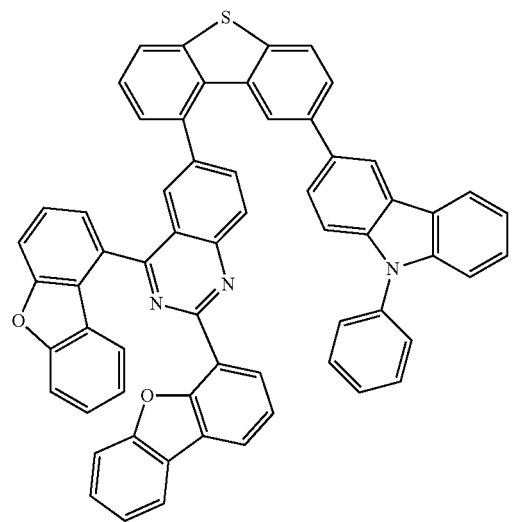 [SMILES: c1ccc(-n2c3ccccc3c3cc(-c4ccc5sc6cccc(-c7ccc8nc(-c9cccc%10c9oc9ccccc9%10)nc(-c9cccc%10oc%11ccccc%11c9%10)c8c7)c6c5c4)ccc32)cc1]
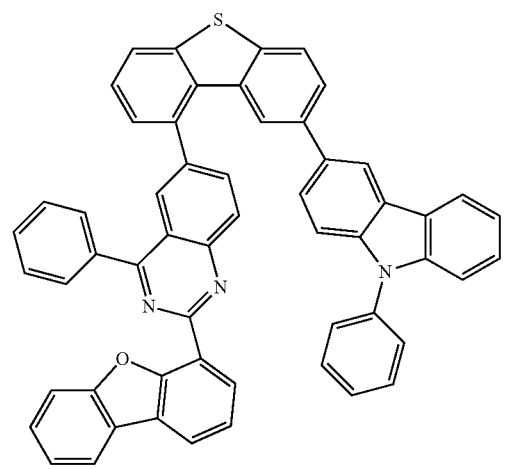 [SMILES: c1ccc(-c2nc(-c3cccc4c3oc3ccccc34)nc3ccc(-c4cccc5sc6ccc(-c7ccc8c(c7)c7ccccc7n8-c7ccccc7)cc6c45)cc23)cc1]
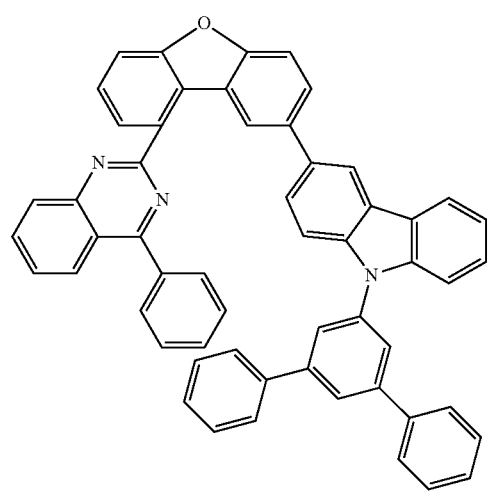 [SMILES: c1ccc(-c2cc(-c3ccccc3)cc(-n3c4ccccc4c4cc(-c5ccc6oc7cccc(-c8nc(-c9ccccc9)c9ccccc9n8)c7c6c5)ccc43)c2)cc1]

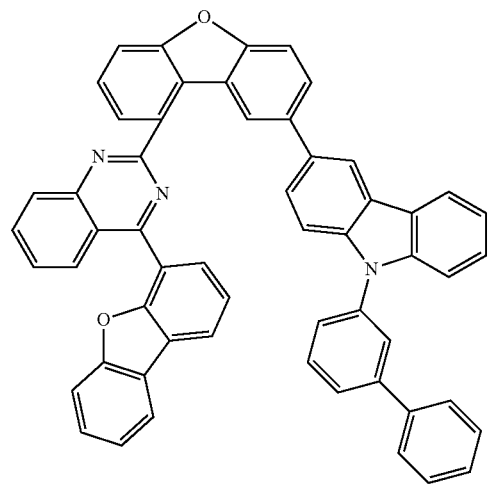 [SMILES: c1ccc(-c2cccc(-n3c4ccccc4c4cc(-c5ccc6oc7cccc(-c8nc(-c9cccc%10c9oc9ccccc9%10)c9ccccc9n8)c7c6c5)ccc43)c2)cc1]
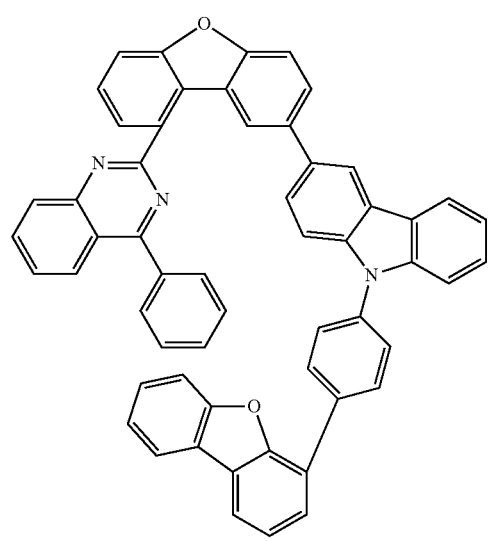 [SMILES: c1ccc(-c2nc(-c3cccc4oc5ccc(-c6ccc7c(c6)c6ccccc6n7-c6ccc(-c7cccc8c7oc7ccccc78)cc6)cc5c34)nc3ccccc23)cc1]
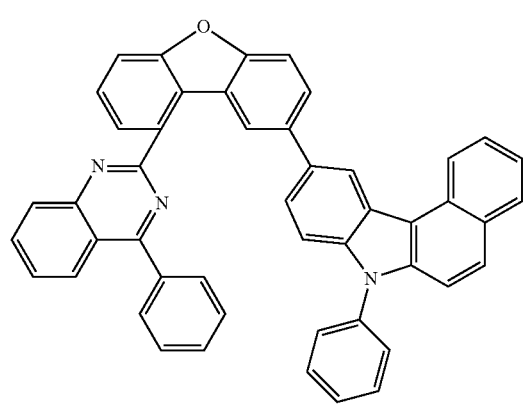 [SMILES: c1ccc(-c2nc(-c3cccc4oc5ccc(-c6ccc7c(c6)c6c8ccccc8ccc6n7-c6ccccc6)cc5c34)nc3ccccc23)cc1]

-continued
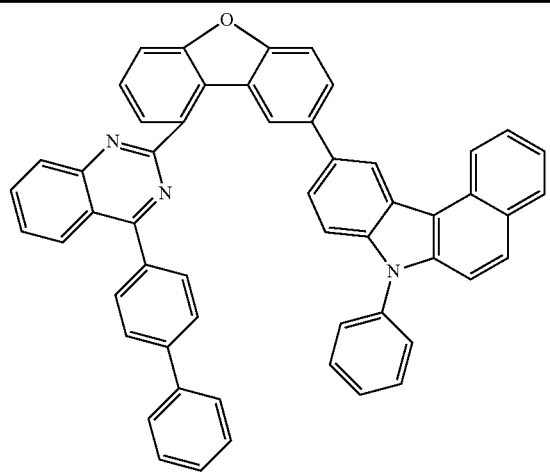
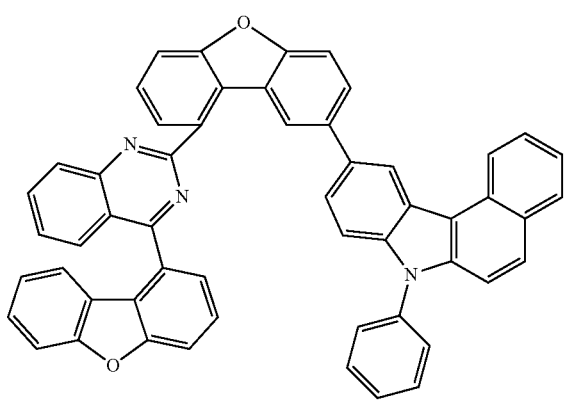 [SMILES: c1ccc(-n2c3ccc(-c4ccc5oc6cccc(-c7nc(-c8cccc9oc%10ccccc%10c89)c8ccccc8n7)c6c5c4)cc3c3c4ccccc4ccc32)cc1]
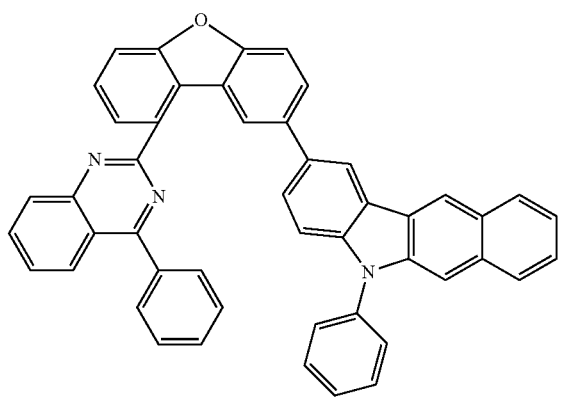 [SMILES: c1ccc(-c2nc(-c3cccc4oc5ccc(-c6ccc7c(c6)c6cc8ccccc8cc6n7-c6ccccc6)cc5c34)nc3ccccc23)cc1]
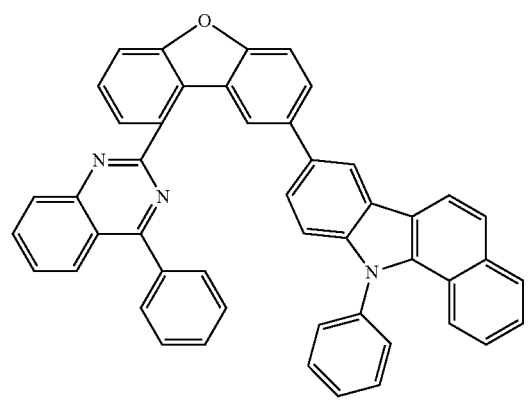 [SMILES: c1ccc(-c2nc(-c3cccc4oc5ccc(-c6ccc7c(c6)c6ccc8ccccc8c6n7-c6ccccc6)cc5c34)nc3ccccc23)cc1]

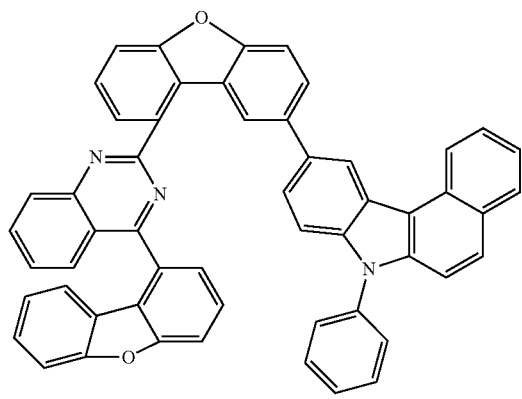 [SMILES: c1ccc(-n2c3ccc(-c4ccc5oc6cccc(-c7nc(-c8cccc9oc%10ccccc%10c89)c8ccccc8n7)c6c5c4)cc3c3c4ccccc4ccc32)cc1]
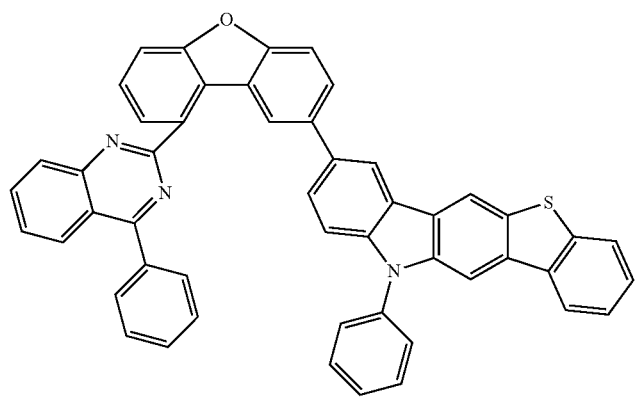 [SMILES: c1ccc(-c2nc(-c3cccc4oc5ccc(-c6ccc7c(c6)c6cc8sc9ccccc9c8cc6n7-c6ccccc6)cc5c34)nc3ccccc23)cc1]
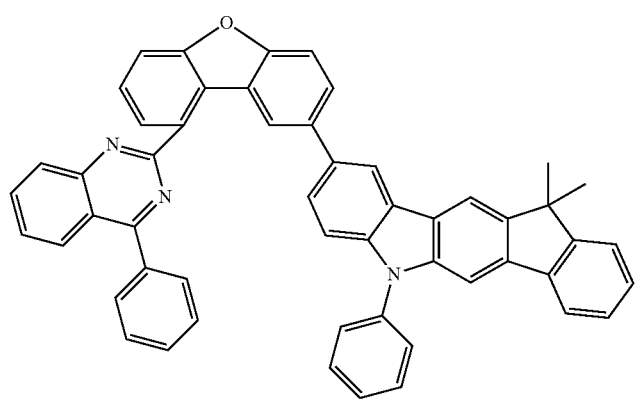 [SMILES: CC1(C)c2ccccc2-c2cc3c(cc21)c1cc(-c2ccc4oc5cccc(-c6nc(-c7ccccc7)c7ccccc7n6)c5c4c2)ccc1n3-c1ccccc1]
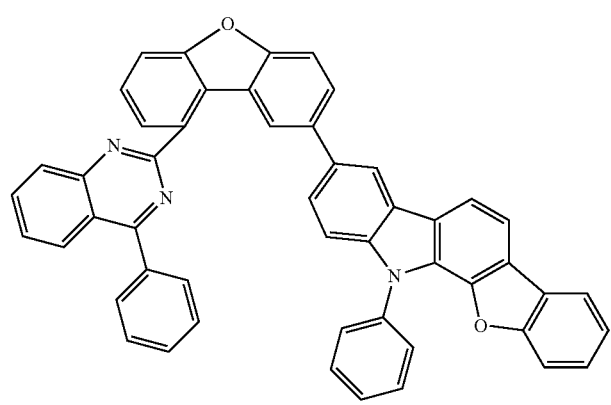 [SMILES: c1ccc(-c2nc(-c3cccc4oc5ccc(-c6ccc7c(c6)c6ccc8c9ccccc9oc8c6n7-c6ccccc6)cc5c34)nc3ccccc23)cc1]

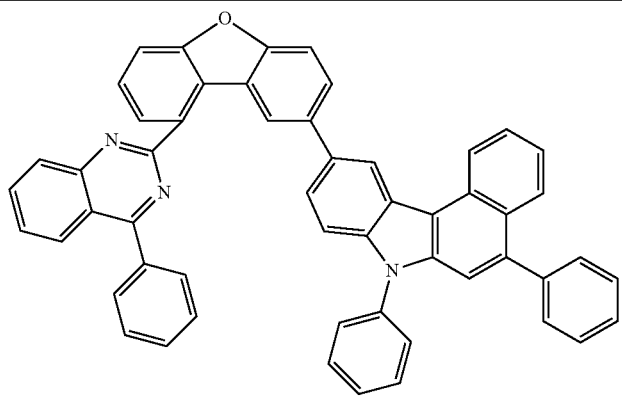
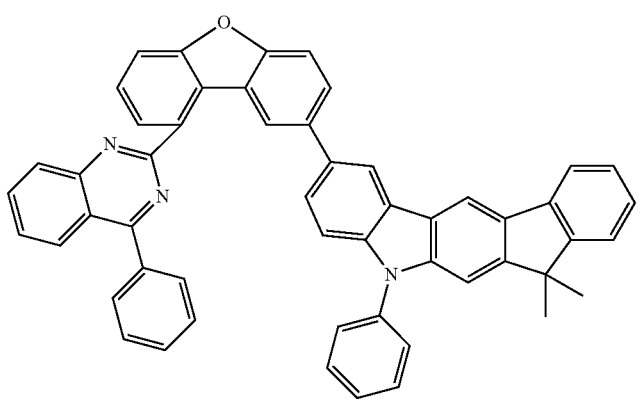 [SMILES: CC1(C)c2ccccc2-c2cc3c4cc(-c5ccc6oc7cccc(-c8nc(-c9ccccc9)c9ccccc9n8)c7c6c5)ccc4n(-c4ccccc4)c3cc21]
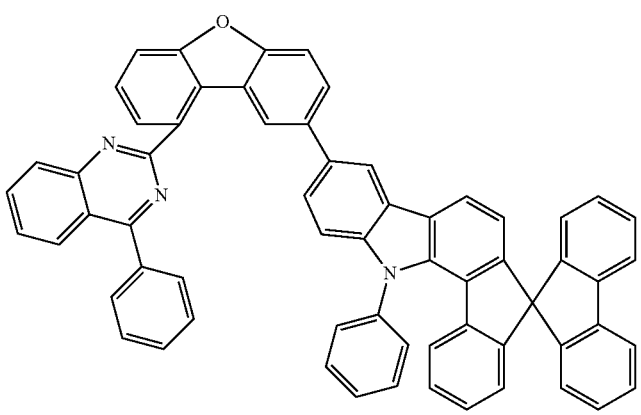 [SMILES: c1ccc(-c2nc(-c3cccc4oc5ccc(-c6ccc7c(c6)c6ccc8c(c6n7-c6ccccc6)-c6ccccc6C86c7ccccc7-c7ccccc76)cc5c34)nc3ccccc23)cc1]
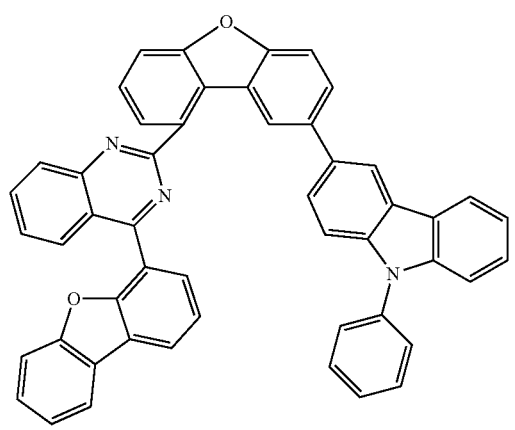 [SMILES: c1ccc(-n2c3ccccc3c3cc(-c4ccc5oc6cccc(-c7nc(-c8cccc9c8oc8ccccc89)c8ccccc8n7)c6c5c4)ccc32)cc1]

-continued
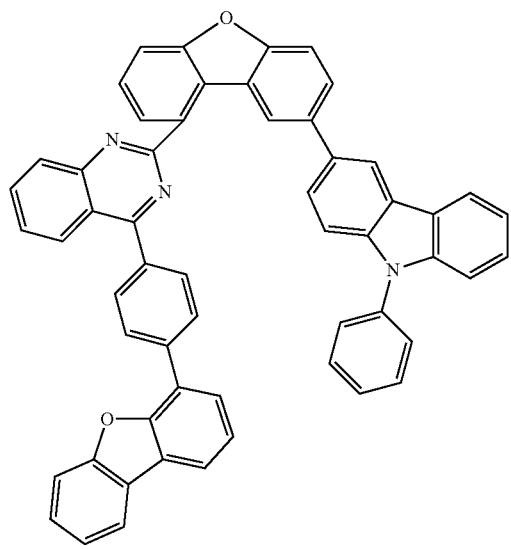 [SMILES: c1ccc(-n2c3ccccc3c3cc(-c4ccc5oc6cccc(-c7nc(-c8ccc(-c9cccc%10c9oc9ccccc9%10)cc8)c8ccccc8n7)c6c5c4)ccc32)cc1]
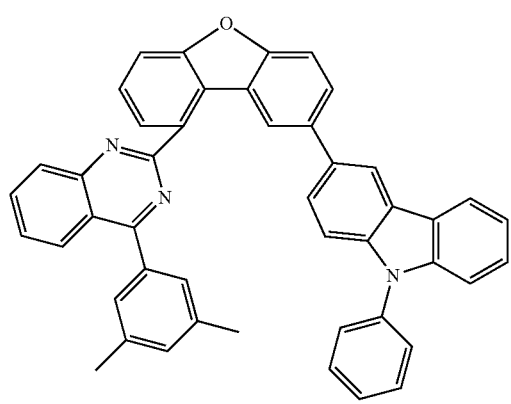 [SMILES: Cc1cc(C)cc(-c2nc(-c3cccc4oc5ccc(-c6ccc7c(c6)c6ccccc6n7-c6ccccc6)cc5c34)nc3ccccc23)c1]
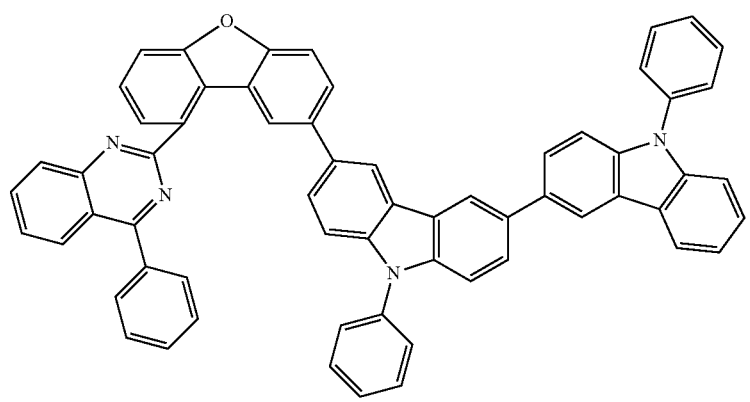

-continued
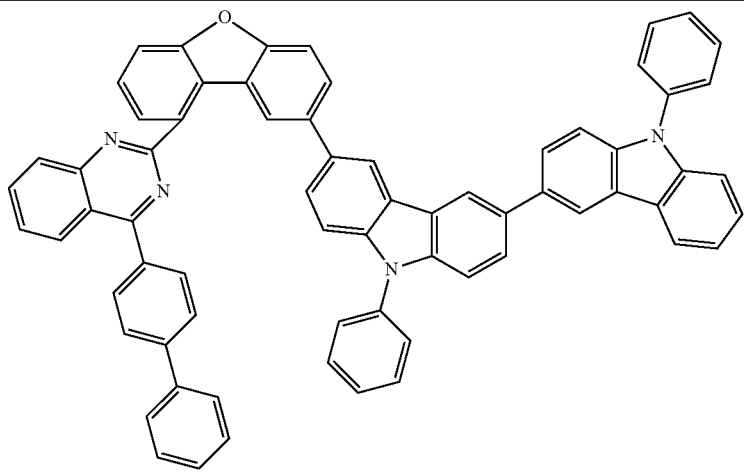
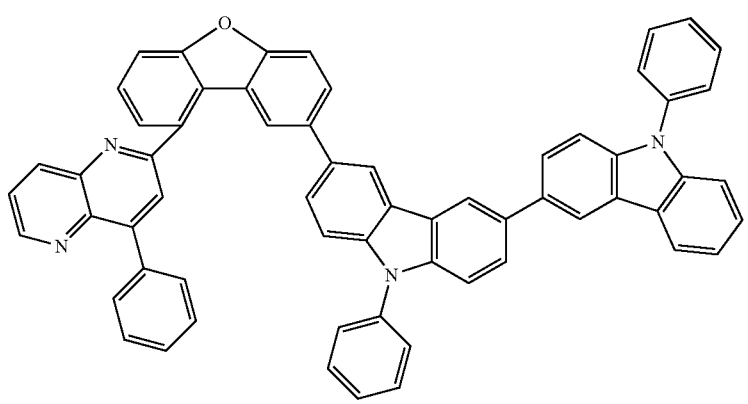 [SMILES: c1ccc(-c2cc(-c3cccc4oc5ccc(-c6ccc7c(c6)c6cc(-c8ccc9c(c8)c8ccccc8n9-c8ccccc8)ccc6n7-c6ccccc6)cc5c34)nc3cccnc23)cc1]
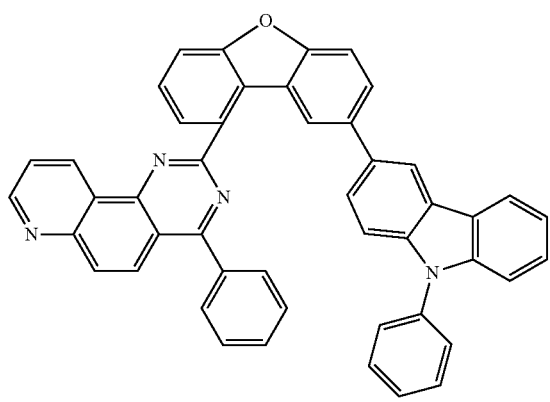 [SMILES: c1ccc(-c2nc(-c3cccc4oc5ccc(-c6ccc7c(c6)c6ccccc6n7-c6ccccc6)cc5c34)nc3c2ccc2ncccc23)cc1]
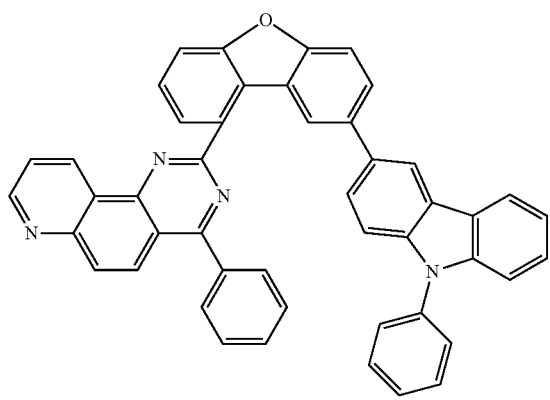 [SMILES: c1ccc(-c2nc(-c3cccc4oc5ccc(-c6ccc7c(c6)c6ccccc6n7-c6ccccc6)cc5c34)nc3c2ccc2ncccc23)cc1]

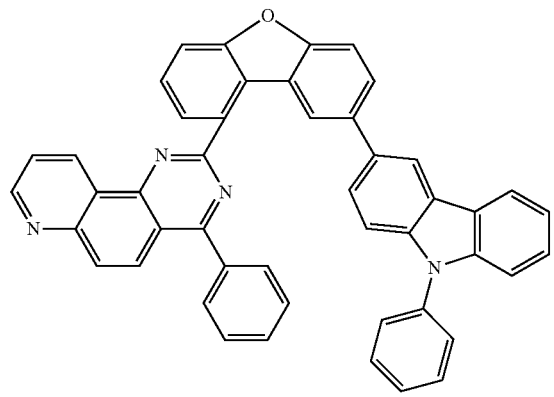 [SMILES: c1ccc(-c2nc(-c3cccc4oc5ccc(-c6ccc7c(c6)c6ccccc6n7-c6ccccc6)cc5c34)nc3c2ccc2ncccc23)cc1]
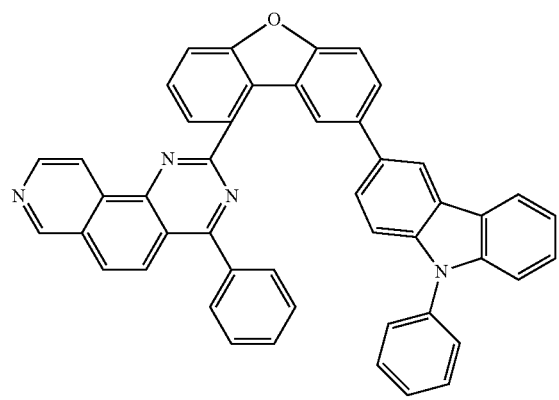 [SMILES: c1ccc(-c2nc(-c3cccc4oc5ccc(-c6ccc7c(c6)c6ccccc6n7-c6ccccc6)cc5c34)nc3c2ccc2cnccc23)cc1]
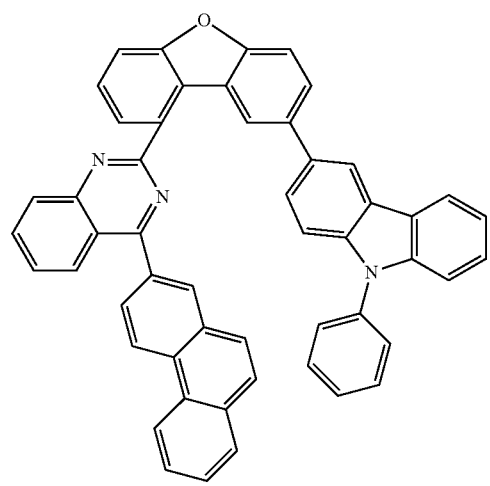 [SMILES: c1ccc(-n2c3ccccc3c3cc(-c4ccc5oc6cccc(-c7nc(-c8ccc9c(ccc%10ccccc%109)c8)c8ccccc8n7)c6c5c4)ccc32)cc1]

-continued
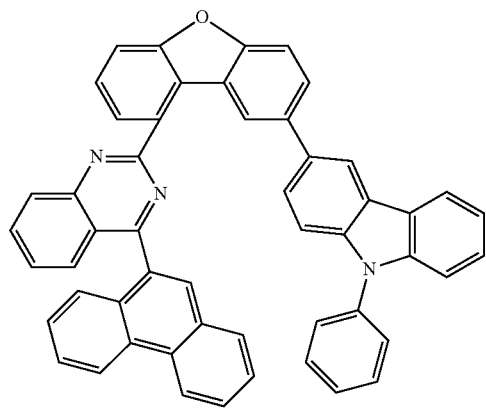 [SMILES: c1ccc(-n2c3ccccc3c3cc(-c4ccc5oc6cccc(-c7nc(-c8cc9ccccc9c9ccccc89)c8ccccc8n7)c6c5c4)ccc32)cc1]
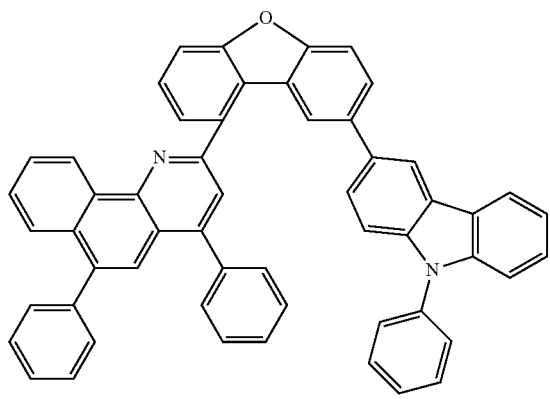 [SMILES: c1ccc(-c2cc3c(-c4ccccc4)cc(-c4cccc5oc6ccc(-c7ccc8c(c7)c7ccccc7n8-c7ccccc7)cc6c45)nc3c3ccccc23)cc1]
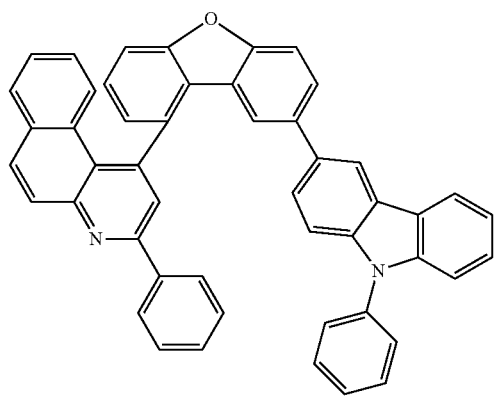 [SMILES: c1ccc(-c2cc(-c3cccc4oc5ccc(-c6ccc7c(c6)c6ccccc6n7-c6ccccc6)cc5c34)c3c(ccc4ccccc43)n2)cc1]
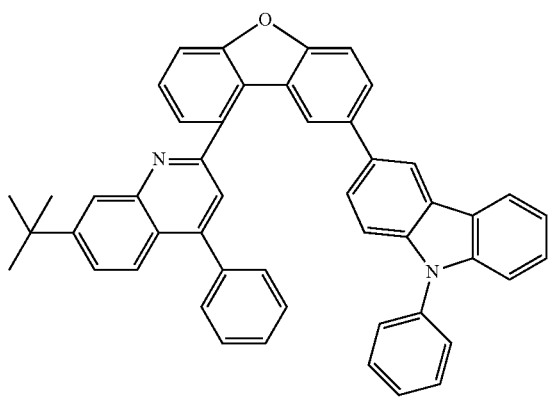 [SMILES: CC(C)(C)c1ccc2c(-c3ccccc3)cc(-c3cccc4oc5ccc(-c6ccc7c(c6)c6ccccc6n7-c6ccccc6)cc5c34)nc2c1]

-continued
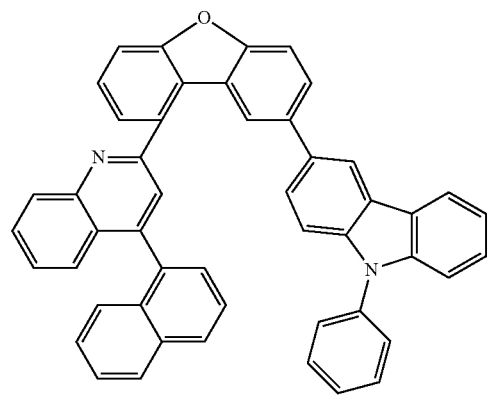 [SMILES: c1ccc(-n2c3ccccc3c3cc(-c4ccc5oc6cccc(-c7cc(-c8cccc9ccccc89)c8ccccc8n7)c6c5c4)ccc32)cc1]
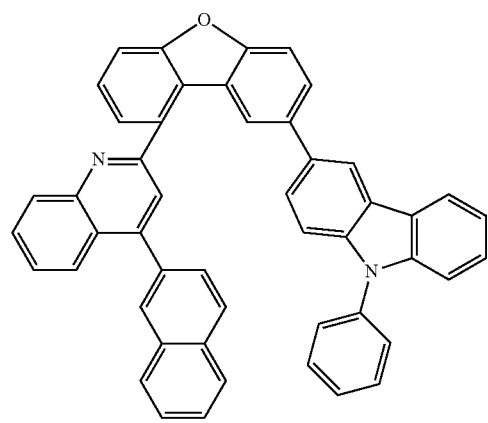 [SMILES: c1ccc(-n2c3ccccc3c3cc(-c4ccc5oc6cccc(-c7cc(-c8ccc9ccccc9c8)c8ccccc8n7)c6c5c4)ccc32)cc1]
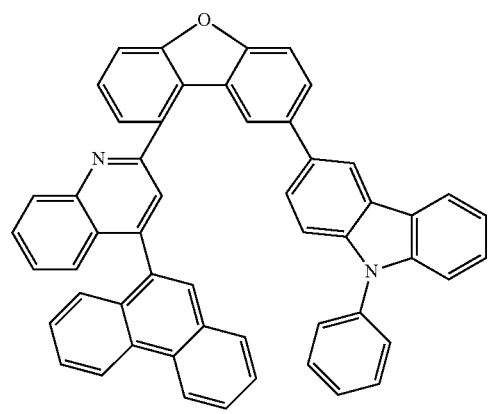
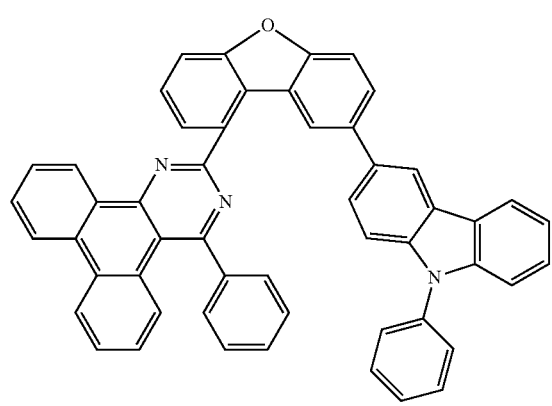 [SMILES: c1ccc(-c2nc(-c3cccc4oc5ccc(-c6ccc7c(c6)c6ccccc6n7-c6ccccc6)cc5c34)nc3c4ccccc4c4ccccc4c23)cc1]

-continued
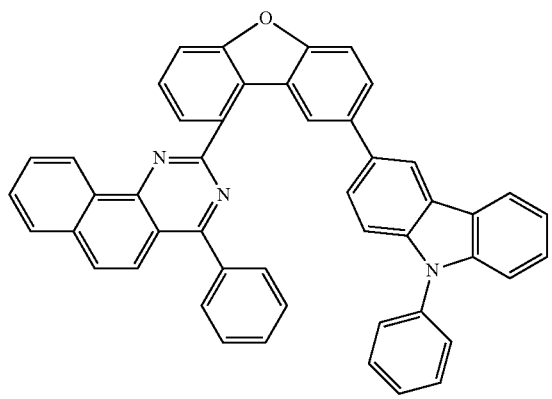
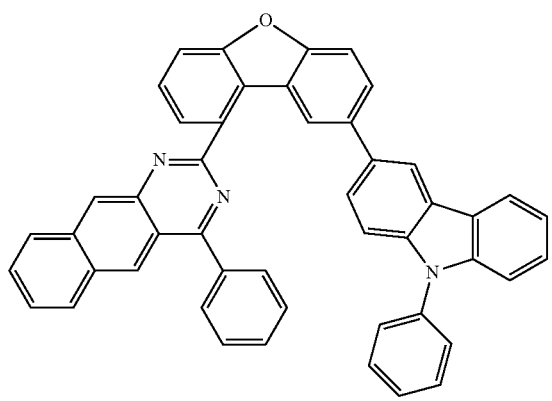 [SMILES: c1ccc(-c2nc(-c3cccc4oc5ccc(-c6ccc7c(c6)c6ccccc6n7-c6ccccc6)cc5c34)nc3cc4ccccc4cc23)cc1]
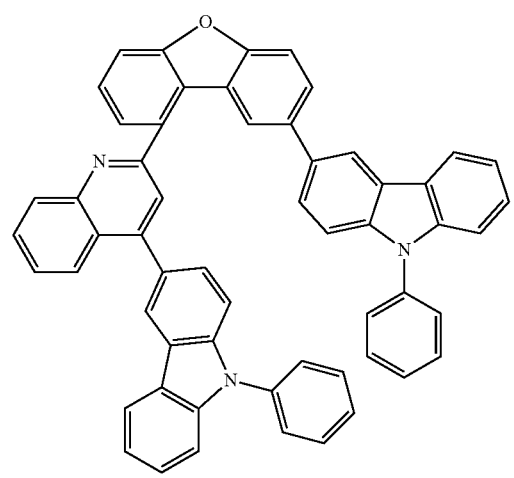 [SMILES: c1ccc(-n2c3ccccc3c3cc(-c4ccc5oc6cccc(-c7cc(-c8ccc9c(c8)c8ccccc8n9-c8ccccc8)c8ccccc8n7)c6c5c4)ccc32)cc1]

-continued
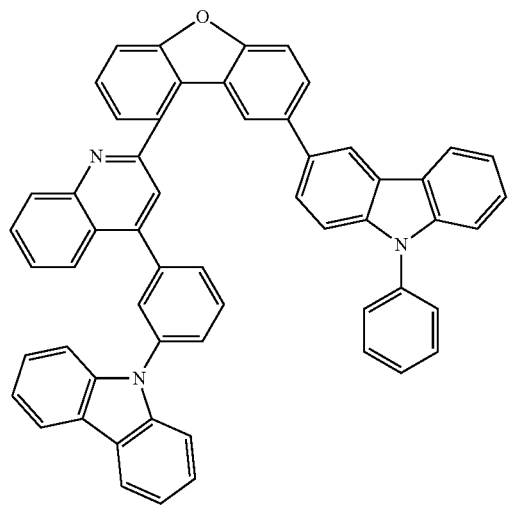 [SMILES: c1ccc(-n2c3ccccc3c3cc(-c4ccc5oc6cccc(-c7cc(-c8cccc(-n9c%10ccccc%10c%10ccccc%109)c8)c8ccccc8n7)c6c5c4)ccc32)cc1]
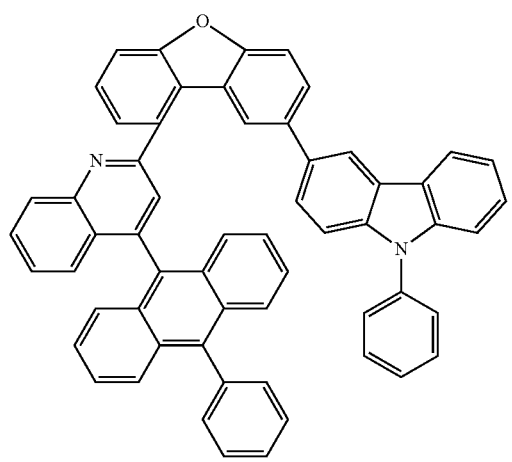 [SMILES: c1ccc(-c2c3ccccc3c(-c3cc(-c4cccc5oc6ccc(-c7ccc8c(c7)c7ccccc7n8-c7ccccc7)cc6c45)nc4ccccc34)c3ccccc23)cc1]
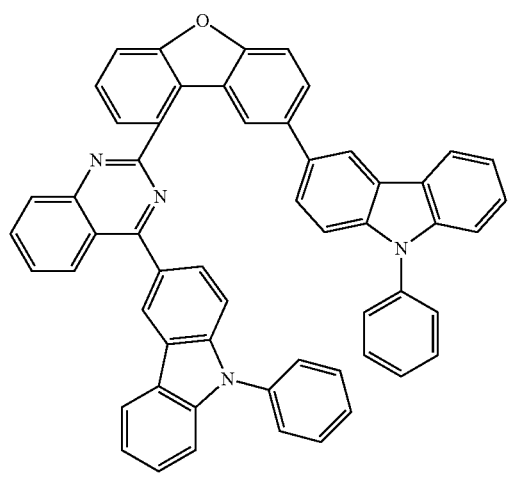 [SMILES: c1ccc(-n2c3ccccc3c3cc(-c4ccc5oc6cccc(-c7nc(-c8ccc9c(c8)c8ccccc8n9-c8ccccc8)c8ccccc8n7)c6c5c4)ccc32)cc1]

-continued
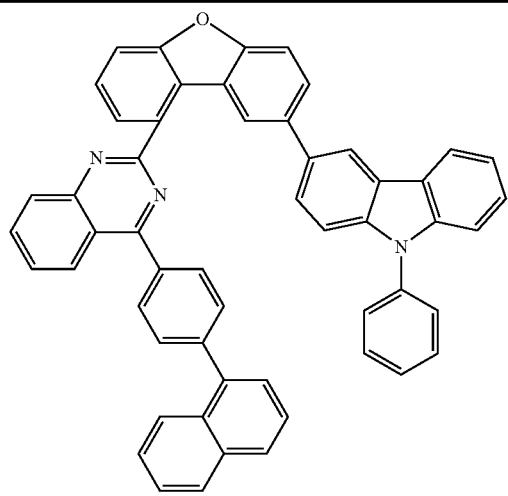
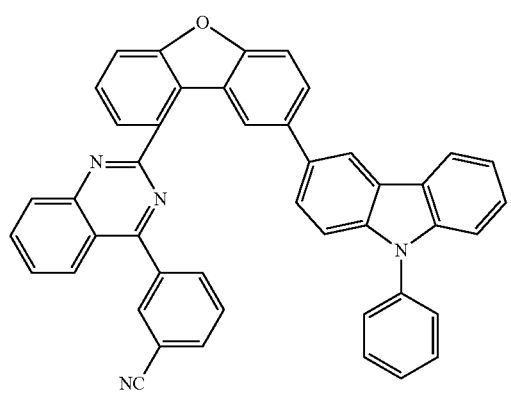 [SMILES: N#Cc1cccc(-c2nc(-c3cccc4oc5ccc(-c6ccc7c(c6)c6ccccc6n7-c6ccccc6)cc5c34)nc3ccccc23)c1]
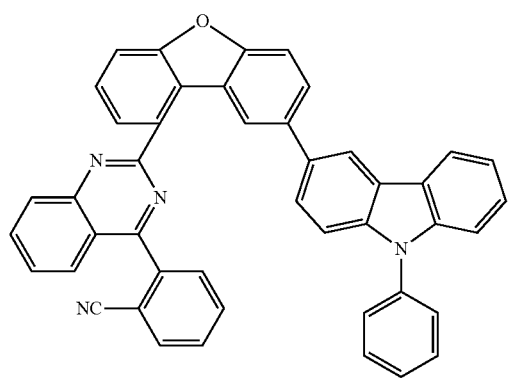 [SMILES: N#Cc1ccccc1-c1nc(-c2cccc3oc4ccc(-c5ccc6c(c5)c5ccccc5n6-c5ccccc5)cc4c23)nc2ccccc12]
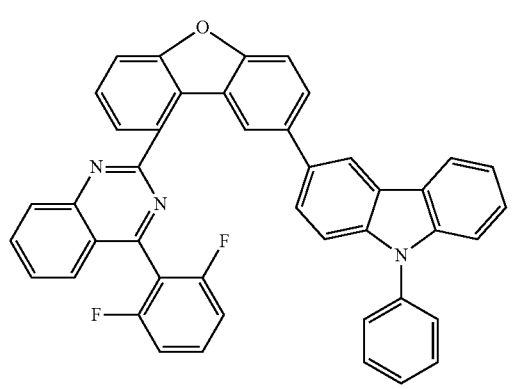 [SMILES: Fc1cccc(F)c1-c1nc(-c2cccc3oc4ccc(-c5ccc6c(c5)c5ccccc5n6-c5ccccc5)cc4c23)nc2ccccc12]

-continued
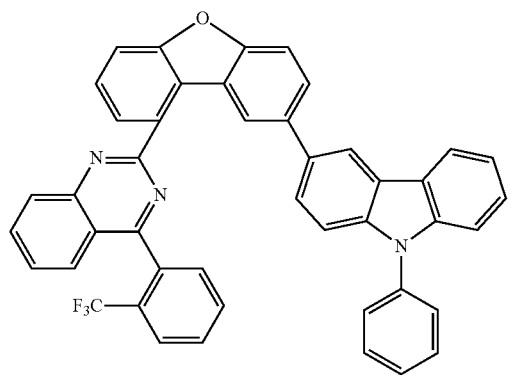
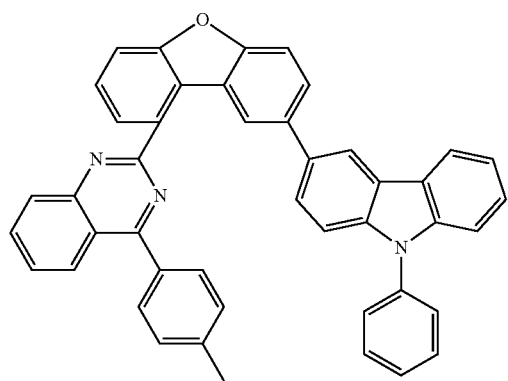
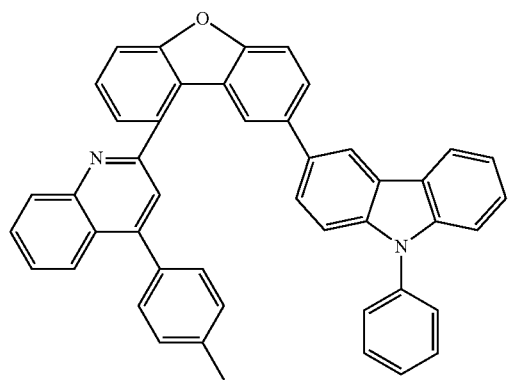 [SMILES: Cc1ccc(-c2cc(-c3cccc4oc5ccc(-c6ccc7c(c6)c6ccccc6n7-c6ccccc6)cc5c34)nc3ccccc23)cc1]
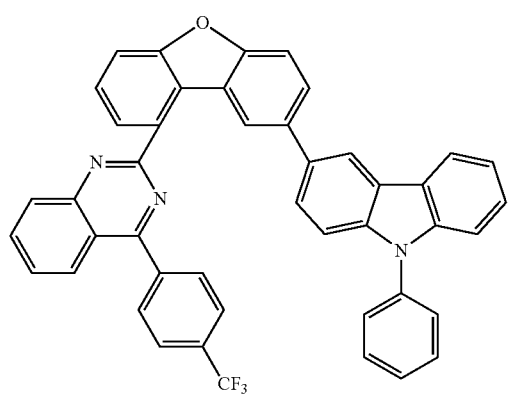 [SMILES: FC(F)(F)c1ccc(-c2nc(-c3cccc4oc5ccc(-c6ccc7c(c6)c6ccccc6n7-c6ccccc6)cc5c34)nc3ccccc23)cc1]

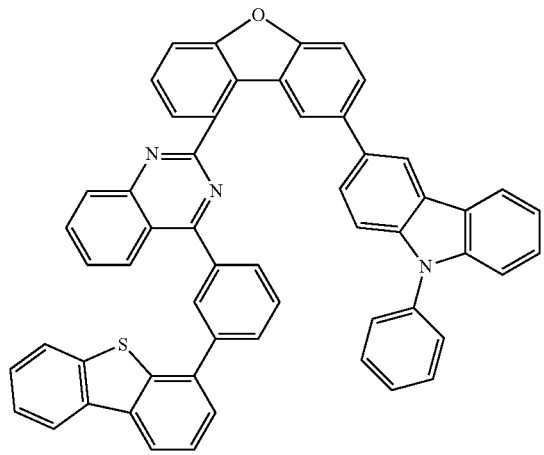 [SMILES: c1ccc(-n2c3ccccc3c3cc(-c4ccc5oc6cccc(-c7nc(-c8cccc(-c9cccc%10c9sc9ccccc9%10)c8)c8ccccc8n7)c6c5c4)ccc32)cc1]
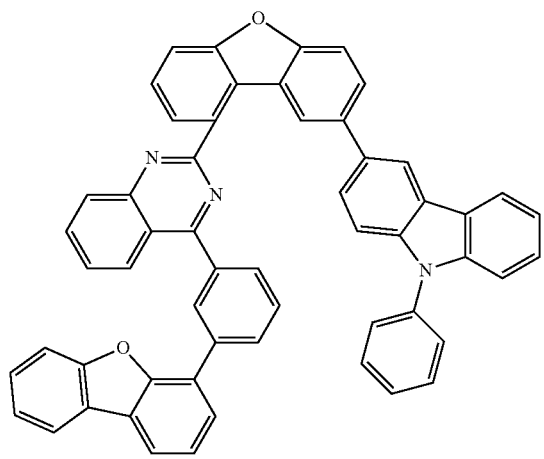
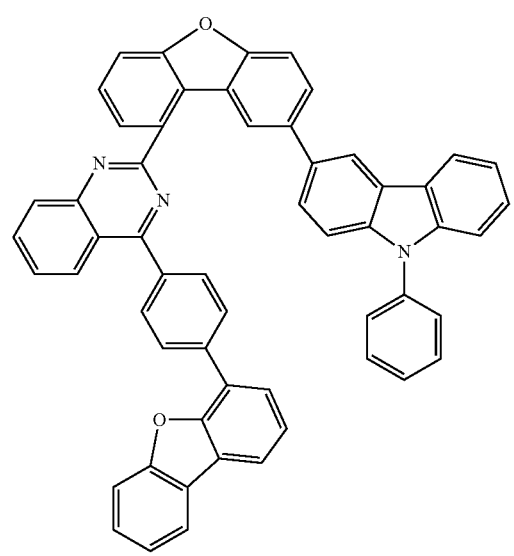 [SMILES: c1ccc(-n2c3ccccc3c3cc(-c4ccc5oc6cccc(-c7nc(-c8ccc(-c9cccc%10c9oc9ccccc9%10)cc8)c8ccccc8n7)c6c5c4)ccc32)cc1]

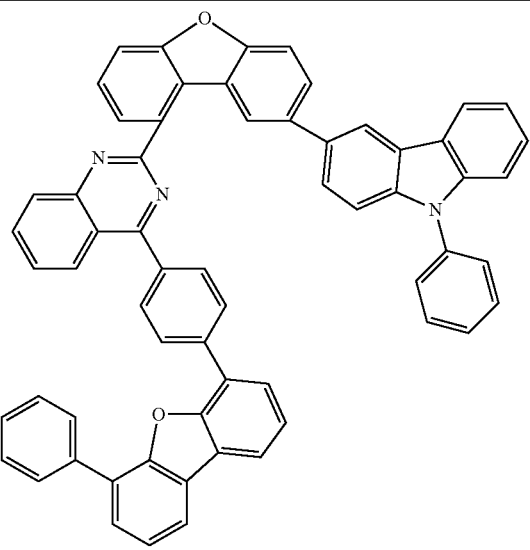
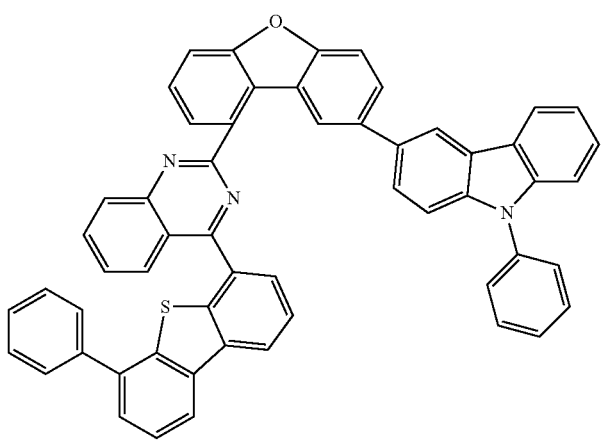 [SMILES: c1ccc(-c2cccc3c2sc2c(-c4nc(-c5cccc6oc7ccc(-c8ccc9c(c8)c8ccccc8n9-c8ccccc8)cc7c56)nc5ccccc45)cccc23)cc1]
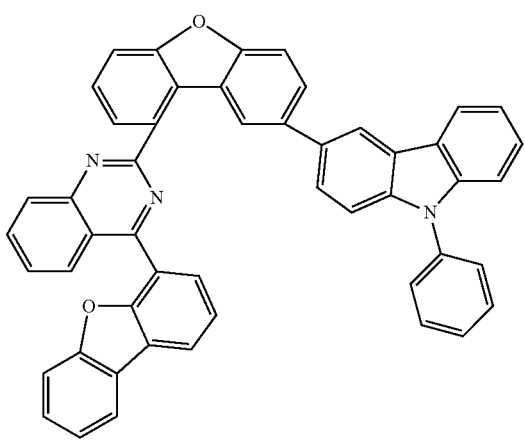 [SMILES: c1ccc(-n2c3ccccc3c3cc(-c4ccc5oc6cccc(-c7nc(-c8cccc9c8oc8ccccc89)c8ccccc8n7)c6c5c4)ccc32)cc1]

-continued
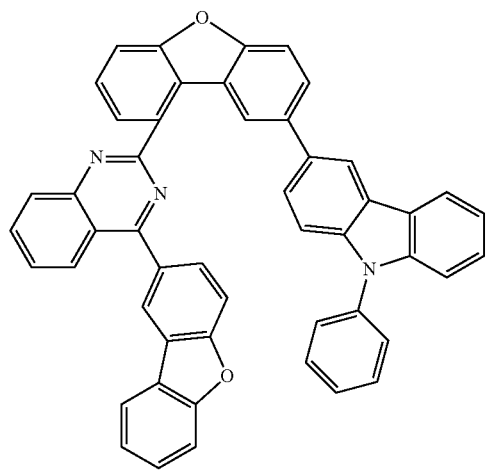 [SMILES: c1ccc(-n2c3ccccc3c3cc(-c4ccc5oc6cccc(-c7nc(-c8ccc9oc%10ccccc%10c9c8)c8ccccc8n7)c6c5c4)ccc32)cc1]
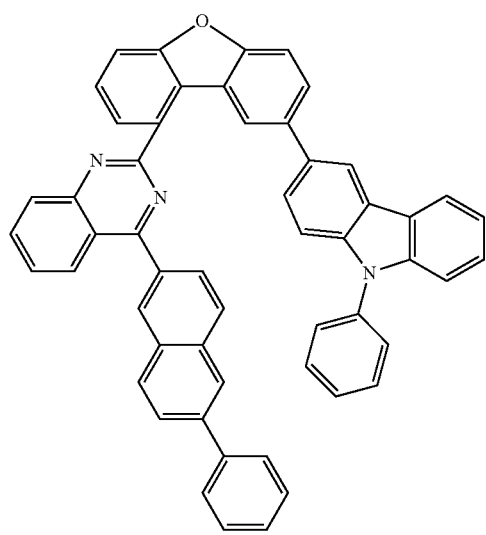 [SMILES: c1ccc(-c2ccc3cc(-c4nc(-c5cccc6oc7ccc(-c8ccc9c(c8)c8ccccc8n9-c8ccccc8)cc7c56)nc5ccccc45)ccc3c2)cc1]
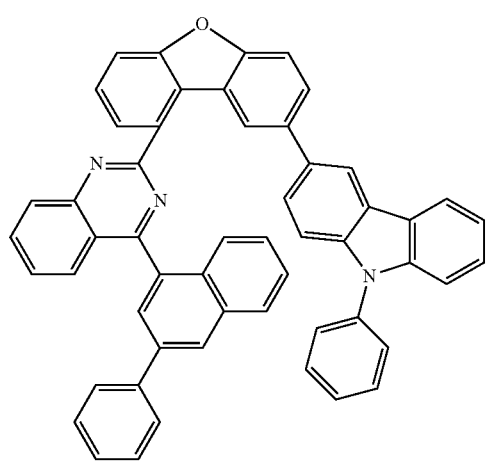 [SMILES: c1ccc(-c2cc(-c3nc(-c4cccc5oc6ccc(-c7ccc8c(c7)c7ccccc7n8-c7ccccc7)cc6c45)nc4ccccc34)c3ccccc3c2)cc1]

-continued
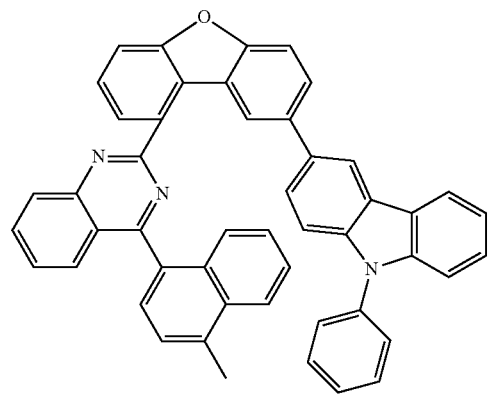 [SMILES: Cc1ccc(-c2nc(-c3cccc4oc5ccc(-c6ccc7c(c6)c6ccccc6n7-c6ccccc6)cc5c34)nc3ccccc23)c2ccccc12]
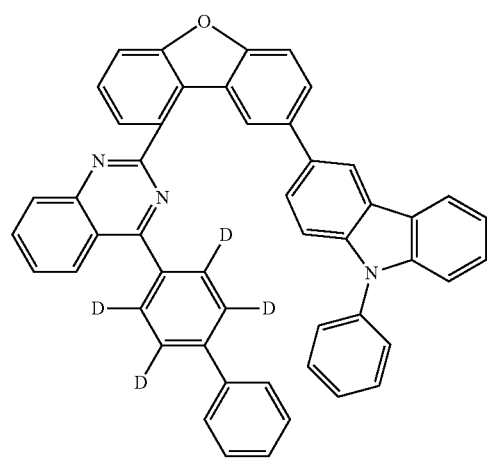 [SMILES: [2H]c1c([2H])c(-c2nc(-c3cccc4oc5ccc(-c6ccc7c(c6)c6ccccc6n7-c6ccccc6)cc5c34)nc3ccccc23)c([2H])c([2H])c1-c1ccccc1]
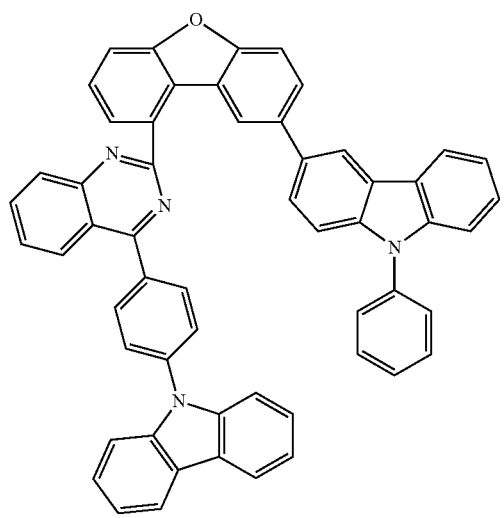 [SMILES: c1ccc(-n2c3ccccc3c3cc(-c4ccc5oc6cccc(-c7nc(-c8ccc(-n9c%10ccccc%10c%10ccccc%109)cc8)c8ccccc8n7)c6c5c4)ccc32)cc1]

-continued
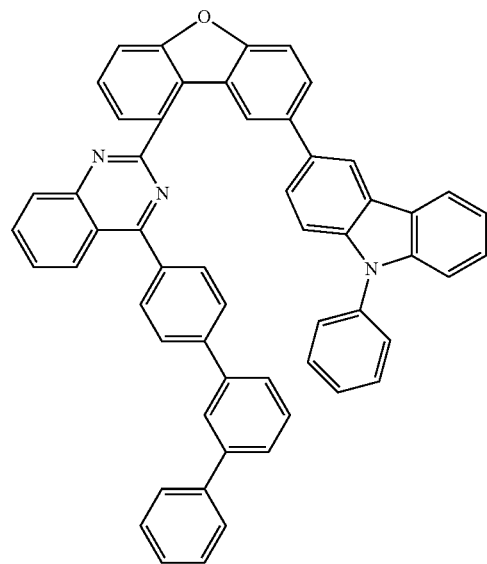 [SMILES: c1ccc(-c2cccc(-c3ccc(-c4nc(-c5cccc6oc7ccc(-c8ccc9c(c8)c8ccccc8n9-c8ccccc8)cc7c56)nc5ccccc45)cc3)c2)cc1]
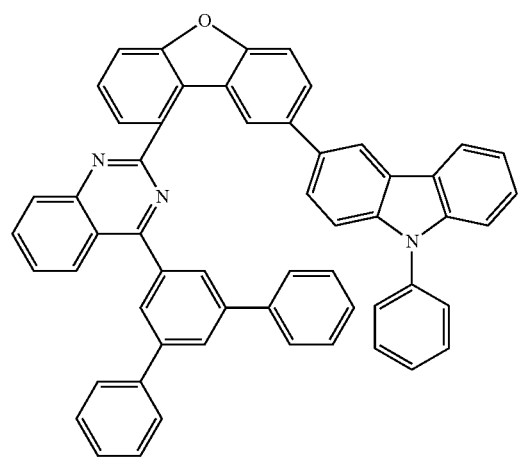 [SMILES: c1ccc(-c2cc(-c3ccccc3)cc(-c3nc(-c4cccc5oc6ccc(-c7ccc8c(c7)c7ccccc7n8-c7ccccc7)cc6c45)nc4ccccc34)c2)cc1]
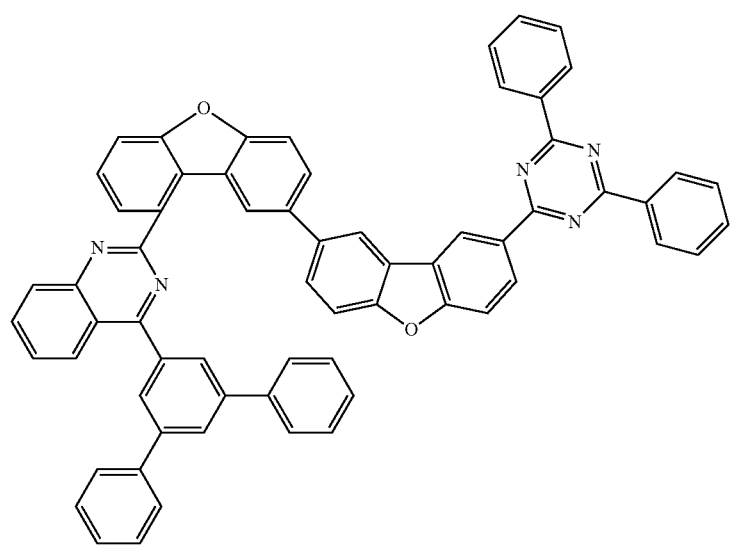 [SMILES: c1ccc(-c2cc(-c3ccccc3)cc(-c3nc(-c4cccc5oc6ccc(-c7ccc8oc9ccc(-c%10nc(-c%11ccccc%11)nc(-c%11ccccc%11)n%10)cc9c8c7)cc6c45)nc4ccccc34)c2)cc1]

-continued
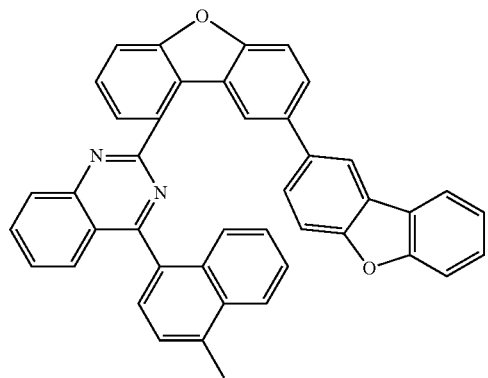 [SMILES: Cc1ccc(-c2nc(-c3cccc4oc5ccc(-c6ccc7oc8ccccc8c7c6)cc5c34)nc3ccccc23)c2ccccc12]
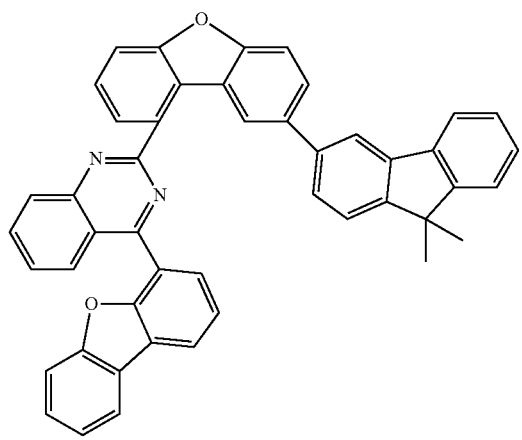 [SMILES: CC1(C)c2ccccc2-c2cc(-c3ccc4oc5cccc(-c6nc(-c7cccc8c7oc7ccccc78)c7ccccc7n6)c5c4c3)ccc21]
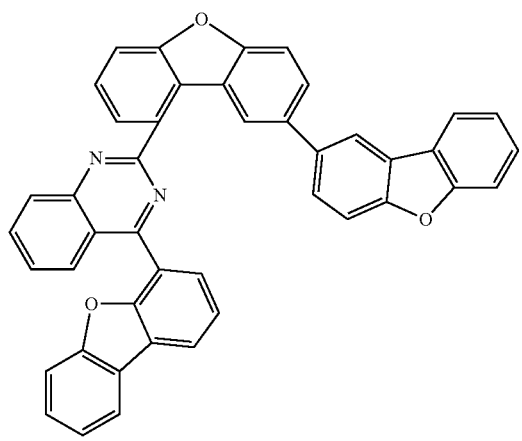 [SMILES: c1ccc2c(-c3cccc4c3oc3ccccc34)nc(-c3cccc4oc5ccc(-c6ccc7oc8ccccc8c7c6)cc5c34)nc2c1]
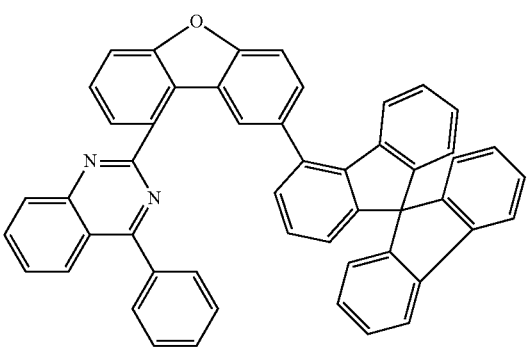 [SMILES: c1ccc(-c2nc(-c3cccc4oc5ccc(-c6cccc7c6-c6ccccc6C76c7ccccc7-c7ccccc76)cc5c34)nc3ccccc23)cc1]

-continued
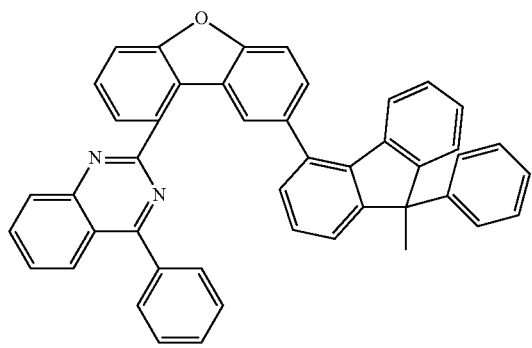 [SMILES: CC1(c2ccccc2)c2ccccc2-c2c(-c3ccc4oc5cccc(-c6nc(-c7ccccc7)c7ccccc7n6)c5c4c3)cccc21]
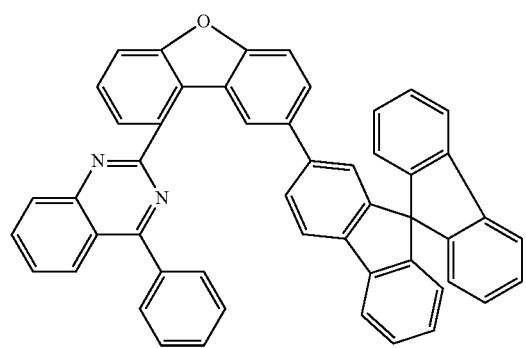 [SMILES: c1ccc(-c2nc(-c3cccc4oc5ccc(-c6ccc7c(c6)C6(c8ccccc8-c8ccccc86)c6ccccc6-7)cc5c34)nc3ccccc23)cc1]
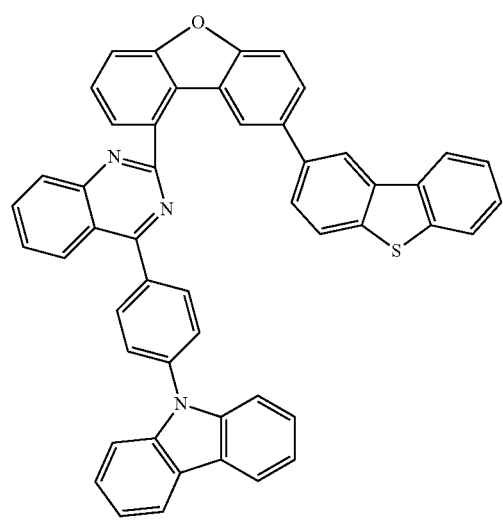 [SMILES: c1ccc2c(-c3ccc(-n4c5ccccc5c5ccccc54)cc3)nc(-c3cccc4oc5ccc(-c6ccc7sc8ccccc8c7c6)cc5c34)nc2c1]

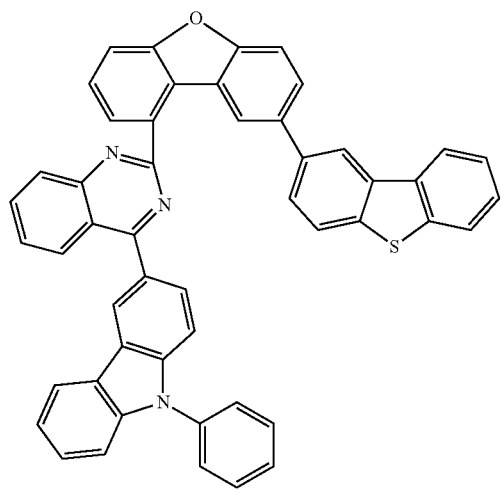 [SMILES: c1ccc(-n2c3ccccc3c3cc(-c4nc(-c5cccc6oc7ccc(-c8ccc9sc%10ccccc%10c9c8)cc7c56)nc5ccccc45)ccc32)cc1]
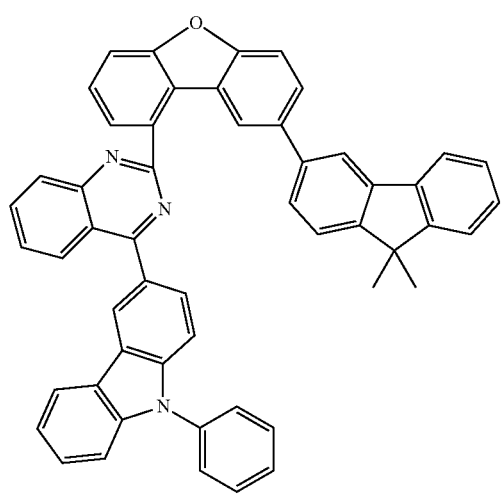 [SMILES: CC1(C)c2ccccc2-c2cc(-c3ccc4oc5cccc(-c6nc(-c7ccc8c(c7)c7ccccc7n8-c7ccccc7)c7ccccc7n6)c5c4c3)ccc21]
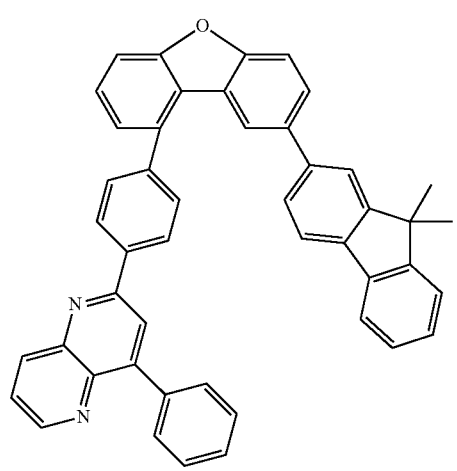 [SMILES: CC1(C)c2ccccc2-c2ccc(-c3ccc4oc5cccc(-c6ccc(-c7cc(-c8ccccc8)c8ncccc8n7)cc6)c5c4c3)cc21]

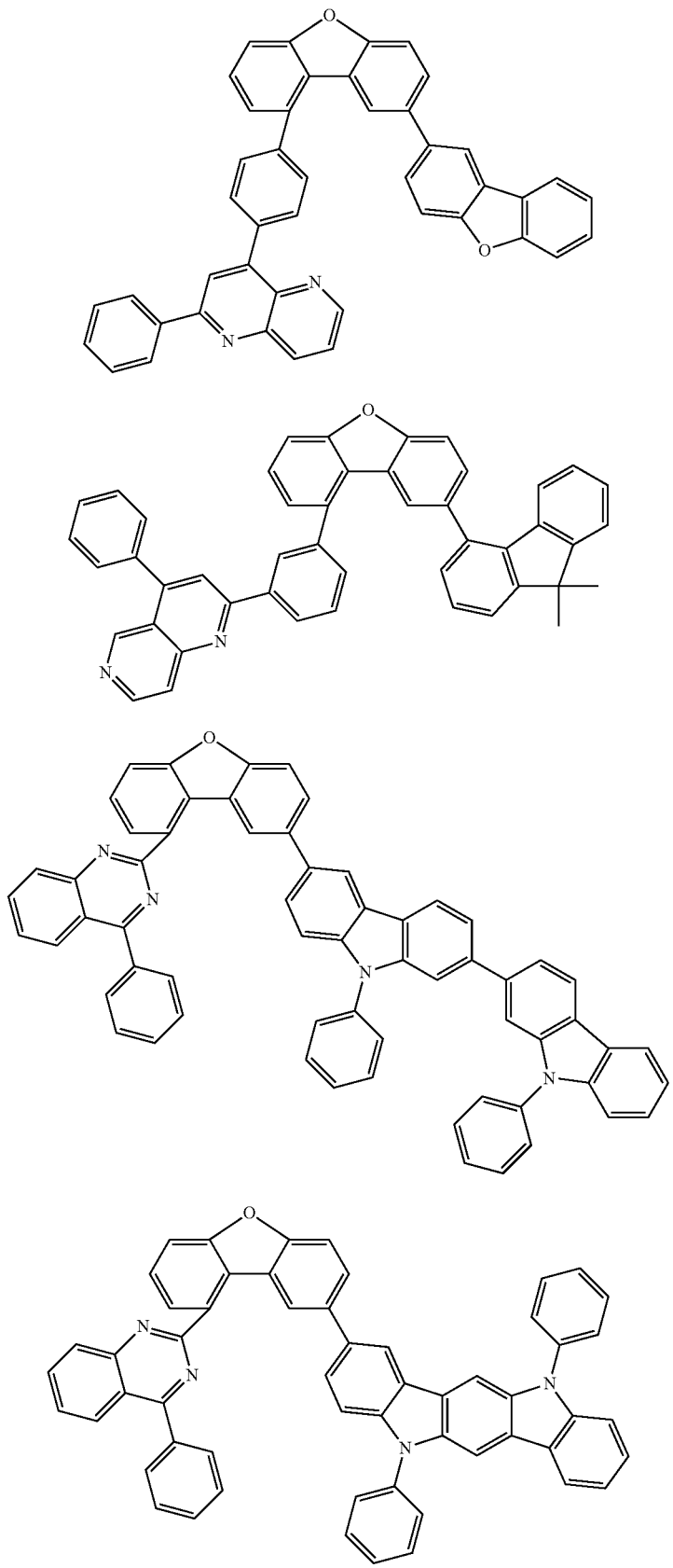

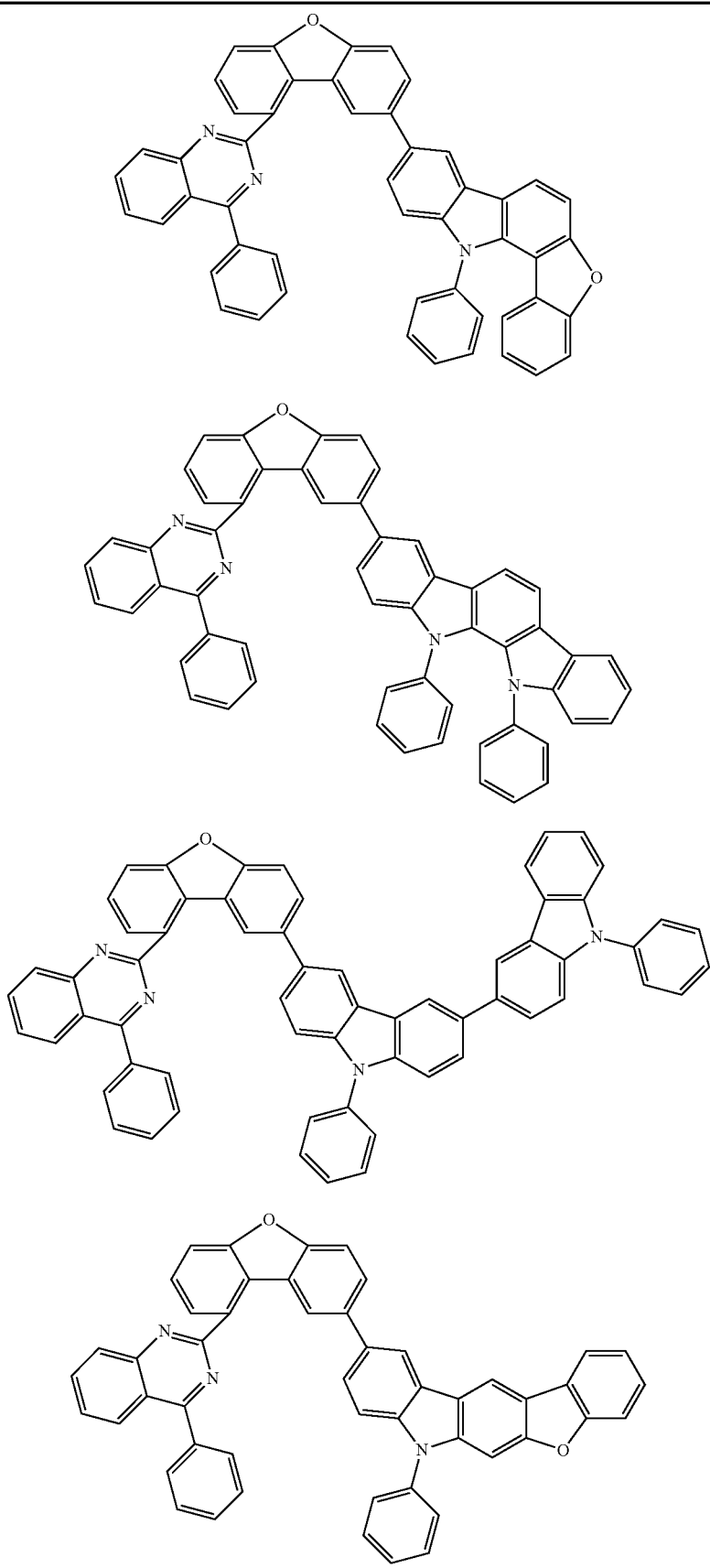

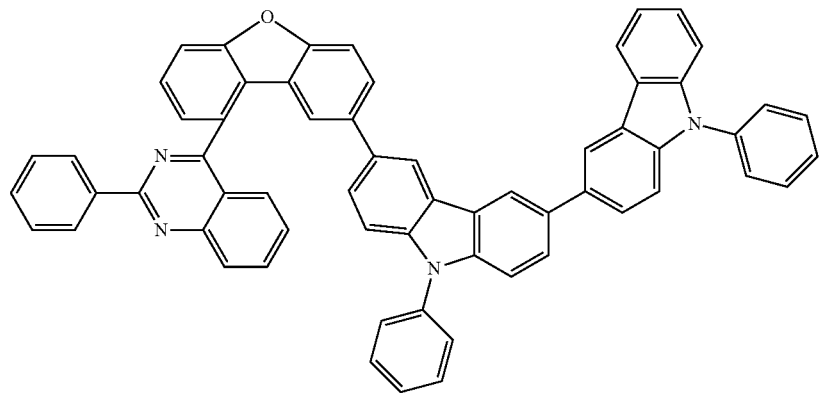 [SMILES: c1ccc(-c2nc(-c3cccc4oc5ccc(-c6ccc7c(c6)c6cc(-c8ccc9c(c8)c8ccccc8n9-c8ccccc8)ccc6n7-c6ccccc6)cc5c34)c3ccccc3n2)cc1]
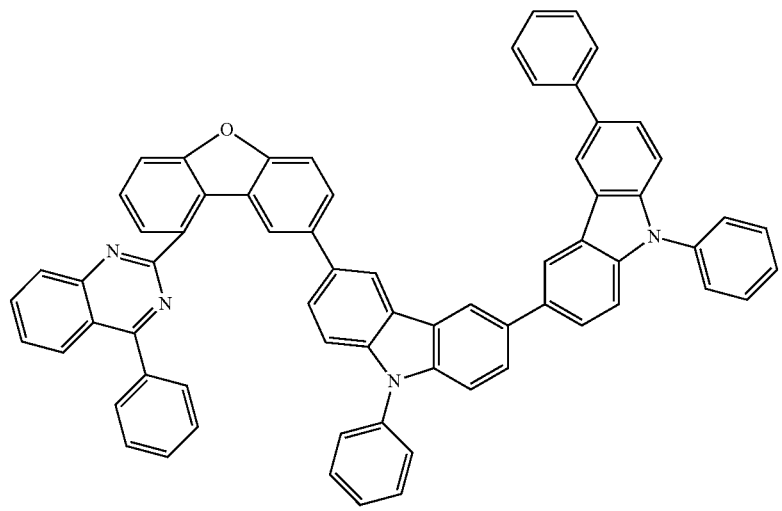 [SMILES: c1ccc(-c2ccc3c(c2)c2cc(-c4ccc5c(c4)c4cc(-c6ccc7oc8cccc(-c9nc(-c%10ccccc%10)c%10ccccc%10n9)c8c7c6)ccc4n5-c4ccccc4)ccc2n3-c2ccccc2)cc1]
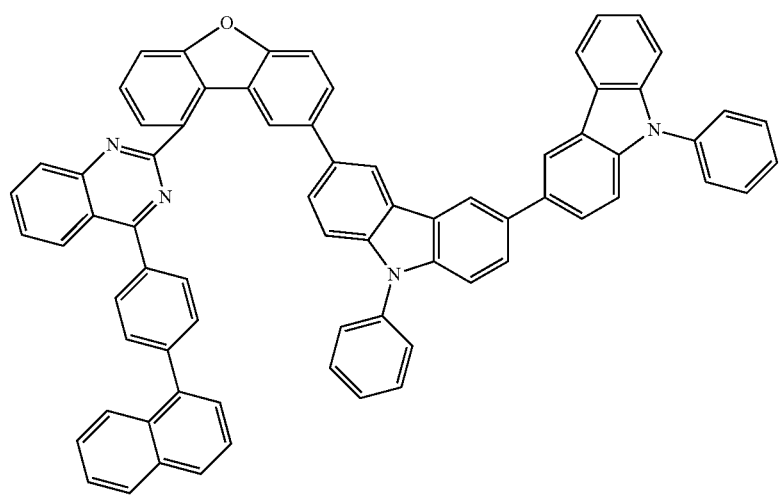 [SMILES: c1ccc(-n2c3ccccc3c3cc(-c4ccc5c(c4)c4cc(-c6ccc7oc8cccc(-c9nc(-c%10ccc(-c%11cccc%12ccccc%11%12)cc%10)c%10ccccc%10n9)c8c7c6)ccc4n5-c4ccccc4)ccc32)cc1]

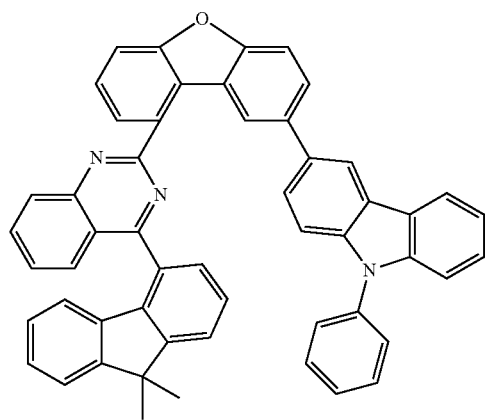 [SMILES: CC1(C)c2ccccc2-c2c(-c3nc(-c4cccc5oc6ccc(-c7ccc8c(c7)c7ccccc7n8-c7ccccc7)cc6c45)nc4ccccc34)cccc21]
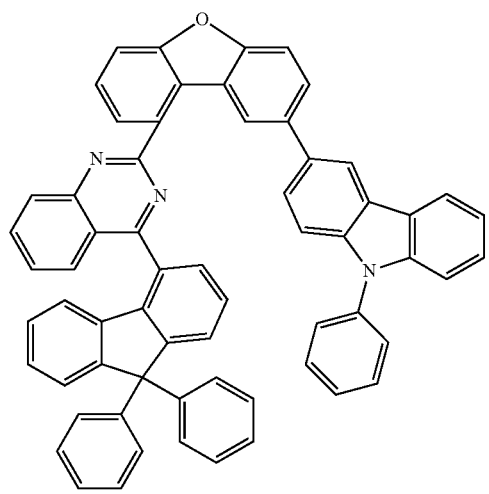 [SMILES: c1ccc(-n2c3ccccc3c3cc(-c4ccc5oc6cccc(-c7nc(-c8cccc9c8-c8ccccc8C9(c8ccccc8)c8ccccc8)c8ccccc8n7)c6c5c4)ccc32)cc1]
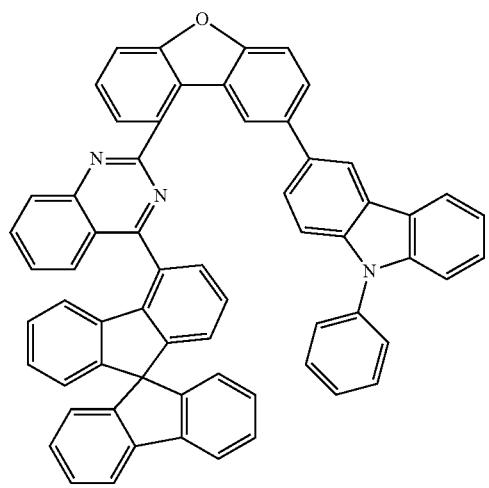 [SMILES: c1ccc(-n2c3ccccc3c3cc(-c4ccc5oc6cccc(-c7nc(-c8cccc9c8-c8ccccc8C98c9ccccc9-c9ccccc98)c8ccccc8n7)c6c5c4)ccc32)cc1]

-continued
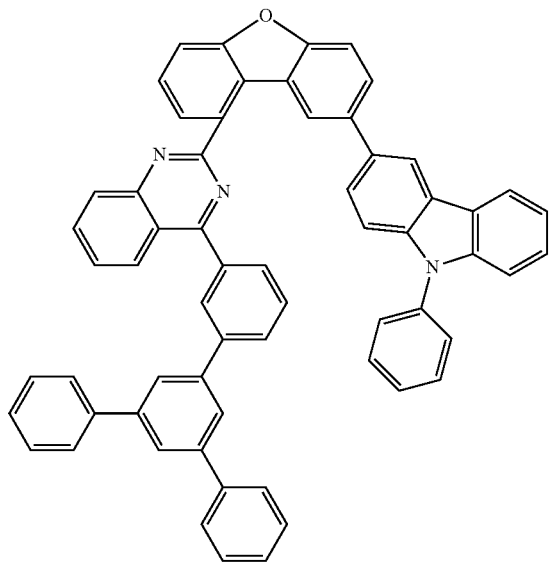 [SMILES: c1ccc(-c2cc(-c3ccccc3)cc(-c3cccc(-c4nc(-c5cccc6oc7ccc(-c8ccc9c(c8)c8ccccc8n9-c8ccccc8)cc7c56)nc5ccccc45)c3)c2)cc1]
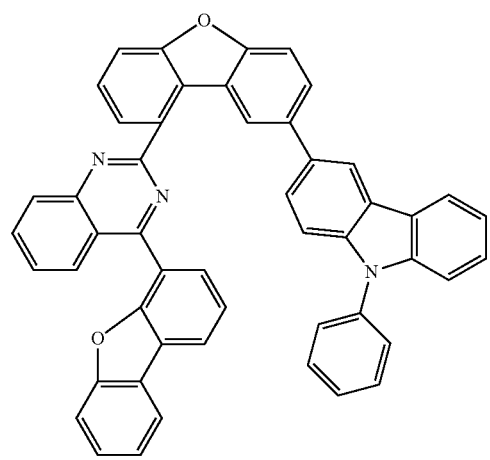 [SMILES: c1ccc(-n2c3ccccc3c3cc(-c4ccc5oc6cccc(-c7nc(-c8cccc9c8oc8ccccc89)c8ccccc8n7)c6c5c4)ccc32)cc1]
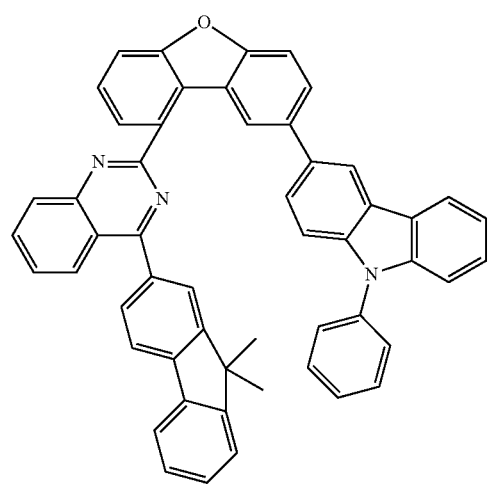 [SMILES: CC1(C)c2ccccc2-c2ccc(-c3nc(-c4cccc5oc6ccc(-c7ccc8c(c7)c7ccccc7n8-c7ccccc7)cc6c45)nc4ccccc34)cc21]

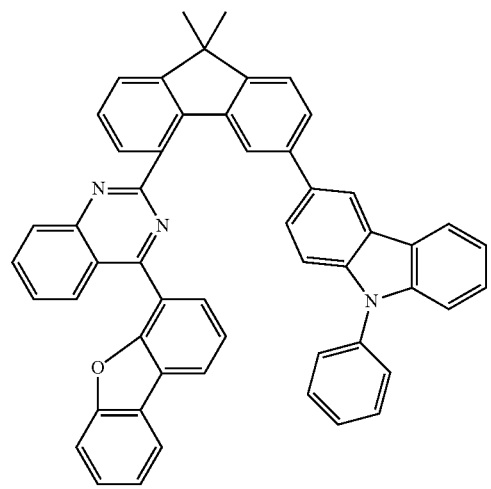 [SMILES: CC1(C)c2ccc(-c3ccc4c(c3)c3ccccc3n4-c3ccccc3)cc2-c2c(-c3nc(-c4cccc5c4oc4ccccc45)c4ccccc4n3)cccc21]
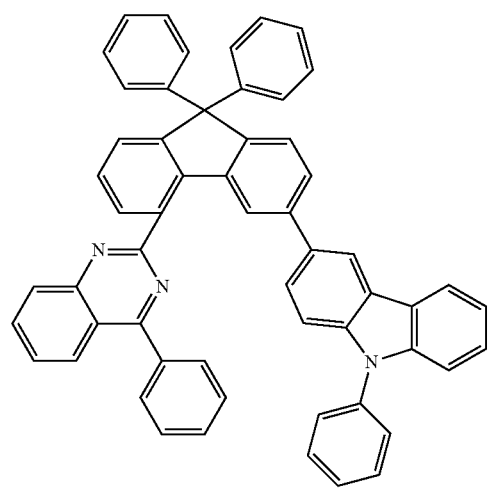 [SMILES: c1ccc(-c2nc(-c3cccc4c3-c3cc(-c5ccc6c(c5)c5ccccc5n6-c5ccccc5)ccc3C4(c3ccccc3)c3ccccc3)nc3ccccc23)cc1]
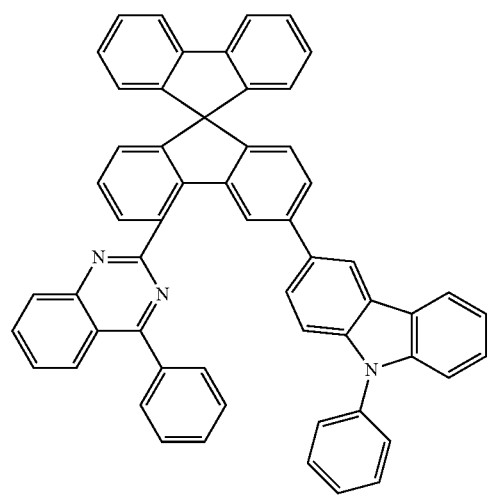 [SMILES: c1ccc(-c2nc(-c3cccc4c3-c3cc(-c5ccc6c(c5)c5ccccc5n6-c5ccccc5)ccc3C43c4ccccc4-c4ccccc43)nc3ccccc23)cc1]

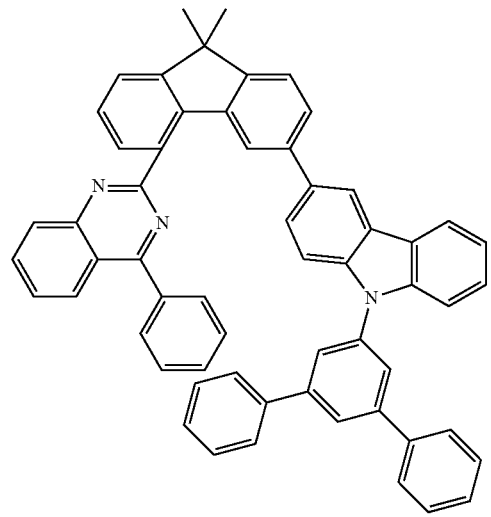 [SMILES: CC1(C)c2ccc(-c3ccc4c(c3)c3ccccc3n4-c3cc(-c4ccccc4)cc(-c4ccccc4)c3)cc2-c2c(-c3nc(-c4ccccc4)c4ccccc4n3)cccc21]
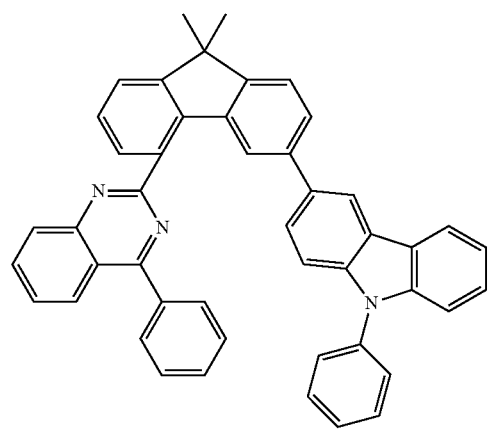 [SMILES: CC1(C)c2ccc(-c3ccc4c(c3)c3ccccc3n4-c3ccccc3)cc2-c2c(-c3nc(-c4ccccc4)c4ccccc4n3)cccc21]
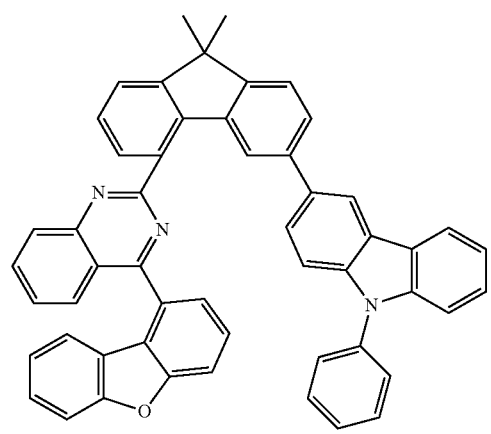 [SMILES: CC1(C)c2ccc(-c3ccc4c(c3)c3ccccc3n4-c3ccccc3)cc2-c2c(-c3nc(-c4cccc5oc6ccccc6c45)c4ccccc4n3)cccc21]

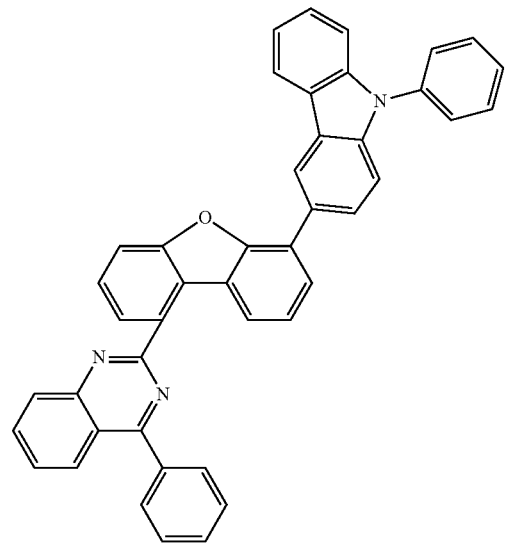 [SMILES: c1ccc(-c2nc(-c3cccc4oc5c(-c6ccc7c(c6)c6ccccc6n7-c6ccccc6)cccc5c34)nc3ccccc23)cc1]
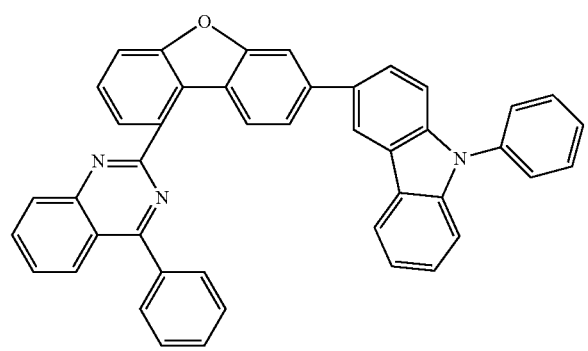 [SMILES: c1ccc(-c2nc(-c3cccc4oc5cc(-c6ccc7c(c6)c6ccccc6n7-c6ccccc6)ccc5c34)nc3ccccc23)cc1]
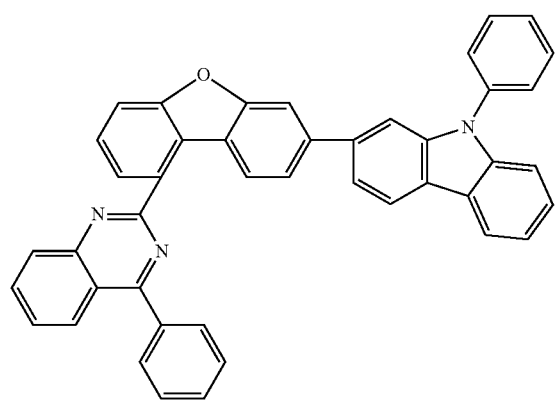 [SMILES: c1ccc(-c2nc(-c3cccc4oc5cc(-c6ccc7c8ccccc8n(-c8ccccc8)c7c6)ccc5c34)nc3ccccc23)cc1]

-continued
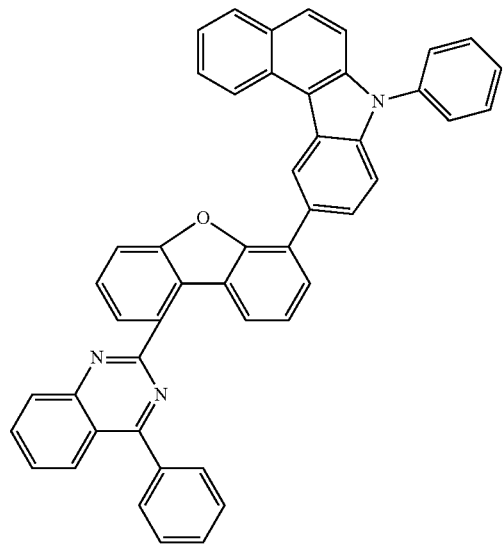 [SMILES: c1ccc(-c2nc(-c3cccc4oc5c(-c6ccc7c(c6)c6c8ccccc8ccc6n7-c6ccccc6)cccc5c34)nc3ccccc23)cc1]
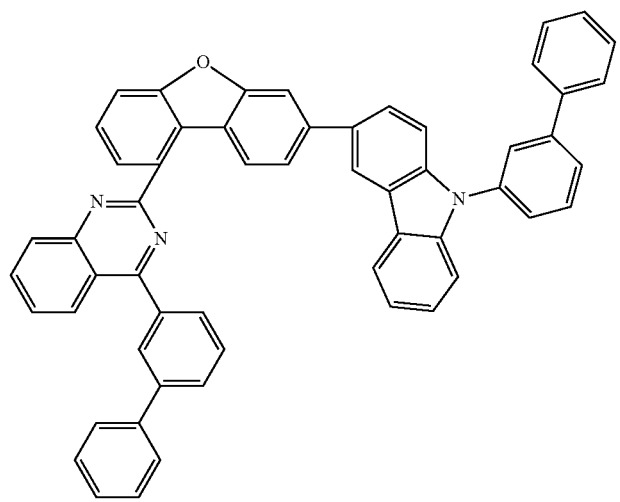 [SMILES: c1ccc(-c2cccc(-c3nc(-c4cccc5oc6cc(-c7ccc8c(c7)c7ccccc7n8-c7cccc(-c8ccccc8)c7)ccc6c45)nc4ccccc34)c2)cc1]
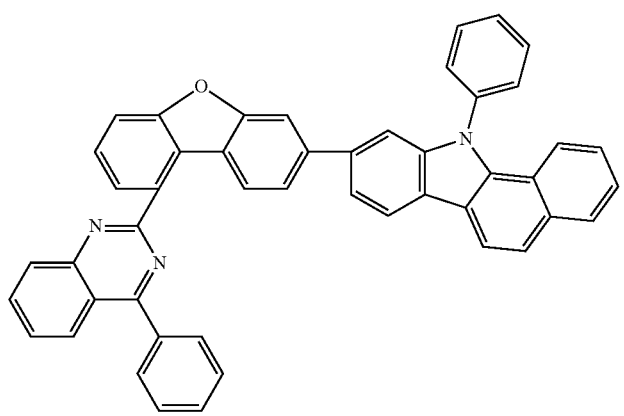 [SMILES: c1ccc(-c2nc(-c3cccc4oc5cc(-c6ccc7c8ccc9ccccc9c8n(-c8ccccc8)c7c6)ccc5c34)nc3ccccc23)cc1]

-continued
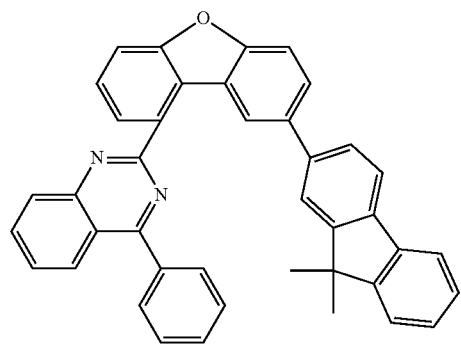 [SMILES: CC1(C)c2ccccc2-c2ccc(-c3ccc4oc5cccc(-c6nc(-c7ccccc7)c7ccccc7n6)c5c4c3)cc21]
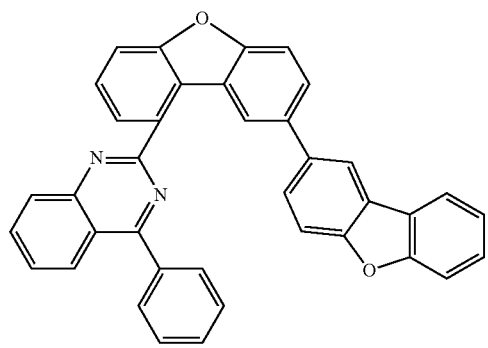 [SMILES: c1ccc(-c2nc(-c3cccc4oc5ccc(-c6ccc7oc8ccccc8c7c6)cc5c34)nc3ccccc23)cc1]
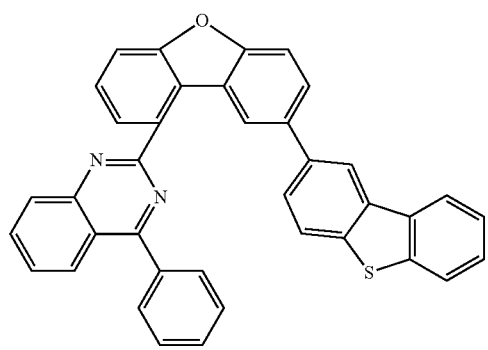
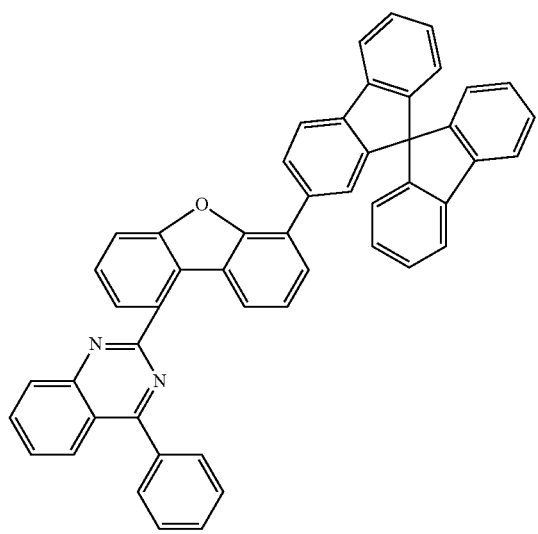 [SMILES: c1ccc(-c2nc(-c3cccc4oc5c(-c6ccc7c(c6)C6(c8ccccc8-c8ccccc86)c6ccccc6-7)cccc5c34)nc3ccccc23)cc1]

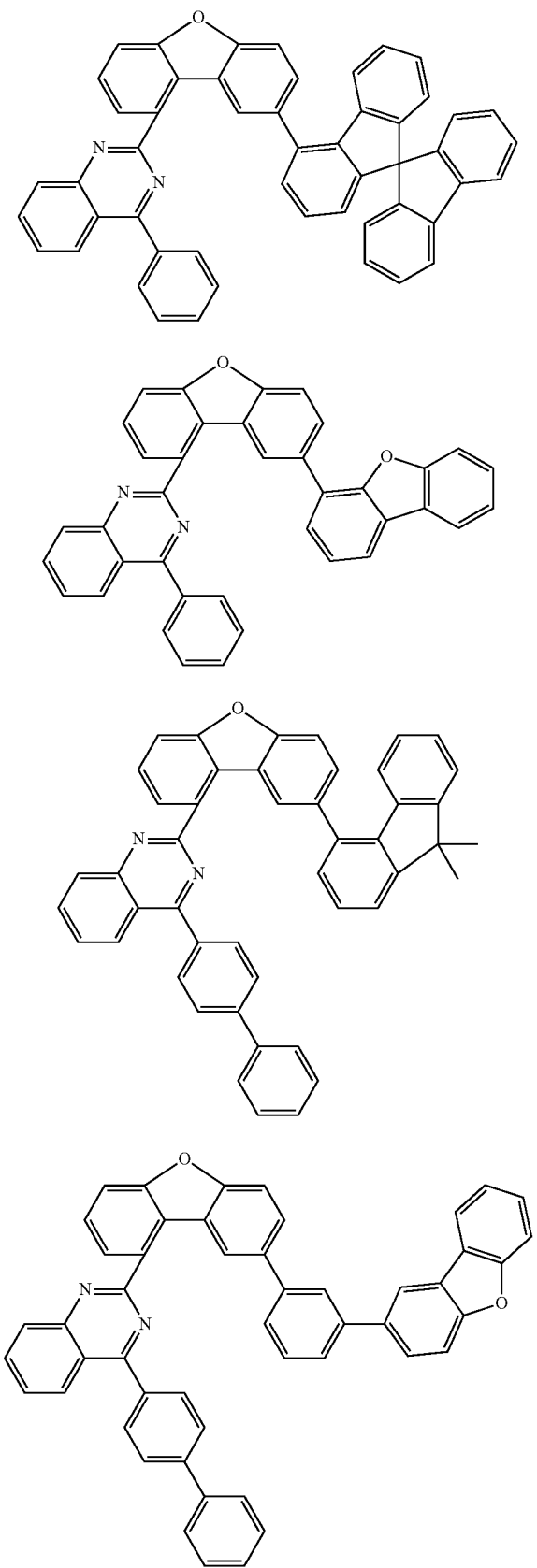

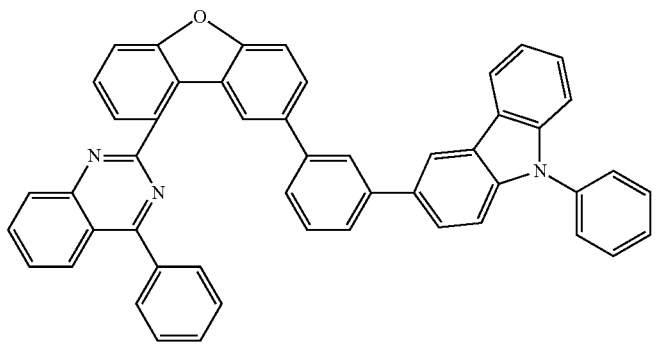 [SMILES: c1ccc(-c2nc(-c3cccc4oc5ccc(-c6cccc(-c7ccc8c(c7)c7ccccc7n8-c7ccccc7)c6)cc5c34)nc3ccccc23)cc1]
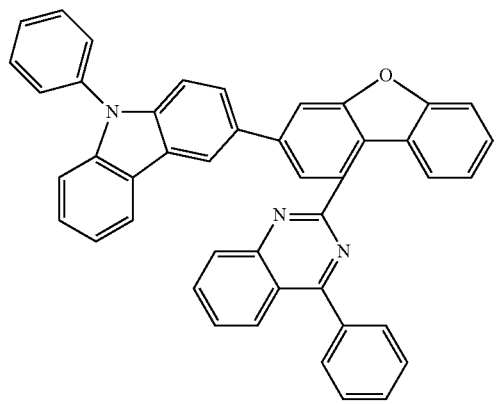 [SMILES: c1ccc(-c2nc(-c3cc(-c4ccc5c(c4)c4ccccc4n5-c4ccccc4)cc4oc5ccccc5c34)nc3ccccc23)cc1]
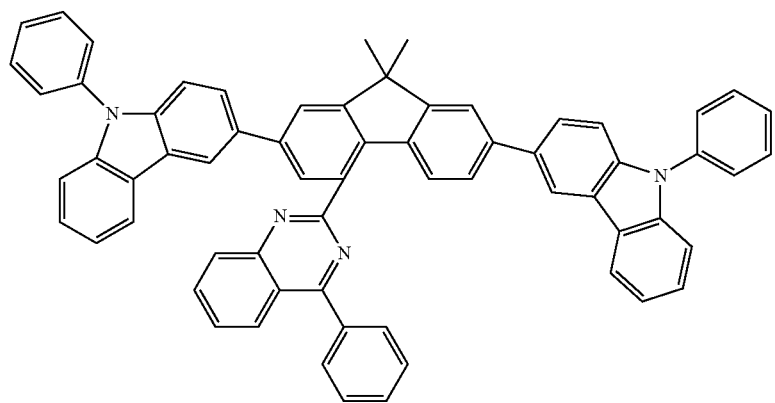 [SMILES: CC1(C)c2cc(-c3ccc4c(c3)c3ccccc3n4-c3ccccc3)ccc2-c2c(-c3nc(-c4ccccc4)c4ccccc4n3)cc(-c3ccc4c(c3)c3ccccc3n4-c3ccccc3)cc21]
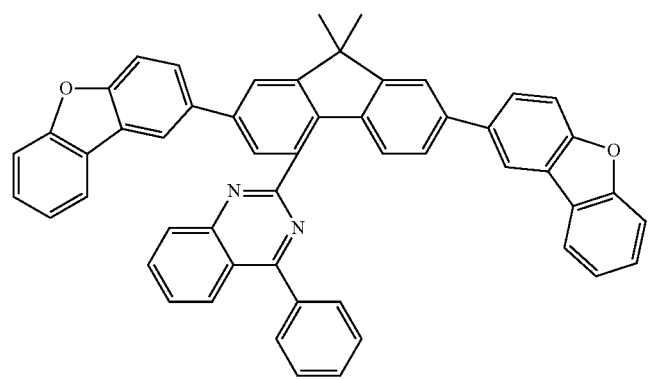 [SMILES: CC1(C)c2cc(-c3ccc4oc5ccccc5c4c3)ccc2-c2c(-c3nc(-c4ccccc4)c4ccccc4n3)cc(-c3ccc4oc5ccccc5c4c3)cc21]

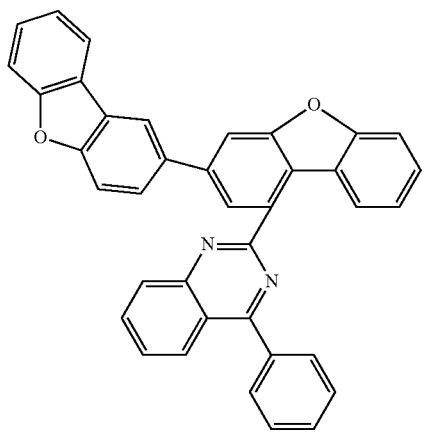
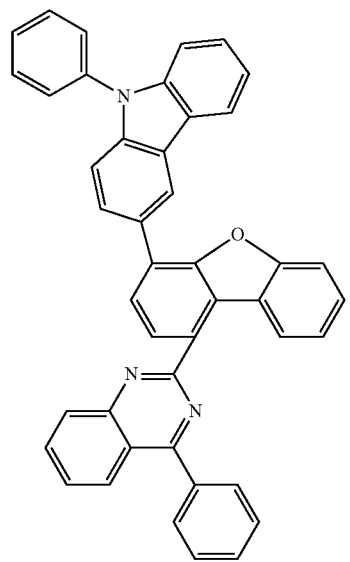 [SMILES: c1ccc(-c2nc(-c3ccc(-c4ccc5c(c4)c4ccccc4n5-c4ccccc4)c4oc5ccccc5c34)nc3ccccc23)cc1]
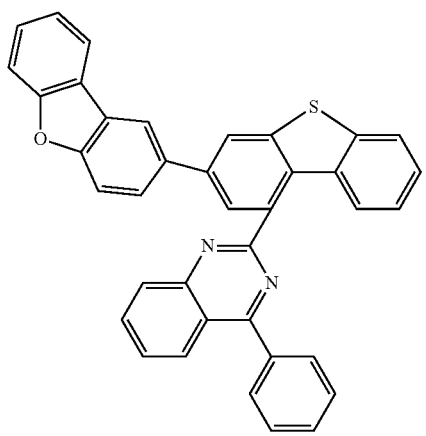 [SMILES: c1ccc(-c2nc(-c3cc(-c4ccc5oc6ccccc6c5c4)cc4sc5ccccc5c34)nc3ccccc23)cc1]

-continued
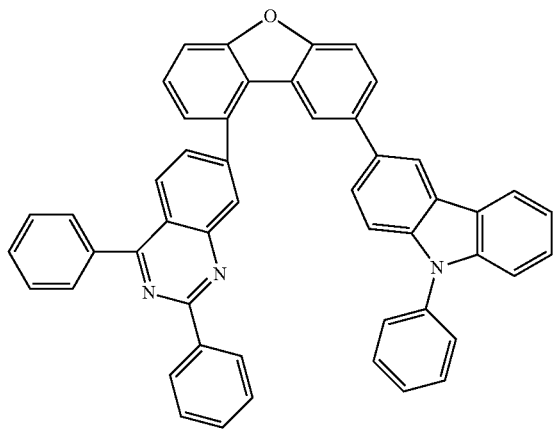 [SMILES: c1ccc(-c2nc(-c3ccccc3)c3ccc(-c4cccc5oc6ccc(-c7ccc8c(c7)c7ccccc7n8-c7ccccc7)cc6c45)cc3n2)cc1]
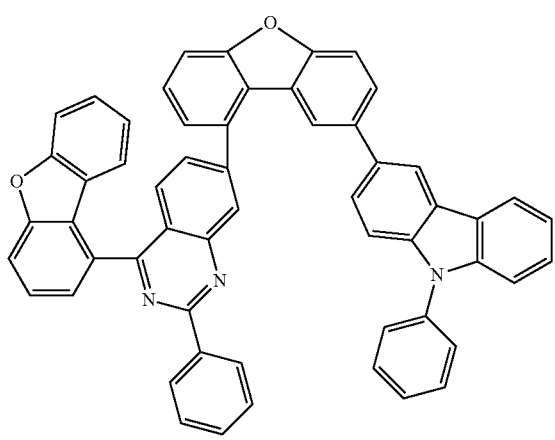 [SMILES: c1ccc(-c2nc(-c3cccc4oc5ccccc5c34)c3ccc(-c4cccc5oc6ccc(-c7ccc8c(c7)c7ccccc7n8-c7ccccc7)cc6c45)cc3n2)cc1]
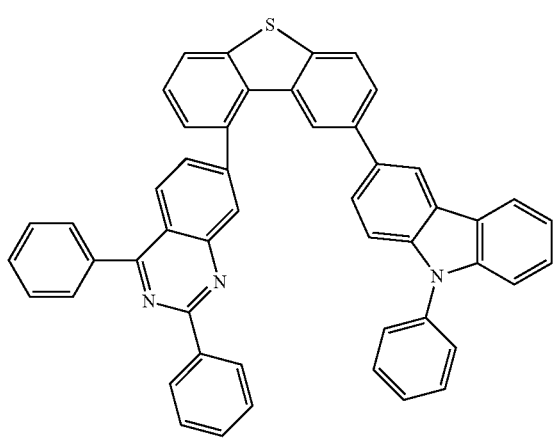

-continued
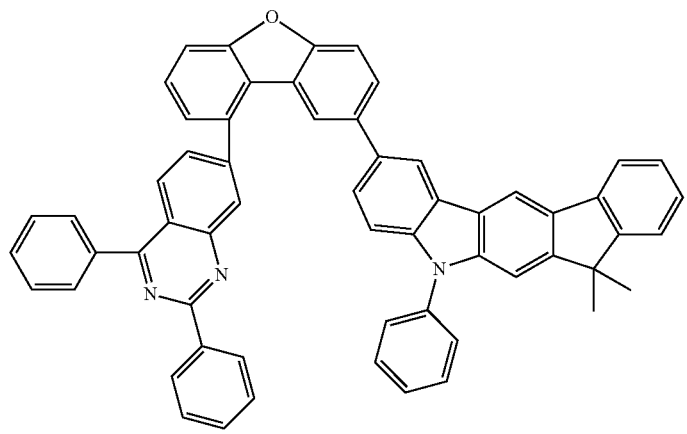 [SMILES: CC1(C)c2ccccc2-c2cc3c4cc(-c5ccc6oc7cccc(-c8ccc9c(-c%10ccccc%10)nc(-c%10ccccc%10)nc9c8)c7c6c5)ccc4n(-c4ccccc4)c3cc21]
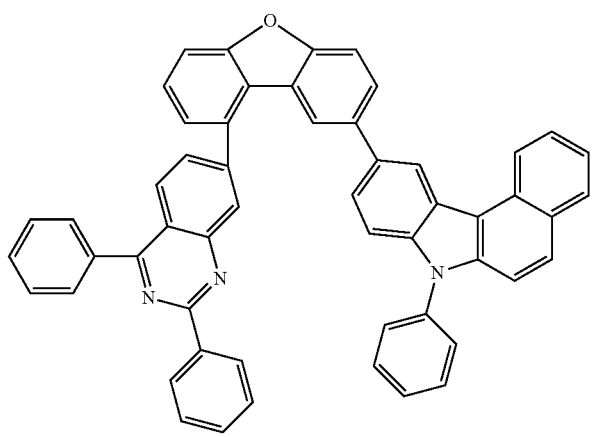 [SMILES: c1ccc(-c2nc(-c3ccccc3)c3ccc(-c4cccc5oc6ccc(-c7ccc8c(c7)c7c9ccccc9ccc7n8-c7ccccc7)cc6c45)cc3n2)cc1]
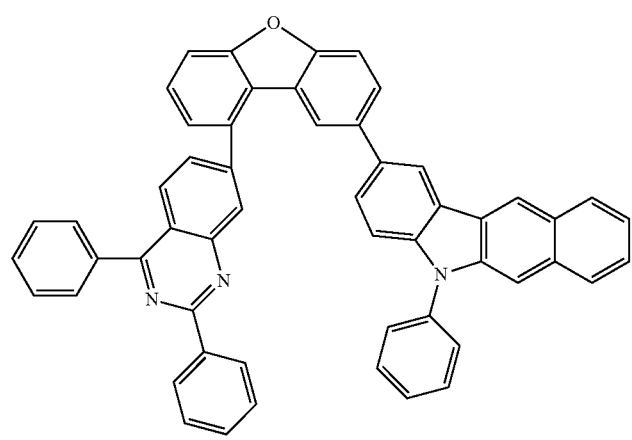 [SMILES: c1ccc(-c2nc(-c3ccccc3)c3ccc(-c4cccc5oc6ccc(-c7ccc8c(c7)c7cc9ccccc9cc7n8-c7ccccc7)cc6c45)cc3n2)cc1]

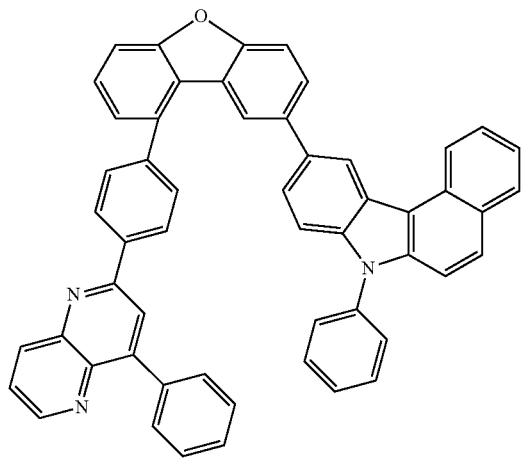 [SMILES: c1ccc(-c2cc(-c3ccc(-c4cccc5oc6ccc(-c7ccc8c(c7)c7c9ccccc9ccc7n8-c7ccccc7)cc6c45)cc3)nc3cccnc23)cc1]
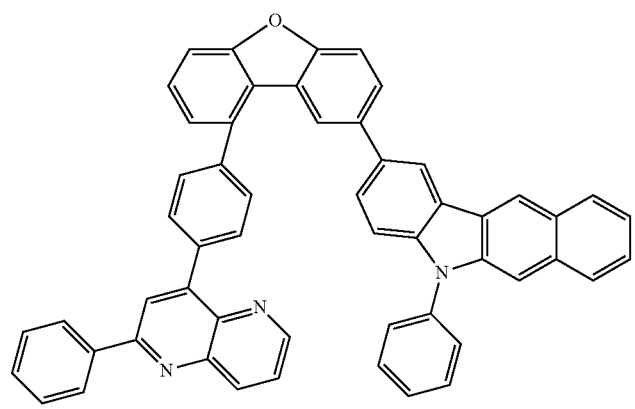 [SMILES: c1ccc(-c2cc(-c3ccc(-c4cccc5oc6ccc(-c7ccc8c(c7)c7cc9ccccc9cc7n8-c7ccccc7)cc6c45)cc3)c3ncccc3n2)cc1]
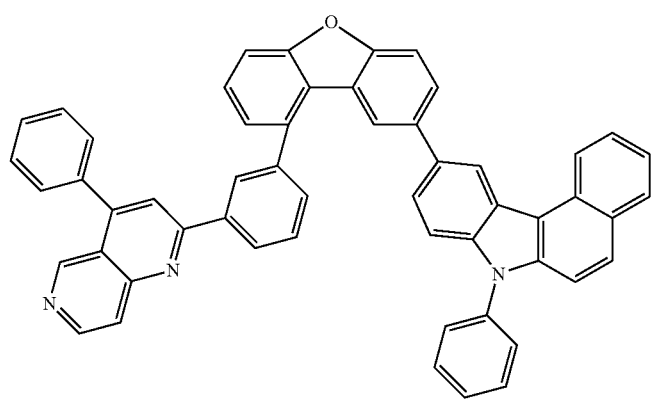 [SMILES: c1ccc(-c2cc(-c3cccc(-c4cccc5oc6ccc(-c7ccc8c(c7)c7c9ccccc9ccc7n8-c7ccccc7)cc6c45)c3)nc3ccncc23)cc1]

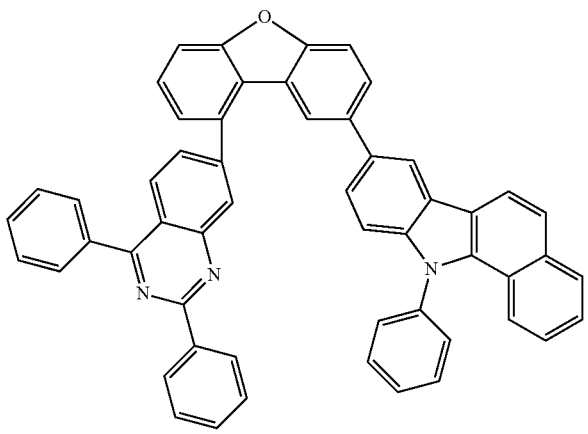 [SMILES: c1ccc(-c2nc(-c3ccccc3)c3ccc(-c4cccc5oc6ccc(-c7ccc8c(c7)c7ccc9ccccc9c7n8-c7ccccc7)cc6c45)cc3n2)cc1]
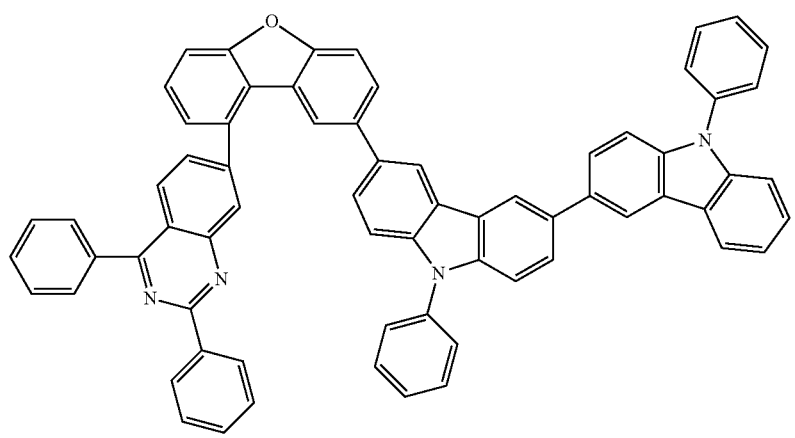 [SMILES: c1ccc(-c2nc(-c3ccccc3)c3ccc(-c4cccc5oc6ccc(-c7ccc8c(c7)c7cc(-c9ccc%10c(c9)c9ccccc9n%10-c9ccccc9)ccc7n8-c7ccccc7)cc6c45)cc3n2)cc1]
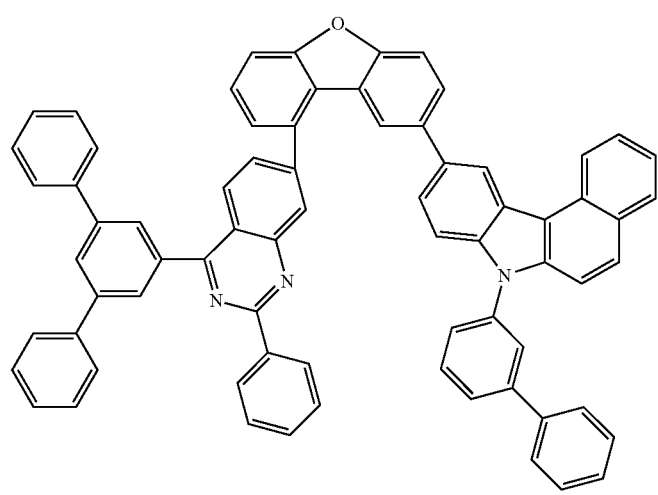 [SMILES: c1ccc(-c2cc(-c3ccccc3)cc(-c3nc(-c4ccccc4)nc4cc(-c5cccc6oc7ccc(-c8ccc9c(c8)c8c%10ccccc%10ccc8n9-c8cccc(-c9ccccc9)c8)cc7c56)ccc34)c2)cc1]

-continued
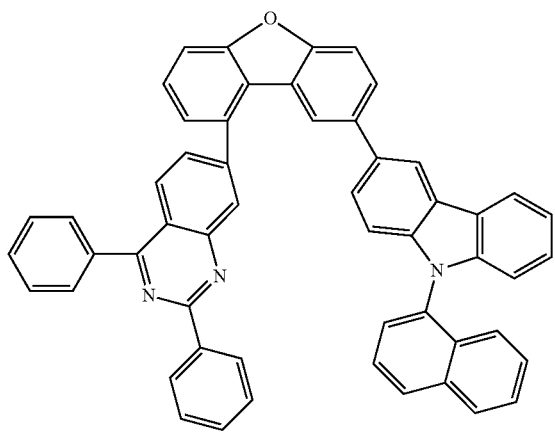 [SMILES: c1ccc(-c2nc(-c3ccccc3)c3ccc(-c4cccc5oc6ccc(-c7ccc8c(c7)c7ccccc7n8-c7cccc8ccccc78)cc6c45)cc3n2)cc1]
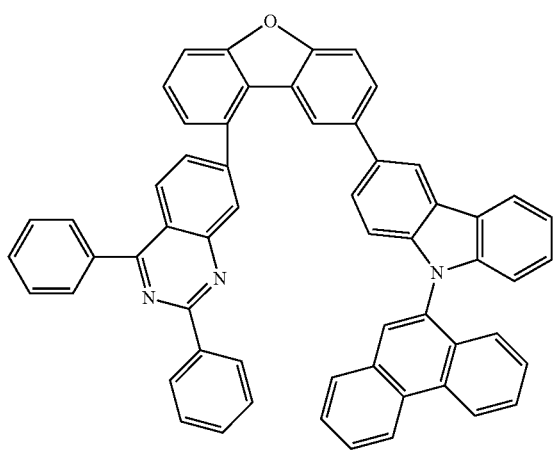 [SMILES: c1ccc(-c2nc(-c3ccccc3)c3ccc(-c4cccc5oc6ccc(-c7ccc8c(c7)c7ccccc7n8-c7cc8ccccc8c8ccccc78)cc6c45)cc3n2)cc1]
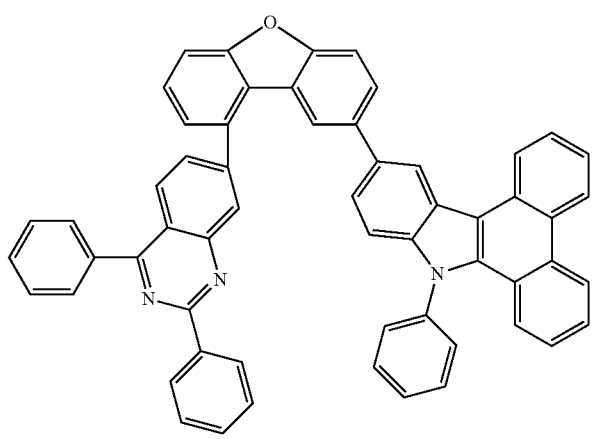 [SMILES: c1ccc(-c2nc(-c3ccccc3)c3ccc(-c4cccc5oc6ccc(-c7ccc8c(c7)c7c9ccccc9c9ccccc9c7n8-c7ccccc7)cc6c45)cc3n2)cc1]

131
-continued
132
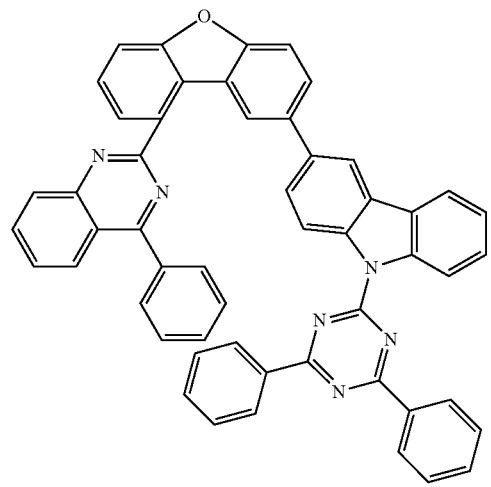
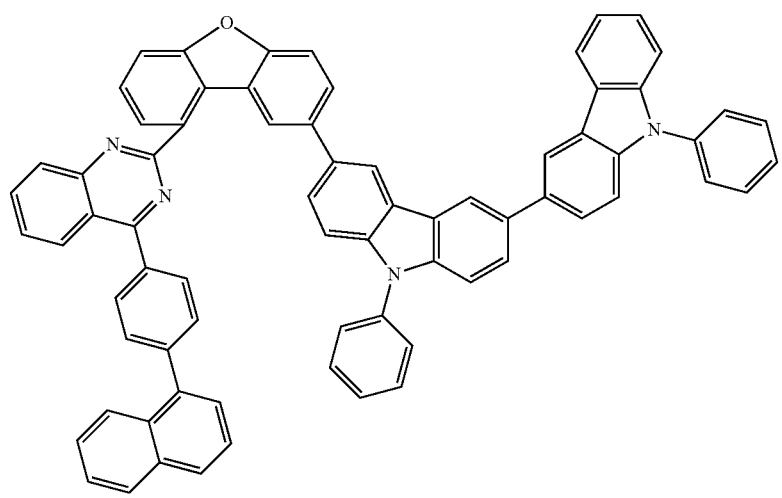 [SMILES: c1ccc(-n2c3ccccc3c3cc(-c4ccc5c(c4)c4cc(-c6ccc7oc8cccc(-c9nc(-c%10ccc(-c%11cccc%12ccccc%11%12)cc%10)c%10ccccc%10n9)c8c7c6)ccc4n5-c4ccccc4)ccc32)cc1]
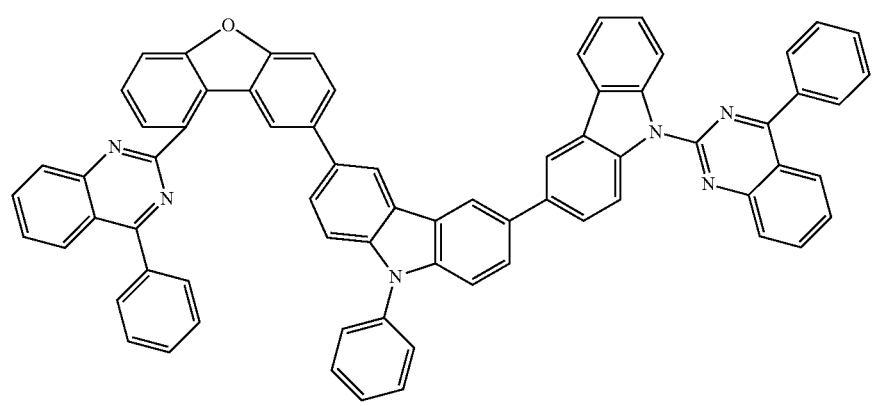 [SMILES: c1ccc(-c2nc(-c3cccc4oc5ccc(-c6ccc7c(c6)c6cc(-c8ccc9c(c8)c8ccccc8n9-c8nc(-c9ccccc9)c9ccccc9n8)ccc6n7-c6ccccc6)cc5c34)nc3ccccc23)cc1]

-continued
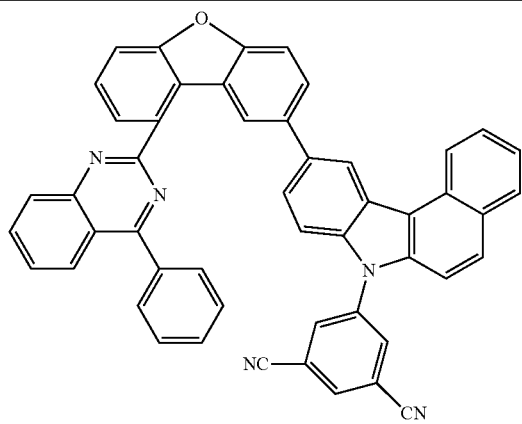
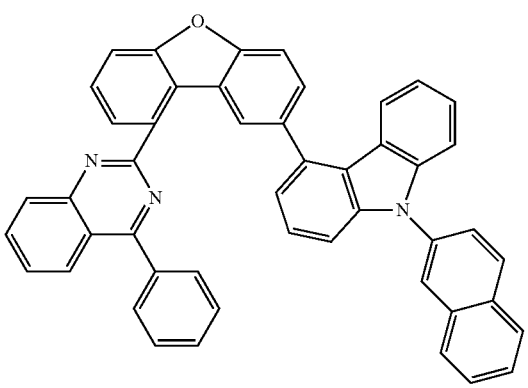 [SMILES: c1ccc(-c2nc(-c3cccc4oc5ccc(-c6cccc7c6c6ccccc6n7-c6ccc7ccccc7c6)cc5c34)nc3ccccc23)cc1]
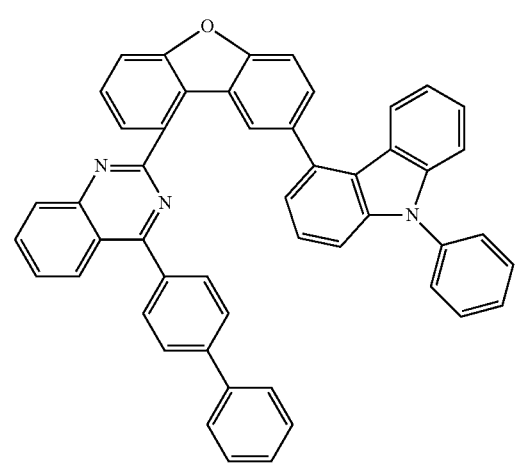 [SMILES: c1ccc(-c2ccc(-c3nc(-c4cccc5oc6ccc(-c7cccc8c7c7ccccc7n8-c7ccccc7)cc6c45)nc4ccccc34)cc2)cc1]
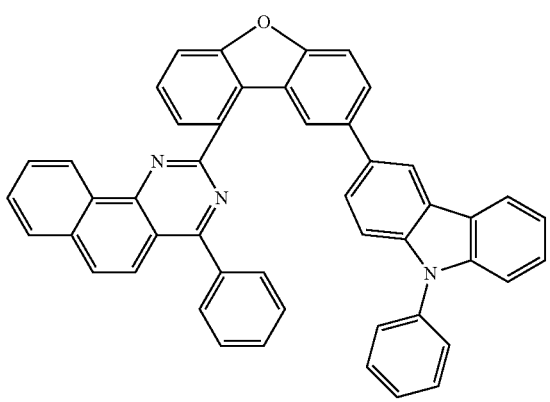

-continued
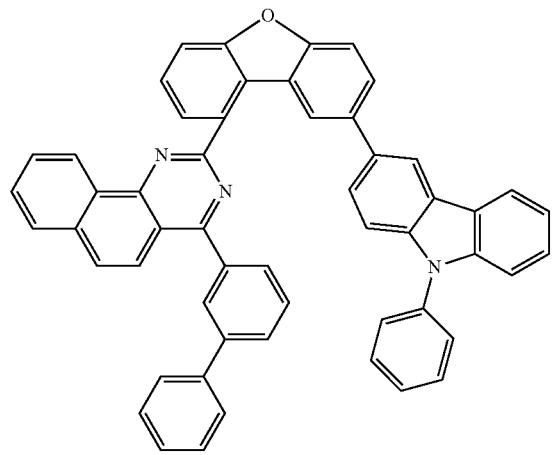 [SMILES: c1ccc(-c2cccc(-c3nc(-c4cccc5oc6ccc(-c7ccc8c(c7)c7ccccc7n8-c7ccccc7)cc6c45)nc4c3ccc3ccccc34)c2)cc1]
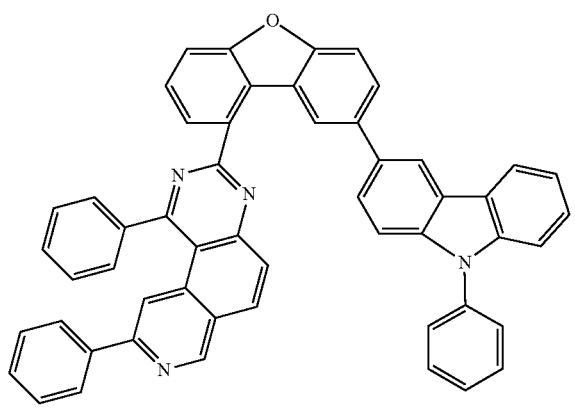 [SMILES: c1ccc(-c2cc3c(ccc4nc(-c5cccc6oc7ccc(-c8ccc9c(c8)c8ccccc8n9-c8ccccc8)cc7c56)nc(-c5ccccc5)c43)cn2)cc1]
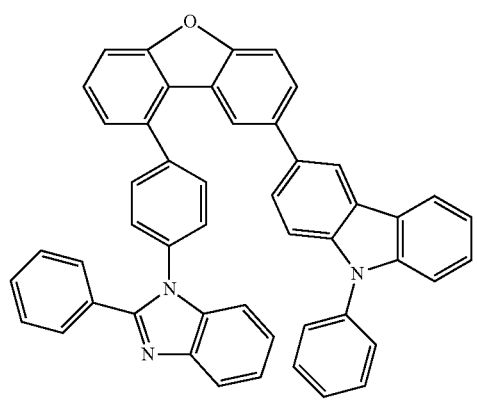 [SMILES: c1ccc(-c2nc3ccccc3n2-c2ccc(-c3cccc4oc5ccc(-c6ccc7c(c6)c6ccccc6n7-c6ccccc6)cc5c34)cc2)cc1]

-continued
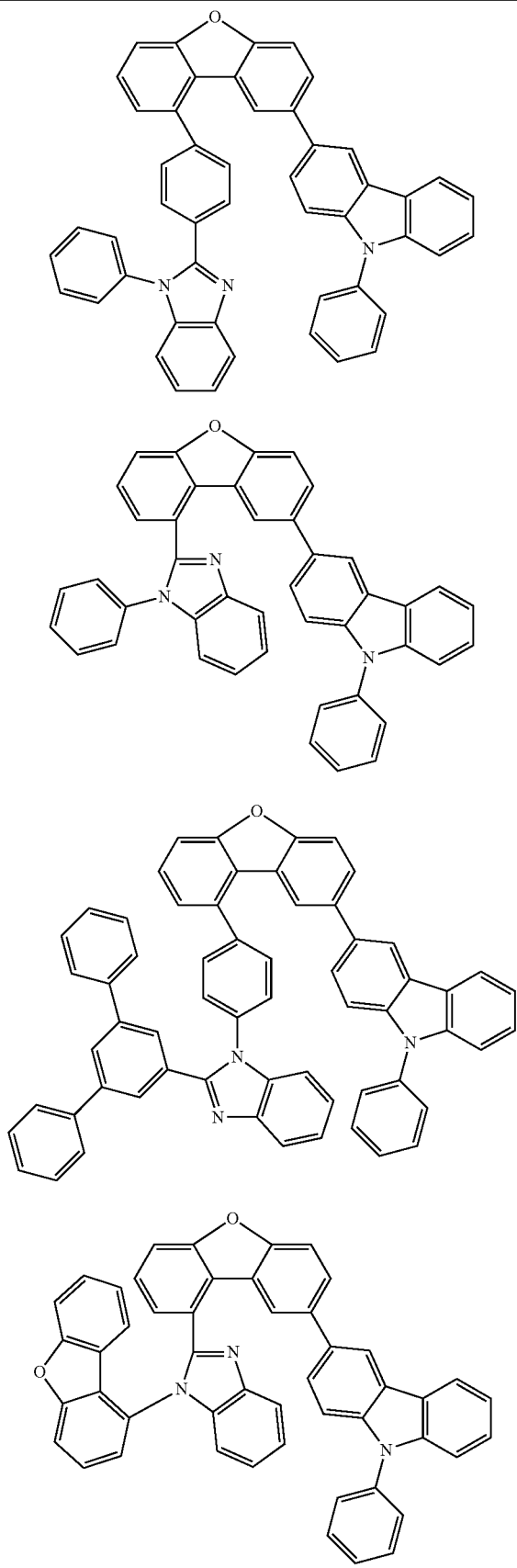

-continued
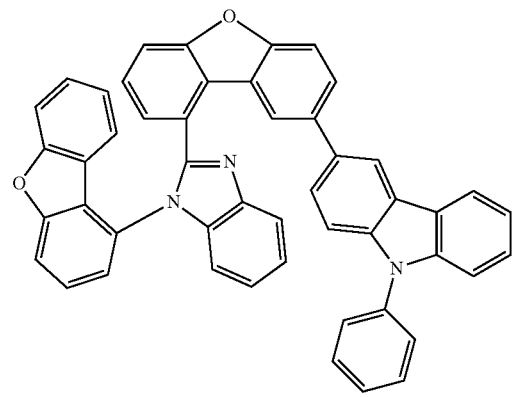 [SMILES: c1ccc(-n2c3ccccc3c3cc(-c4ccc5oc6cccc(-c7nc8ccccc8n7-c7cccc8oc9ccccc9c78)c6c5c4)ccc32)cc1]
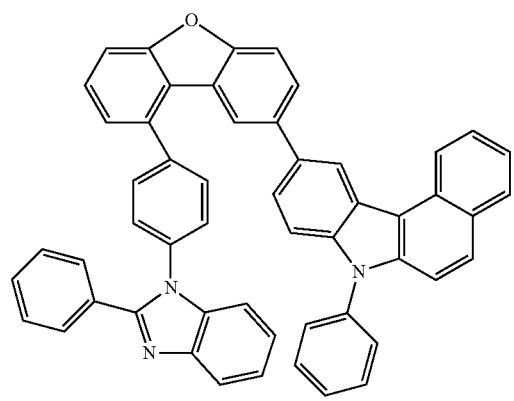 [SMILES: c1ccc(-c2nc3ccccc3n2-c2ccc(-c3cccc4oc5ccc(-c6ccc7c(c6)c6c8ccccc8ccc6n7-c6ccccc6)cc5c34)cc2)cc1]
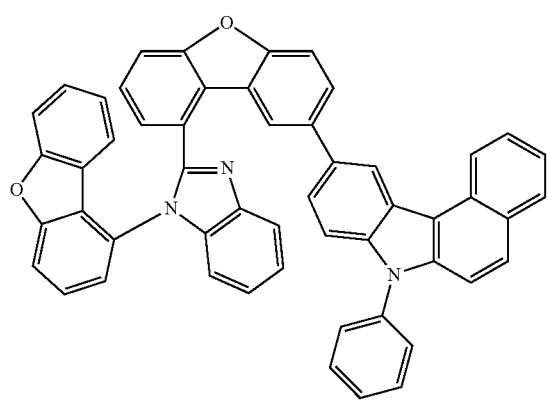 [SMILES: c1ccc(-n2c3ccc(-c4ccc5oc6cccc(-c7nc8ccccc8n7-c7cccc8oc9ccccc9c78)c6c5c4)cc3c3c4ccccc4ccc32)cc1]
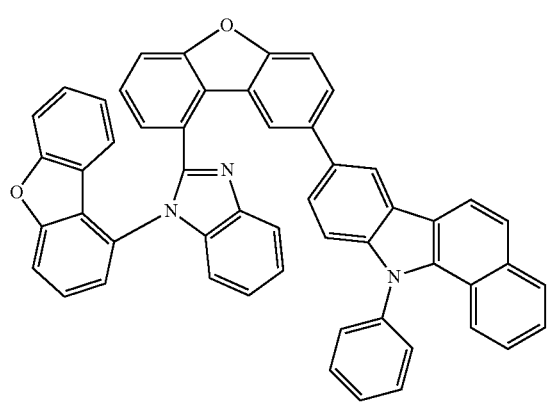 [SMILES: c1ccc(-n2c3ccc(-c4ccc5oc6cccc(-c7nc8ccccc8n7-c7cccc8oc9ccccc9c78)c6c5c4)cc3c3ccc4ccccc4c32)cc1]

-continued
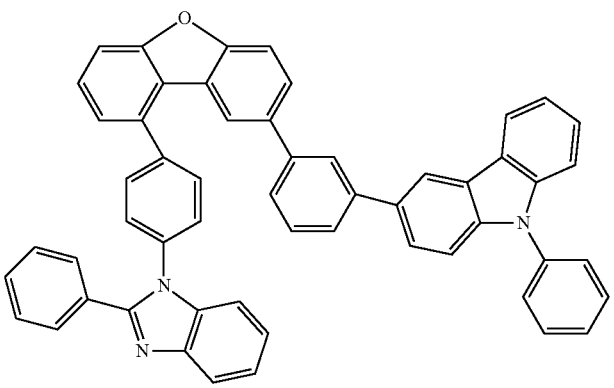 [SMILES: c1ccc(-c2nc3ccccc3n2-c2ccc(-c3cccc4oc5ccc(-c6cccc(-c7ccc8c(c7)c7ccccc7n8-c7ccccc7)c6)cc5c34)cc2)cc1]
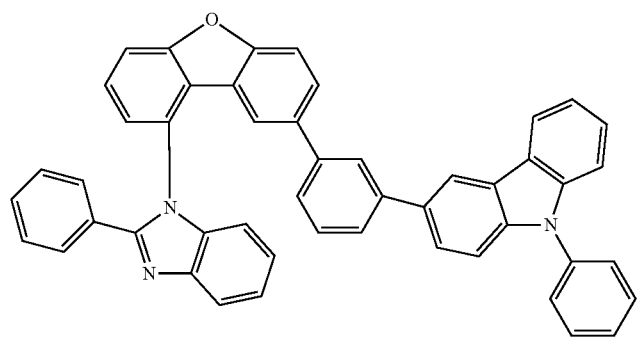 [SMILES: c1ccc(-c2nc3ccccc3n2-c2cccc3oc4ccc(-c5cccc(-c6ccc7c(c6)c6ccccc6n7-c6ccccc6)c5)cc4c23)cc1]
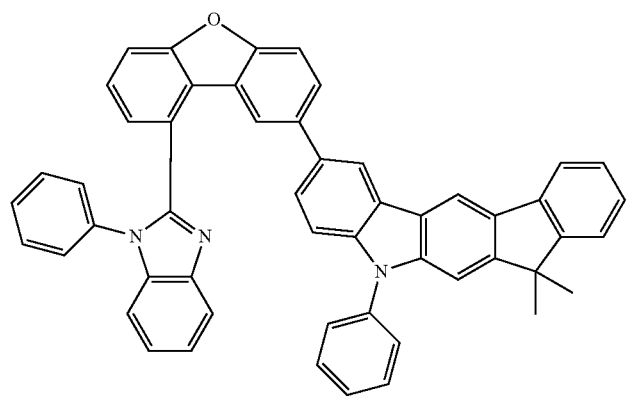 [SMILES: CC1(C)c2ccccc2-c2cc3c4cc(-c5ccc6oc7cccc(-c8nc9ccccc9n8-c8ccccc8)c7c6c5)ccc4n(-c4ccccc4)c3cc21]
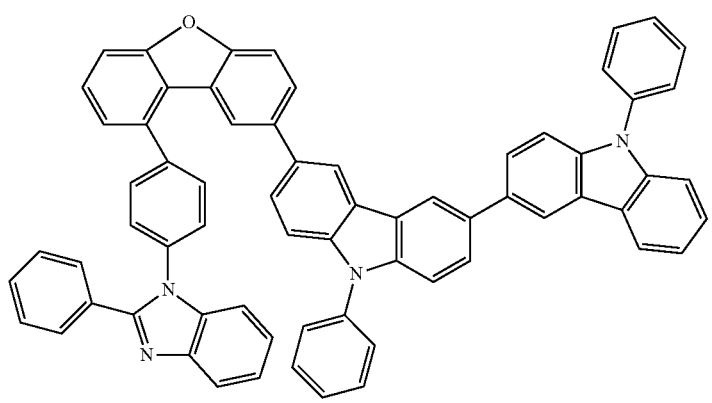 [SMILES: c1ccc(-c2nc3ccccc3n2-c2ccc(-c3cccc4oc5ccc(-c6ccc7c(c6)c6cc(-c8ccc9c(c8)c8ccccc8n9-c8ccccc8)ccc6n7-c6ccccc6)cc5c34)cc2)cc1]

-continued
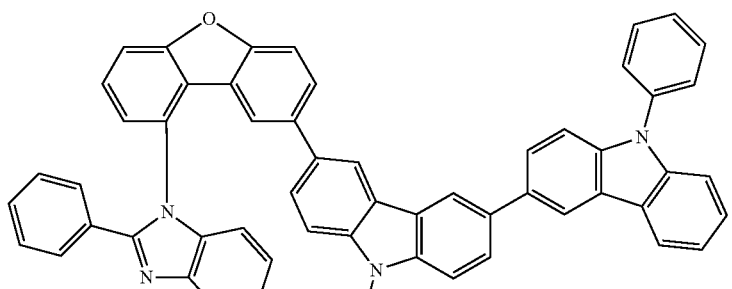
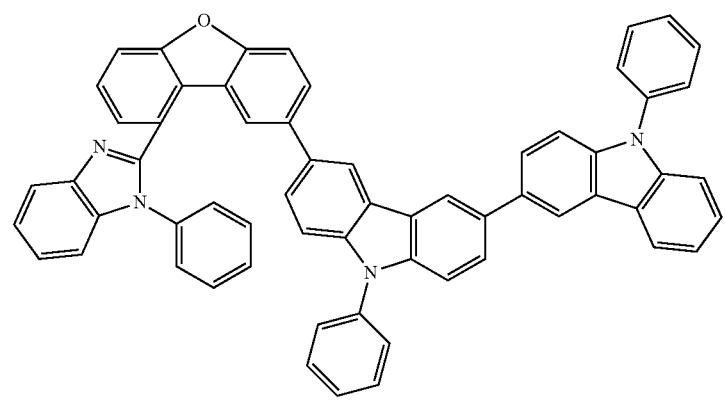 [SMILES: c1ccc(-n2c(-c3cccc4oc5ccc(-c6ccc7c(c6)c6cc(-c8ccc9c(c8)c8ccccc8n9-c8ccccc8)ccc6n7-c6ccccc6)cc5c34)nc3ccccc32)cc1]
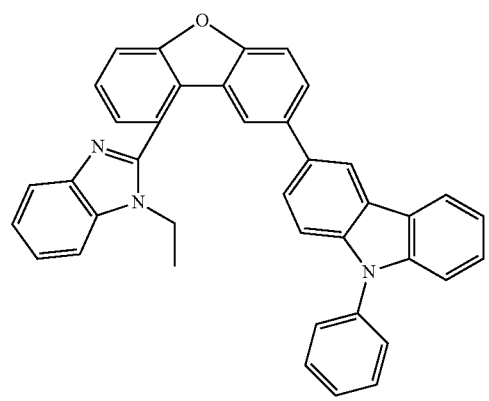 [SMILES: CCn1c(-c2cccc3oc4ccc(-c5ccc6c(c5)c5ccccc5n6-c5ccccc5)cc4c23)nc2ccccc21]
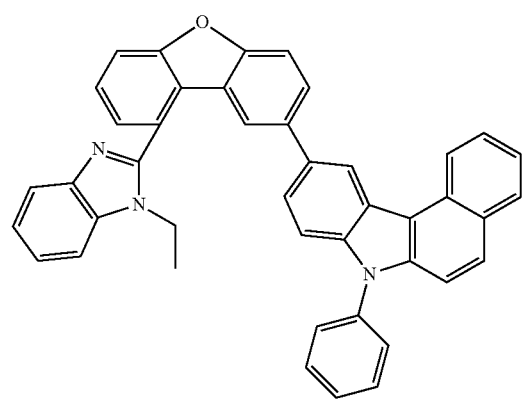

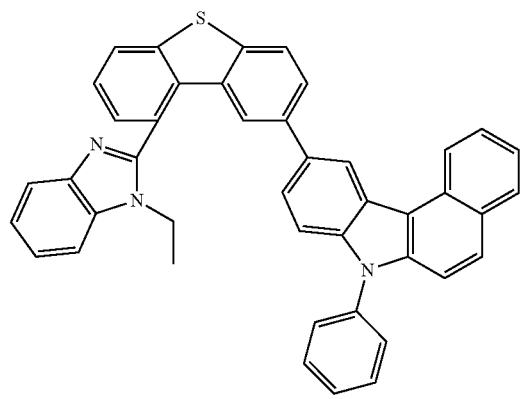 [SMILES: CCn1c(-c2cccc3sc4ccc(-c5ccc6c(c5)c5c7ccccc7ccc5n6-c5ccccc5)cc4c23)nc2ccccc21]
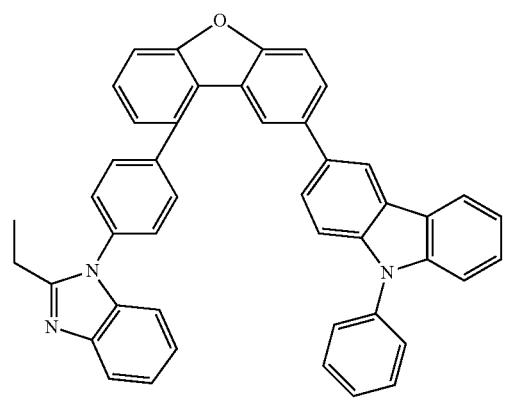 [SMILES: CCc1nc2ccccc2n1-c1ccc(-c2cccc3sc4ccc(-c5ccc6c(c5)c5ccccc5n6-c5ccccc5)cc4c23)cc1]
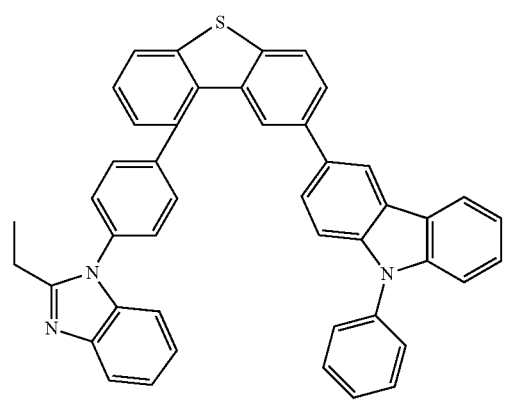
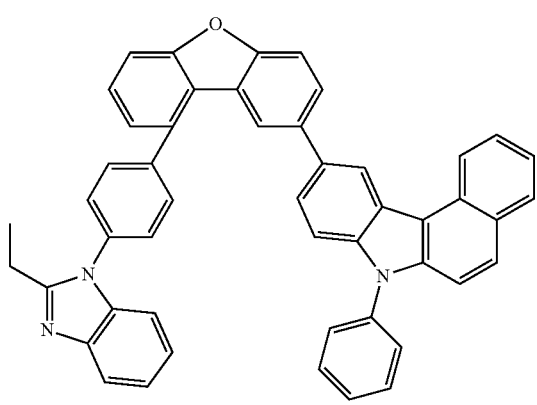 [SMILES: CCc1nc2ccccc2n1-c1ccc(-c2cccc3oc4ccc(-c5ccc6c(c5)c5c7ccccc7ccc5n6-c5ccccc5)cc4c23)cc1]

-continued
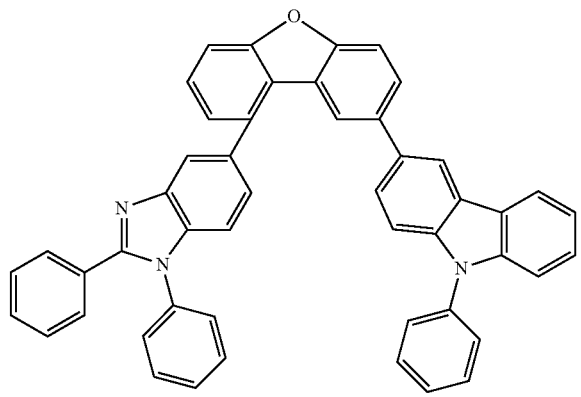 [SMILES: c1ccc(-c2nc3cc(-c4cccc5oc6ccc(-c7ccc8c(c7)c7ccccc7n8-c7ccccc7)cc6c45)ccc3n2-c2ccccc2)cc1]
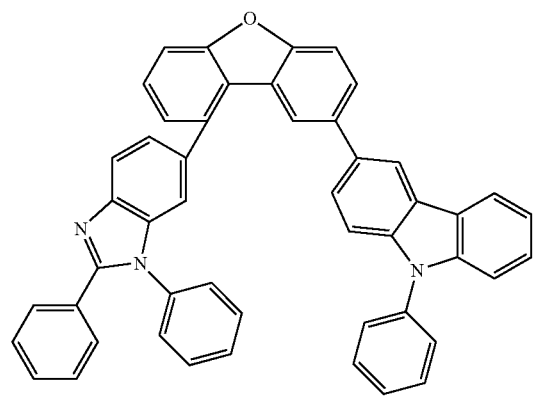 [SMILES: c1ccc(-c2nc3ccc(-c4cccc5oc6ccc(-c7ccc8c(c7)c7ccccc7n8-c7ccccc7)cc6c45)cc3n2-c2ccccc2)cc1]
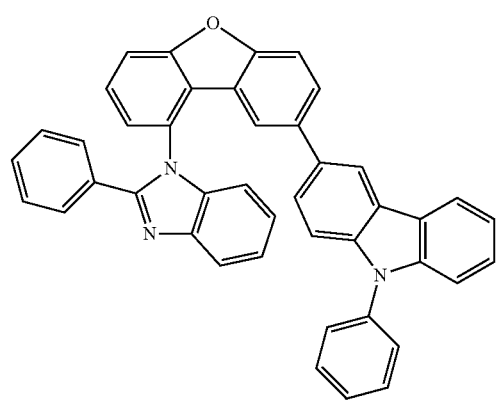 [SMILES: c1ccc(-c2nc3ccccc3n2-c2cccc3oc4ccc(-c5ccc6c(c5)c5ccccc5n6-c5ccccc5)cc4c23)cc1]
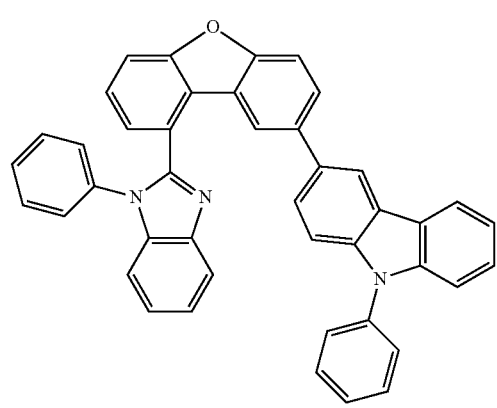 [SMILES: c1ccc(-n2c(-c3cccc4oc5ccc(-c6ccc7c(c6)c6ccccc6n7-c6ccccc6)cc5c34)nc3ccccc32)cc1]

-continued
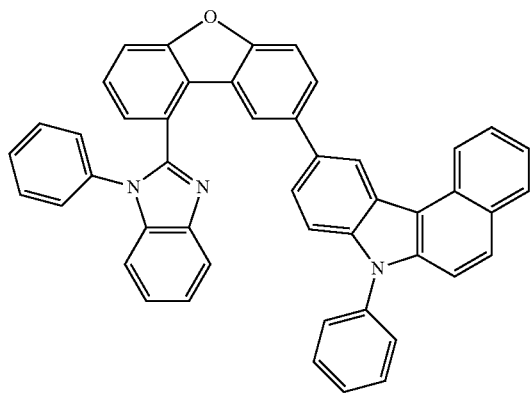 [SMILES: c1ccc(-n2c(-c3cccc4oc5ccc(-c6ccc7c(c6)c6c8ccccc8ccc6n7-c6ccccc6)cc5c34)nc3ccccc32)cc1]
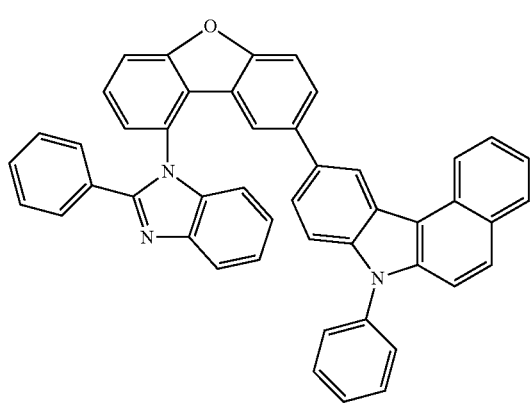 [SMILES: c1ccc(-c2nc3ccccc3n2-c2cccc3oc4ccc(-c5ccc6c(c5)c5c7ccccc7ccc5n6-c5ccccc5)cc4c23)cc1]
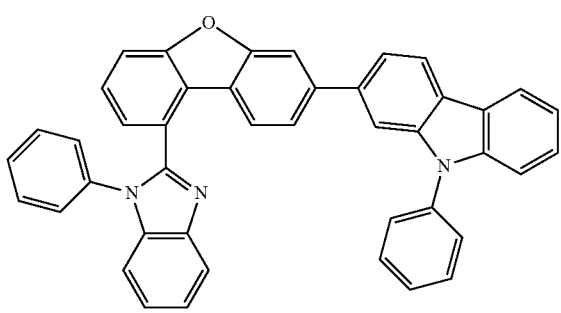 [SMILES: c1ccc(-n2c(-c3cccc4oc5cc(-c6ccc7c8ccccc8n(-c8ccccc8)c7c6)ccc5c34)nc3ccccc32)cc1]
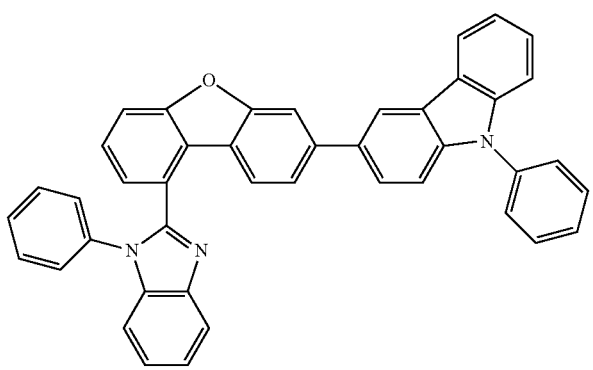 [SMILES: c1ccc(-n2c(-c3cccc4oc5cc(-c6ccc7c(c6)c6ccccc6n7-c6ccccc6)ccc5c34)nc3ccccc32)cc1]

-continued
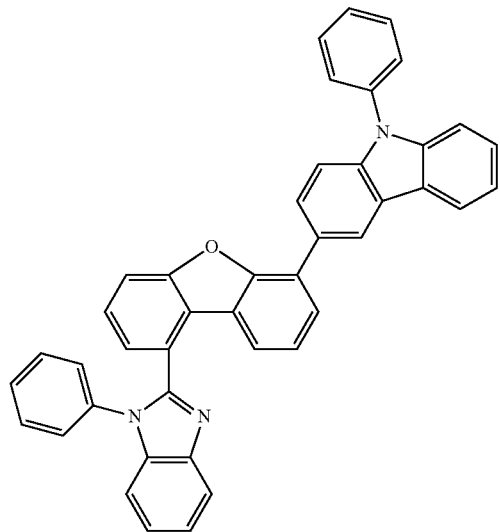 [SMILES: c1ccc(-n2c(-c3cccc4oc5c(-c6ccc7c(c6)c6ccccc6n7-c6ccccc6)cccc5c34)nc3ccccc32)cc1]
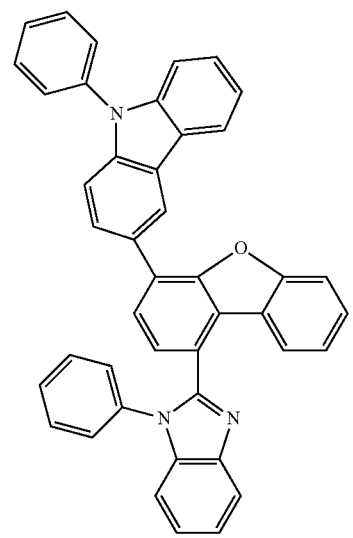 [SMILES: c1ccc(-n2c(-c3ccc(-c4ccc5c(c4)c4ccccc4n5-c4ccccc4)c4oc5ccccc5c34)nc3ccccc32)cc1]
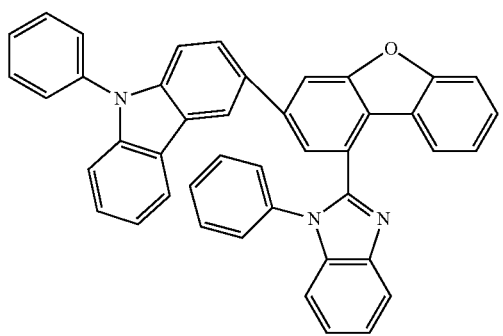 [SMILES: c1ccc(-n2c(-c3cc(-c4ccc5c(c4)c4ccccc4n5-c4ccccc4)cc4oc5ccccc5c34)nc3ccccc32)cc1]

-continued
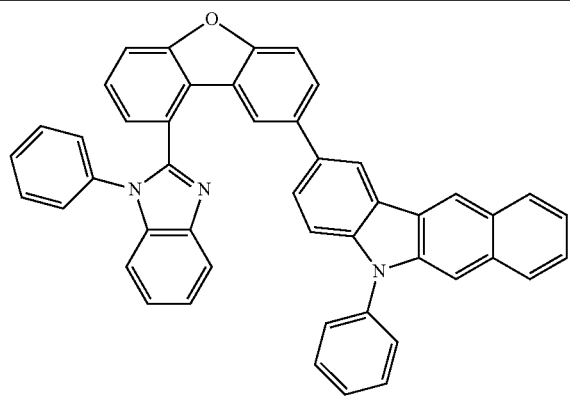
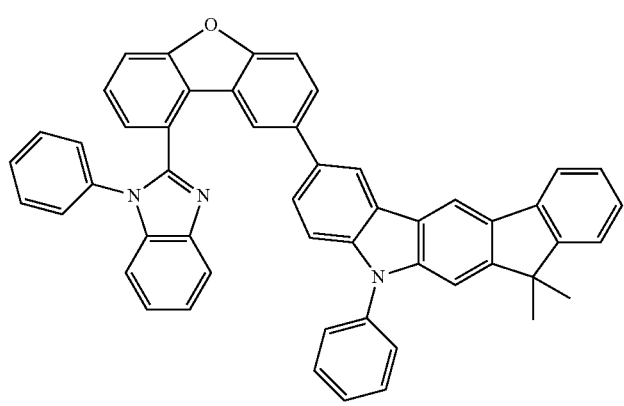 [SMILES: CC1(C)c2ccccc2-c2cc3c4cc(-c5ccc6oc7cccc(-c8nc9ccccc9n8-c8ccccc8)c7c6c5)ccc4n(-c4ccccc4)c3cc21]
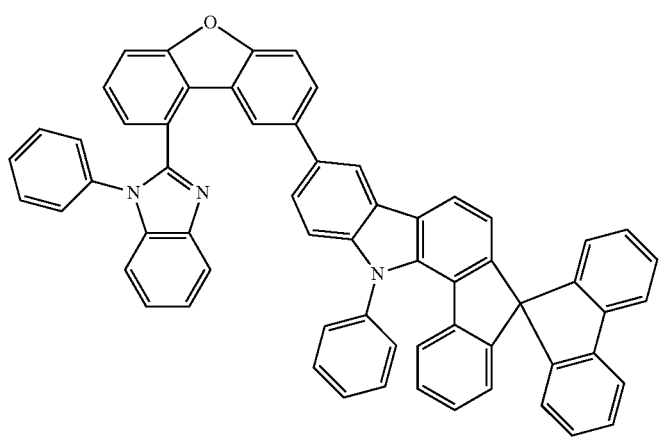 [SMILES: c1ccc(-n2c(-c3cccc4oc5ccc(-c6ccc7c(c6)c6ccc8c(c6n7-c6ccccc6)-c6ccccc6C86c7ccccc7-c7ccccc76)cc5c34)nc3ccccc32)cc1]
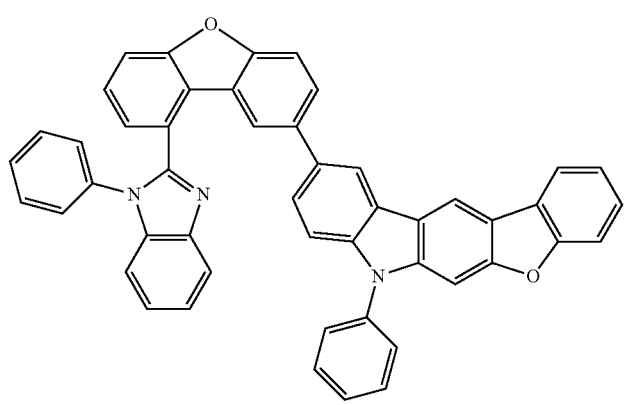 [SMILES: c1ccc(-n2c(-c3cccc4oc5ccc(-c6ccc7c(c6)c6cc8c(cc6n7-c6ccccc6)oc6ccccc68)cc5c34)nc3ccccc32)cc1]

-continued
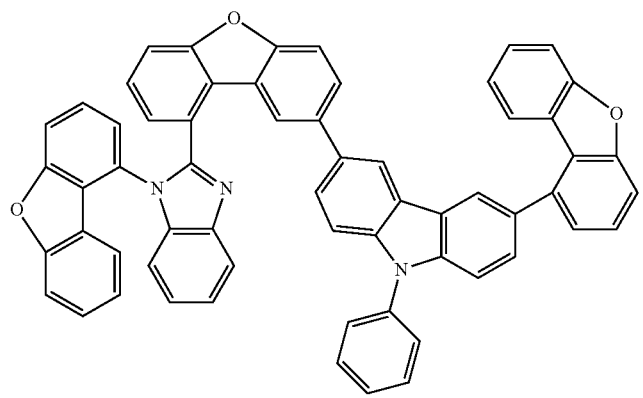 [SMILES: c1ccc(-n2c3ccc(-c4ccc5oc6cccc(-c7nc8ccccc8n7-c7cccc8oc9ccccc9c78)c6c5c4)cc3c3cc(-c4cccc5oc6ccccc6c45)ccc32)cc1]
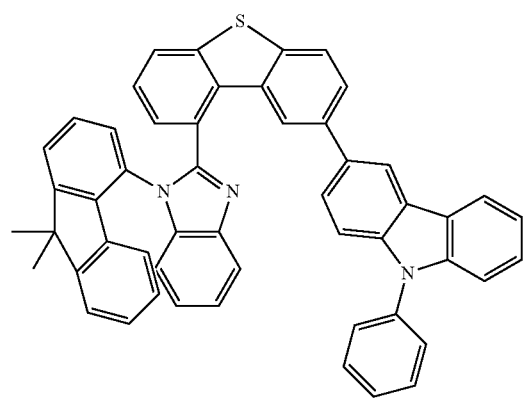 [SMILES: CC1(C)c2ccccc2-c2c(-n3c(-c4cccc5sc6ccc(-c7ccc8c(c7)c7ccccc7n8-c7ccccc7)cc6c45)nc4ccccc43)cccc21]
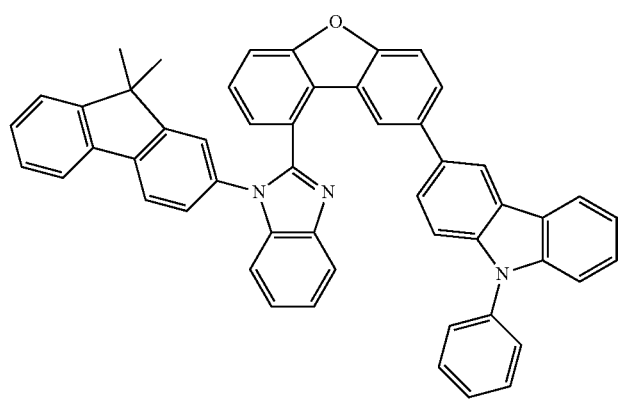 [SMILES: CC1(C)c2ccccc2-c2ccc(-n3c(-c4cccc5oc6ccc(-c7ccc8c(c7)c7ccccc7n8-c7ccccc7)cc6c45)nc4ccccc43)cc21]
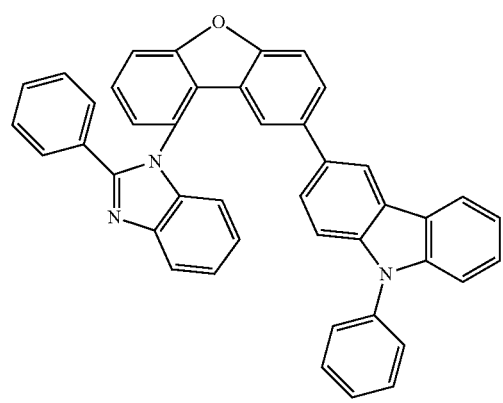 [SMILES: c1ccc(-c2nc3ccccc3n2-c2cccc3oc4ccc(-c5ccc6c(c5)c5ccccc5n6-c5ccccc5)cc4c23)cc1]

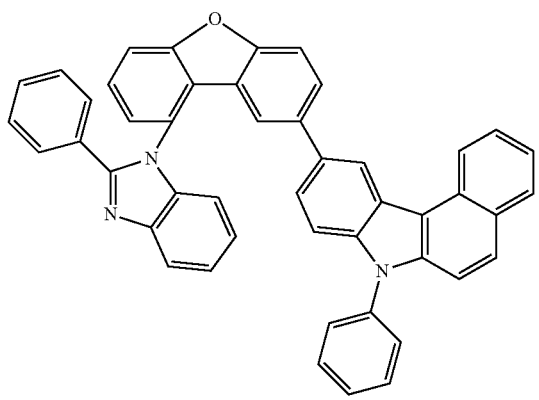 [SMILES: c1ccc(-c2nc3ccccc3n2-c2cccc3oc4ccc(-c5ccc6c(c5)c5c7ccccc7ccc5n6-c5ccccc5)cc4c23)cc1]
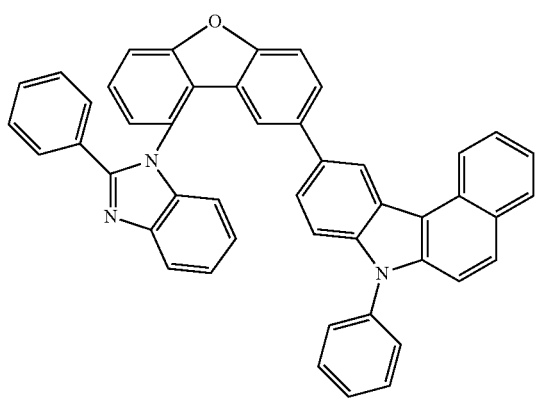 [SMILES: c1ccc(-c2nc3ccccc3n2-c2cccc3oc4ccc(-c5ccc6c(c5)c5c7ccccc7ccc5n6-c5ccccc5)cc4c23)cc1]
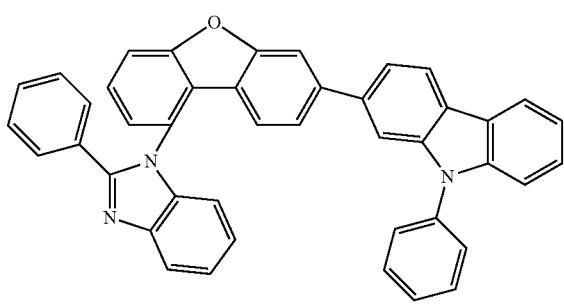 [SMILES: c1ccc(-c2nc3ccccc3n2-c2cccc3oc4cc(-c5ccc6c7ccccc7n(-c7ccccc7)c6c5)ccc4c23)cc1]
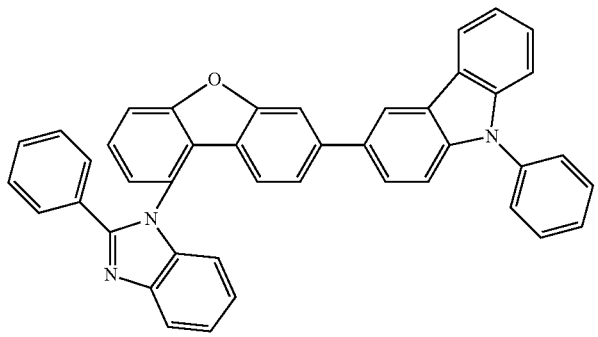 [SMILES: c1ccc(-c2nc3ccccc3n2-c2cccc3oc4cc(-c5ccc6c(c5)c5ccccc5n6-c5ccccc5)ccc4c23)cc1]

-continued
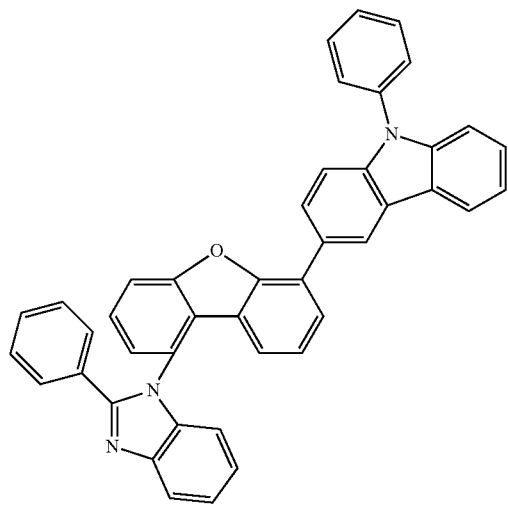 [SMILES: c1ccc(-c2nc3ccccc3n2-c2cccc3oc4c(-c5ccc6c(c5)c5ccccc5n6-c5ccccc5)cccc4c23)cc1]
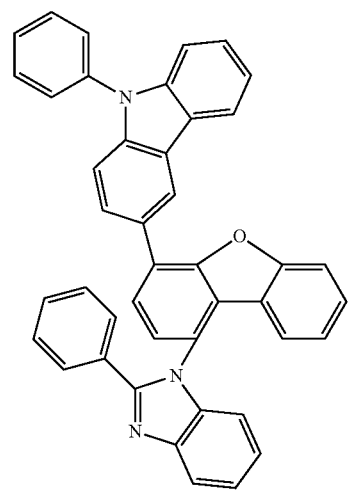 [SMILES: c1ccc(-c2nc3ccccc3n2-c2ccc(-c3ccc4c(c3)c3ccccc3n4-c3ccccc3)c3oc4ccccc4c23)cc1]
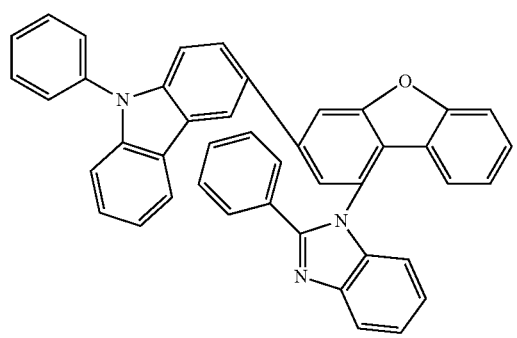 [SMILES: c1ccc(-c2nc3ccccc3n2-c2cc(-c3ccc4c(c3)c3ccccc3n4-c3ccccc3)cc3oc4ccccc4c23)cc1]

-continued
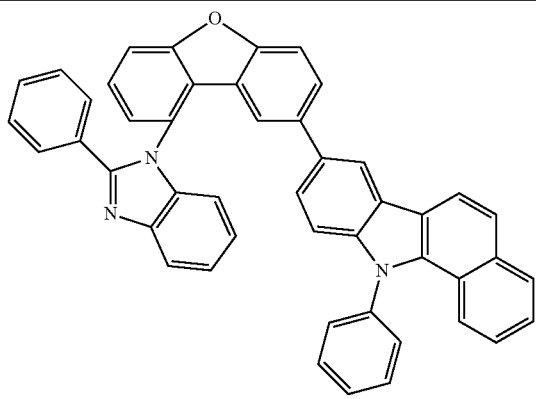
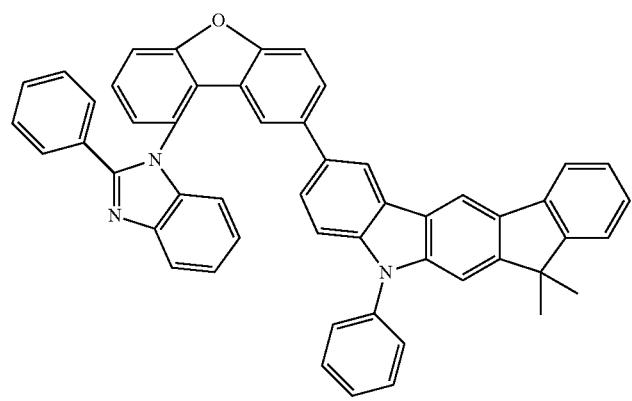 [SMILES: CC1(C)c2ccccc2-c2cc3c4cc(-c5ccc6oc7cccc(-n8c(-c9ccccc9)nc9ccccc98)c7c6c5)ccc4n(-c4ccccc4)c3cc21]
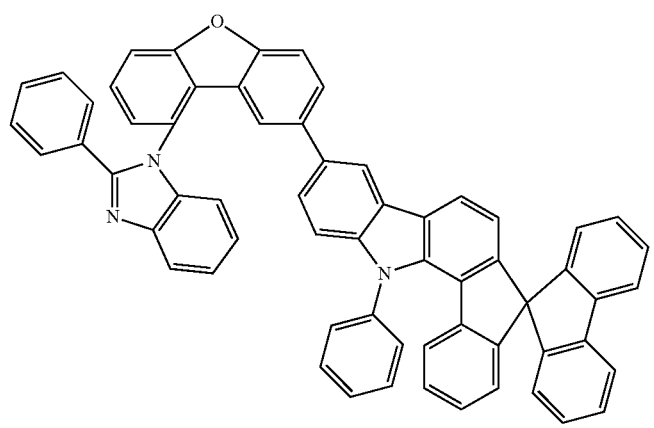 [SMILES: c1ccc(-c2nc3ccccc3n2-c2cccc3oc4ccc(-c5ccc6c(c5)c5ccc7c(c5n6-c5ccccc5)-c5ccccc5C75c6ccccc6-c6ccccc65)cc4c23)cc1]
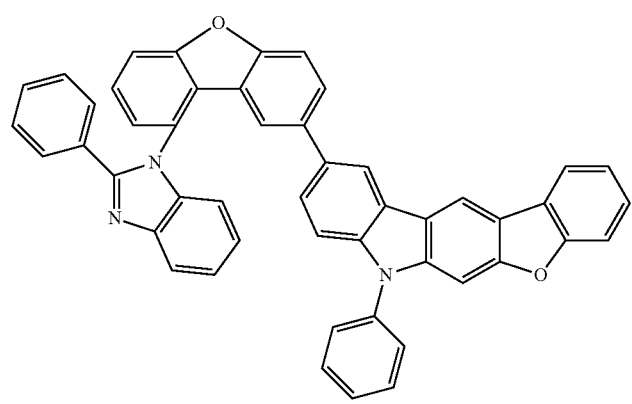 [SMILES: c1ccc(-c2nc3ccccc3n2-c2cccc3oc4ccc(-c5ccc6c(c5)c5cc7c(cc5n6-c5ccccc5)oc5ccccc57)cc4c23)cc1]

-continued
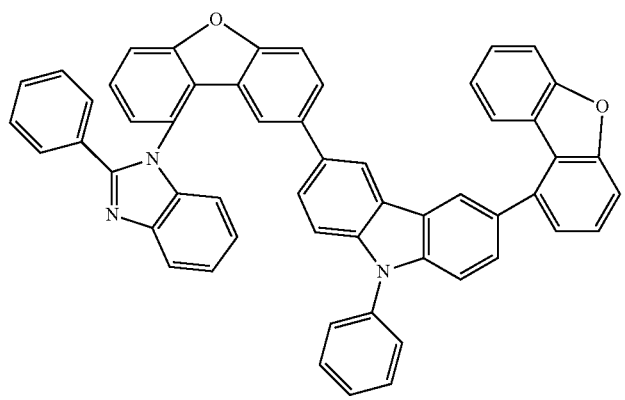 [SMILES: c1ccc(-c2nc3ccccc3n2-c2cccc3oc4ccc(-c5ccc6c(c5)c5cc(-c7cccc8oc9ccccc9c78)ccc5n6-c5ccccc5)cc4c23)cc1]
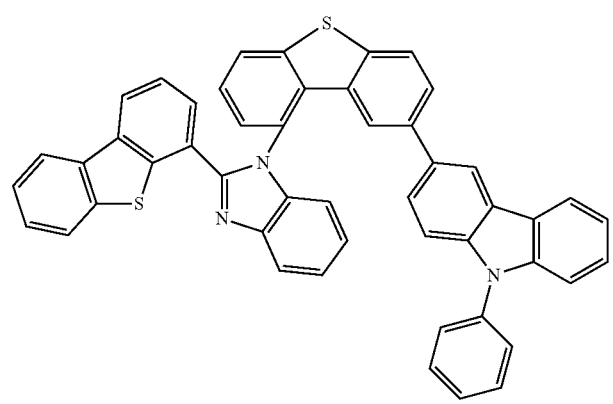 [SMILES: c1ccc(-n2c3ccccc3c3cc(-c4ccc5sc6cccc(-n7c(-c8cccc9c8sc8ccccc89)nc8ccccc87)c6c5c4)ccc32)cc1]
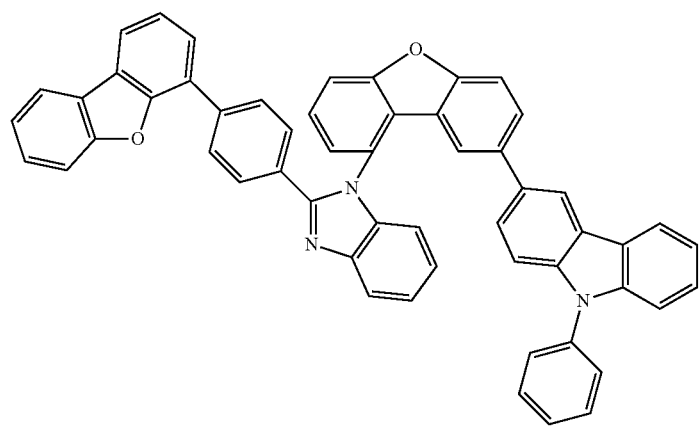 [SMILES: c1ccc(-n2c3ccccc3c3cc(-c4ccc5oc6cccc(-n7c(-c8ccc(-c9cccc%10c9oc9ccccc9%10)cc8)nc8ccccc87)c6c5c4)ccc32)cc1]

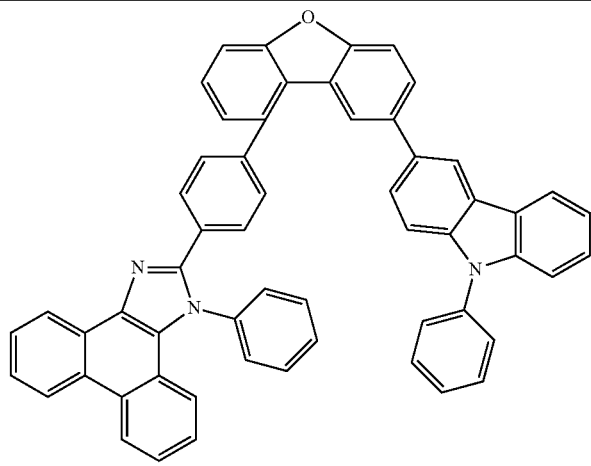
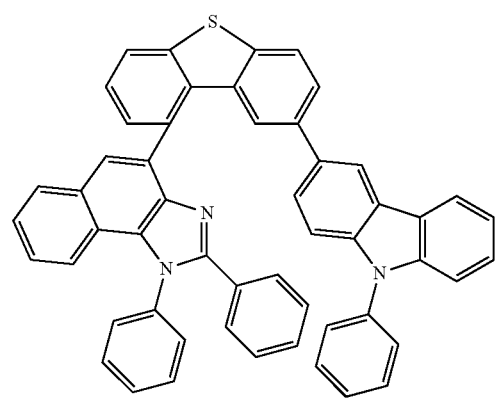 [SMILES: c1ccc(-c2nc3c(-c4cccc5sc6ccc(-c7ccc8c(c7)c7ccccc7n8-c7ccccc7)cc6c45)cc4ccccc4c3n2-c2ccccc2)cc1]
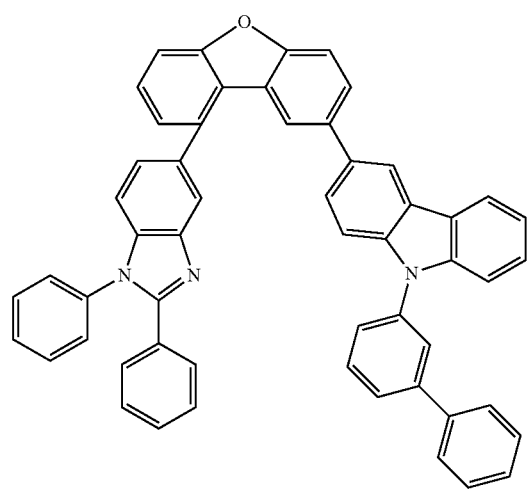 [SMILES: c1ccc(-c2cccc(-n3c4ccccc4c4cc(-c5ccc6oc7cccc(-c8ccc9c(c8)nc(-c8ccccc8)n9-c8ccccc8)c7c6c5)ccc43)c2)cc1]

-continued
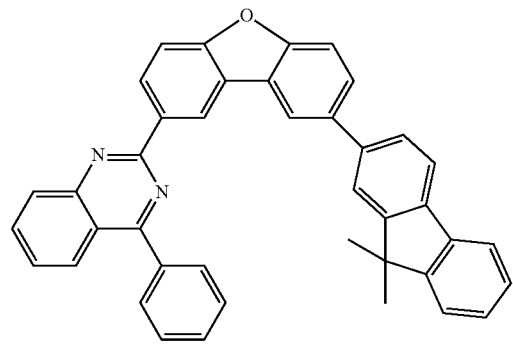 [SMILES: CC1(C)c2ccccc2-c2ccc(-c3ccc4oc5ccc(-c6nc(-c7ccccc7)c7ccccc7n6)cc5c4c3)cc21]
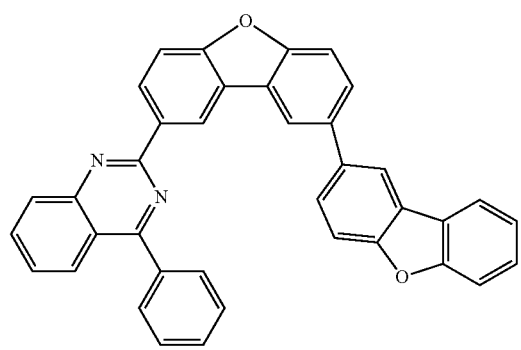
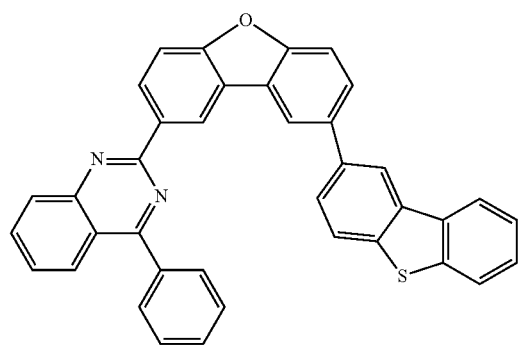 [SMILES: c1ccc(-c2nc(-c3ccc4oc5ccc(-c6ccc7oc8ccccc8c7c6)cc5c4c3)nc3ccccc23)cc1]
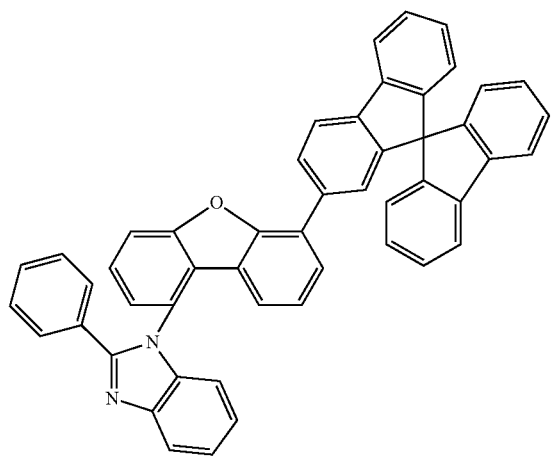 [SMILES: c1ccc(-c2nc3ccccc3n2-c2cccc3oc4c(-c5ccc6c(c5)C5(c7ccccc7-c7ccccc75)c5ccccc5-6)cccc4c23)cc1]

-continued
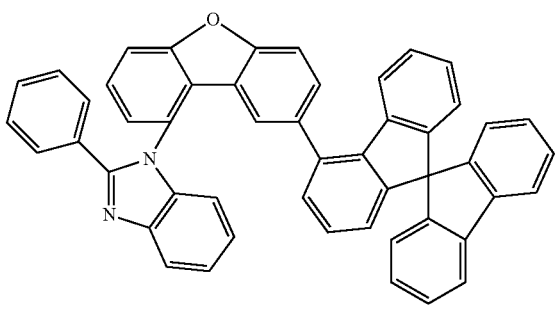 [SMILES: c1ccc(-c2nc3ccccc3n2-c2cccc3oc4ccc(-c5cccc6c5-c5ccccc5C65c6ccccc6-c6ccccc65)cc4c23)cc1]
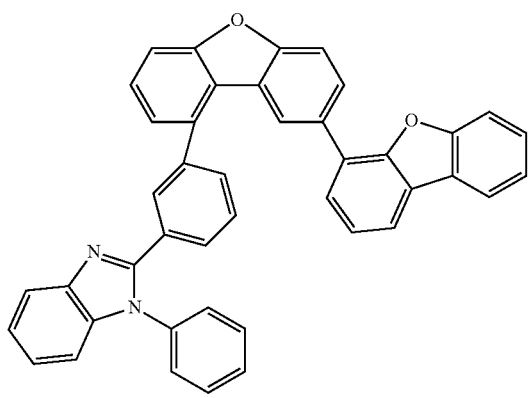 [SMILES: c1ccc(-n2c(-c3cccc(-c4cccc5oc6ccc(-c7cccc8c7oc7ccccc78)cc6c45)c3)nc3ccccc32)cc1]
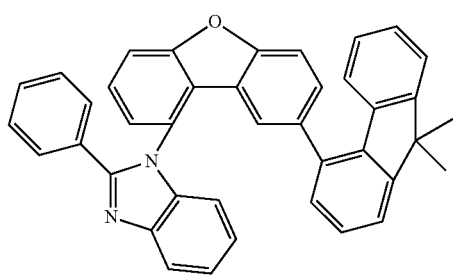 [SMILES: CC1(C)c2ccccc2-c2c(-c3ccc4oc5cccc(-n6c(-c7ccccc7)nc7ccccc76)c5c4c3)cccc21]
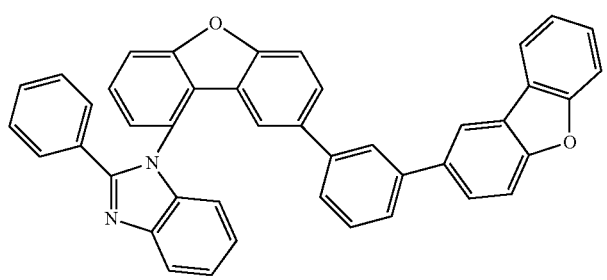 [SMILES: c1ccc(-c2nc3ccccc3n2-c2cccc3oc4ccc(-c5cccc(-c6ccc7oc8ccccc8c7c6)c5)cc4c23)cc1]
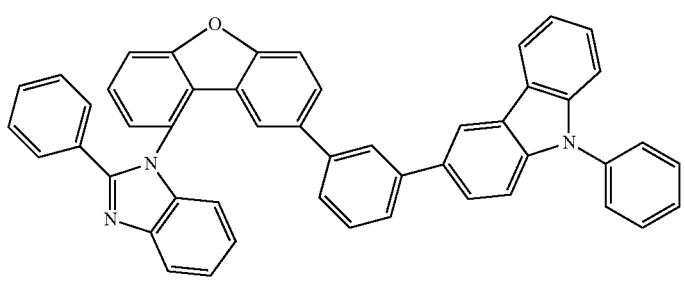 [SMILES: c1ccc(-c2nc3ccccc3n2-c2cccc3oc4ccc(-c5cccc(-c6ccc7c(c6)c6ccccc6n7-c6ccccc6)c5)cc4c23)cc1]

-continued
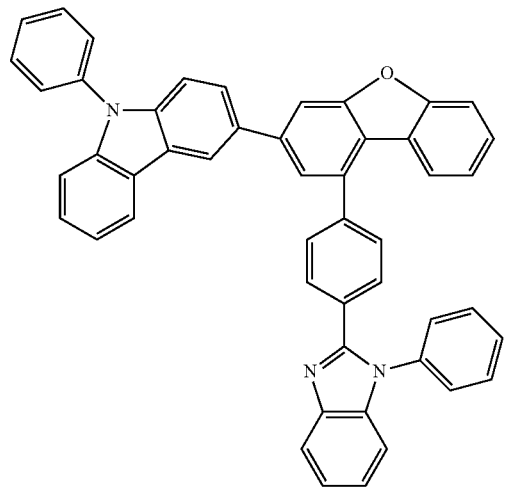 [SMILES: c1ccc(-n2c(-c3ccc(-c4cc(-c5ccc6c(c5)c5ccccc5n6-c5ccccc5)cc5oc6ccccc6c45)cc3)nc3ccccc32)cc1]
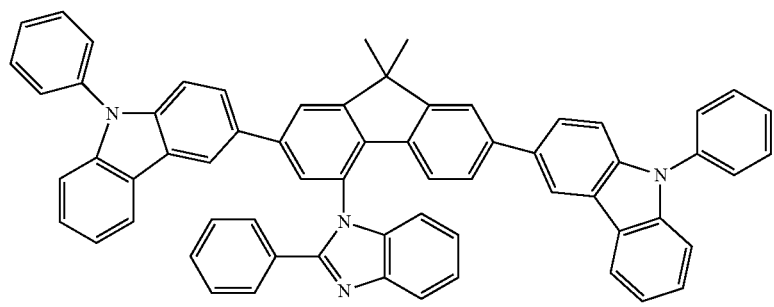 [SMILES: CC1(C)c2cc(-c3ccc4c(c3)c3ccccc3n4-c3ccccc3)ccc2-c2c(-n3c(-c4ccccc4)nc4ccccc43)cc(-c3ccc4c(c3)c3ccccc3n4-c3ccccc3)cc21]
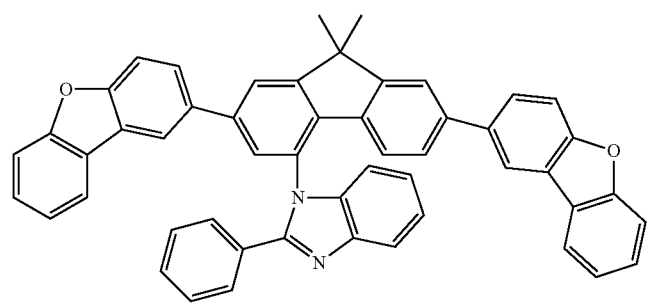 [SMILES: CC1(C)c2cc(-c3ccc4oc5ccccc5c4c3)ccc2-c2c(-n3c(-c4ccccc4)nc4ccccc43)cc(-c3ccc4oc5ccccc5c4c3)cc21]
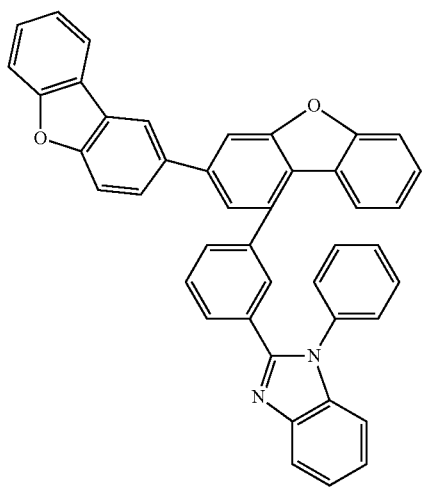 [SMILES: c1ccc(-n2c(-c3cccc(-c4cc(-c5ccc6oc7ccccc7c6c5)cc5oc6ccccc6c45)c3)nc3ccccc32)cc1]

-continued
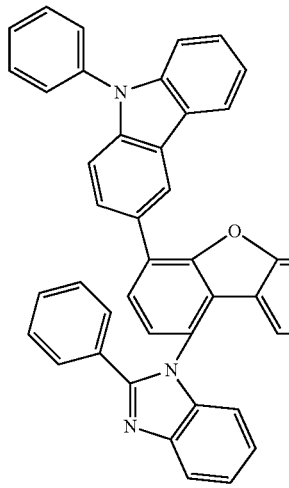
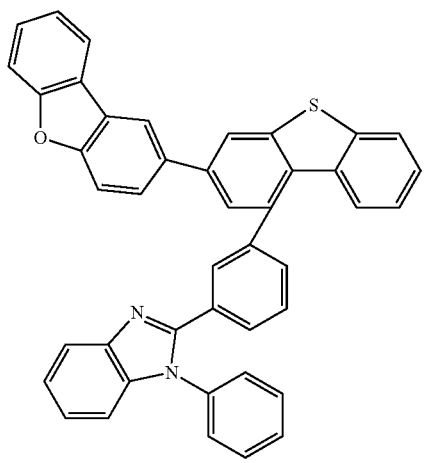 [SMILES: c1ccc(-n2c(-c3cccc(-c4cc(-c5ccc6oc7ccccc7c6c5)cc5sc6ccccc6c45)c3)nc3ccccc32)cc1]
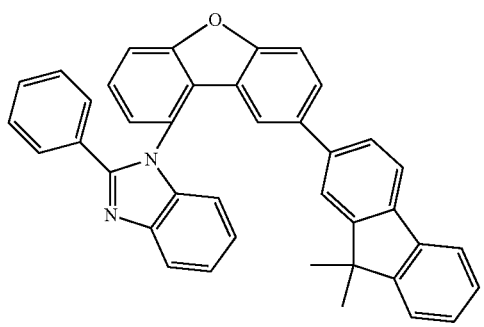 [SMILES: CC1(C)c2ccccc2-c2ccc(-c3ccc4oc5cccc(-n6c(-c7ccccc7)nc7ccccc76)c5c4c3)cc21]
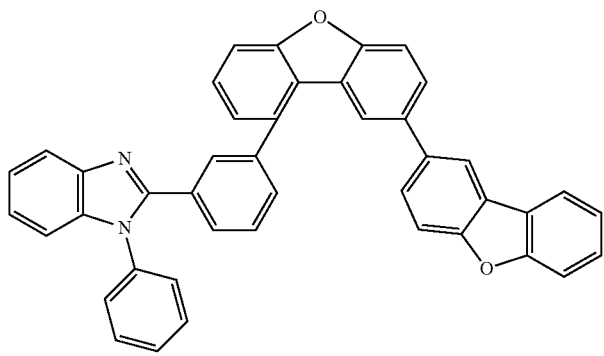 [SMILES: c1ccc(-n2c(-c3cccc(-c4cccc5oc6ccc(-c7ccc8oc9ccccc9c8c7)cc6c45)c3)nc3ccccc32)cc1]

-continued
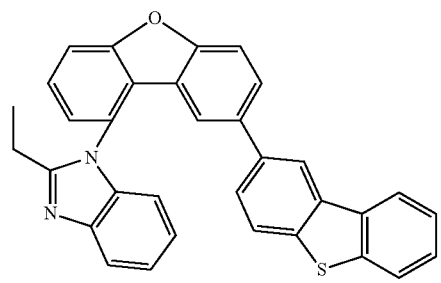 [SMILES: CCc1nc2ccccc2n1-c1cccc2oc3ccc(-c4ccc5sc6ccccc6c5c4)cc3c12]
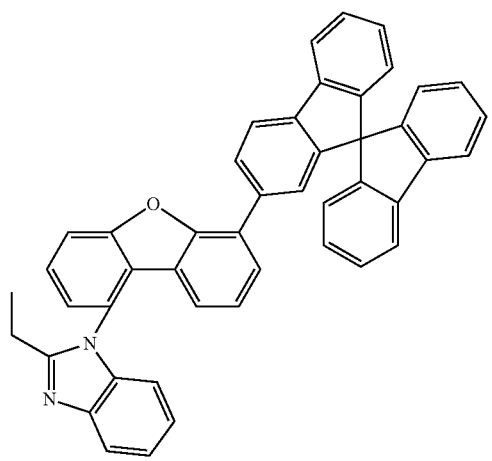 [SMILES: CCc1nc2ccccc2n1-c1cccc2oc3c(-c4ccc5c(c4)C4(c6ccccc6-c6ccccc64)c4ccccc4-5)cccc3c12]
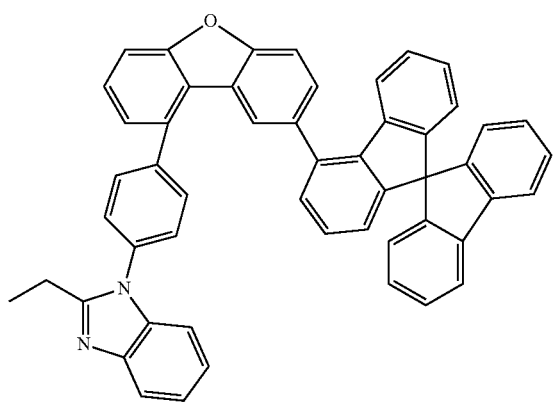 [SMILES: CCc1nc2ccccc2n1-c1ccc(-c2cccc3oc4ccc(-c5cccc6c5-c5ccccc5C65c6ccccc6-c6ccccc65)cc4c23)cc1]
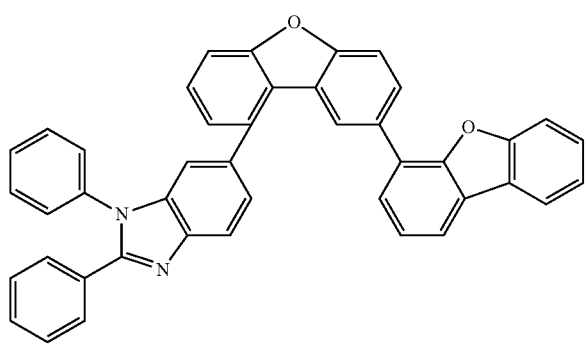 [SMILES: c1ccc(-c2nc3ccc(-c4cccc5oc6ccc(-c7cccc8c7oc7ccccc78)cc6c45)cc3n2-c2ccccc2)cc1]

-continued
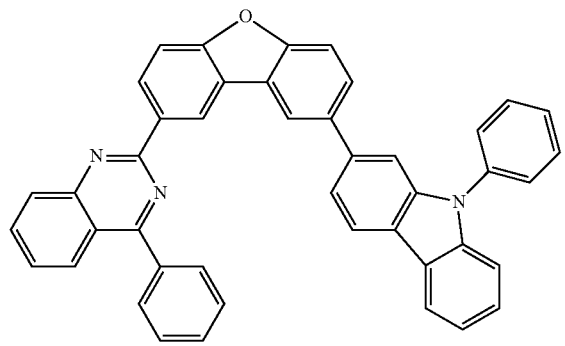 [SMILES: c1ccc(-c2nc(-c3ccc4oc5ccc(-c6ccc7c8ccccc8n(-c8ccccc8)c7c6)cc5c4c3)nc3ccccc23)cc1]
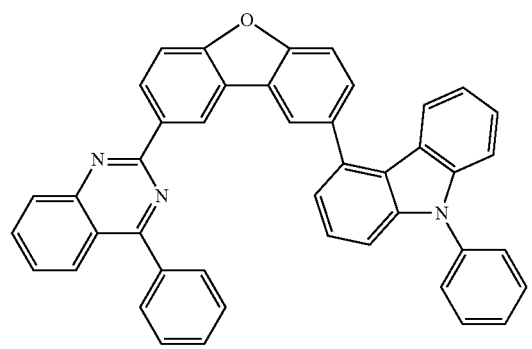 [SMILES: c1ccc(-c2nc(-c3ccc4oc5ccc(-c6cccc7c6c6ccccc6n7-c6ccccc6)cc5c4c3)nc3ccccc23)cc1]
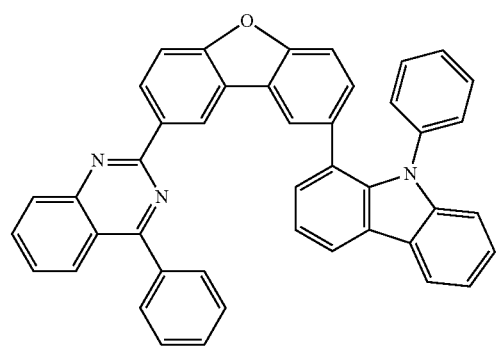 [SMILES: c1ccc(-c2nc(-c3ccc4oc5ccc(-c6cccc7c8ccccc8n(-c8ccccc8)c67)cc5c4c3)nc3ccccc23)cc1]
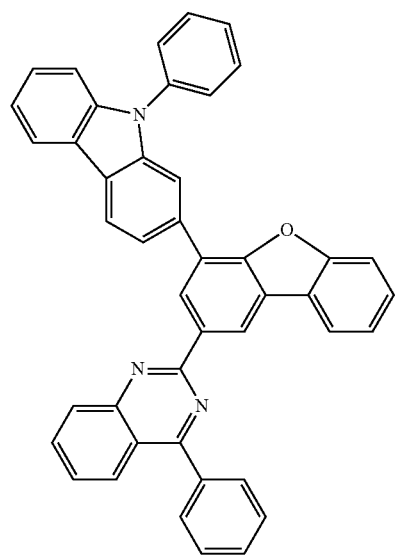 [SMILES: c1ccc(-c2nc(-c3cc(-c4ccc5c6ccccc6n(-c6ccccc6)c5c4)c4oc5ccccc5c4c3)nc3ccccc23)cc1]

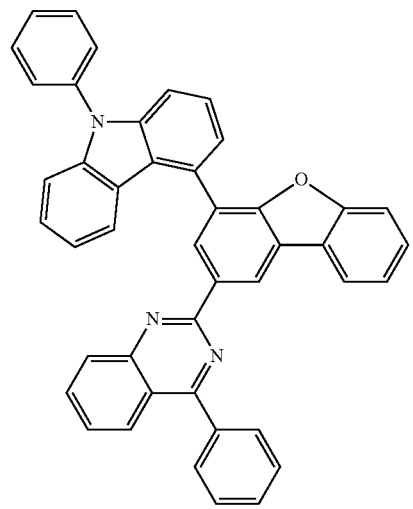 [SMILES: c1ccc(-c2nc(-c3cc(-c4cccc5c4c4ccccc4n5-c4ccccc4)c4oc5ccccc5c4c3)nc3ccccc23)cc1]
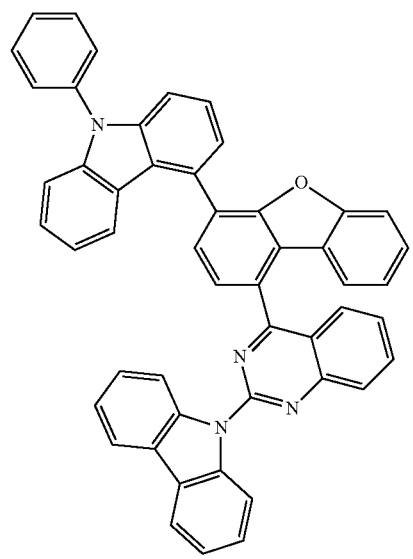 [SMILES: c1ccc(-n2c3ccccc3c3c(-c4ccc(-c5nc(-n6c7ccccc7c7ccccc76)nc6ccccc56)c5c4oc4ccccc45)cccc32)cc1]
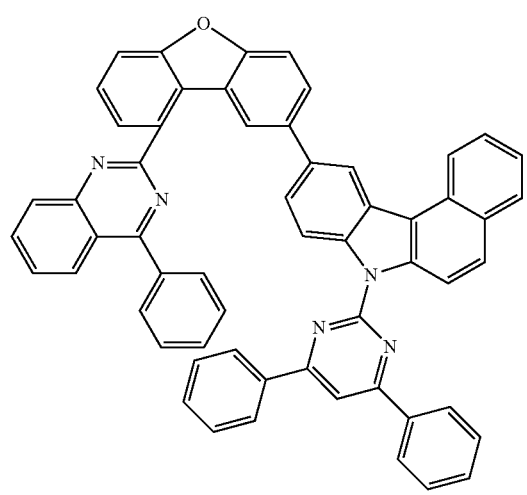 [SMILES: c1ccc(-c2cc(-c3ccccc3)nc(-n3c4ccc(-c5ccc6oc7cccc(-c8nc(-c9ccccc9)c9ccccc9n8)c7c6c5)cc4c4c5ccccc5ccc43)n2)cc1]

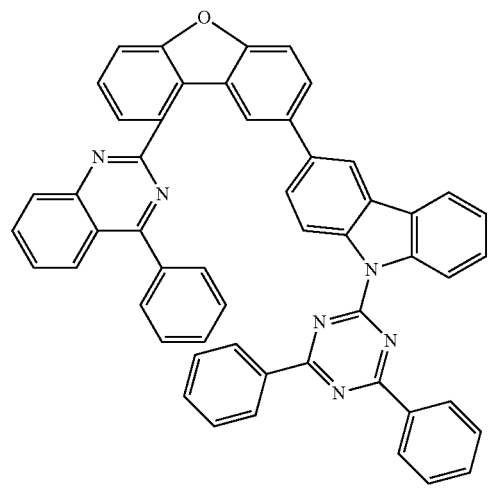
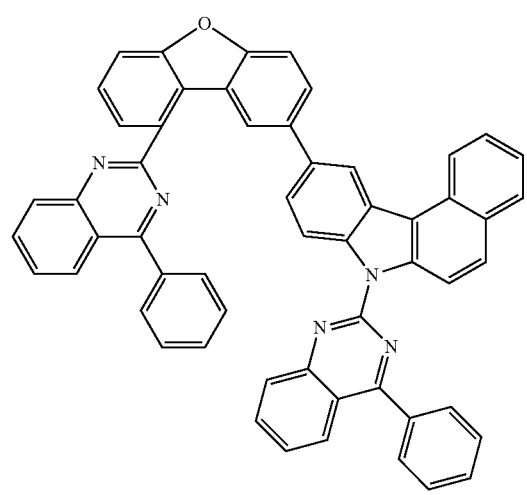 [SMILES: c1ccc(-c2nc(-c3cccc4oc5ccc(-c6ccc7c(c6)c6c8ccccc8ccc6n7-c6nc(-c7ccccc7)c7ccccc7n6)cc5c34)nc3ccccc23)cc1]
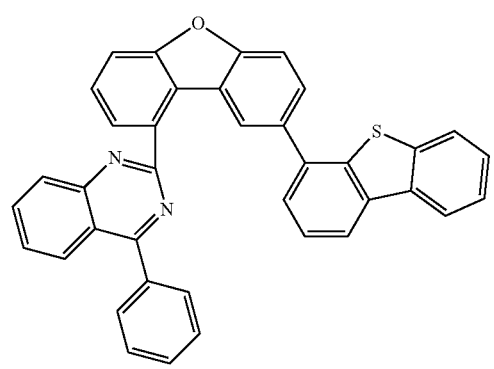 [SMILES: c1ccc(-c2nc(-c3cccc4oc5ccc(-c6cccc7c6sc6ccccc67)cc5c34)nc3ccccc23)cc1]

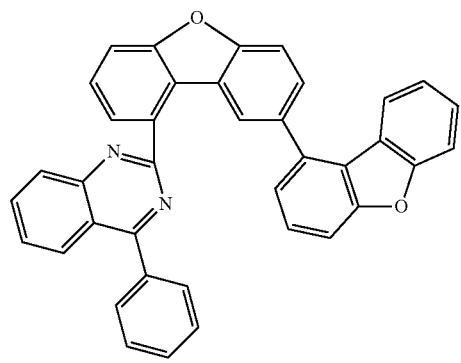 [SMILES: c1ccc(-c2nc(-c3cccc4oc5ccc(-c6cccc7oc8ccccc8c67)cc5c34)nc3ccccc23)cc1]
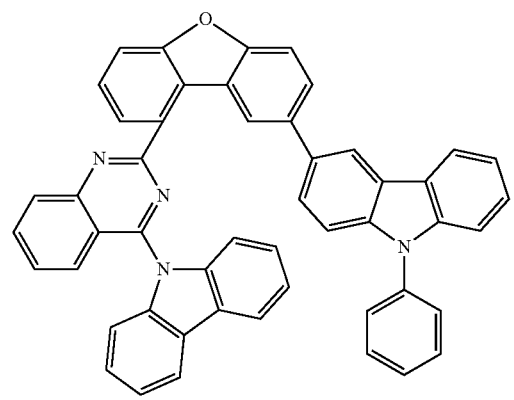 [SMILES: c1ccc(-n2c3ccccc3c3cc(-c4ccc5oc6cccc(-c7nc(-n8c9ccccc9c9ccccc98)c8ccccc8n7)c6c5c4)ccc32)cc1]
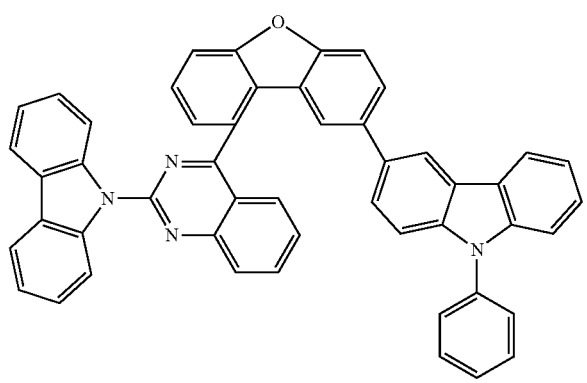 [SMILES: c1ccc(-n2c3ccccc3c3cc(-c4ccc5oc6cccc(-c7nc(-n8c9ccccc9c9ccccc98)nc8ccccc78)c6c5c4)ccc32)cc1]
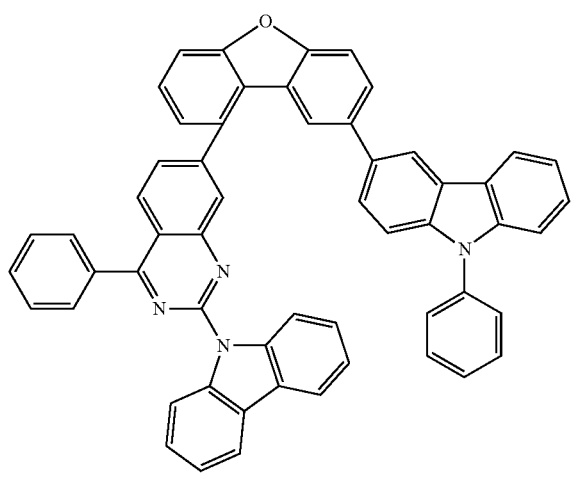 [SMILES: c1ccc(-c2nc(-n3c4ccccc4c4ccccc43)nc3cc(-c4cccc5oc6ccc(-c7ccc8c(c7)c7ccccc7n8-c7ccccc7)cc6c45)ccc23)cc1]

-continued
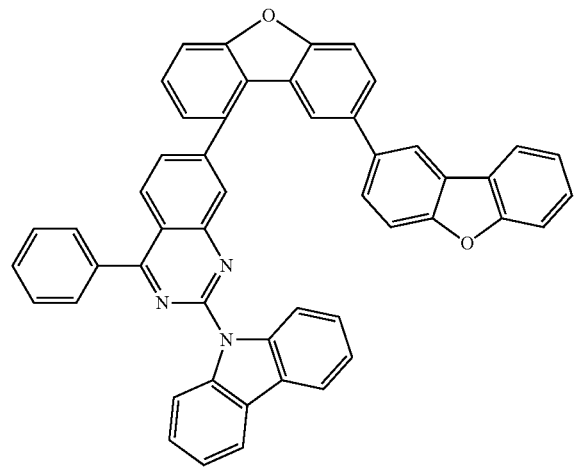 [SMILES: c1ccc(-c2nc(-n3c4ccccc4c4ccccc43)nc3cc(-c4cccc5oc6ccc(-c7ccc8oc9ccccc9c8c7)cc6c45)ccc23)cc1]
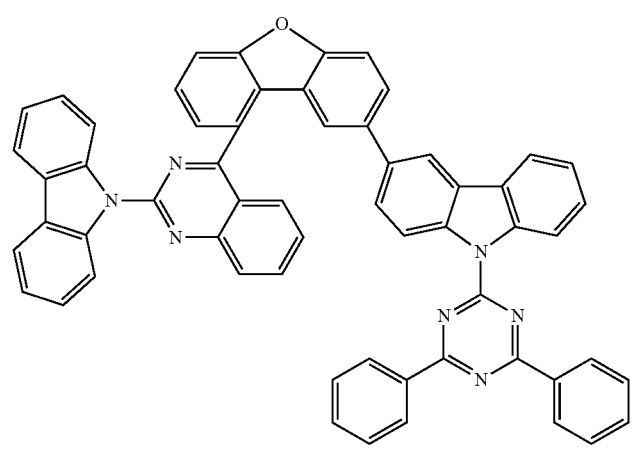 [SMILES: c1ccc(-c2nc(-c3ccccc3)nc(-n3c4ccccc4c4cc(-c5ccc6oc7cccc(-c8nc(-n9c%10ccccc%10c%10ccccc%109)nc9ccccc89)c7c6c5)ccc43)n2)cc1]
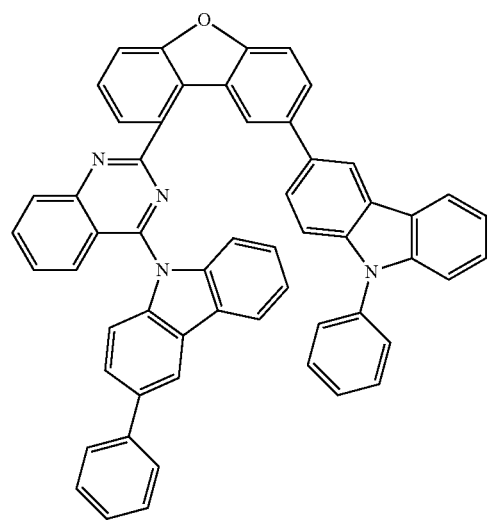 [SMILES: c1ccc(-c2ccc3c(c2)c2ccccc2n3-c2nc(-c3cccc4oc5ccc(-c6ccc7c(c6)c6ccccc6n7-c6ccccc6)cc5c34)nc3ccccc23)cc1]

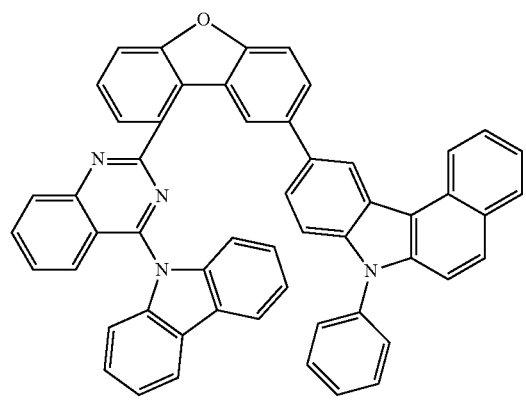 [SMILES: c1ccc(-n2c3ccc(-c4ccc5oc6cccc(-c7nc(-n8c9ccccc9c9ccccc98)c8ccccc8n7)c6c5c4)cc3c3c4ccccc4ccc32)cc1]
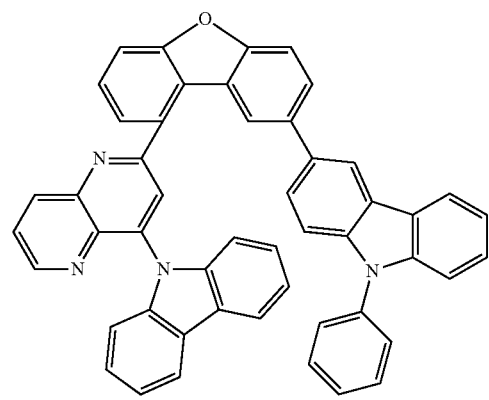 [SMILES: c1ccc(-n2c3ccccc3c3cc(-c4ccc5oc6cccc(-c7cc(-n8c9ccccc9c9ccccc98)c8ncccc8n7)c6c5c4)ccc32)cc1]
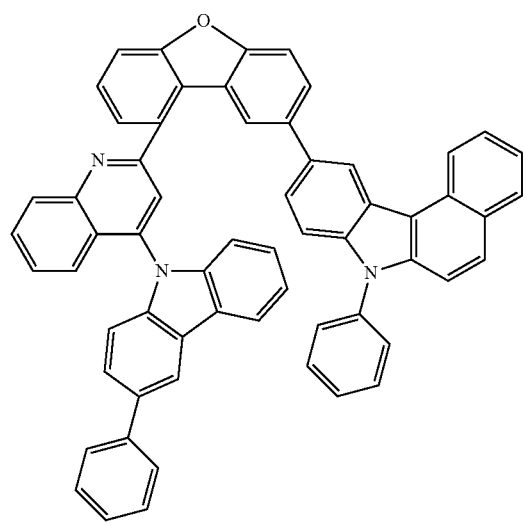 [SMILES: c1ccc(-c2ccc3c(c2)c2ccccc2n3-c2cc(-c3cccc4oc5ccc(-c6ccc7c(c6)c6c8ccccc8ccc6n7-c6ccccc6)cc5c34)nc3ccccc23)cc1]

-continued

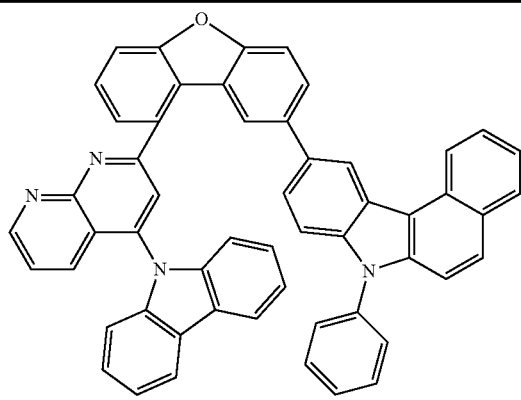

The compounds according to the invention are suitable for use in an electronic device, in particular in an organic electroluminescent device. The present invention therefore furthermore relates to the use of a compound according to the invention in an electronic device, in particular in an organic electroluminescent device. The present invention still furthermore relates to an electronic device comprising at least one compound according to the invention. An electronic device in the sense of the present invention is a device which comprises at least one layer which comprises at least one organic compound. The component may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and "organic plasmon emitting devices", but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). The organic electroluminescent device according to the invention may also be a tandem OLED, in particular also for white-emitting OLEDs.

The compound according to the invention in accordance with the embodiments indicated above can be employed in various layers, depending on the precise structure. Preference is given to an organic electroluminescent device comprising a compound of the formulae (1) or (2) or the preferred embodiments indicated above as matrix material for phosphorescent or fluorescent emitters, in particular for phosphorescent emitters, and/or in an electron-blocking or exciton-blocking layer and/or in a hole-transport layer and/or in a hole-blocking layer and/or in a hole-blocking or electron-transport layer, depending on the precise substitution.

In a preferred embodiment of the invention, the compound according to the invention is employed as matrix material for a phosphorescent compound in an emitting layer. The organic electroluminescent device here may comprise one emitting layer, or it may comprise a plurality of emitting layers, where at least one emitting layer comprises at least one compound according to the invention as matrix material.

If the compound according to the invention is employed as matrix material for a phosphorescent compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state>1, in particular from an excited triplet state. In the sense of this application, all luminescent complexes containing transition metals or lanthanides, in particular all iridium, platinum and copper complexes, are to be regarded as phosphorescent compounds.

The mixture of the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example in accordance with WO 2007/063754 or WO 2008/056746, indenocarbazole derivatives, for example in accordance with WO 2010/136109, WO 2011/000455, WO 2013/041176 or WO 2013/056776, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with WO 2011/042107, WO 2011/060867, WO 2011/088877 and WO 2012/143080, or triphenylene derivatives, for example in accordance with WO 2012/048781. A further phosphorescent emitter which emits at shorter wavelength than the actual emitter may likewise be present in the mixture as co-host, or a compound which does not participate in the charge transport to a significant extent, if at all, as described, for example, in WO 2010/108579.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531 and WO 2013/020631. Also suitable are, for example, the metal complexes disclosed in the unpublished applications EP 12005187.5 and EP 12005715.3. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

The compounds according to the invention are also suitable, in particular, as matrix materials for phosphorescent emitters in organic electroluminescent devices, as described, for example, in US 2011/0248247 and US 2012/0223633. In these multicoloured display components, an additional blue emission layer is applied by vapour deposition over the entire area to all pixels, also those having a colour other than blue. It has been found here, surprisingly, that the compounds according to the invention, when employed as matrix materials for the red and/or green pixels, continue to result in very good lifetime and emission together with the vapour-deposited blue emission layer.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is the same as or similar to the metal complex in the emitting layer as hole-transport or hole-injection material directly adjacent to the emitting layer, as described, for example, in WO 2009/030981.

In a further embodiment of the invention, the compound according to the invention is employed in a hole-transport layer or in an electron-blocking layer or exciton-blocking layer.

In still a further preferred embodiment of the invention, the compound according to the invention is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxy-quinolinate) or with an alkali metal, such as Li.

In still a further preferred embodiment of the invention, the compound according to the invention is employed in a hole-blocking layer. A hole-blocking layer is taken to mean a layer which is directly adjacent to an emitting layer on the cathode side.

In the further layers of the organic electroluminescent device according to the invention, all materials can be used as are usually employed in accordance with the prior art. The person skilled in the art will therefore be able to employ all materials which are known for organic electroluminescent devices in combination with the compounds of the formula (1) according to the invention or the preferred embodiments indicated above without inventive step.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. Also possible are hybrid processes, in which, for example, one or more layers are applied from solution and one or more further layers are applied by vapour deposition.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, hexamethylindane, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound and/or a further matrix material. Suitable emitting compounds and further matrix materials are indicated above in connection with the organic electroluminescent device. This further compound may also be polymeric.

dibenzofuran, dibenzothiophene or a fluorene group substituted in the 1-position, either directly or through a linking group, to a carbon atom of a heteroaromatic group with one or two nitrogen atoms in a bicyclic 6/6 core, or to a carbon or nitrogen atom of a heteroaromatic group with two nitrogen atoms in a bicyclic 5/6 core and are further substituted with a group selected from dibenzofuran, dibenzothiophene, fluorene or carbazole.

All of the above processes are generally known to the person skilled in the art and can be applied without inventive step to organic electroluminescent devices comprising the compounds according to the invention.

The compounds according to the invention and the organic electroluminescent devices according to the invention are distinguished by one or more of the following surprising advantages over the prior art:

1. The compounds according to the invention, employed as matrix material for fluorescent or phosphorescent emitters, result in long lifetimes. This applies, in particular, if the compounds are employed as matrix material for a phosphorescent emitter.

2. The compounds according to the invention result in very low operating voltages. This applies, in particular, if the compounds are employed as matrix material for a phosphorescent emitter.

These above-mentioned advantages are not accompanied by an impairment in the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

The following syntheses are carried out, unless indicated otherwise, under a protective-gas atmosphere in dried solvents. The solvents and reagents can be purchased from ALDRICH or ABCR. The numbers indicated in the case of the starting materials which are not commercially available are the corresponding CAS numbers.

Generally, there are two general processes for forming compounds of formulae (1) or (2). The first (illustrated in Scheme 2) is where an intermediate with a group containing X (i.e. dibenzofuran, dibenzothiophene or a fluorene group) and the group containing Y (i.e. dibenzofuran, dibenzothiophene, fluorene or carbazole) is obtained by a C—C coupling, such as Suzuki, Negishi, Yamamoto, Grignard-Cross, Stille, Hartwig-Buchwald or Ullmann, between the two groups. The heterocyclic A (or $L_1$-A) group is added to this intermediate by subsequent functionization (i.e. halogenation, followed by formation of a boron containing group) and another C—C coupling reaction with A (or $L_1$-A) compound. In the case where A is a benzotriazole attached via nitrogen, the coupling reaction is by any known C—N coupling reactions including both a nucleophilic aromatic substitution reaction or a Pd-catalysed coupling reaction. Alternatively, a second process (illustrated in Schemes 1 and 3) is where the A (or $L_1$-A) group is attached to the group containing X by any of same methods described above. The resulting intermediate is then functionized by any of the methods described for the first process, and the group containing Y is then added to the intermediate by a C—C coupling reaction. For example, some of the compounds of the invention may be made by the following synthetic schemes:

Scheme 1
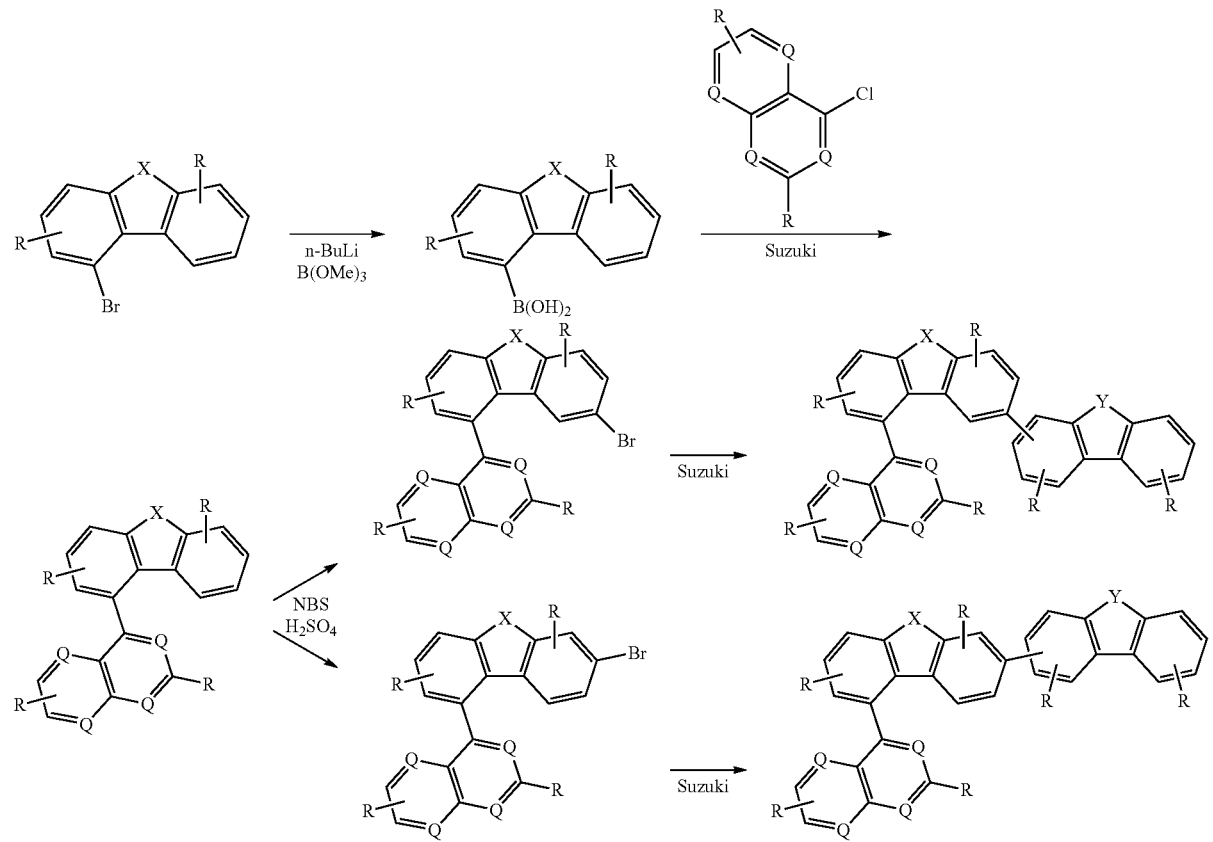

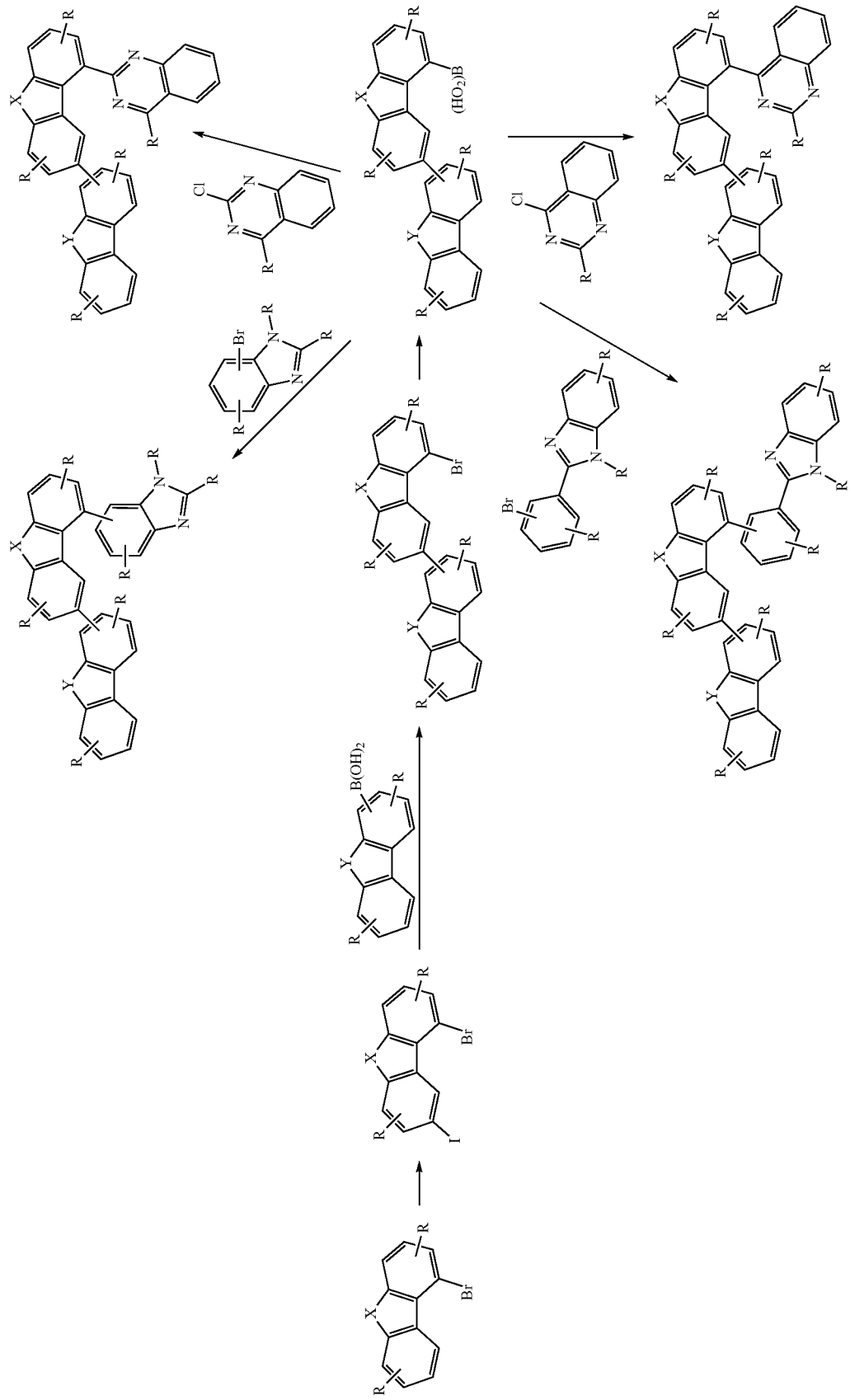
Scheme 2

Scheme 3

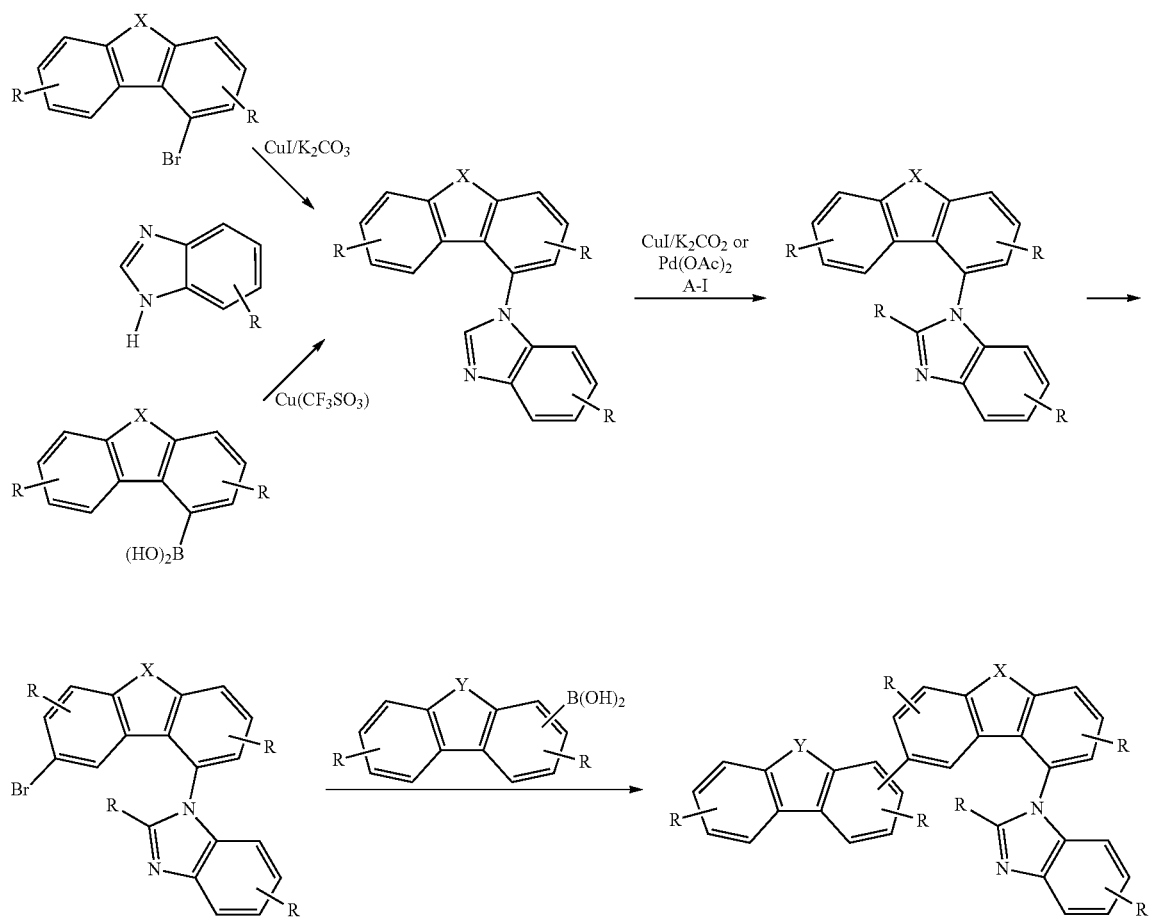

Synthesis Examples a) 4-bromo-9-methyl-9-phenyl-9H-fluorene

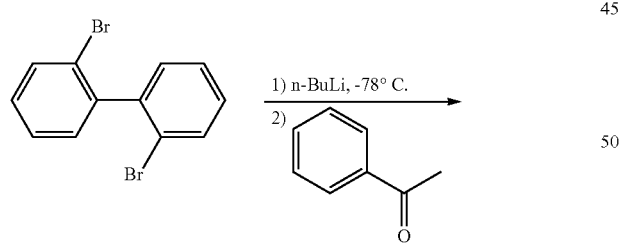

30 g (94 mmol) of 2,2'-dibromobiphenyl are dissolved in 200 ml of dried THF in a flask which has been dried by heating. The reaction mixture is cooled to −78° C. 37.7 ml of a 2.5 M solution of n-butyllithium in hexane (94 mmol) are slowly added dropwise (duration: about 1 h) at this temperature. The batch is stirred at −70° C. for a further 1 h. 11.1 ml of acetophenone (94 mmol) are subsequently dissolved in 100 ml of THF and added dropwise at −70° C. When the addition is complete, the reaction mixture is slowly warmed to room temperature, quenched using NH$_4$Cl and subsequently evaporated in a rotary evaporator. 300 ml of acetic acid are carefully added to the evaporated solution, and 50 ml of fuming HCl are subsequently added. The batch is heated to 75° C. and kept there for 6 h, during which a white solid precipitates out.

b) 4-bromo-9,9-diphenyl-9H-fluorene

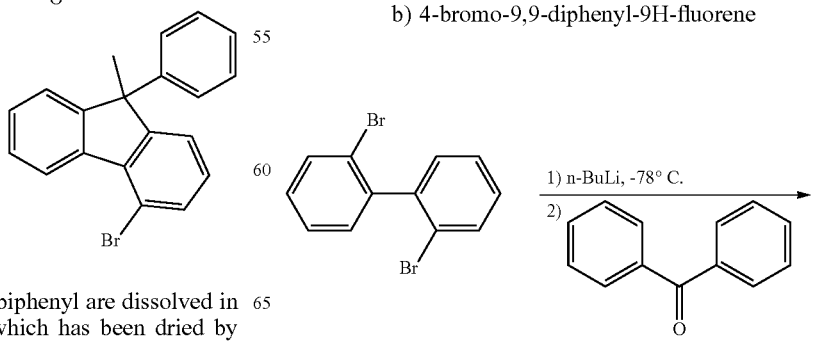

c) 6-Bromo-2-fluoro-2'-methoxy-biphenyl

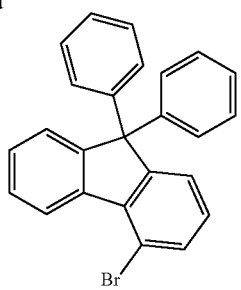

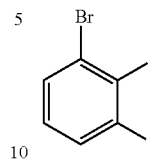

37 g (152 mmol) of 2,2'-dibromobiphenyl are dissolved in 300 ml of dried THF in a flask which has been dried by heating. The reaction mixture is cooled to −78° C. 75 ml of a 15% solution of n-butyllithium in hexane (119 mmol) are slowly added dropwise (duration: about 1 hour) at this temperature. The batch is stirred at −70° C. for a further 1 h. 21.8 g of benzophenone (119 mmol) are subsequently dissolved in 100 ml of THF and added dropwise at −70° C. When the addition is complete, the reaction mixture is slowly warmed to room temperature, quenched using NH$_4$Cl and subsequently evaporated in a rotary evaporator. 510 ml of acetic acid are carefully added to the evaporated solution, and 100 ml of fuming HCl are subsequently added. The batch is heated to 75° C. and kept at this temperature for 4 h, during which a white solid precipitates out. The batch is then cooled to room temperature, and the solid which has precipitated out is filtered off with suction and rinsed with methanol. The residue is dried at 40° C. in vacuo. The yield is 33.2 g (83 mmol) (70% of theory).

The following brominated compounds b1-b3 were prepared analogously:

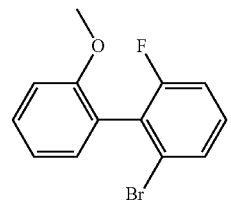

200 g (664 mmol) of 1-bromo-3-fluoro-2-iodobenzene, 101 g (664 mmol) of 2-methoxyphenylboronic acid and 137.5 g (997 mmol) of sodium tetraborate are dissolved in 1000 ml of THF and 600 ml of water and degassed. 9.3 g (13.3 mmol) of bis(triphenylphosphine)palladium(II) chloride and 1 g (20 mmol) of hydrazinium hydroxide are added. The reaction mixture is subsequently stirred at 70° C. for 48 h under a protective-gas atmosphere. The cooled solution is diluted with toluene, washed a number of times with water, dried and evaporated. The product is purified by column chromatography on silica gel with toluene/heptane (1:2). Yield: 155 g (553 mmol), 83% of theory.

| | Reactant 1 | Reactant 2 | Product | Yield |
|---|---|---|---|---|
| b1 | 2,2'-dibromobiphenyl | cyclohexanone | spiro fluorene-cyclohexane bromide | 78% |
| b2 | 2,2'-dibromobiphenyl | acetone | 9,9-dimethyl-bromofluorene | 70% |
| b3 | 2,2'-dibromobiphenyl | 4,4'-dimethylbenzophenone | 9,9-bis(4-tolyl)-bromofluorene | 82% |

The following compound c1 was prepared analogously:

| Reactant 1 | Reactant 2 | Product | Yield |
|---|---|---|---|
| c1 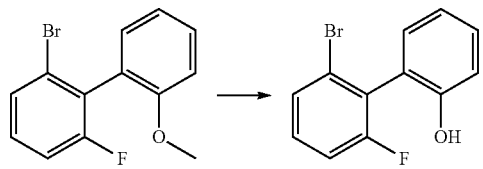 [SMILES: COc1ccccc1-c1c(F)cccc1Br ; Oc1ccccc1-c1c(F)cccc1Br] [1000576-09-9] | | | 77% | d) 6'-bromo-2'-fluoro-biphenyl-2-ol 112 g (418 mmol) of 6-bromo-2-fluoro-2'-methoxybiphenyl are dissolved in 2 l of dichloromethane and cooled to 5° C. 41.01 ml (431 mmol) of boron tribromide are added dropwise to this solution over the course of 90 min., and stirring is continued overnight. Water is subsequently slowly added to the mixture, and the organic phase is washed three times with water, dried over Na$_2$SO$_4$, evaporated in a rotary evaporator and purified by chromatography. Yield: 104 g (397 mmol), 98% of theory.

The following compound d1 was prepared analogously:

| Reactant | Product | Yield |
|---|---|---|
| d1 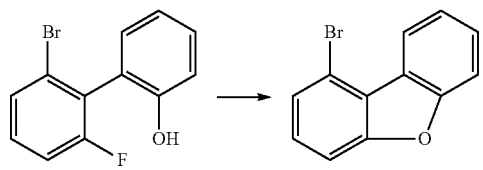 [SMILES: Oc1ccccc1-c1c(F)cccc1Br ; Brc1cccc2oc3ccccc3c12] | | 92% | e) 1-Bromo-dibenzofuran 111 g (416 mmol) of 6'-bromo-2'-fluorobiphenyl-2-ol are dissolved in 2 l of SeccoSolv® DMF (max 0.003% of H$_2$O) and cooled to 5° C. 20 g (449 mmol) of sodium hydride (60% suspension in paraffin oil) are added in portions to this solution, and the mixture is stirred for a further 20 min. after the addition is complete and then heated at 100° C. for 45 min. After cooling, 500 ml of ethanol are slowly added to the mixture, which is then evaporated to dryness in a rotary evaporator and purified by chromatography. Yield: 90 g (367 mmol), 88.5% of theory.

The following compound e1 was prepared analogously:

| Reactant | Product | Yield |
|---|---|---|
| e1 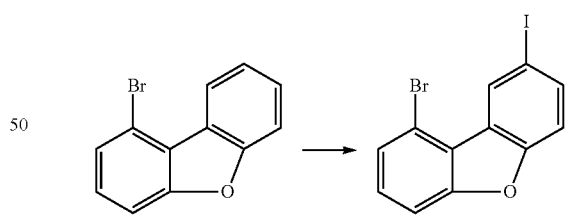 | | 81% | f) 1-bromo-8-iodo-dibenzofuran 20 g (80 mmol) of dibenzofuran-1-boronic acid, 2.06 g (40.1 mmol) of iodine, 3.13 g (17.8 mmol) of iodic acid, 80 ml of acetic acid, 5 ml of sulfuric acid, 5 ml of water and 2 ml of chloroform are stirred at 65° for 3 hours. After cooling, water is added to the mixture, and the solid which has precipitated out is filtered off with suction and washed three times with water. The residue is recrystallised from toluene and from dichloromethane/heptane. The yield is 25.6 g (68 mmol), corresponding to 85% of theory.

The following compounds were prepared analogously:

| Reactant | Product | Yield |
|---|---|---|
| f1 | | 81% |
| f2 | | 84% |
| f3 | | 78% | g) 3-(1-bromo-dibenzothiophene-3-yl)-9-phenyl-9H-carbazole

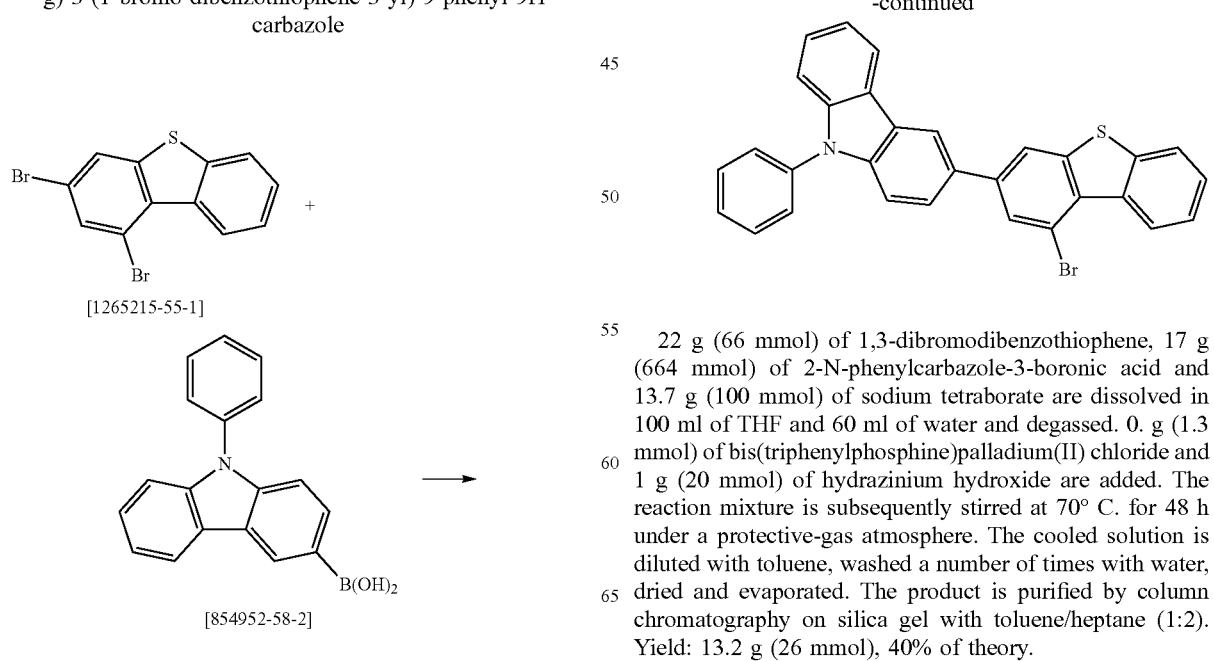

22 g (66 mmol) of 1,3-dibromodibenzothiophene, 17 g (664 mmol) of 2-N-phenylcarbazole-3-boronic acid and 13.7 g (100 mmol) of sodium tetraborate are dissolved in 100 ml of THF and 60 ml of water and degassed. 0. g (1.3 mmol) of bis(triphenylphosphine)palladium(II) chloride and 1 g (20 mmol) of hydrazinium hydroxide are added. The reaction mixture is subsequently stirred at 70° C. for 48 h under a protective-gas atmosphere. The cooled solution is diluted with toluene, washed a number of times with water, dried and evaporated. The product is purified by column chromatography on silica gel with toluene/heptane (1:2). Yield: 13.2 g (26 mmol), 40% of theory.

The following compounds were prepared analogously:

| | Reactant 1 | Reactant 2 | Product | Yield |
|---|---|---|---|---|
| g1 | [1225467-30-0] | [854952-58-2] | | 27% |
| g2 | [1225467-28-6] | [854952-58-2] | | 24% |
| g3 | [1453088-13-5] | [854952-58-2] | | 31% | h) dibenzofuran-1-boronic acid

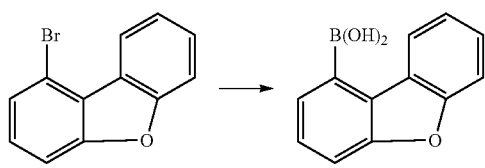 [SMILES: Brc1cccc2oc3ccccc3c12 ; OB(O)c1cccc2oc3ccccc3c12]

180 g (728 mmol) of 1-bromodibenzofuran are dissolved in 1500 ml of dry THF and cooled to −78° C. 305 ml (764 mmol/2.5 M in hexane) of n-butyllithium are added over the course of about 5 min. at this temperature, and the mixture is subsequently stirred at −78° C. for a further 2.5 h. 151 g (1456 mmol) of trimethyl borate are added as rapidly as possible at this temperature, and the reaction is slowly allowed to come to room temperature (about 18 h). The reaction solution is washed with water, and the solid which has precipitated out and the organic phase are dried azeotropically with toluene. The crude product is washed by stirring with toluene/methylene chloride at about 40° C. and filtered off with suction. Yield: 146 g (690 mmol), 95% of theory.

The following compounds were prepared analogously:

| Reactant | Product | Yield |
|---|---|---|
| h1 | | 81% |
| h2 [65642-94-6] | | 73% |
| h3 | | 78% |
| h4 | | 81% |
| h5 | | 86% |
| h6 | | 83% |

-continued
| | Reactant | Product | Yield |
|---|---|---|---|
| h7 | 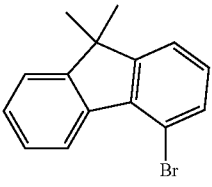 [SMILES: CC1(C)c2ccccc2-c2c(Br)cccc21] | 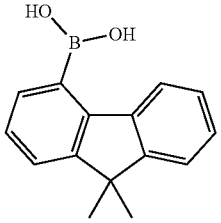 [SMILES: CC1(C)c2ccccc2-c2c(B(O)O)cccc21] | 85% |
| h8 | 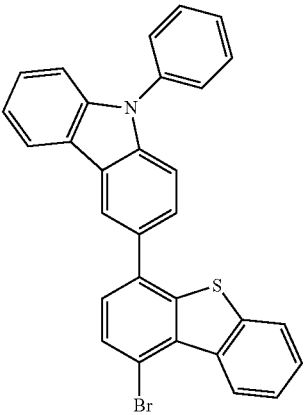 [SMILES: Brc1ccc(-c2ccc3c(c2)c2ccccc2n3-c2ccccc2)c2sc3ccccc3c12] | 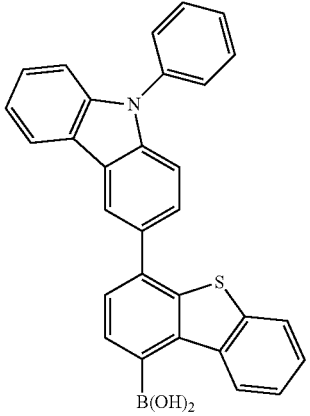 | 80% |
| h9 | 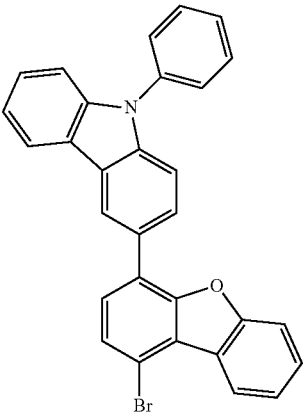 | 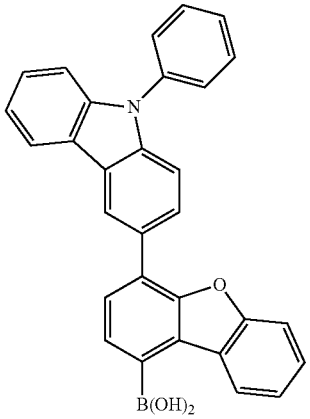 | 83% |
| h10 | 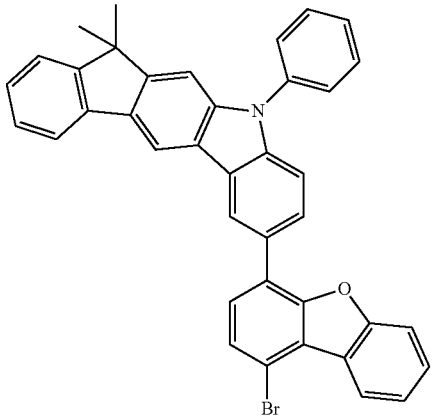 [SMILES: CC1(C)c2ccccc2-c2cc3c4cc(-c5ccc(Br)c6c5oc5ccccc56)ccc4n(-c4ccccc4)c3cc21] | 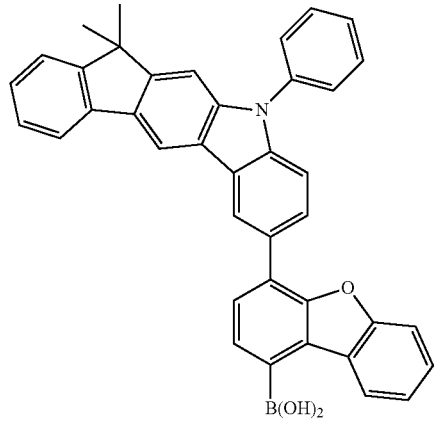 [SMILES: CC1(C)c2ccccc2-c2cc3c4cc(-c5ccc(B(O)O)c6c5oc5ccccc56)ccc4n(-c4ccccc4)c3cc21] | 82% |

-continued

| | Reactant | Product | Yield |
|---|---|---|---|
| h11 | 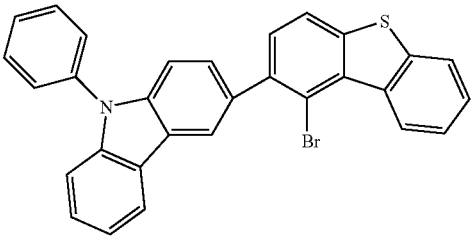 [SMILES: Brc1c(-c2ccc3c(c2)c2ccccc2n3-c2ccccc2)ccc2sc3ccccc3c12] | 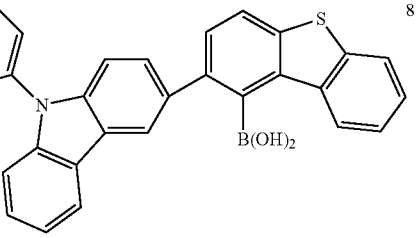 | 81% | j) 2-Dibenzofuran-1-yl-4-phenyl-quinazoline

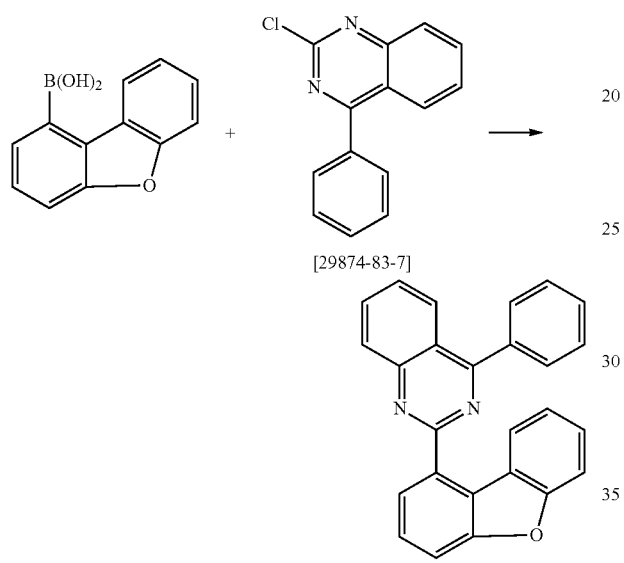

[29874-83-7]

23 g (110.0 mmol) of dibenzofuran-1-boronic acid, 29.5 g (110.0 mmol) of 2-chloro-4-phenyl-quinazoline and 26 g (210.0 mmol) of sodium carbonate are suspended in 500 ml of ethylene glycol diamine ether and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/heptane. The yield is 32 g (86 mmol), corresponding to 80% of theory.

The following compounds were prepared analogously:

| | Reactant 1 | Reactant 2 | Product | Yield |
|---|---|---|---|---|
| j1 | 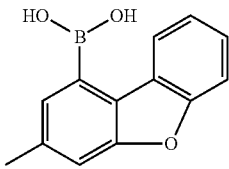 [SMILES: Cc1cc(B(O)O)c2c(c1)oc1ccccc12] | 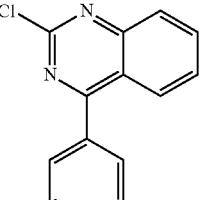 [29874-83-7] | 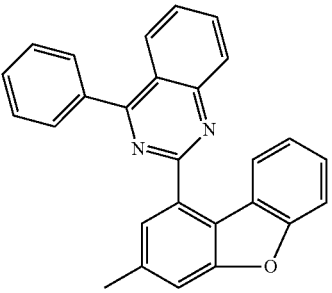 [SMILES: Cc1cc(-c2nc(-c3ccccc3)c3ccccc3n2)c2c(c1)oc1ccccc12] | 78% |
| j2 | 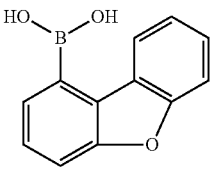 [SMILES: OB(O)c1cccc2oc3ccccc3c12] | 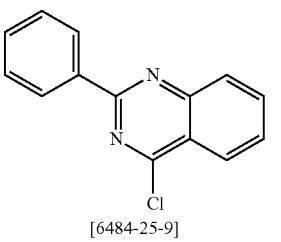 [6484-25-9] | 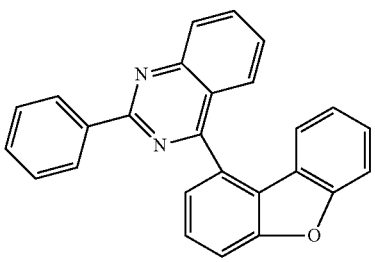 [SMILES: c1ccc(-c2nc(-c3cccc4oc5ccccc5c34)c3ccccc3n2)cc1] | 70% |

-continued

| | Reactant 1 | Reactant 2 | Product | Yield |
|---|---|---|---|---|
| j3 | (dibenzofuran-1-yl)boronic acid | 2-chloro-4-(3-cyanophenyl)quinazoline [1292317-90-8] | 4-phenyl-2-(dibenzofuran-1-yl)quinazoline derivative | 71% |
| j4 | (dibenzothiophen-1-yl)boronic acid | 2-chloro-4-phenylquinazoline [29874-83-7] | 4-phenyl-2-(dibenzothiophen-1-yl)quinazoline | 77% |
| j5 | (dibenzothiophen-1-yl)boronic acid | 4-chloro-2-phenylquinazoline [6484-25-9] | 2-phenyl-4-(dibenzothiophen-1-yl)quinazoline | 76% |
| j6 | (9,9-dimethyl-9H-fluoren-4-yl)boronic acid | 2-chloro-4-phenylquinazoline [29874-83-7] | 4-phenyl-2-(9,9-dimethyl-9H-fluoren-4-yl)quinazoline | 74% |

-continued

| Reactant 1 | Reactant 2 | Product | Yield |
|---|---|---|---|
| j7 | [29874-83-7] | | 75% |
| j8 | [6484-25-9] | | 71% |
| j9 | [29874-83-7] | | 64% |

| Reactant 1 | Reactant 2 | Product | Yield |
|---|---|---|---|
| j10 | [29874-83-7] | | 59% |
| j11 | [760212-40-6] | | 67% |
| j12 | [30169-34-7] | | 71% | i) 2-(8-bromo-dibenzofuran-1-yl)-4-phenyl-quinazoline

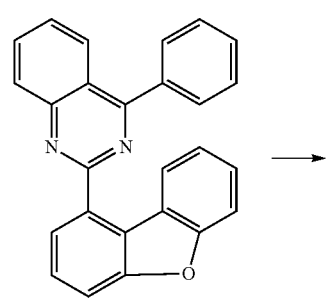

→

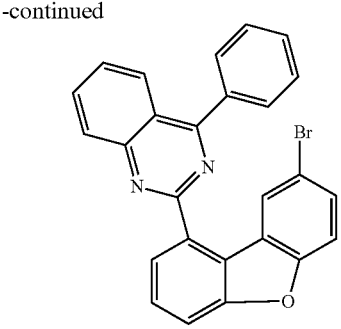

70.6 g (190.0 mmol) of 2-dibenzofuran-1-yl-4-phenylquinazoline are suspended in 2000 ml of acetic acid (100%) and 2000 ml of sulfuric acid (95-98%). 34 g (190 mmol) of NBS are added in portions to this suspension, and the mixture is stirred in the dark for 2 hours. Water/ice are then added, and the solid is separated off and rinsed with ethanol. The residue is recrystallised from toluene. The yield is 59 g (130 mmol), corresponding to 69% of theory.

In the case of the thiophene derivatives, nitrobenzene is employed instead of sulfuric acid and elemental bromine is employed instead of NBS.

The following compounds were prepared analogously:
| | Reactant | Product | Yield |
|---|---|---|---|
| i1 | 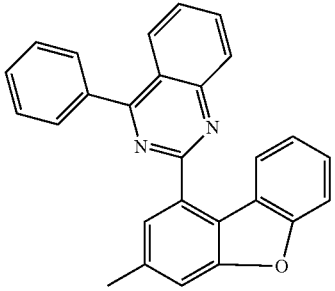 [SMILES: Cc1cc(-c2nc(-c3ccccc3)c3ccccc3n2)c2c(c1)oc1ccccc12] | 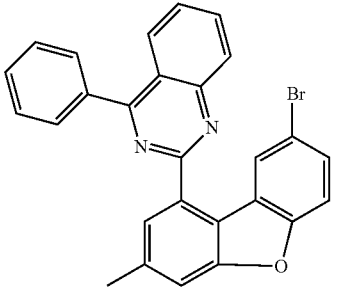 [SMILES: Cc1cc(-c2nc(-c3ccccc3)c3ccccc3n2)c2c(c1)oc1ccc(Br)cc12] | 70% |
| i2 | 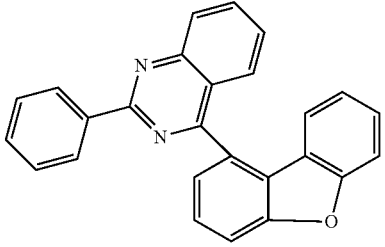 [SMILES: c1ccc(-c2nc(-c3cccc4oc5ccccc5c34)c3ccccc3n2)cc1] | 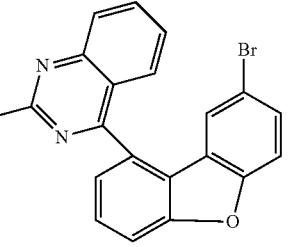 | 73% |
| i3 | 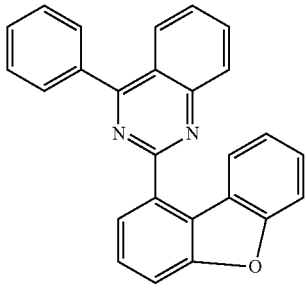 [SMILES: c1ccc(-c2nc(-c3cccc4oc5ccccc5c34)nc3ccccc23)cc1] | 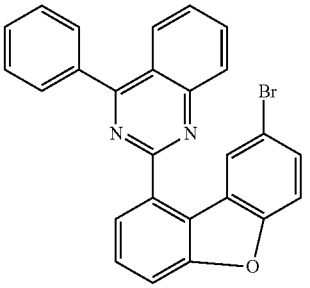 [SMILES: Brc1ccc2oc3cccc(-c4nc(-c5ccccc5)c5ccccc5n4)c3c2c1] | 71% |
| i4 | 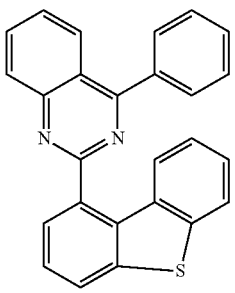 [SMILES: c1ccc(-c2nc(-c3cccc4sc5ccccc5c34)nc3ccccc23)cc1] | 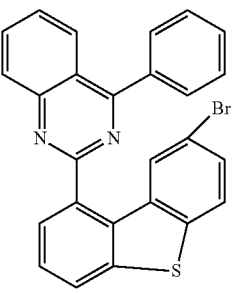 [SMILES: Brc1ccc2sc3cccc(-c4nc(-c5ccccc5)c5ccccc5n4)c3c2c1] | 62% |
| i5 | 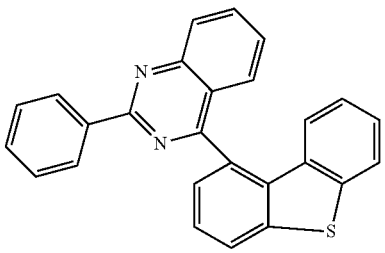 [SMILES: c1ccc(-c2nc(-c3cccc4sc5ccccc5c34)c3ccccc3n2)cc1] | 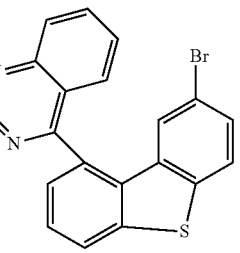 | 60% |

-continued

| Reactant | Product | Yield |
|---|---|---|
| i6 | | 65% |
| i7 | | 69% | k) 9-Phenyl-3-[9-(4-phenyl-quinazolin-2-yl)-dibenzofuran-2-yl]-9H-carbazole

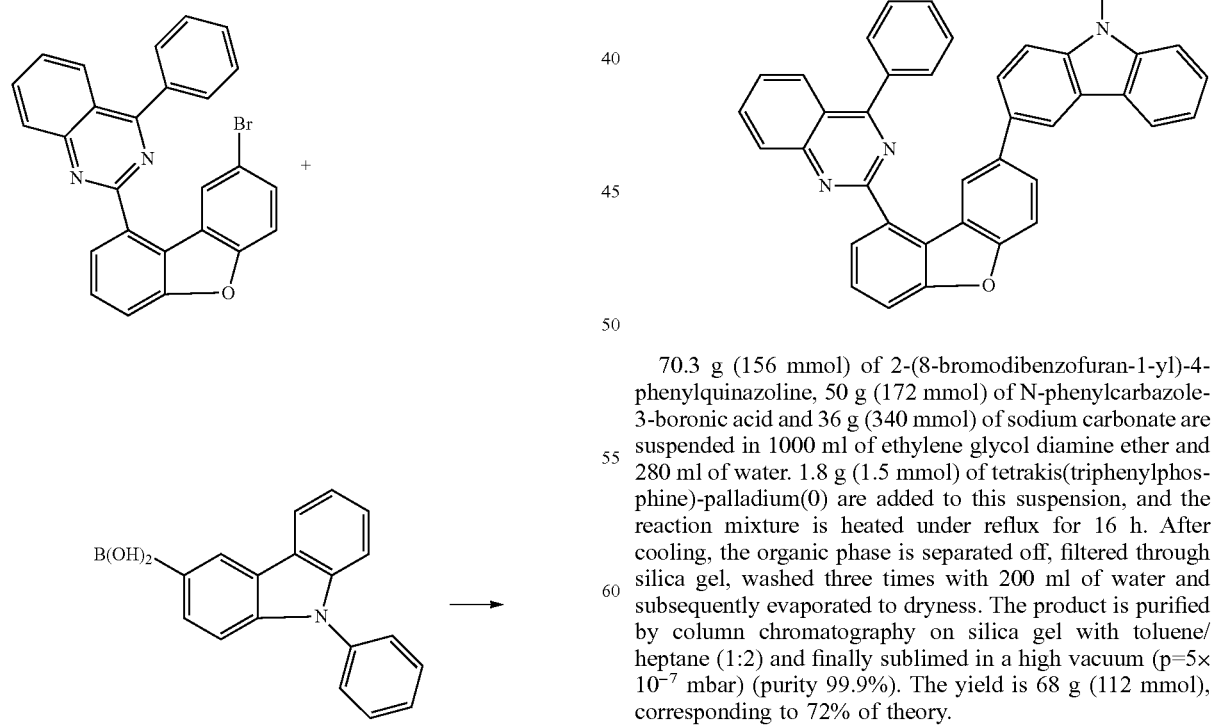

-continued 70.3 g (156 mmol) of 2-(8-bromodibenzofuran-1-yl)-4-phenylquinazoline, 50 g (172 mmol) of N-phenylcarbazole-3-boronic acid and 36 g (340 mmol) of sodium carbonate are suspended in 1000 ml of ethylene glycol diamine ether and 280 ml of water. 1.8 g (1.5 mmol) of tetrakis(triphenylphosphine)-palladium(0) are added to this suspension, and the reaction mixture is heated under reflux for 16 h. After cooling, the organic phase is separated off, filtered through silica gel, washed three times with 200 ml of water and subsequently evaporated to dryness. The product is purified by column chromatography on silica gel with toluene/heptane (1:2) and finally sublimed in a high vacuum (p=5× $10^{-7}$ mbar) (purity 99.9%). The yield is 68 g (112 mmol), corresponding to 72% of theory.

The following compounds were prepared analogously:

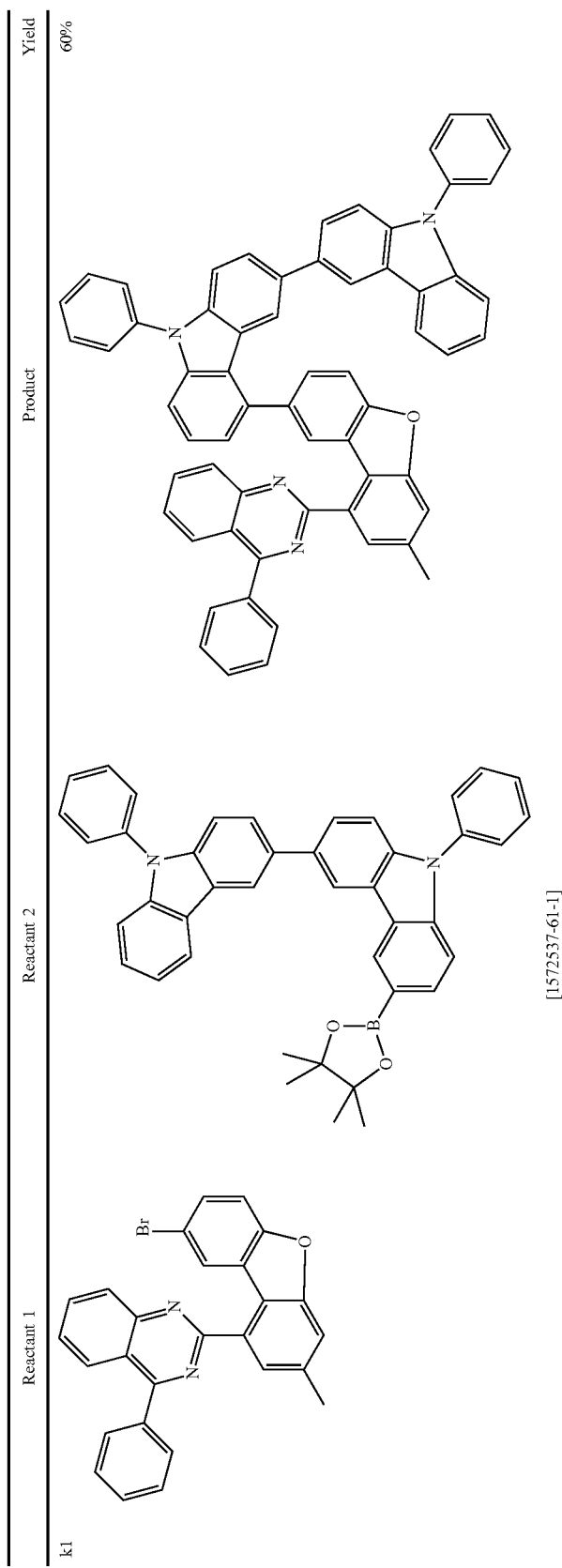

-continued
| | Reactant 1 | Reactant 2 | Product | Yield |
|---|---|---|---|---|
| k2 | 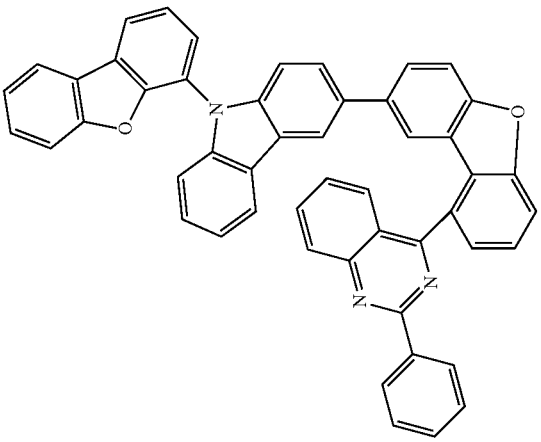 | 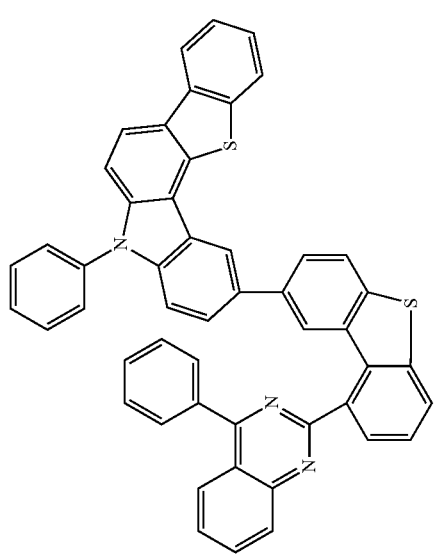 [1547397-15-8] | 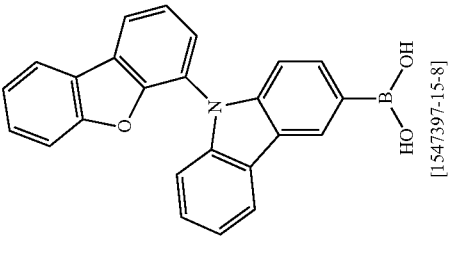 | 65% |
| k4 | 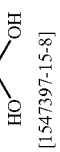 | 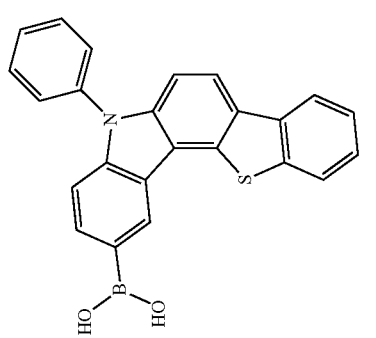 [1391729-63-7] | 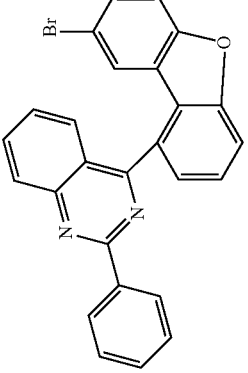 | 53% |

| | Reactant 1 | Reactant 2 | Product | Yield |
|---|---|---|---|---|
| k5 | | [1379585-25-7] | | 58% |
| k6 | | [1373359-67-1] | | 52% |

-continued

| | Reactant 1 | Reactant 2 | Product | Yield |
|---|---|---|---|---|
| k7 | | 854952-58-2 | | 69% |
| k8 | | [1314019-74-3] | | 67% |

-continued

| | Reactant 1 | Reactant 2 | Product | Yield |
|---|---|---|---|---|
| k9 | | [854952-60-6] | | 69% |
| k10 | | [854952-60-6] | | 55% |

-continued
| | Reactant 1 | Reactant 2 | Product | Yield |
|---|---|---|---|---|
| k11 | 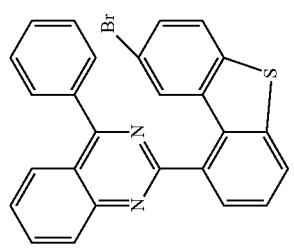 | 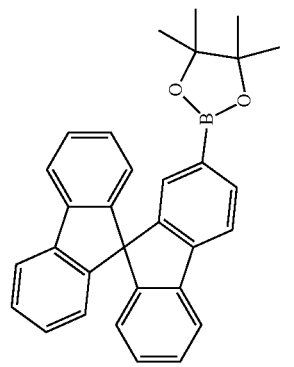 [1557257-88-1] | 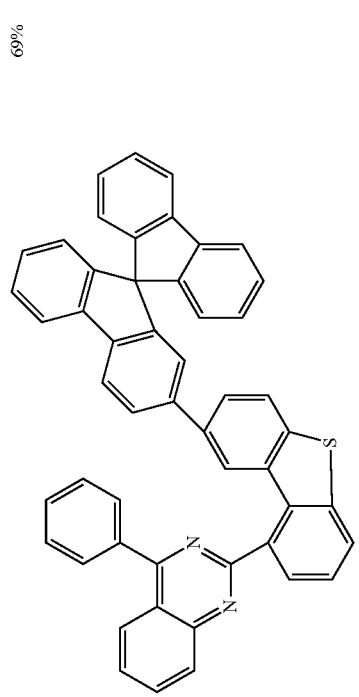 | 69% |
| k12 | 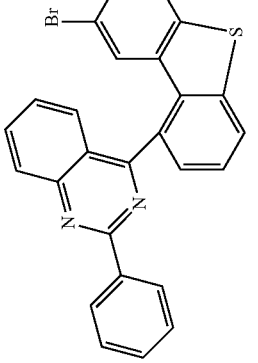 | 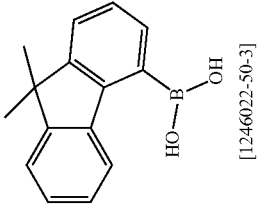 [1246022-50-3] | 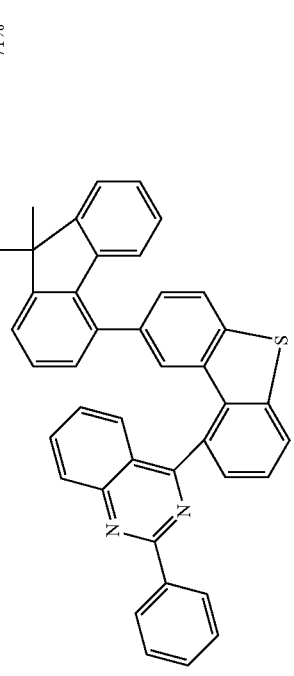 | 71% |
| k13 | 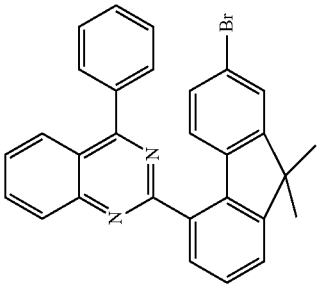 | 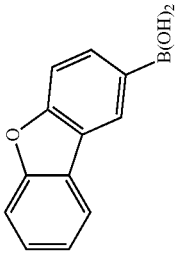 [402936-15-6] | 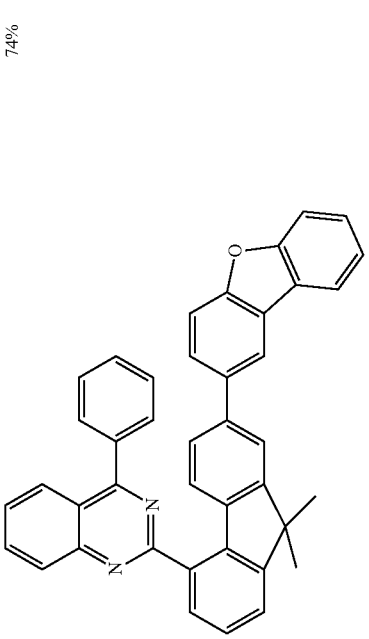 | 74% |

-continued
| | Reactant 1 | Reactant 2 | Product | Yield |
|---|---|---|---|---|
| k14 | 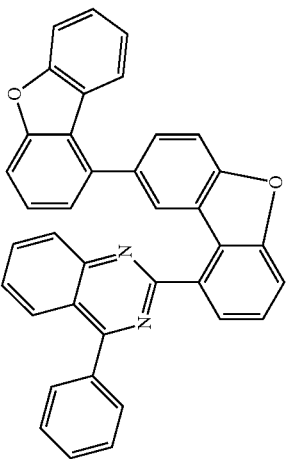 | 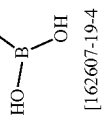  [162607-19-4] | 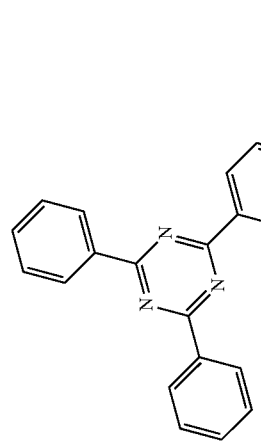 | 67% |
| k15 | 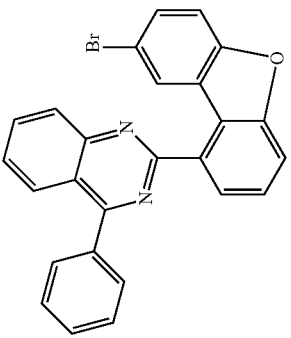 | 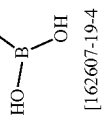 | 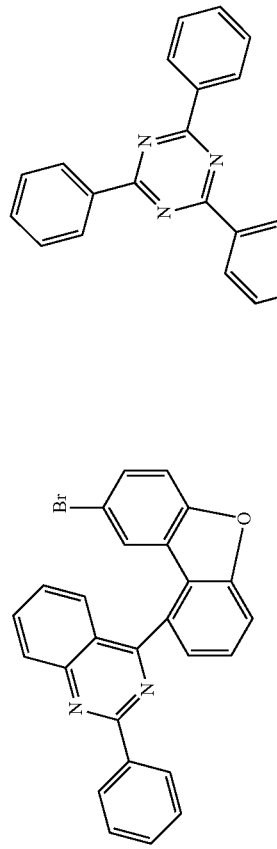 | 65% |

-continued

| | Reactant 1 | Reactant 2 | Product | Yield |
|---|---|---|---|---|
| k16 | | [1572537-61-1] | | 82% |
| k17 | | 854952-58-2 | | 51% |

| | Reactant 1 | Reactant 2 | Product | Yield |
|---|---|---|---|---|
| k18 | | [1556069-50-1] | | 62% |
| k19 | | [1434286-69-7] | | 77% |

-continued
| | Reactant 1 | Reactant 2 | Product | Yield |
|---|---|---|---|---|
| k20 | 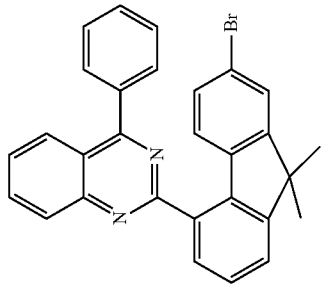 | 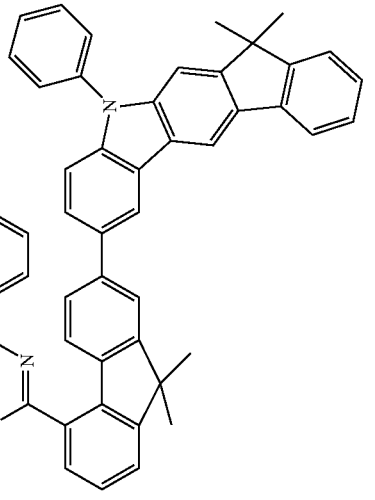 [1379585-25-7] | 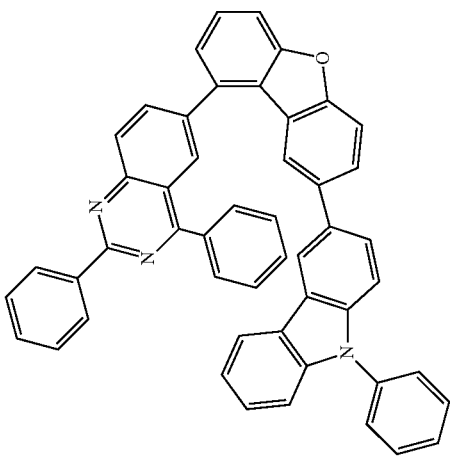 | 64% |
| k21 | 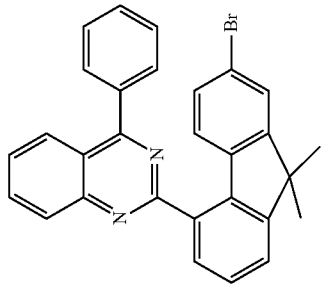 | 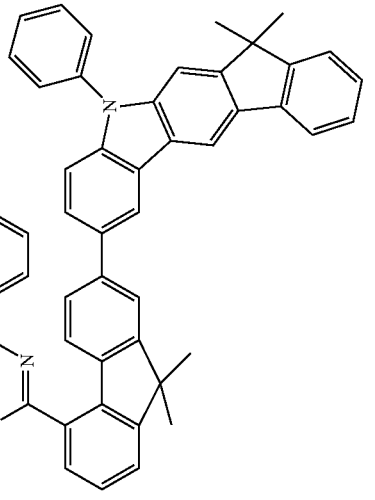 854952-58-2 | 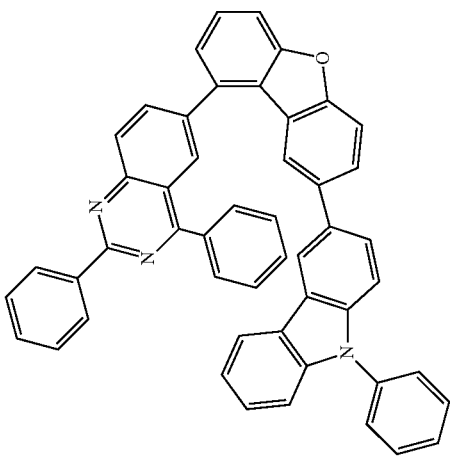 | 72% |

| | Reactant 1 | Reactant 2 | Product | Yield |
|---|---|---|---|---|
| k22 | 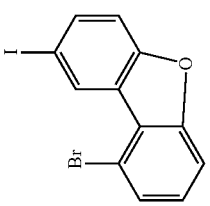 | 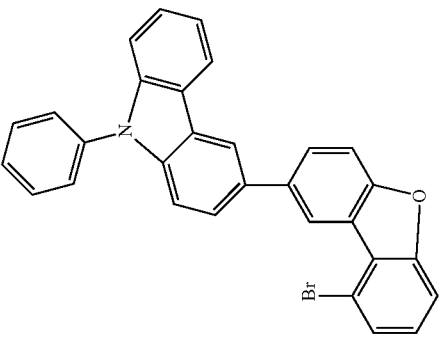 854952-58-2 | 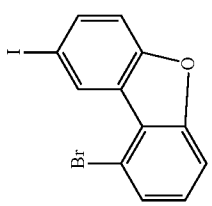 | 66% |
| k23 | 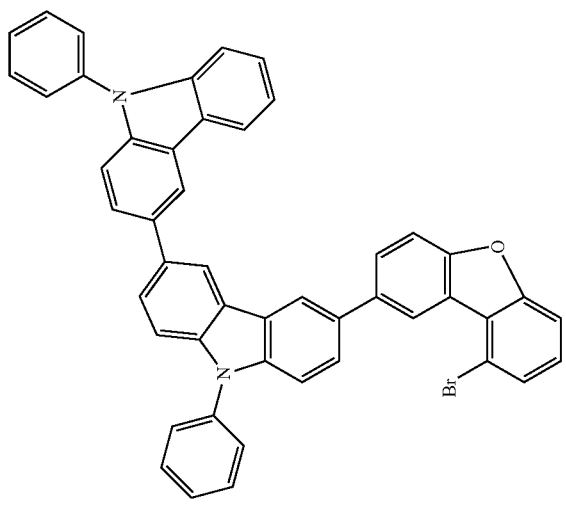 | 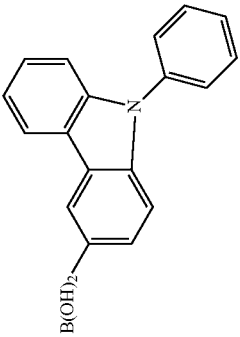 [1572537-61-1] | 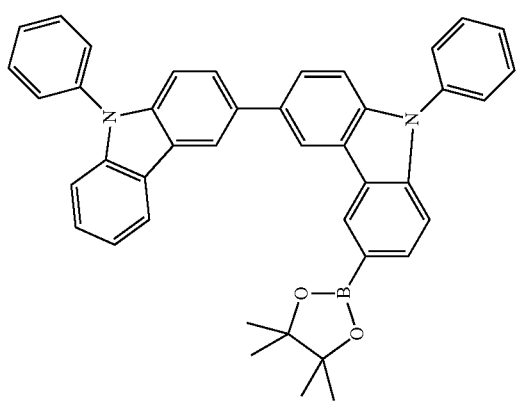 | 75% |

-continued

| | Reactant 1 | Reactant 2 | Product | Yield |
|---|---|---|---|---|
| k24 | | 854952-58-2 | | 78% |
| k25 | | 854952-58-2 | | 70% |

-continued
| | Reactant 1 | Reactant 2 | Product | Yield |
|---|---|---|---|---|
| k26 | 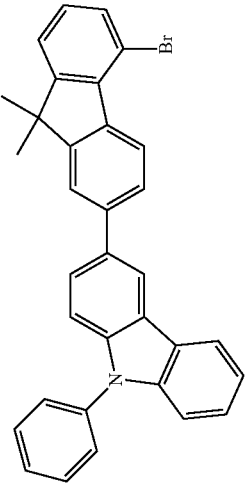 | 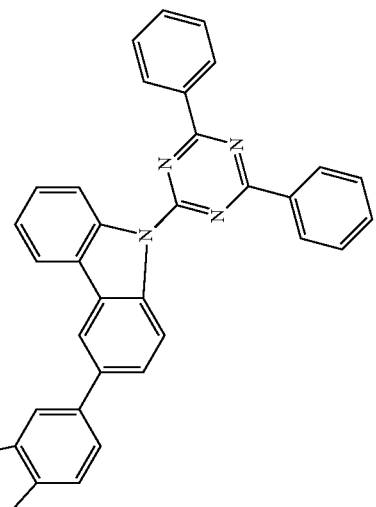
854952-58-2 | | 76% |
| k27 | 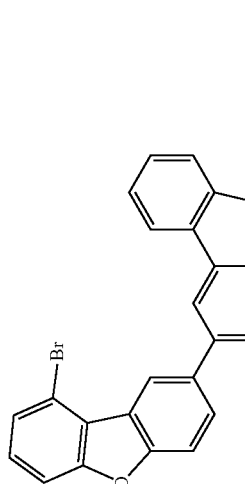 | 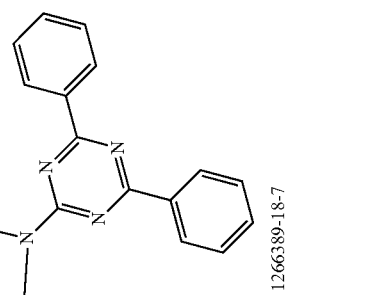
1266389-18-7 | | 70% |

| | Reactant 1 | Reactant 2 | Product | Yield |
|---|---|---|---|---|
| k28 | | 1246562-39-9 | | 74% |
| k29 | | 1357572-68-9 | | 73% |

| | Reactant 1 | Reactant 2 | Product | Yield |
|---|---|---|---|---|
| k30 | 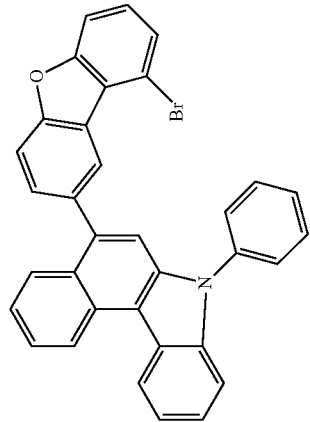 | 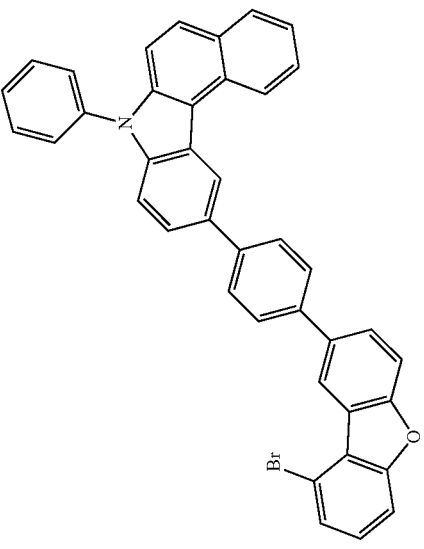 1357573-03-5 | 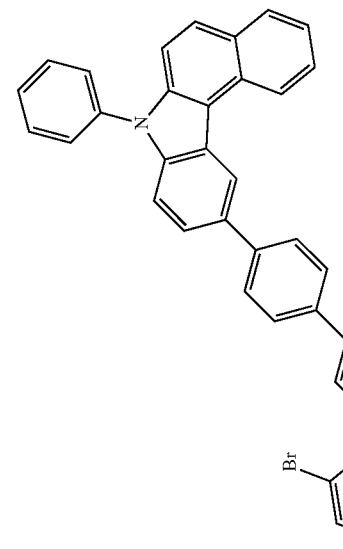 | 72% |
| k31 | 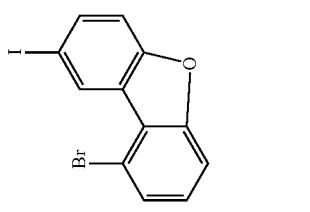 | 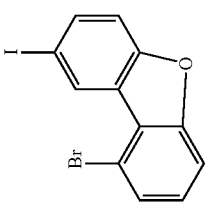 1426392-81-5 | 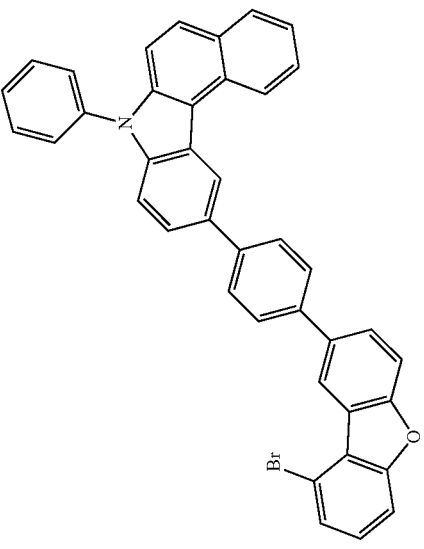 | 69% |

1) 8-(9-phenyl-9H-carbazol-3-yl)-dibenzofuran-1-boronic acid

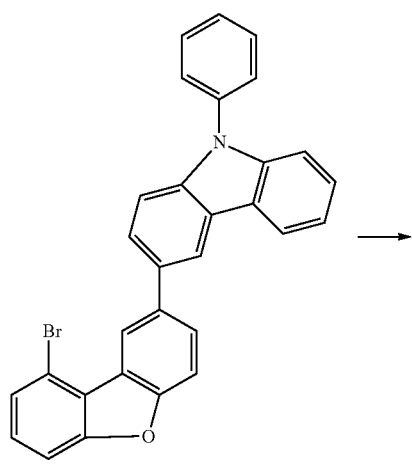

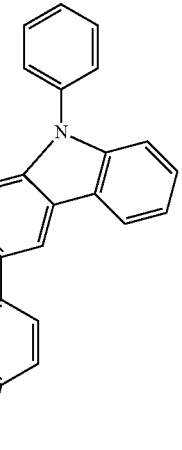

20 g (182 mmol) of 3-(9-bromodibenzofuran-2-yl)-9-phenyl-9H-carbazole are dissolved in 400 ml of dry THF and cooled to −78° C. 77 ml (190 mmol/2.5 M in hexane) of n-butyllithium are added over the course of about 5 min. at this temperature, and the mixture is subsequently stirred at −78° C. for a further 2.5 h. 38 g (365 mmol) of trimethyl borate are added as rapidly as possible at this temperature, and the reaction is slowly allowed to come to RT (about 18 h). The reaction solution is washed with water, and the solid which has precipitated out and the organic phase are dried azeotropically with toluene. The crude product is washed by stirring with toluene/methylene chloride at about 40° C. and filtered off with suction. Yield: 16.7 g (690 mmol), 90% of theory.

The following compounds were prepared analogously:

| | Reactant | Product | Yield |
|---|---|---|---|
| l1 | | | 81% |

-continued
| | Reactant | Product | Yield |
|---|---|---|---|
| 12 | 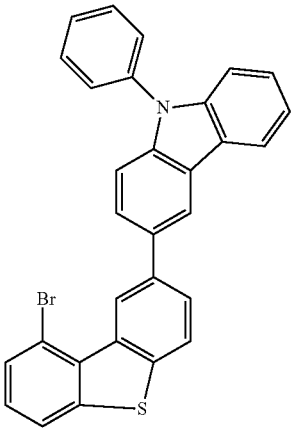 [SMILES: Brc1cccc2sc3ccc(-c4ccc5c(c4)c4ccccc4n5-c4ccccc4)cc3c12] | 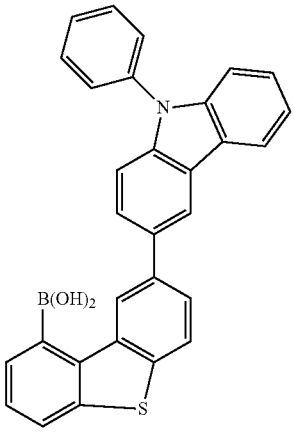 | 84% |
| 13 | 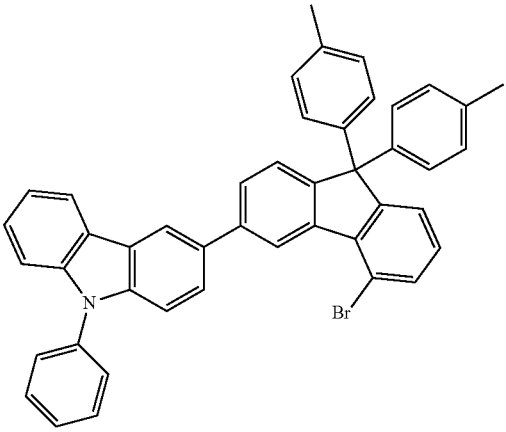 [SMILES: Cc1ccc(C2(c3ccc(C)cc3)c3ccc(-c4ccc5c(c4)c4ccccc4n5-c4ccccc4)cc3-c3c(Br)cccc32)cc1] | 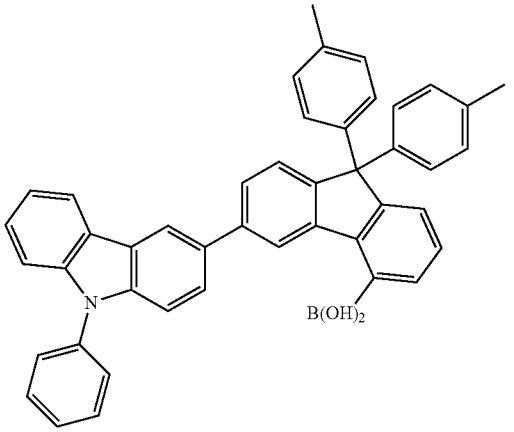 [SMILES: Cc1ccc(C2(c3ccc(C)cc3)c3ccc(-c4ccc5c(c4)c4ccccc4n5-c4ccccc4)cc3-c3c(B(O)O)cccc32)cc1] | 78% |
| 14 | 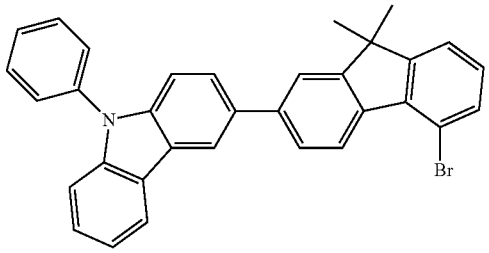 [SMILES: CC1(C)c2cc(-c3ccc4c(c3)c3ccccc3n4-c3ccccc3)ccc2-c2c(Br)cccc21] | 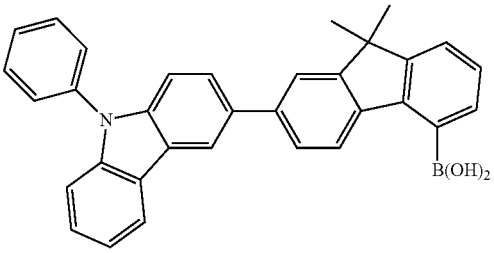 [SMILES: CC1(C)c2cc(-c3ccc4c(c3)c3ccccc3n4-c3ccccc3)ccc2-c2c(B(O)O)cccc21] | 77% |
| 15 | 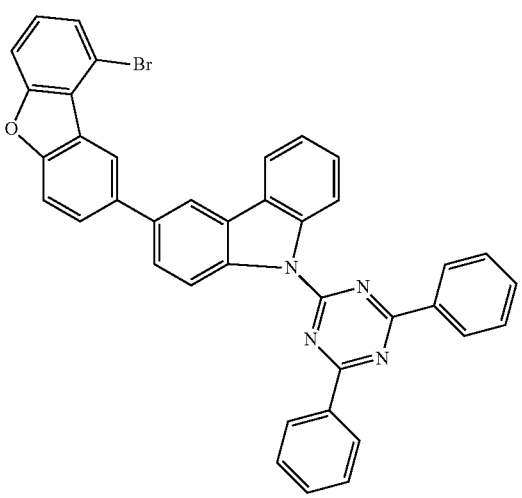 [SMILES: Brc1cccc2oc3ccc(-c4ccc5c(c4)c4ccccc4n5-c4nc(-c5ccccc5)nc(-c5ccccc5)n4)cc3c12] | 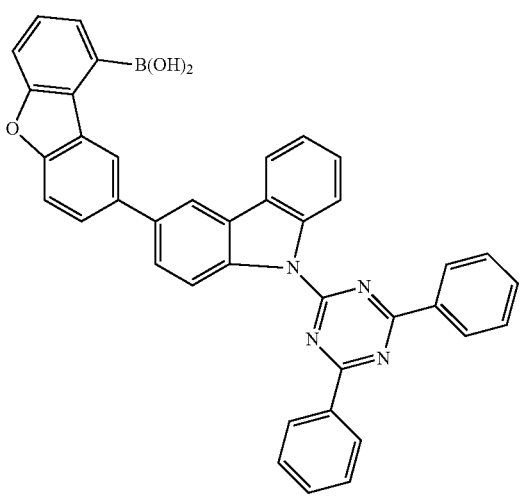 [SMILES: OB(O)c1cccc2oc3ccc(-c4ccc5c(c4)c4ccccc4n5-c4nc(-c5ccccc5)nc(-c5ccccc5)n4)cc3c12] | 72% |

-continued

| | Reactant | Product | Yield |
|---|---|---|---|
| 16 | | | 77% |
| 17 | | | 75% |
| 18 | | | 70% |
| 19 | | | 71% | m) 3-[9-(4-biphenyl-4-yl-quinazolin-2-yl)-dibenzo-furan-2-yl]-9-phenyl-9H-carbazole

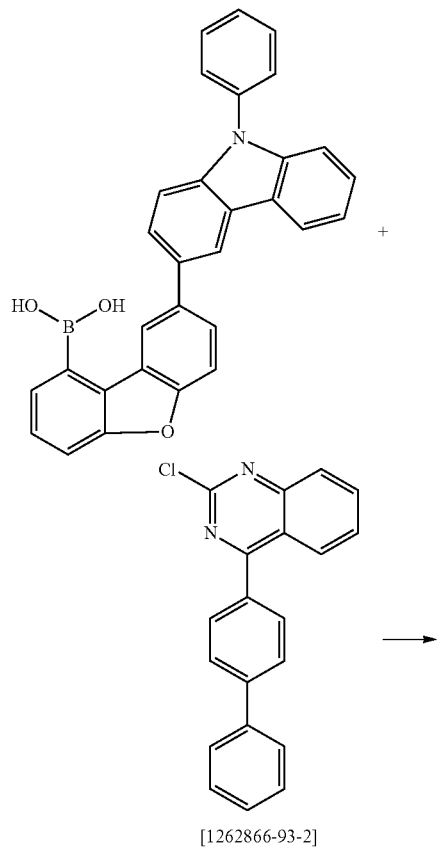

[1262866-93-2]

+

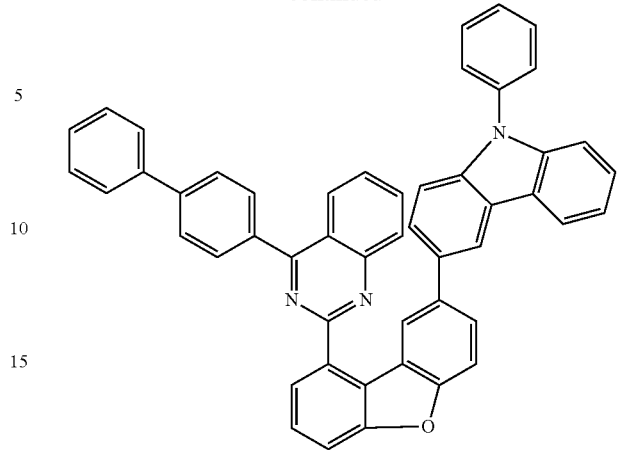

49.8 g (110.0 mmol) of 8-(9-phenyl-9H-carbazol-3-yl) dibenzofuran-1-boronic acid, 34 g (110.0 mmol) of 4-biphenyl-4-yl-2-chloroquinazoline and 26 g (210.0 mmol) of sodium carbonate are suspended in 500 ml of ethylene glycol diamine ether and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The product is purified by column chromatography on silica gel with toluene/heptane (1:2) and finally sublimed in a high vacuum (p=5× $10^{-7}$ mbar) (purity 99.9%). The yield is 60 g (87 mmol), corresponding to 80% of theory.

The following compounds were prepared analogously:

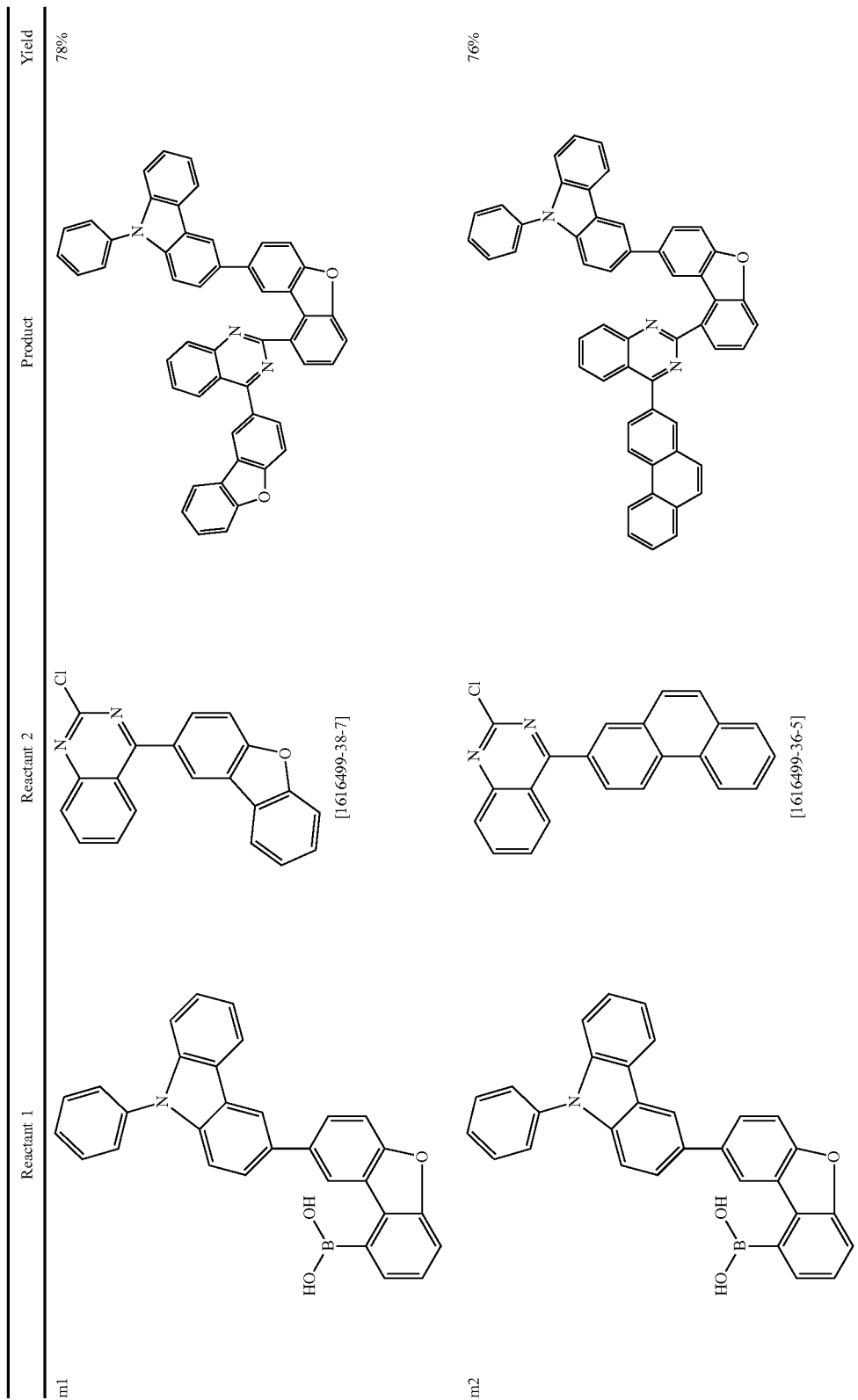

-continued

| Reactant 1 | Reactant 2 | Product | Yield |
|---|---|---|---|
| m3 | [1403252-58-3] | | 72% |
| m4 | [1373265-66-7] | | 69% |

-continued

| Reactant 1 | Reactant 2 | Product | Yield |
|---|---|---|---|
| m5 | [1373317-91-9] | | 81% |
| m6 | [643017-61-2] | | 88% |

-continued

| | Reactant 1 | Reactant 2 | Product | Yield |
|---|---|---|---|---|
| m7 | | [857206-12-3] | | 79% |
| m8 | | [760212-55-3] | | 75% |

| | Reactant 1 | Reactant 2 | Product | Yield |
|---|---|---|---|---|
| m9 | 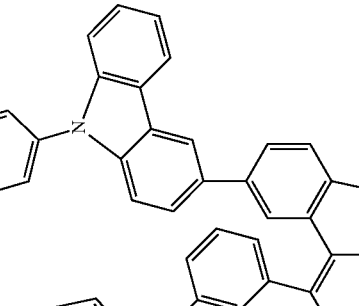 | 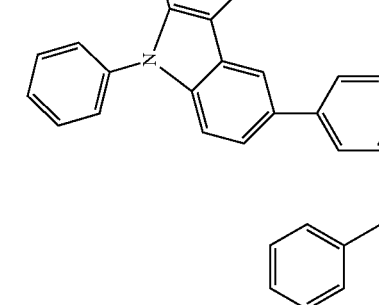 [1171247-63-4] | 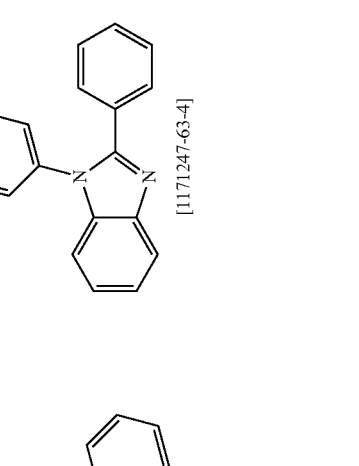 | 83% |
| m10 | 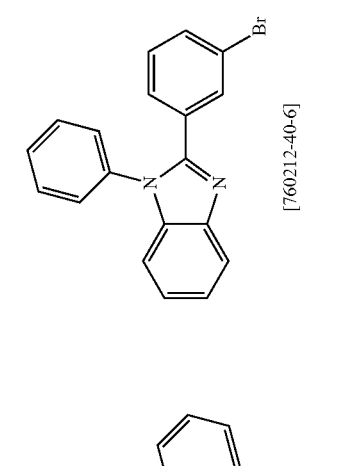 | 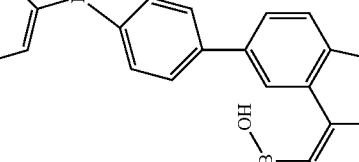 [760212-40-6] | 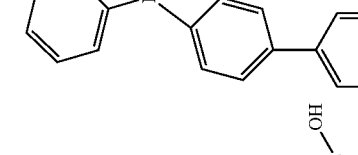 | 76% |

| | Reactant 1 | Reactant 2 | Product | Yield |
|---|---|---|---|---|
| m11 | 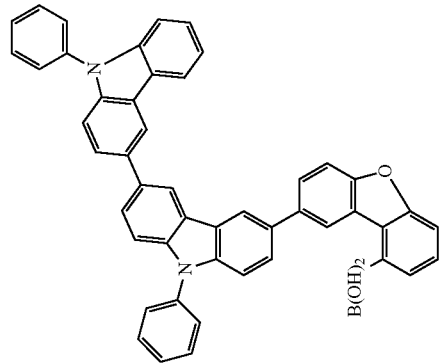 | 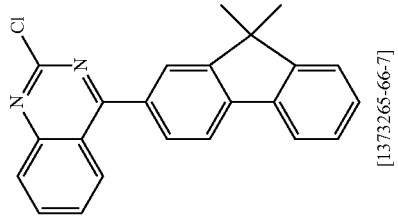 [1373265-66-7] | 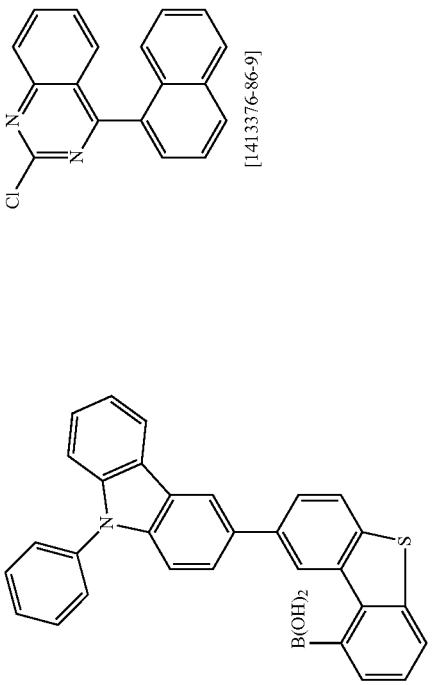 | 71% |
| m12 | 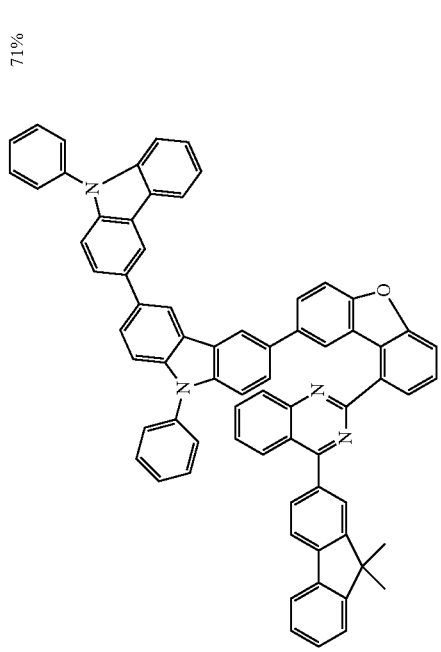 | 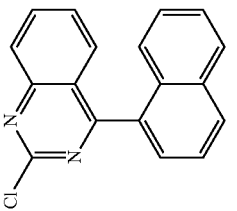 [1413376-86-9] | 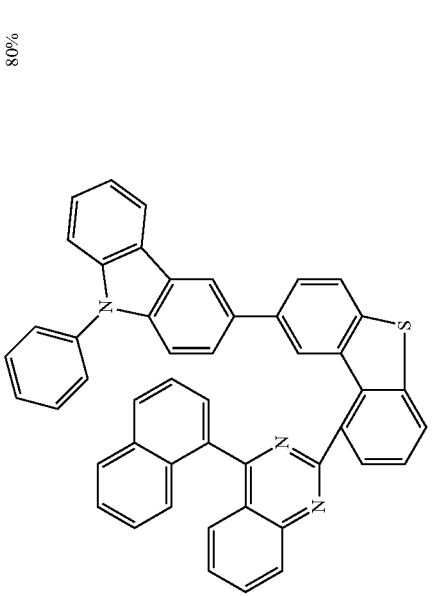 | 80% |

-continued

| | Reactant 1 | Reactant 2 | Product | Yield |
|---|---|---|---|---|
| m13 | | [14003252-55-0] | | 75% |
| m14 | | [5855-56-1] | | 74% |

-continued

| | Reactant 1 | Reactant 2 | Product | Yield |
|---|---|---|---|---|
| m15 | (structure with B(OH)₂-fluorene-carbazole) | (3-bromophenyl-N-phenylbenzimidazole) [760212-40-6] | (product structure) | 73% |
| m16 | (carbazole-dibenzothiophene-B(OH)₂ structure) | (6-chloro-2,4-diphenylquinazoline) [30169-34-7] | (product structure) | 69% |

| Reactant 1 | Reactant 2 | Product | Yield |
|---|---|---|---|
| m17 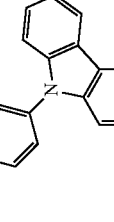 | 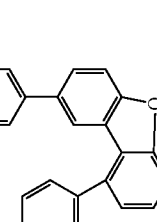 [1257084-12-0] | 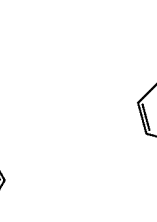 | 59% |
| m18  | m17 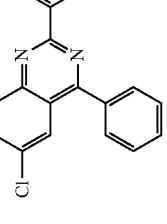 |  | 73% |

| Reactant 1 | Reactant 2 | Product | Yield |
|---|---|---|---|
| m19 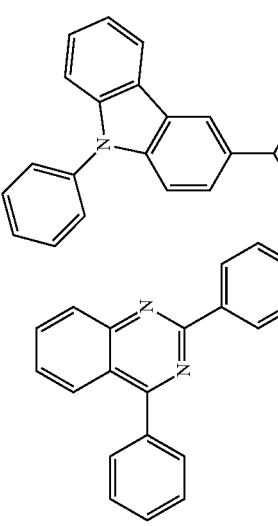 | 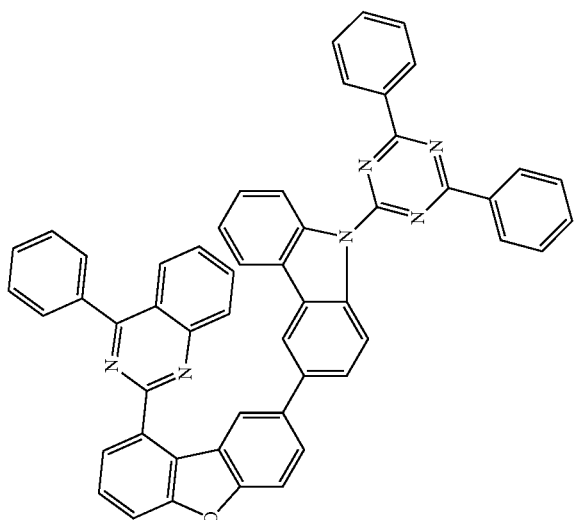 [540466-42-0] | 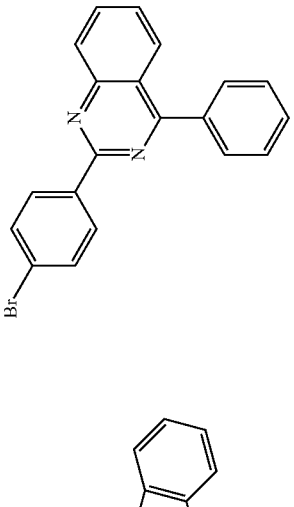 | 78% |
| m20 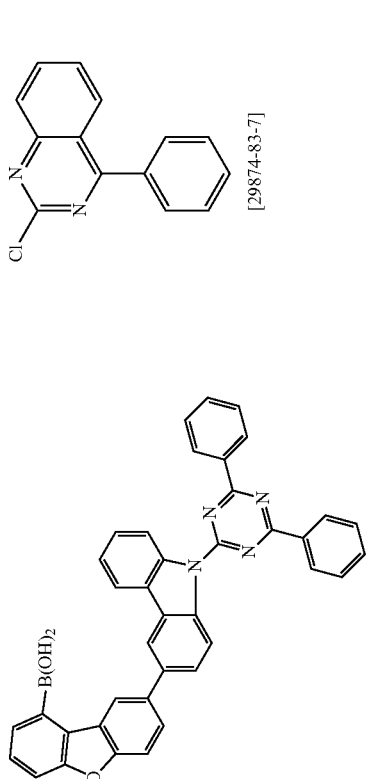 | [29874-83-7] | | 70% |

-continued
| | Reactant 1 | Reactant 2 | Product | Yield |
|---|---|---|---|---|
| m21 | 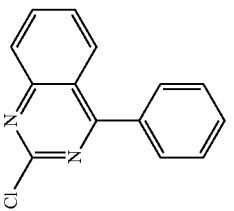 | 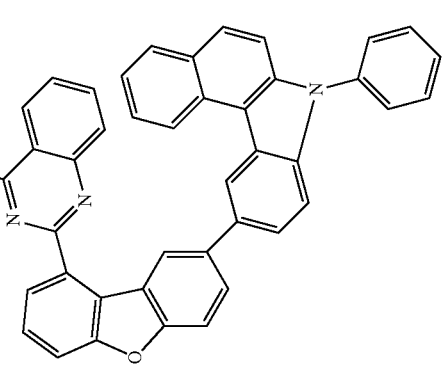 [29874-83-7] | 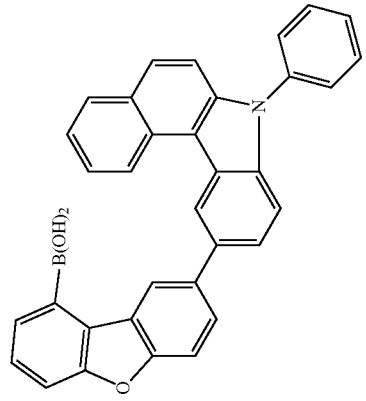 | 73% |
| m22 | 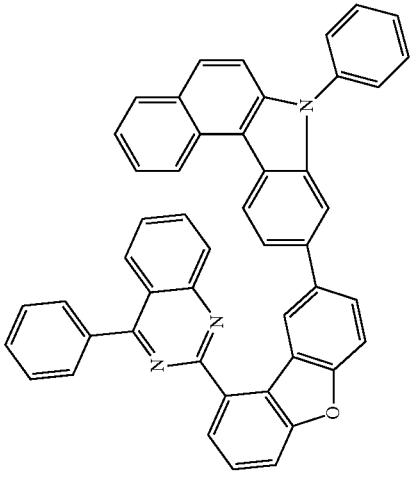 | 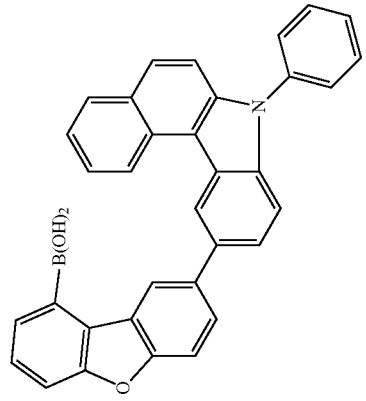 [29874-83-7] | 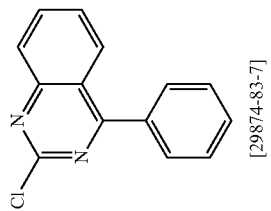 | 67% |

-continued

| | Reactant 1 | Reactant 2 | Product | Yield |
|---|---|---|---|---|
| m23 | (dibenzofuran-B(OH)₂ with N-phenyl benzo-fused carbazole substituent) | 2-chloro-4-phenylquinazoline [29874-83-7] | (corresponding coupled product) | 68% |
| m24 | (dibenzofuran-B(OH)₂ with N-phenyl benzo-fused carbazole substituent) | 4-chloro-2-phenylquinazoline [6484-25-9] | (corresponding coupled product) | 76% |

| | Reactant 1 | Reactant 2 | Product | Yield |
|---|---|---|---|---|
| m25 | | [6484-25-9] | | 79% |
| m26 | | [6484-25-9] | | 77% |

| | Reactant 1 | Reactant 2 | Product | Yield |
|---|---|---|---|---|
| m27 | 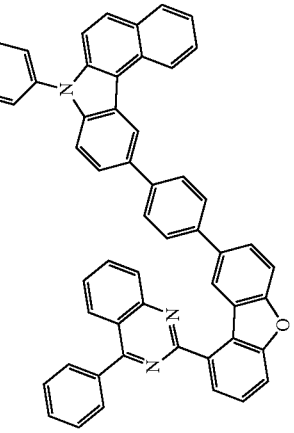 | 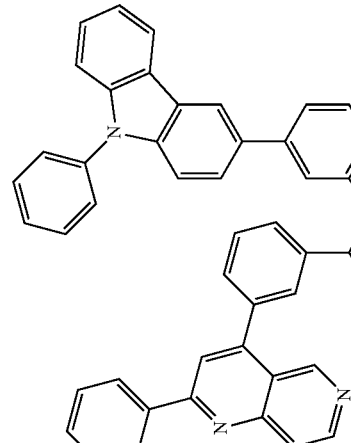 | | 78% |
| m30 | 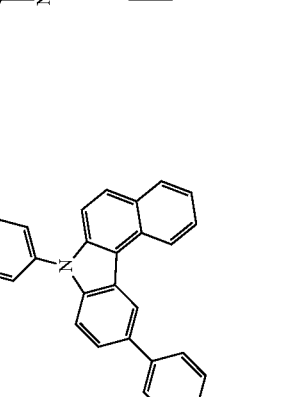 | 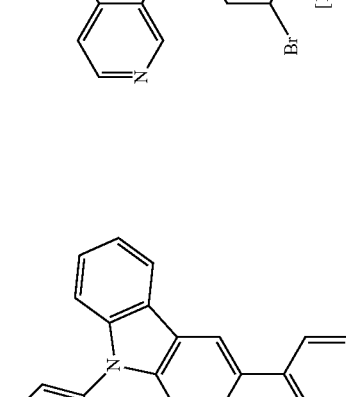 | | 75% |

-continued

| Reactant 1 | Reactant 2 | Product | Yield |
|---|---|---|---|
| m31 | [1632307-97-1] | | 76% |
| m32 | [1632307-96-0] | | 78% |

| | Reactant 1 | Reactant 2 | Product | Yield |
|---|---|---|---|---|
| m33 | 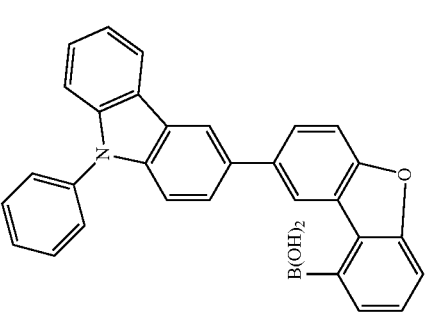 | 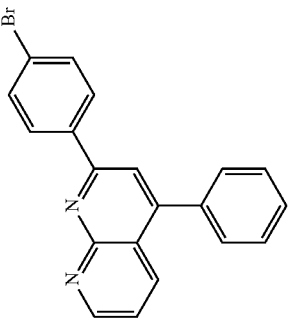  [1632294-77-9] | 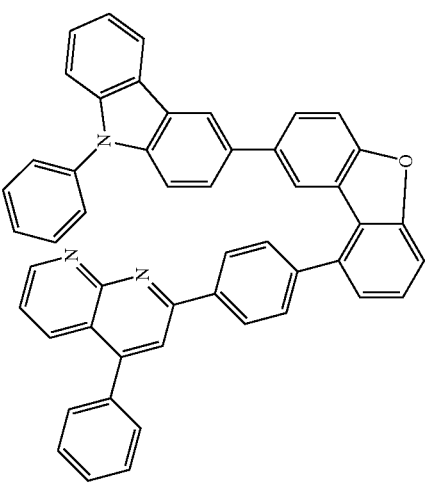 | 73% | n) 3-(9-benzimidazol-1-yl-dibenzofuran-2-yl)-9-phenyl-9H-carbazole

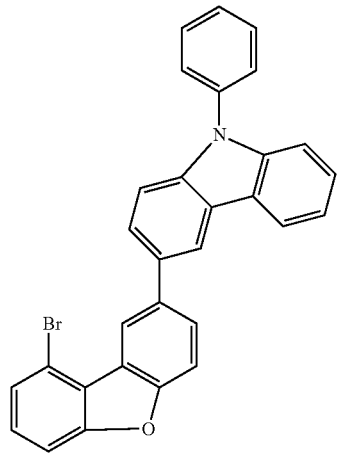

k21

+

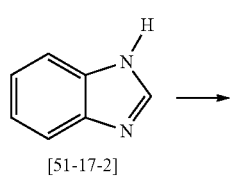

[51-17-2]

→

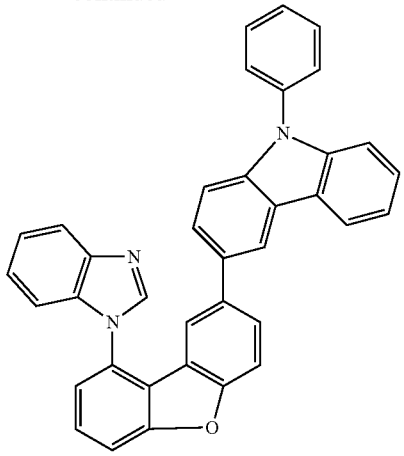

10 g (84.7 mmol) of benzimidazole, 42 g (127.4 mmol) of $CsCO_3$, 2.4 g (14.7 mmol) of CuI and 30.7 g (63 mmol) of 3-(9-bromodibenzofuran-2-yl)-9-phenyl-9H-carbazole are suspended in 100 ml of degassed DMF under a protective gas, and the reaction mixture is heated under reflux at 120° C. for 40 h. After cooling, the solvent is removed in vacuo, the residue is dissolved in dichloromethane, and water is added. The organic phase is then separated off and filtered through silica gel. The yield is 28 g (53 mmol), corresponding to 87% of theory.

The following compounds are prepared analogously:

| | Reactant 1 | Reactant 2 | Product | Yield |
|---|---|---|---|---|
| n1 | k22 | [51-17-2] | | 80% |

| Reactant 1 | Reactant 2 | Product | Yield |
|---|---|---|---|
| n2 k23 | [51-17-2] | | 83% |
| n3 k24 | [51-17-2] | | 79% |
| n4 K25 | [51-17-2] | | 86% | o) 9-phenyl-3-[9-(2-phenyl-benzimidazol-1-yl)-dibenzofuran-2-yl]-9H-carbazole

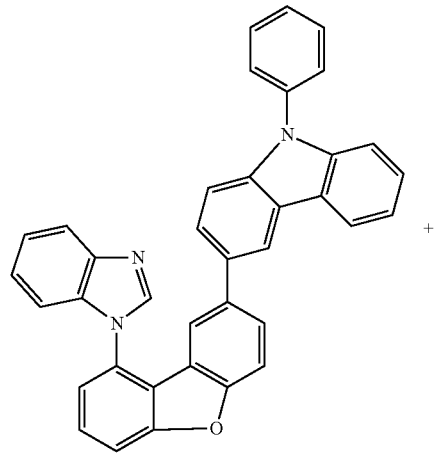

+

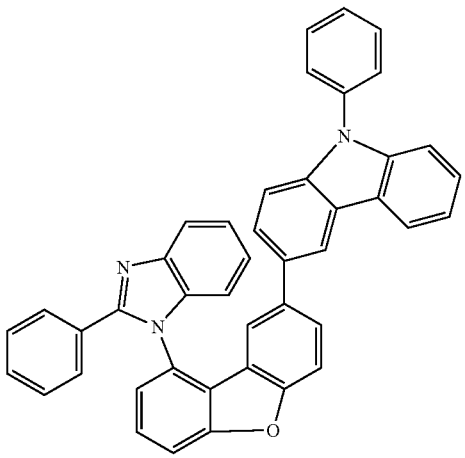

26 g (50 mmol) of 3-(9-benzimidazol-1-yldibenzofuran-2-yl)-9-phenyl-9H-carbazole, 560 mg (25 mmol) of Pd(OAc)$_2$, 19.3 g (118 mmol) of CuI and 20.8 g (100 mmol) of iodobenzene are suspended in 300 ml of degassed DMF under a protective gas, and the reaction mixture is heated under reflux at 140° C. for 24 h. After cooling, the solvent is removed in vacuo, the residue is dissolved in dichloromethane, and water is added. The organic phase is then separated off and filtered through silica gel. The product is purified by column chromatography on silica gel with toluene/heptane (1:2) and finally sublimed in a high vacuum (p=5×10$^{-7}$ mbar) (purity 99.9%). The yield is 17.8 g (30 mmol), corresponding to 60% of theory.

The following compounds were prepared analogously:

| | Reactant 1 | Reactant 2 | Product | Yield |
|---|---|---|---|---|
| o1 | | 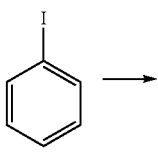  [144981-85-1] | | 55% |

-continued

| Reactant 1 | Reactant 2 | Product | Yield |
|---|---|---|---|
| o2 | I-Ph | | 53% |
| o3 | [65344-26-5] | | 47% |
| o4 | I-Ph | | 44% |
| o5 | I-Ph | | 51% |

Fabrication of OLEDs

The following examples V1-V7 and E1-E11 (see Table 1 and 2) show data for various OLEDs.

Substrate pre-treatment of examples V1-7 and E1-E1a: Glass plates with structured ITO (50 nm, indium tin oxide) form the substrates on which the OLEDs are processed. Before evaporation of the OLED materials, the substrates are pre-baked for 15 minutes at 250° C., followed by an O₂ plasma treatment for 130 seconds.

The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The exact layer structure (and layer thickness) is denoted in Table 1. The materials used for the OLED fabrication are presented in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:M1:TEG1 (55%:35%:10%) here means that material IC1 is present in the layer in a proportion by volume of 55%, M1 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (CE1000, measured in cd/A at 1000 cd/m$^2$), the luminous efficacy (LE1000, measured in lm/W at 1000 cd/m$^2$), the external quantum efficiency (EQE1000, measured in % at 1000 cd/m$^2$) and the voltage (U1000, measured at 1000 cd/m$^2$ in V) are determined from current/voltage/luminance characteristic lines (IUL characteristic lines) assuming a Lambertian emission profile. The electroluminescence (EL) spectra are recorded at a luminous density of $10^3$ (1000) cd/m$^2$ and the CIE 1931 x and y coordinates are then calculated from the EL spectrum.

For selected experiments, the lifetime is determined. The lifetime is defined as the time after which the luminous density has dropped to a certain proportion from a certain initial luminous density $L_1$ when the OLED is driven at a constant current. The starting condition $L_0$; $j_0$=4000 cd/m$^2$ and $L_1$=70% in Table 2 indicates that the in column LT denoted lifetime corresponds to the time in hours (h) needed to fade the OLED from a starting luminous density of 4000 cd/m$^2$ to 2800 cd/m$^2$. Accordingly, the lifetime of the starting condition $L_0$; $j_0$=20 mA/cm$^2$, $L_1$=80% is the time needed to fade the OLED operated at the constant current of 20 mA/cm$^2$ to 80% of the initial luminous density.

The device data of various OLEDs is summarized in Table 2. The examples V1-V7 are comparison examples according to the state-of-the-art using comparison compounds XXCE1 to XXCE7. The examples E1-E11 show data of inventive OLEDs using inventive examples Inv-1 to Inv-11.

TABLE 1

OLED structure

| No. | HTL | IL | EBL | EML | HBL | ETL |
|-----|-----|----|----|-----|-----|-----|
| V1 | SpMA1 140 nm | — | — | XXCE1:TER4 (95%:5%) 40 nm | — | ST2:LiQ (50%:50%) 35 nm |
| V2 | SpA1 70 nm | HATCN 5 nm | SpMA1 110 nm | IC1:TEG1 (90%:10%) 30 nm | XXCE2 10 nm | ST2:LiQ (50%:50%) 30 nm |
| V3 | SpA1 70 nm | HATCN 5 nm | SpMA1 110 nm | IC1:TEG1 (90%:10%) 30 nm | XXCE3 10 nm | ST2:LiQ (50%:50%) 30 nm |
| V4 | SpMA1 140 nm | — | — | XXCE4:TER4 (95%:5%) 40 nm | — | ST2:LiQ (50%:50%) 35 nm |
| V5 | SpMA1 140 nm | — | — | XXCE5:TER4 (95%:5%) 40 nm | — | ST2:LiQ (50%:50%) 35 nm |
| V6 | SpMA1 140 nm | — | — | XXCE6:TER4 (95%:5%) 40 nm | — | ST2:LiQ (50%:50%) 35 nm |
| V7 | SpMA1 140 nm | — | — | IC1:TER4 (95%:5%) 40 nm | XXCE7 10 nm | ST2:LiQ (50%:50%) 25 nm |
| E1 | SpMA1 140 nm | — | — | Inv-1:TER4 (95%:5%) 40 nm | — | ST2:LiQ (50%:50%) 35 nm |
| E2 | SpMA1 140 nm | — | — | Inv-2:TER4 (95%:5%) 40 nm | — | ST2:LiQ (50%:50%) 35 nm |
| E3 | SpMA1 140 nm | — | — | Inv-3:TEG1:TER4 (80%:15%:5%) 40 nm | — | ST2:LiQ (50%:50%) 35 nm |
| E4 | SpMA1 140 nm | — | — | Inv-4:SpMA1:TER4 (65%:30%:5%) 40 nm | — | ST2:LiQ (50%:50%) 35 nm |
| E5 | SpMA1 140 nm | — | — | Inv-5:TEG1:TER4 (85%:10%:5%) 40 nm | — | ST2:LiQ (50%:50%) 35 nm |
| E6 | SpMA1 140 nm | — | — | Inv-6:TER4 (97%:3%) 40 nm | — | ST2:LiQ (50%:50%) 35 nm |
| E7 | SpMA1 140 nm | — | — | Inv-7:TEG1:TER4 (85%:10%:5%) 40 nm | — | ST2:LiQ (50%:50%) 35 nm |
| E8 | SpMA1 140 nm | — | — | Inv-8:TER4 (95%:5%) 40 nm | — | ST2:LiQ (50%:50%) 35 nm |
| E9 | SpA1 70 nm | HATCN 5 nm | SpMA1 110 nm | IC1:TEG1 (90%:10%) 30 nm | Inv-9 10 nm | ST2:LiQ (50%:50%) 30 nm |
| E10 | SpA1 70 nm | HATCN 5 nm | SpMA1 110 nm | IC1:TEG1 (90%:10%) 30 nm | — | Inv-10:LiQ (50%:50%) 30 nm |
| E11 | SpMA1 140 nm | — | — | Inv-11:TER4 (97%:3%) 40 nm | IC1 10 nm | ST2:LiQ (50%:50%) 25 nm |

TABLE 2

| | | | OLED device data | | | | | |
|---|---|---|---|---|---|---|---|---|
| Example | U1000 (V) | CE1000 (cd/A) | LE1000 (lm/W) | EQE 1000 | CIE x/y at $10^3$ cd/m$^2$ | $L_0$; $j_0$ | $L_1$ % | LT (h) |
| V1 | 4.8 | 16.1 | 10.5 | 14.4% | 0.67/0.33 | 20 mA/cm$^2$ | 80 | 740 |
| V2 | 3.5 | 61 | 55 | 17.3% | 0.33/0.62 | 20 mA/cm$^2$ | 80 | 120 |
| V3 | 3.3 | 63 | 60 | 17.5% | 0.32/0.63 | 20 mA/cm$^2$ | 80 | 125 |
| V4 | 4.7 | 16.6 | 11.1 | 14.7% | 0.67/0.33 | 20 mA/cm$^2$ | 80 | 870 |
| V5 | 4.5 | 16.9 | 11.8 | 14.9% | 0.66/0.34 | 20 mA/cm$^2$ | 80 | 820 |
| V6 | 4.8 | 16.7 | 10.9 | 14.6% | 0.66/0.34 | 20 mA/cm$^2$ | 80 | 770 |
| V7 | 4.8 | 16.8 | 11.0 | 14.7% | 0.66/0.33 | 20 mA/cm$^2$ | 80 | 1010 |
| E1 | 4.7 | 16.7 | 11.2 | 14.8% | 0.67/0.33 | 20 mA/cm$^2$ | 80 | 1120 |
| E2 | 4.6 | 16.8 | 11.5 | 14.9% | 0.67/0.33 | 20 mA/cm$^2$ | 80 | 900 |
| E3 | 4.2 | 19.6 | 14.7 | 17.8% | 0.67/0.33 | 20 mA/cm$^2$ | 80 | 1330 |
| E4 | 4.4 | 17.4 | 12.4 | 15.6% | 0.67/0.33 | 20 mA/cm$^2$ | 80 | 1170 |
| E5 | 4.3 | 19.5 | 14.2 | 17.0% | 0.66/0.34 | 20 mA/cm$^2$ | 80 | 1240 |
| E6 | 4.6 | 17.0 | 11.6 | 15.0% | 0.67/0.33 | 20 mA/cm$^2$ | 80 | 1090 |
| E7 | 4.3 | 19.1 | 14.0 | 16.9% | 0.67/0.33 | 20 mA/cm$^2$ | 80 | 1140 |
| E8 | 4.7 | 16.5 | 11.0 | 14.6% | 0.67/0.33 | 20 mA/cm$^2$ | 80 | 1020 |
| E9 | 3.5 | 63 | 57 | 17.1% | 0.33/0.63 | 20 mA/cm$^2$ | 80 | 135 |
| E10 | 3.6 | 64 | 56 | 17.2% | 0.33/0.63 | 20 mA/cm$^2$ | 80 | 115 |
| E11 | 4.6 | 17.3 | 11.8 | 15.1% | 0.66/0.34 | 20 mA/cm$^2$ | 80 | 1100 |

TABLE 3

Structures of OLED Materials

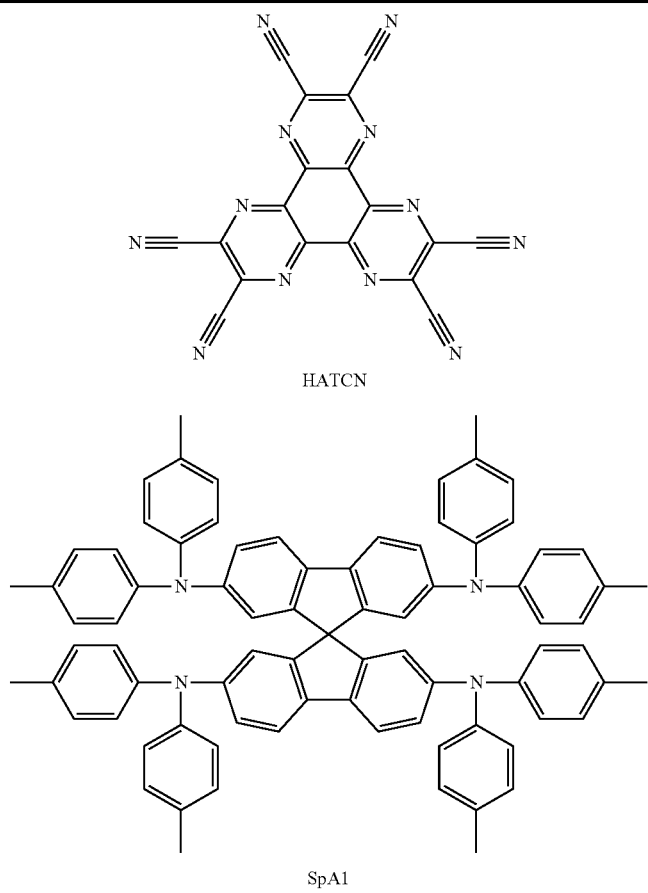

HATCN

SpA1

TABLE 3-continued
Structures of OLED Materials
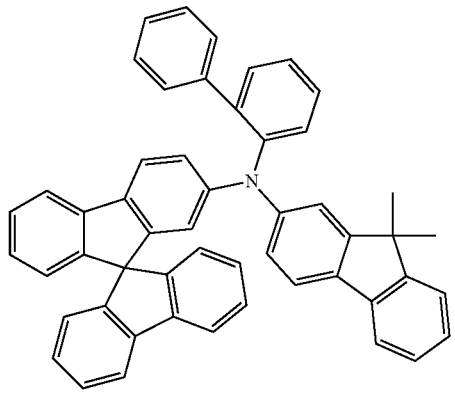
SpMA1
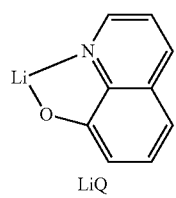
LiQ
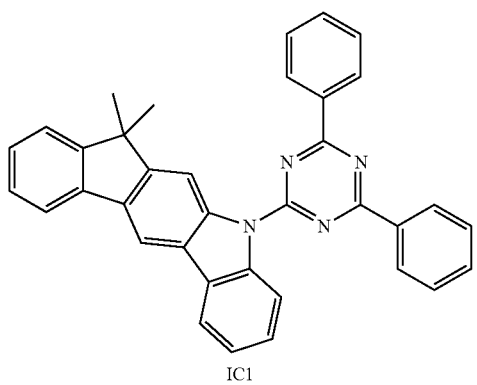
IC1
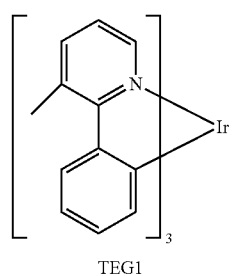
TEG1

TABLE 3-continued
Structures of OLED Materials
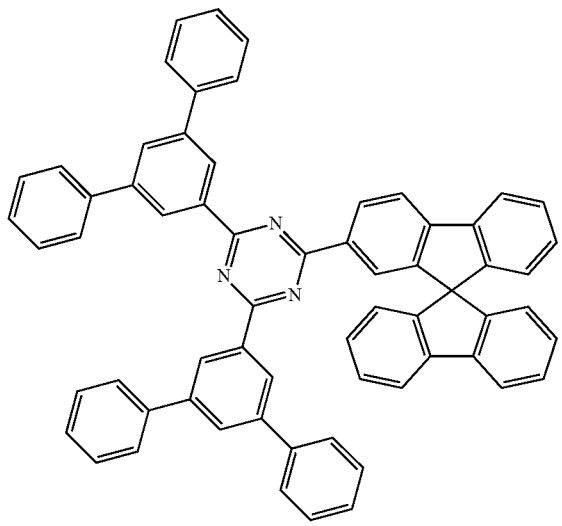
ST2
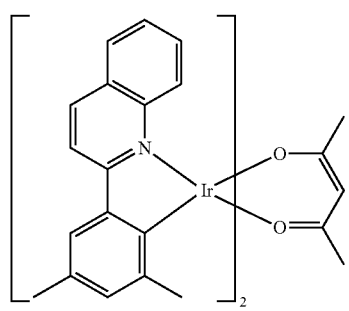
TER4
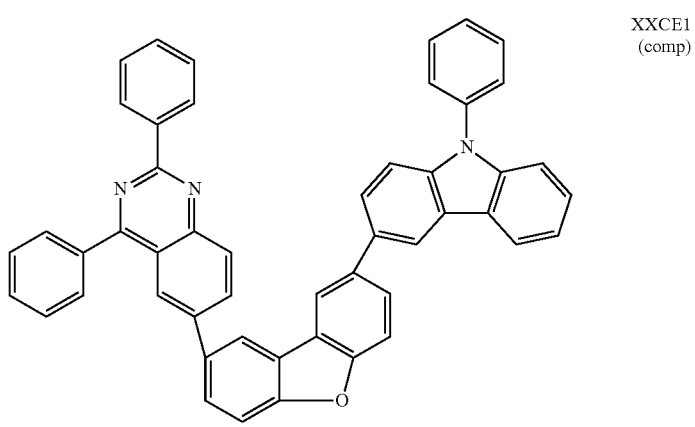
XXCE1 (comp)
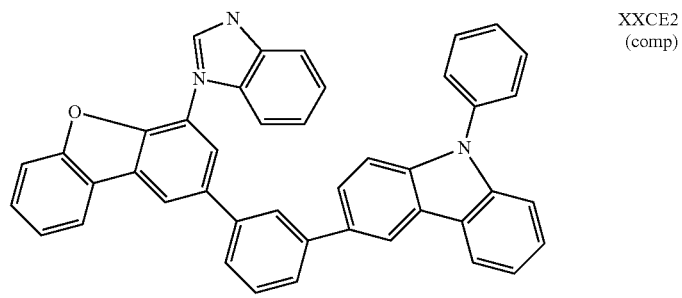
XXCE2 (comp)

TABLE 3-continued
Structures of OLED Materials
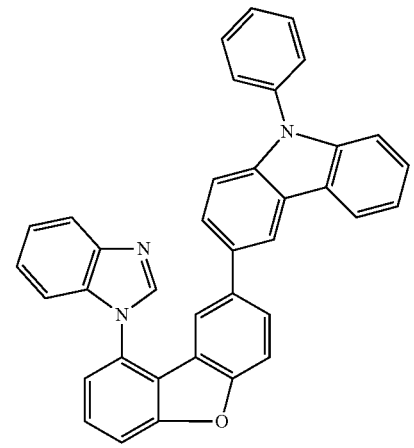 [SMILES: c1ccc(-n2c3ccccc3c3cc(-c4ccc5oc6cccc(-n7cnc8ccccc87)c6c5c4)ccc32)cc1]
XXCE3
(comp)
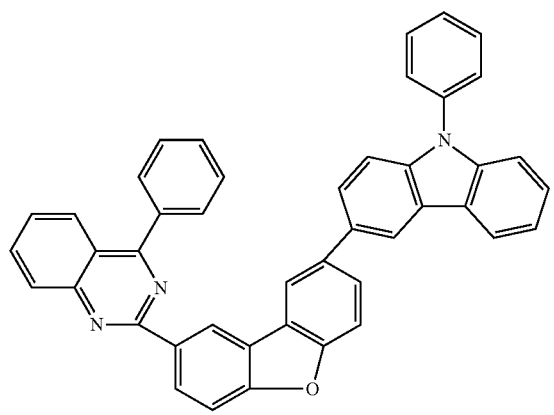 [SMILES: c1ccc(-c2nc(-c3ccc4oc5ccc(-c6ccc7c(c6)c6ccccc6n7-c6ccccc6)cc5c4c3)nc3ccccc23)cc1]
XXCE4
(comp)
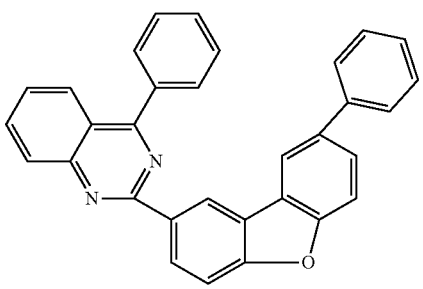 [SMILES: c1ccc(-c2ccc3oc4ccc(-c5nc(-c6ccccc6)c6ccccc6n5)cc4c3c2)cc1]
XXCE5
(comp)
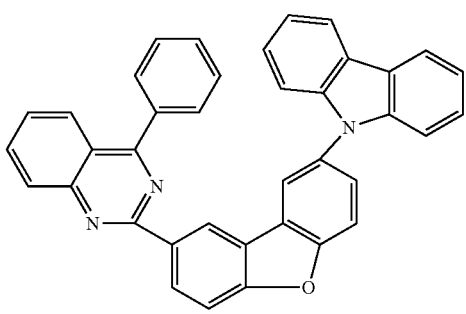 [SMILES: c1ccc(-c2nc(-c3ccc4oc5ccc(-n6c7ccccc7c7ccccc76)cc5c4c3)nc3ccccc23)cc1]
XXCE6
(comp)

TABLE 3-continued
Structures of OLED Materials
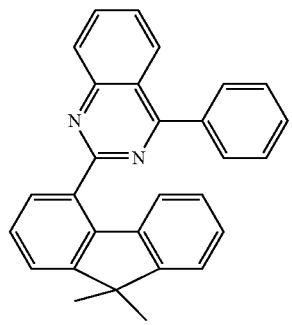 [SMILES: CC1(C)c2ccccc2-c2c(-c3nc(-c4ccccc4)c4ccccc4n3)cccc21]
XXCE7
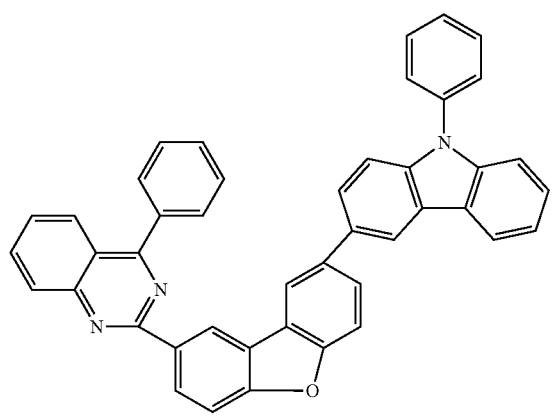 [SMILES: c1ccc(-c2nc(-c3ccc4oc5ccc(-c6ccc7c(c6)c6ccccc6n7-c6ccccc6)cc5c4c3)nc3ccccc23)cc1]
Inv-1
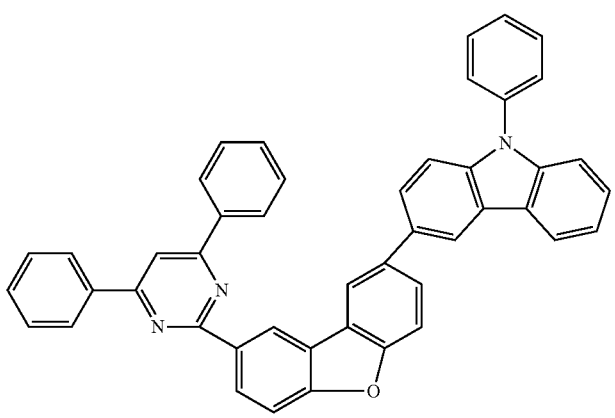 [SMILES: c1ccc(-c2cc(-c3ccccc3)nc(-c3ccc4oc5ccc(-c6ccc7c(c6)c6ccccc6n7-c6ccccc6)cc5c4c3)n2)cc1]
Inv-2
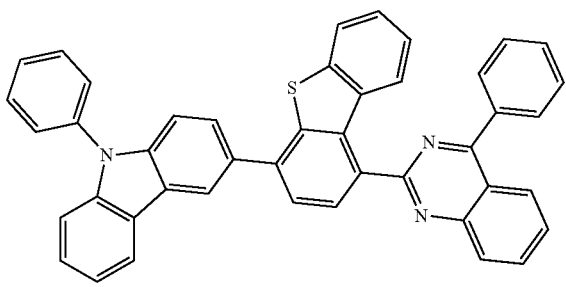 [SMILES: c1ccc(-c2nc(-c3ccc(-c4ccc5c(c4)c4ccccc4n5-c4ccccc4)c4sc5ccccc5c34)nc3ccccc23)cc1]
Inv-3

TABLE 3-continued
Structures of OLED Materials
Inv-4
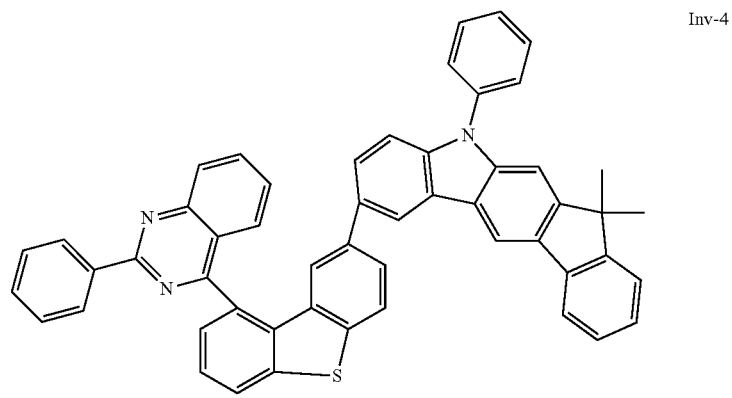
Inv-5
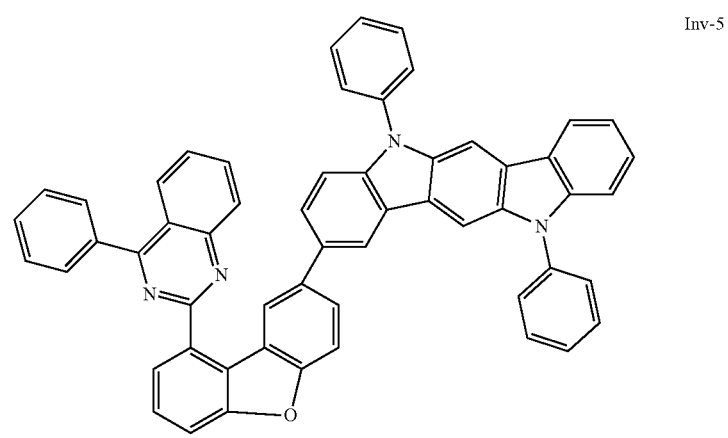
Inv-6
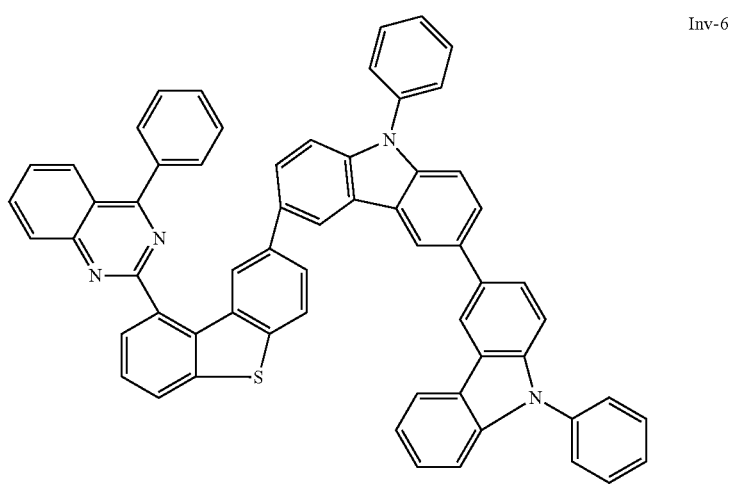

TABLE 3-continued
Structures of OLED Materials
Inv-7
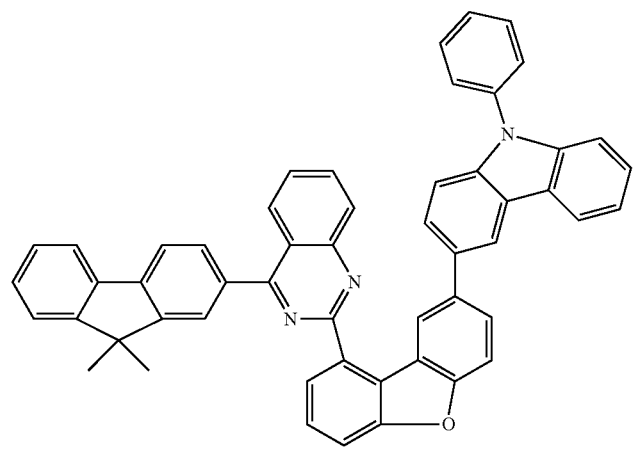 [SMILES: CC1(C)c2ccccc2-c2ccc(-c3nc(-c4cccc5oc6ccc(-c7ccc8c(c7)c7ccccc7n8-c7ccccc7)cc6c45)nc4ccccc34)cc21]
Inv-8
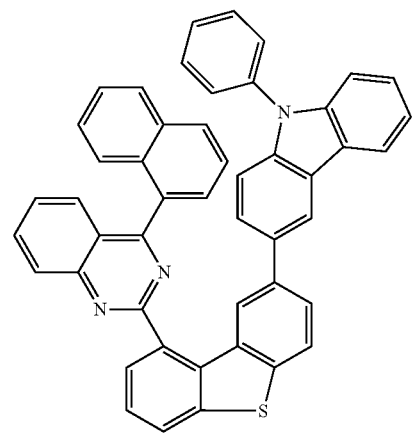 [SMILES: c1ccc(-n2c3ccccc3c3cc(-c4ccc5sc6cccc(-c7nc(-c8cccc9ccccc89)c8ccccc8n7)c6c5c4)ccc32)cc1]
Inv-9
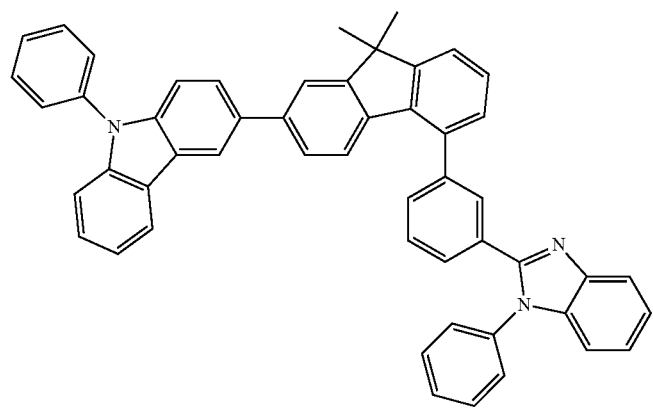 [SMILES: CC1(C)c2cc(-c3ccc4c(c3)c3ccccc3n4-c3ccccc3)ccc2-c2c(-c3cccc(-c4nc5ccccc5n4-c4ccccc4)c3)cccc21]

TABLE 3-continued

Structures of OLED Materials

Inv-10

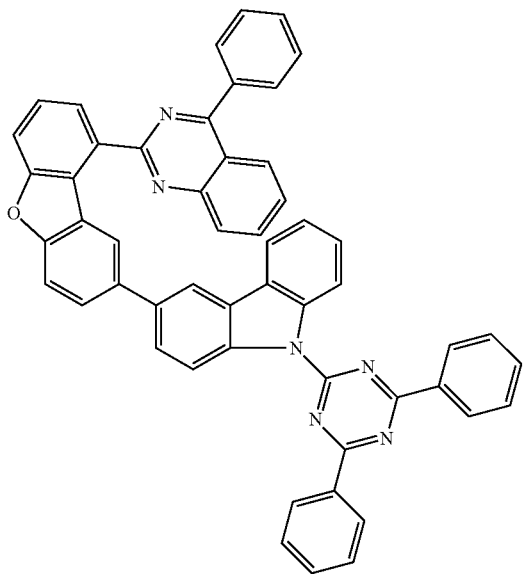 [SMILES: c1ccc(-c2nc(-c3ccccc3)nc(-n3c4ccccc4c4cc(-c5ccc6oc7cccc(-c8nc(-c9ccccc9)c9ccccc9n8)c7c6c5)ccc43)n2)cc1]

Inv-11

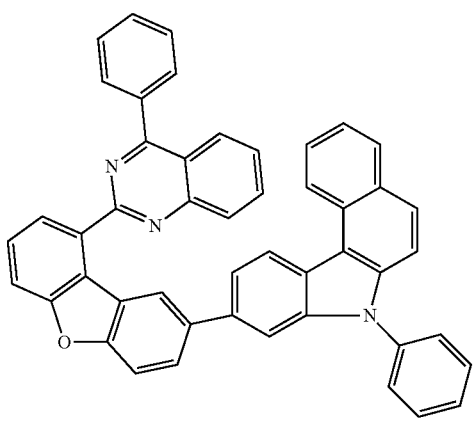 [SMILES: c1ccc(-c2nc(-c3cccc4oc5ccc(-c6ccc7c8c9ccccc9ccc8n(-c8ccccc8)c7c6)cc5c34)nc3ccccc23)cc1]

As can been seen in Table 2, OLEDs containing the compounds of the invention provide improved performance, without regard to whether it is located in the light-emitting layer as a host (i.e. E1-E8), in a hole-blocking layer (i.e. E9) or in an electron-transporting layer (i.e. E10). For example, inventive OLEDs E1, E2, E6 and E8, using inventive compounds as a host for a red phosphorescent emitter, are the same as comparative OLEDs V1 and V4-6 but have improved lifetime. In particular, comparison compound XXCE4 (V4), which has a diazine heterocycle in the 2-position, has a LT of 870 h. However, E1, which is identical to V4 except for using the inventive compound Inv-1, which is identical for XXCE4 except that the diazine is located in the 1-position, has a LT of 1120 h, for an improvement of 29%. Likewise, E9, where an inventive compound is used as a host for a green phosphorescent emitter, shows better lifetime than V2 and V3. Even better results are seen when an inventive compound is used in more than one layer (i.e. E11) is compared to a comparative (i.e. V7) without the inventive compound.

The invention claimed is:

1. An oligomer, polymer or dendrimer containing one or more of the compounds according to Formula (1) or (2):

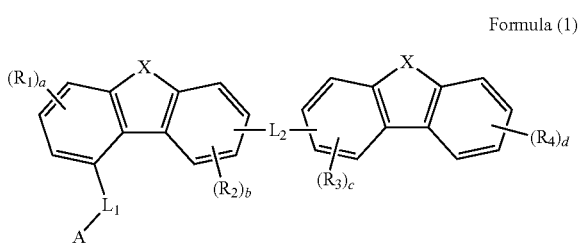

Formula (1)

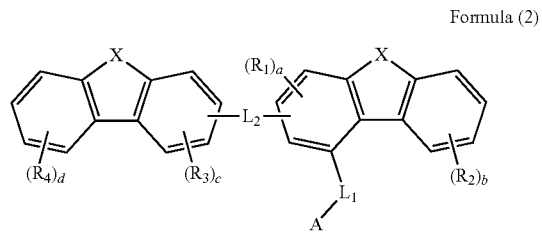

Formula (2)

where:

X is oxygen, sulfur or $CZ_1Z_2$;

Y is oxygen, sulfur, $CZ_1Z_2$ or $NAr_1$;

Z₁ and Z₂ are on each occurrence, identically or differently, H, D, F, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R_5$, where one or more, non-adjacent $CH_2$ groups may be replaced by $(R_5)C=C(R_5)$, $C≡C$, $Si(R_5)_2$, $Ge(R_5)_2$, $Sn(R_5)_2$, $C=O$, $C=S$, $C=Se$, $C=N(R_5)$, $P(=O)(R_5)$, SO, $SO_2$, $N(R_5)_2$, O, S or $CON(R_5)_2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R_5$, or an aryloxy or heteroaryloxy group having 5 to 60 aromatic ring atoms, which may be substituted by one or more radicals $R_5$, where $Z_1$ and $Z_2$ may be connected together to form a spiro ring system;

$R_1$, $R_2$, $R_3$ and $R_4$ is on each occurrence, identically or differently, selected from the group consisting of H, D, F, Cl, Br, I, CN, $Si(R_5)_3$, a straight-chain alkyl, alkoxy or thioalkyl group having 1 to 40 C atoms or a branched or cyclic alkyl, alkoxy or thioalkyl with 3-40 C atoms which may be substituted by one or more radicals $R_5$, wherein each one or more non-adjacent $CH_2$ groups by may be replaced $Si(R_5)_2$, $C=NR_5$, $P(=O)(R_5)$, SO, $SO_2$, $NR_5$, O, S or $CONR_5$ and where one or more H atoms may be replaced by D, F, Cl, Br or I, an aromatic or heteroaromatic ring system having 6 to 40 carbon atoms which may be substituted by one or more radicals $R_5$, an aryloxy group having 5 to 60 aromatic ring atoms which may be substituted by one or more radicals $R_5$, or an aralkyl group having 5 to 60 aromatic ring atoms, which may be substituted by one or more radicals $R_5$, where two or more adjacent substituents $R_1$, $R_2$, $R_3$ and $R_4$ can form a mono- or poly-cyclic, aliphatic, aromatic or heteroaromatic ring system with one another and which may be substituted with one or more radicals $R_5$;

$R_5$ is selected from the group consisting of H, D, F, an aliphatic hydrocarbon radical having 1 to 20 carbon atoms or an aromatic or heteroaromatic ring system having 5 to 30 C atoms;

$Ar_1$ is an aromatic or heteroaromatic ring system having 5 to 30 aromatic ring atoms, which may be substituted by one or more radicals $R_5$ and where optionally two or more adjacent substituents $R_5$ can form a mono- or polycyclic, aliphatic, aromatic or heteroaromatic ring system with one another;

a, b, c are on each occurrence, identically or differently, are 0, 1, 2 or 3, where a is not 3 in Formula (2), and d is independently 0, 1, 2, 3 or 4;

$L_1$ and $L_2$ are on each occurrence, identically or differently, a direct bond or an aromatic or heteroaromatic ring system having 5-30 aromatic ring atoms, which may be substituted by one or more non-aromatic radicals $R_5$;

A is a heterocyclic group selected from the group of Formula $A_1$,

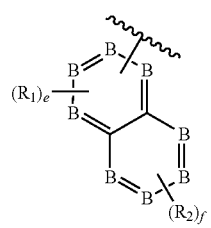

where only one or two of B are nitrogen atoms and the others are carbon atoms, $R_1$ and $R_2$ are as previously defined, e is 0, 1, 2 or 3, f is 0, 1, 2, 3 or 4, and wherein $A_1$ is connected to the remainder of the compound through a carbon atom; or A is a heterocyclic group selected from the group of Formula A2 or A3:

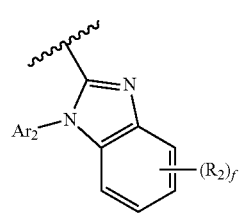

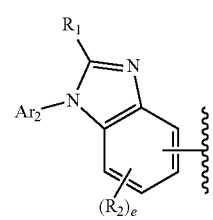

where $R_1$, $R_2$, e and f are as previously defined; and $Ar_2$ is an aromatic or heteroaromatic ring system having 5 to 30 aromatic ring atoms, which may be substituted by one or more radicals $R_5$ and where optionally two or more adjacent substituents $R_5$ can form a mono- or polycyclic, aliphatic, aromatic or heteroaromatic ring system with one another;

or A is a heterocyclic group according to $A_4$:

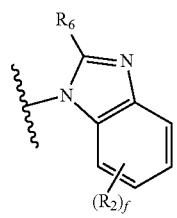

where $R_2$, e and f are as previously defined; and $R_6$ is the same as $R_1$ but excluding H or D, where one or more bonds from the compound to the polymer, oligomer or dendrimer are present instead of substituents at one or more positions.

2. The oligomer, polymer or dendrimer according to claim 1, wherein $A_1$ is according to formula W:

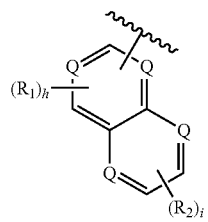

where only one or two of Q are nitrogen atoms and the others are carbon atoms.

3. The oligomer, polymer or dendrimer according to claim 1, wherein X is oxygen and Y is $NAr_1$.

4. The oligomer, polymer or dendrimer according to claim 1, wherein c is 0, d is 0 or 2 and when d is 2, the two $R_4$ groups are adjacent and form a monocyclic- or polycyclic, aromatic or heteroaromatic annulated ring system.

5. The oligomer, polymer or dendrimer according to claim 1, wherein the compound is according to any one of Formulae (11) to (18);

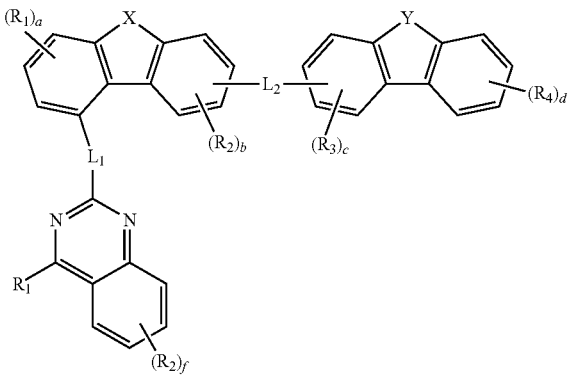

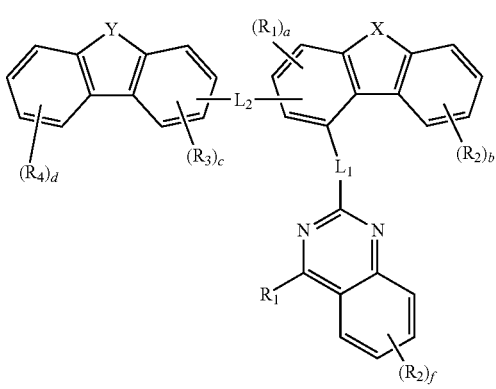

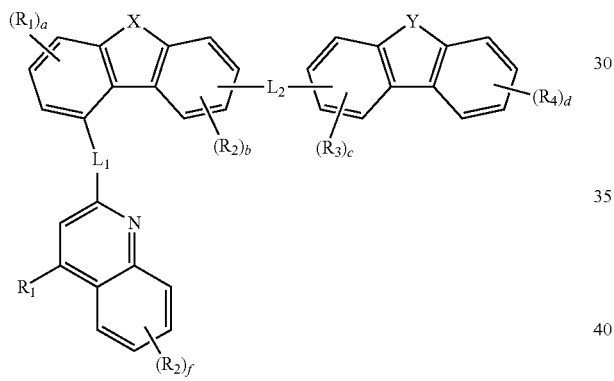

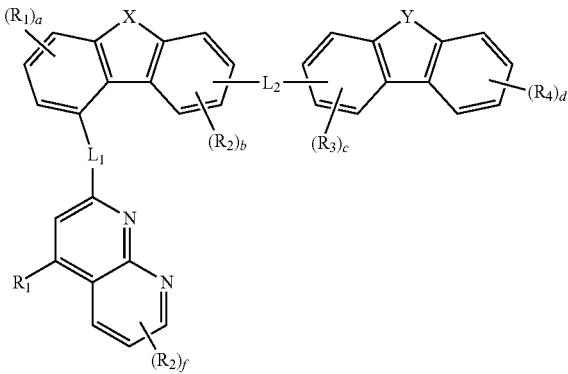

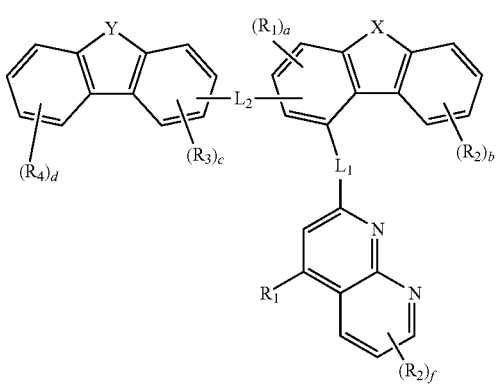

(17)

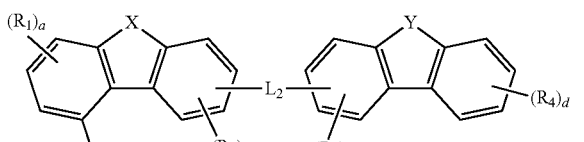

(18)

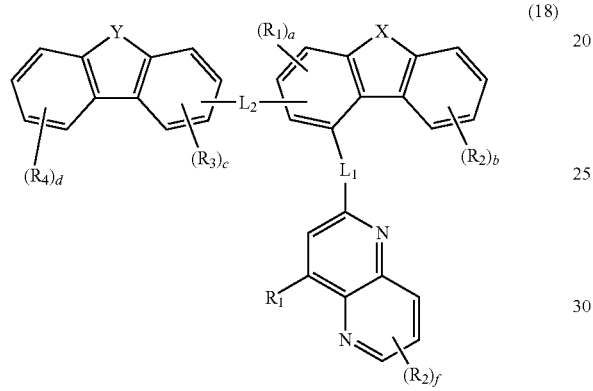

where the symbols and indices are defined as in claim 1.

6. The oligomer, polymer or dendrimer according to claim 1, wherein the compound contains no condensed aryl or heteroaryl groups in which more than two six-membered rings are condensed directly onto one another.

7. A formulation comprising the oligomer, polymer or dendrimer according to claim 1 and at least one solvent.

8. An electronic device comprising the oligomer, polymer or dendrimer according to claim 1.

9. The electronic device according to claim 8, wherein the device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

10. An organic electroluminescent device which comprises the oligomer, polymer or dendrimer according to claim 1 is employed as matrix material for phosphorescent or fluorescent emitters and/or in an electron-blocking or exciton-blocking layer and/or in a hole-transport layer and/or in a hole-blocking layer and/or in a hole-blocking or electron-transport layer.

11. The oligomer, polymer or dendrimer according to claim 2, wherein one Q is nitrogen so that W group is according to $A_1$-a or $A_1$-b or where two Q are nitrogen so that W is according to any of $A_1$-c, $A_1$-d and $A_1$-e:

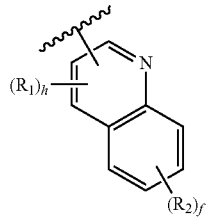
$A_1$-a

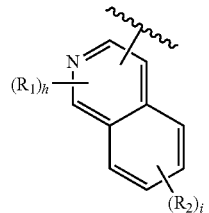
$A_1$-b

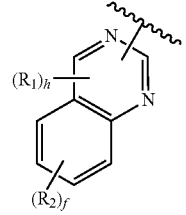
$A_1$-c

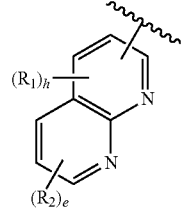
$A_1$-d

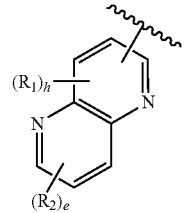
$A_1$-e $R_1$ and $R_2$, is on each occurrence, identically or differently, selected from the group consisting of H, D, F, Cl, Br, I, CN, $Si(R_5)_3$, a straight-chain alkyl, alkoxy or thioalkyl group having 1 to 40 C atoms or a branched or cyclic alkyl, alkoxy or thioalkyl with 3-40 C atoms which may be substituted by one or more radicals $R_5$, wherein each one or more non-adjacent $CH_2$ groups by may be replaced $Si(R_5)_2$, C=$NR_5$, P(=O)($R_5$), SO, $SO_2$, $NR_5$, O, S or $CONR_5$ and where one or more H atoms may be replaced by D, F, Cl, Br or I, an aromatic or heteroaromatic ring system having 6 to 40 carbon atoms which may be substituted by one or more radicals $R_5$, an aryloxy group having 5 to 60 aromatic ring atoms which may be substituted by one or more radicals $R_5$, or an aralkyl group having 5 to 60 aromatic ring atoms, which may be substituted by one or more radicals $R_5$, where two or more adjacent substituents $R_1$ and $R_2$ can form a mono- or polycyclic, aliphatic, aromatic or heteroaromatic ring system with one another and which may be substituted with one or more radicals $R_5$;

$R_5$ is selected from the group consisting of H, D, F, an aliphatic hydrocarbon radical having 1 to 20 carbon atoms or an aromatic or heteroaromatic ring system having 5 to 30 C atoms;

e is 0, 1, 2 or 3;
f is 0, 1, 2, 3 or 4;
h is 0, 1 or 2; and
i is 0 or 1.

12. The oligomer, polymer or dendrimer according to claim 11, wherein W group is $A_1$-a or $A_1$-b.

13. The oligomer, polymer or dendrimer according to claim 11, wherein W group is $A_1$-c or $A_1$-d.

14. The oligomer, polymer or dendrimer according to claim 11, wherein W group is $A_1$-e.

15. A compound according to Formula (1) or (2):

Formula (1)

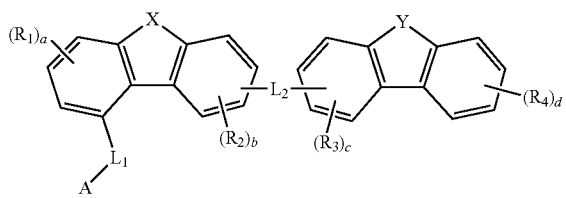

Formula (2)

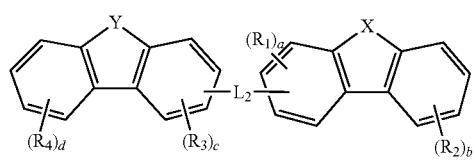

where:
X is oxygen, sulfur or $CZ_1Z_2$;
Y is oxygen, sulfur, $CZ_1Z_2$ or $NAr_1$;
$Z_1$ and $Z_2$ are on each occurrence, identically or differently, H, D, F, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R_5$, where one or more, non-adjacent $CH_2$ groups may be replaced by $(R_5)C=C(R_5)$, $C≡C$, $Si(R_5)_2$, $Ge(R_5)_2$, $Sn(R_5)_2$, $C=O$, $C=S$, $C=Se$, $C=N(R_5)$, $P(=O)(R_5)$, SO, $SO_2$, $N(R_5)_2$, O, S or $CON(R_5)_2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R_5$, or an aryloxy or heteroaryloxy group having 5 to 60 aromatic ring atoms, which may be substituted by one or more radicals $R_5$, where $Z_1$ and $Z_2$ may be connected together to form a spiro ring system;

$R_1$, $R_2$, $R_3$ and $R_4$ is on each occurrence, identically or differently, selected from the group consisting of H, D, F, Cl, Br, I, CN, $Si(R_5)_3$, a straight-chain alkyl, alkoxy or thioalkyl group having 1 to 40 C atoms or a branched or cyclic alkyl, alkoxy or thioalkyl with 3-40 C atoms which may be substituted by one or more radicals $R_5$, wherein each one or more non-adjacent $CH_2$ groups by may be replaced $Si(R_5)_2$, $C=NR_5$, $P(=O)(R_5)$, SO, $SO_2$, $NR_5$, O, S or $CONR_5$ and where one or more H atoms may be replaced by D, F, Cl, Br or I, an aromatic or heteroaromatic ring system having 6 to 40 carbon atoms which may be substituted by one or more radicals $R_5$, an aryloxy group having 5 to 60 aromatic ring atoms which may be substituted by one or more radicals $R_5$, or an aralkyl group having 5 to 60 aromatic ring atoms, which may be substituted by one or more radicals $R_5$, where two or more adjacent substituents $R_1$, $R_2$, $R_3$ and $R_4$ can form a mono- or poly-cyclic, aliphatic, aromatic or heteroaromatic ring system with one another and which may be substituted with one or more radicals $R_5$;

$R_5$ is selected from the group consisting of H, D, F, an aliphatic hydrocarbon radical having 1 to 20 carbon atoms or an aromatic or heteroaromatic ring system having 5 to 30 C atoms;

$Ar_1$ is an aromatic or heteroaromatic ring system having 5 to 30 aromatic ring atoms, which may be substituted by one or more radicals $R_5$ and where optionally two or more adjacent substituents $R_5$ can form a mono- or polycyclic, aliphatic, aromatic or heteroaromatic ring system with one another;

a, b, c are on each occurrence, identically or differently, are 0, 1, 2 or 3, where a is not 3 in Formula (2), and is independently 0, 1, 2, 3 or 4;

$L_1$ and $L_2$ are on each occurrence, identically or differently, a direct bond or an aromatic or heteroaromatic ring system having 5-30 aromatic ring atoms, which may be substituted by one or more non-aromatic radicals $R_5$;

A is a heterocyclic group selected from the group of Formula $A_2$ or $A_3$:

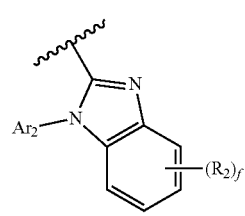

$A_2$

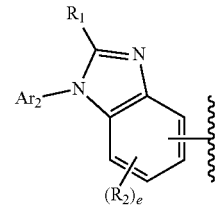

$A_3$ where $R_1$, $R_2$, e and f are as previously defined; and
$Ar_2$ is an aromatic or heteroaromatic ring system having 5 to 30 aromatic ring atoms, which may be substituted by one or more radicals $R_5$ and where optionally two or more adjacent substituents $R_5$ can form a mono- or polycyclic, aliphatic, aromatic or heteroaromatic ring system with one another;

or A is a heterocyclic group according to $A_4$:

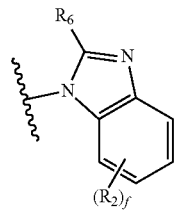

e is 0, 1, 2 or 3 and f is 0, 1, 2, 3 or 4 and $R_6$ is the same as $R_1$ but excluding H or D.

16. The compound according to claim 15, wherein X is oxygen and Y is $NAr_1$.

17. The compound according to claim 15, wherein $L_1$ is a direct bond or a phenylene group.

18. The compound according to claim 15, wherein $L_2$ is a direct bond or a phenylene group.

19. The compound according to claim 15, wherein whenever X or Y is $CZ_1Z_2$, $Z_1$ and $Z_2$ are identical alkyl groups of 1-10 carbon atoms or aryl groups of between 6-30 carbon atoms.

20. The compound according to claim 15, wherein c is 0, d is 0 or 2 and when d is 2, the two $R_4$ groups are adjacent and form a monocyclic- or polycyclic, aromatic or heteroaromatic annulated ring system.

21. The compound according to claim 15, wherein the compound contains no condensed aryl or heteroaryl groups in which more than two six-membered rings are condensed directly onto one another.

22. An oligomer, polymer or dendrimer containing one or more of the compounds according to claim 15, where one or more bonds from the compound to the polymer, oligomer or dendrimer are present instead of substituents at one or more positions.

23. A formulation comprising at least one compound according to claim 15 and at least one solvent.

24. An electronic device comprising the compound according to claim 15.

25. The electronic device according to claim 24, wherein the device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

26. An organic electroluminescent device which comprises the compound according to claim 15 is employed as matrix material for phosphorescent or fluorescent emitters and/or in an electron-blocking or exciton-blocking layer and/or in a hole-transport layer and/or in a hole-blocking layer and/or in a hole-blocking or electron-transport layer.

* * * * *